(12) United States Patent
Patrick et al.

(10) Patent No.: US 9,067,015 B2
(45) Date of Patent: Jun. 30, 2015

(54) SYSTEM FOR INJECTING FLUIDS IN A SUBJECT

(71) Applicant: Carticept Medical, Inc., Alpharetta, GA (US)

(72) Inventors: Timothy Patrick, Alpharetta, GA (US); Richard Knostman, Alpharetta, GA (US); Michael Axelrod, Roswell, GA (US); Carribeth Ramey, Suwanee, GA (US)

(73) Assignee: Carticept Medical, Inc., Alpharetta, GA (US)

( * ) Notice: Subject to any disclaimer, the term of this patent is extended or adjusted under 35 U.S.C. 154(b) by 0 days.

(21) Appl. No.: 14/040,283

(22) Filed: Sep. 27, 2013

(65) Prior Publication Data

US 2014/0031751 A1   Jan. 30, 2014

Related U.S. Application Data

(63) Continuation of application No. 12/823,004, filed on Jun. 24, 2010, now Pat. No. 8,545,440, which is a continuation-in-part of application No. 12/340,595, filed on Dec. 19, 2008, now Pat. No. 8,002,736.

(60) Provisional application No. 61/220,175, filed on Jun. 24, 2009, provisional application No. 61/016,395, filed on Dec. 21, 2007.

(51) Int. Cl.
*A61M 37/00* (2006.01)
*A61M 5/168* (2006.01)
(Continued)

(52) U.S. Cl.
CPC ......... *A61M 5/16827* (2013.01); *A61B 5/4839* (2013.01); *A61B 8/00* (2013.01);
(Continued)

(58) Field of Classification Search
USPC ............. 604/82, 83, 85, 89, 65–67, 131, 151, 604/152, 154, 155, 257–259, 500, 506, 507, 604/511, 518–520, 191
See application file for complete search history.

(56) References Cited

U.S. PATENT DOCUMENTS 3,176,538 A   4/1965   Hurlow
3,556,079 A   1/1971   Omizo
(Continued)

FOREIGN PATENT DOCUMENTS

EP   0 223 548   5/1987
EP   0 302 752   8/1988
(Continued)

OTHER PUBLICATIONS

Caglar-Yagci et al. "Safety and Efficacy of Ultrasound-Guided Intra-Articular Hylan G-F 20 Injection in Osteoarthritis of the Hip: A Pilot Study". Physical Medicine and Rehabilitation Department, Rheumatol Int. Jun. 2005;25(5):341-4. Epub Mar. 5, 2004. Ankara Physical Medicine and Rehabilitation Education and Research Hospital, Ankara, Turkey.

(Continued)

*Primary Examiner* — Scott Medway
(74) *Attorney, Agent, or Firm* — Knobbe, Martens, Olson & Bear, LLP

(57) ABSTRACT

Devices and systems for injecting fluids and/or other materials into a targeted anatomical location, in particular, a joint or intra-articular space, include a handpiece assembly having a needle extending from its distal end, a fluid delivery module comprising a cassette and a fluid transfer device. A conduit is generally configured to place the fluid delivery module in fluid communication with the handpiece assembly. Medicaments, formulations and/or other fluids or materials contained within vials that are secured to a cassette or other portion of the fluid delivery module can be selectively delivered into an anatomy through a needle located at the distal end of the handpiece assembly. In some embodiments, ultrasound or other imaging technologies can be used to locate a joint or other targeted anatomical location.

18 Claims, 105 Drawing Sheets

(51) Int. Cl.
  *A61B 8/00* (2006.01)
  *A61M 5/145* (2006.01)
  *A61B 5/00* (2006.01)
  *A61B 17/34* (2006.01)
  *A61B 19/00* (2006.01)
  *A61M 5/142* (2006.01)
  *A61M 5/162* (2006.01)
  *A61M 39/24* (2006.01)

(52) U.S. Cl.
  CPC . *A61B2017/3413* (2013.01); *A61B 2019/5276* (2013.01); *A61M 5/14216* (2013.01); *A61M 5/1452* (2013.01); *A61M 5/162* (2013.01); *A61M 2039/242* (2013.01); *A61M 2039/246* (2013.01); *A61M 2205/505* (2013.01)

(56) References Cited

U.S. PATENT DOCUMENTS

| | | | |
|---|---|---|---|
| 3,807,048 | A | 4/1974 | Malmin |
| 4,005,614 | A | 2/1977 | Moore et al. |
| 4,236,880 | A | 12/1980 | Archibald |
| 4,559,036 | A | 12/1985 | Wunsch |
| 4,563,175 | A * | 1/1986 | LaFond .................. 604/155 |
| 4,676,256 | A | 6/1987 | Golden |
| 4,747,824 | A | 5/1988 | Spinello |
| 4,790,823 | A | 12/1988 | Charton et al. |
| 4,795,441 | A | 1/1989 | Bhatt |
| 4,877,934 | A | 10/1989 | Spinello |
| 4,950,245 | A | 8/1990 | Brown et al. |
| 4,978,336 | A | 12/1990 | Capozzi et al. |
| 5,125,837 | A | 6/1992 | Warrin et al. |
| 5,147,323 | A | 9/1992 | Haber et al. |
| 5,176,643 | A | 1/1993 | Kramer et al. |
| 5,180,371 | A | 1/1993 | Spinello |
| 5,188,603 | A | 2/1993 | Vaillancourt |
| 5,199,949 | A | 4/1993 | Haber et al. |
| 5,207,642 | A | 5/1993 | Orkin et al. |
| 5,243,982 | A | 9/1993 | Mostl et al. |
| 5,253,578 | A | 10/1993 | Hsu |
| 5,271,527 | A | 12/1993 | Haber et al. |
| 5,281,198 | A | 1/1994 | Haber et al. |
| 5,298,023 | A | 3/1994 | Haber et al. |
| 5,314,412 | A | 5/1994 | Rex |
| 5,318,522 | A | 6/1994 | D'Antonio |
| 5,324,258 | A | 6/1994 | Rohrbough |
| 5,336,188 | A | 8/1994 | Kriesel |
| 5,354,284 | A | 10/1994 | Haber et al. |
| 5,360,410 | A | 11/1994 | Wacks |
| 5,378,231 | A | 1/1995 | Johnson et al. |
| 5,378,233 | A | 1/1995 | Haber et al. |
| 5,395,326 | A | 3/1995 | Haber et al. |
| 5,411,490 | A | 5/1995 | Tennican et al. |
| 5,425,366 | A | 6/1995 | Reinhardt et al. |
| 5,445,614 | A | 8/1995 | Haber et al. |
| 5,478,323 | A | 12/1995 | Westwood et al. |
| 5,505,704 | A | 4/1996 | Pawelka et al. |
| 5,520,658 | A | 5/1996 | Holm |
| 5,542,934 | A | 8/1996 | Silver |
| 5,584,815 | A | 12/1996 | Pawelka et al. |
| 5,588,432 | A | 12/1996 | Crowley |
| 5,599,312 | A | 2/1997 | Higashikawa |
| 5,611,783 | A | 3/1997 | Mikkelsen |
| 5,620,479 | A | 4/1997 | Diederich |
| 5,647,373 | A | 7/1997 | Paltieli |
| 5,656,016 | A | 8/1997 | Ogden |
| 5,658,247 | A | 8/1997 | Henley |
| 5,666,946 | A | 9/1997 | Langenback |
| 5,667,487 | A | 9/1997 | Henley |
| 5,698,787 | A | 12/1997 | Parzuchowski et al. |
| 5,704,918 | A | 1/1998 | Higashikawa |
| 5,707,365 | A | 1/1998 | Haber et al. |
| 5,725,494 | A | 3/1998 | Brisken |
| 5,735,811 | A | 4/1998 | Brisken |
| 5,752,515 | A | 5/1998 | Jolesz et al. |
| 5,794,612 | A | 8/1998 | Wachter et al. |
| 5,800,421 | A | 9/1998 | Lemelson |
| 5,814,022 | A | 9/1998 | Antanavich et al. |
| 5,830,187 | A | 11/1998 | Kriesel et al. |
| 5,833,627 | A | 11/1998 | Shmulewitz et al. |
| RE35,986 | E | 12/1998 | Ritson et al. |
| 5,876,380 | A | 3/1999 | Manganini et al. |
| 5,908,158 | A | 6/1999 | Cheiman |
| 5,917,828 | A | 6/1999 | Thompson |
| 5,924,997 | A | 7/1999 | Campbell |
| 5,927,977 | A | 7/1999 | Sale et al. |
| 5,935,111 | A | 8/1999 | Bunyan |
| 5,951,517 | A | 9/1999 | Lampropoulos et al. |
| 5,961,494 | A | 10/1999 | Hogan |
| 5,980,509 | A | 11/1999 | Magruder et al. |
| 5,984,889 | A | 11/1999 | Christ et al. |
| 5,997,497 | A | 12/1999 | Nita et al. |
| 6,022,337 | A | 2/2000 | Herbst et al. |
| 6,024,718 | A | 2/2000 | Chen et al. |
| D422,361 | S | 4/2000 | Herbst et al. |
| D423,665 | S | 4/2000 | Herbst et al. |
| 6,045,533 | A | 4/2000 | Kriesel et al. |
| D427,314 | S | 6/2000 | Herbst et al. |
| 6,126,600 | A | 10/2000 | Oxaal et al. |
| 6,132,400 | A | 10/2000 | Waldenburg |
| 6,132,414 | A | 10/2000 | Herbst et al. |
| 6,152,734 | A | 11/2000 | Herbst et al. |
| 6,199,554 | B1 | 3/2001 | Mann et al. |
| 6,200,289 | B1 | 3/2001 | Hochman et al. |
| 6,223,936 | B1 | 5/2001 | Jeanbourquin |
| 6,234,990 | B1 | 5/2001 | Rowe et al. |
| 6,245,043 | B1 * | 6/2001 | Villette .................. 604/154 |
| 6,264,064 | B1 | 7/2001 | Birtcher et al. |
| 6,273,864 | B1 | 8/2001 | Duarte et al. |
| 6,308,714 | B1 | 10/2001 | Peterson et al. |
| 6,322,532 | B1 | 11/2001 | D'Sa et al. |
| 6,350,245 | B1 | 2/2002 | Cimino |
| 6,352,683 | B1 | 3/2002 | ten Cate |
| 6,390,815 | B1 | 5/2002 | Pond |
| 6,394,956 | B1 | 5/2002 | Chandrasekaran et al. |
| 6,416,740 | B1 | 7/2002 | Unger |
| 6,428,517 | B1 | 8/2002 | Hochman et al. |
| 6,461,296 | B1 | 10/2002 | Desai |
| 6,475,148 | B1 | 11/2002 | Jackson et al. |
| 6,487,447 | B1 | 11/2002 | Weimann et al. |
| 6,488,628 | B1 | 12/2002 | Reiss |
| 6,491,657 | B2 | 12/2002 | Rowe et al. |
| 6,508,783 | B2 | 1/2003 | DeVore |
| 6,508,791 | B1 | 1/2003 | Guerrero |
| 6,527,718 | B1 | 3/2003 | Connor et al. |
| 6,537,249 | B2 | 3/2003 | Kriesell et al. |
| 6,565,538 | B2 | 5/2003 | Quinn et al. |
| 6,565,539 | B1 | 5/2003 | Zinger et al. |
| 6,585,696 | B2 | 7/2003 | Petersen et al. |
| 6,589,158 | B2 | 7/2003 | Winkler |
| 6,595,948 | B2 | 7/2003 | Suzuki et al. |
| 6,601,581 | B1 | 8/2003 | Babaev |
| 6,607,502 | B1 | 8/2003 | Maguire et al. |
| 6,610,033 | B1 | 8/2003 | Melanson et al. |
| 6,610,042 | B2 | 8/2003 | Leon et al. |
| 6,620,138 | B1 | 9/2003 | Marrgi et al. |
| 6,635,017 | B1 | 10/2003 | Moehring et al. |
| 6,645,181 | B1 | 11/2003 | Lavi et al. |
| 6,652,482 | B2 | 11/2003 | Hochman |
| 6,659,950 | B2 | 12/2003 | Taheri |
| 6,689,067 | B2 | 2/2004 | Sauer et al. |
| 6,689,108 | B2 | 2/2004 | Lavi et al. |
| 6,695,786 | B2 | 2/2004 | Wang et al. |
| 6,702,749 | B2 | 3/2004 | Paladini et al. |
| 6,716,168 | B2 | 4/2004 | Nock et al. |
| 6,719,729 | B2 | 4/2004 | Sogaro |
| 6,723,064 | B2 | 4/2004 | Babaev |
| 6,723,068 | B2 | 4/2004 | Lavi et al. |
| 6,726,650 | B2 | 4/2004 | Schneider et al. |
| 6,726,658 | B2 | 4/2004 | Hochman |
| 6,731,971 | B2 | 5/2004 | Evans et al. |
| 6,733,451 | B2 | 5/2004 | Rabiner et al. |
| 6,786,885 | B2 | 9/2004 | Hochman et al. |

(56) References Cited

U.S. PATENT DOCUMENTS

| | | |
|---|---|---|
| 6,796,964 B2 | 9/2004 | Eidson et al. |
| 6,808,514 B2 | 10/2004 | Schneider et al. |
| 6,842,641 B2 | 1/2005 | Weimann et al. |
| 6,858,020 B2 | 2/2005 | Rusnak |
| 6,875,179 B2 | 4/2005 | Ferguson et al. |
| 6,887,216 B2 | 5/2005 | Hochman et al. |
| 6,905,482 B2 | 6/2005 | Hochman |
| 6,908,433 B1 | 6/2005 | Pruter |
| 6,917,828 B2 | 7/2005 | Fukuda |
| 6,929,609 B2 | 8/2005 | Asafusa |
| 6,936,033 B2 | 8/2005 | McIntosh et al. |
| 6,939,329 B1 | 9/2005 | Verkaart |
| 6,945,954 B2 | 9/2005 | Hochman et al. |
| 6,966,899 B2 | 11/2005 | Hochman et al. |
| 6,972,005 B2 | 12/2005 | Boehm et al. |
| 6,994,686 B2 | 2/2006 | Cruise et al. |
| 7,037,269 B2 | 5/2006 | Nix et al. |
| 7,041,081 B2 | 5/2006 | Minezaki et al. |
| 7,077,827 B2 | 7/2006 | Greenfield |
| 7,078,015 B2 | 7/2006 | Unger |
| 7,169,128 B2 | 1/2007 | Kriesel et al. |
| 7,182,107 B2 | 2/2007 | Sommer et al. |
| 7,214,210 B2* | 5/2007 | Kamen et al. .................. 604/131 |
| 7,235,063 B2 | 6/2007 | D'Antonio et al. |
| D558,340 S | 12/2007 | Hochman et al. |
| D566,265 S | 4/2008 | Hochman et al. |
| 7,361,163 B2 | 4/2008 | Cohen |
| 7,418,981 B2 | 9/2008 | Baker et al. |
| D579,540 S | 10/2008 | Hochman et al. |
| D579,546 S | 10/2008 | Birath et al. |
| 7,445,125 B2 | 11/2008 | Ellsworth et al. |
| 7,449,008 B2 | 11/2008 | Hochman |
| 7,473,432 B2 | 1/2009 | Cevc et al. |
| 7,488,309 B2* | 2/2009 | Kissinger et al. ............. 604/246 |
| 7,510,397 B2 | 3/2009 | Hochman |
| 7,618,409 B2 | 11/2009 | Hochman |
| 7,625,354 B2 | 12/2009 | Hochman |
| 7,789,552 B2 | 9/2010 | Girvin et al. |
| 7,815,605 B2 | 10/2010 | Souter |
| 7,837,651 B2 | 11/2010 | Bishop et al. |
| 7,975,922 B2 | 7/2011 | Fago et al. |
| 8,002,736 B2 | 8/2011 | Patrick et al. |
| 8,007,487 B2 | 8/2011 | Patrick et al. |
| 8,079,976 B2 | 12/2011 | Patrick et al. |
| 8,142,414 B2 | 3/2012 | Patrick et al. |
| 8,425,463 B2 | 4/2013 | Patrick et al. |
| 8,425,464 B2 | 4/2013 | Patrick et al. |
| 8,545,440 B2 | 10/2013 | Patrick et al. |
| 2001/0049608 A1 | 12/2001 | Hochman |
| 2001/0051798 A1 | 12/2001 | Hochman |
| 2001/0055610 A1 | 12/2001 | Nagata et al. |
| 2002/0016569 A1* | 2/2002 | Critchlow et al. ............ 604/131 |
| 2002/0045850 A1 | 4/2002 | Rowe et al. |
| 2002/0055702 A1 | 5/2002 | Atala et al. |
| 2002/0077588 A1 | 6/2002 | Schneider et al. |
| 2002/0123678 A1 | 9/2002 | Lerner et al. |
| 2002/0133101 A1 | 9/2002 | DeVore |
| 2002/0150539 A1* | 10/2002 | Unger ......................... 424/9.52 |
| 2002/0151868 A1 | 10/2002 | Taheri |
| 2002/0156376 A1 | 10/2002 | Wang et al. |
| 2002/0183701 A1 | 12/2002 | Hochman et al. |
| 2003/0028112 A1 | 2/2003 | Paladini et al. |
| 2003/0040700 A1 | 2/2003 | Hickle et al. |
| 2003/0073908 A1 | 4/2003 | Desai |
| 2003/0078533 A1 | 4/2003 | Weimann et al. |
| 2003/0120154 A1 | 6/2003 | Sauer |
| 2003/0120201 A1 | 6/2003 | Abergel |
| 2003/0120217 A1 | 6/2003 | Abergel |
| 2003/0204141 A1 | 10/2003 | Nock et al. |
| 2003/0229304 A1 | 12/2003 | Babaev |
| 2003/0233046 A1 | 12/2003 | Ferguson |
| 2004/0002647 A1 | 1/2004 | Desai |
| 2004/0019318 A1 | 1/2004 | Wilson et al. |
| 2004/0039368 A1 | 2/2004 | Reilly et al. |
| 2004/0064102 A1 | 4/2004 | Yamada |
| 2004/0092821 A1 | 5/2004 | Hering |
| 2004/0097805 A1 | 5/2004 | Verard et al. |
| 2004/0097806 A1 | 5/2004 | Hunter |
| 2004/0162484 A1 | 8/2004 | Nemoto |
| 2005/0038387 A1 | 2/2005 | Kriesel et al. |
| 2005/0043681 A1 | 2/2005 | Rusnak |
| 2005/0075620 A1 | 4/2005 | Iger |
| 2005/0123482 A1 | 6/2005 | Unger |
| 2005/0165096 A1 | 7/2005 | Lee |
| 2005/0171486 A1 | 8/2005 | Hochman |
| 2005/0177054 A1 | 8/2005 | Yi et al. |
| 2005/0203413 A1 | 9/2005 | Fichtinger et al. |
| 2005/0228256 A1 | 10/2005 | Labadie et al. |
| 2005/0260084 A1 | 11/2005 | Rusnak |
| 2005/0283110 A1 | 12/2005 | Atala et al. |
| 2006/0106283 A1 | 5/2006 | Wallace et al. |
| 2006/0122555 A1 | 6/2006 | Hochman |
| 2006/0217655 A1 | 9/2006 | Vitullo et al. |
| 2006/0247578 A1 | 11/2006 | Arguedas et al. |
| 2006/0258977 A1 | 11/2006 | Lee |
| 2007/0032723 A1 | 2/2007 | Glossop |
| 2007/0073235 A1 | 3/2007 | Estes et al. |
| 2007/0073267 A1 | 3/2007 | Muller |
| 2007/0083155 A1 | 4/2007 | Muller |
| 2007/0088268 A1 | 4/2007 | Edwards |
| 2007/0088271 A1 | 4/2007 | Richards |
| 2007/0129630 A1 | 6/2007 | Shimko |
| 2007/0156092 A1 | 7/2007 | Estes et al. |
| 2007/0167905 A1 | 7/2007 | Estes et al. |
| 2007/0191781 A1 | 8/2007 | Richards et al. |
| 2007/0197954 A1 | 8/2007 | Keenan |
| 2007/0213660 A1 | 9/2007 | Richards et al. |
| 2007/0233185 A1* | 10/2007 | Anderson et al. ............. 606/213 |
| 2007/0244442 A1 | 10/2007 | Chowhan |
| 2007/0282221 A1 | 12/2007 | Wang et al. |
| 2007/0299398 A1 | 12/2007 | Alferness et al. |
| 2007/0299399 A1 | 12/2007 | Alferness et al. |
| 2007/0299400 A1 | 12/2007 | Alferness et al. |
| 2008/0015512 A1 | 1/2008 | D'Antonio et al. |
| 2008/0045902 A1 | 2/2008 | Estes et al. |
| 2008/0045925 A1* | 2/2008 | Stepovich et al. ............ 604/518 |
| 2008/0058711 A1 | 3/2008 | Neftel et al. |
| 2008/0058732 A1 | 3/2008 | Harris |
| 2008/0060970 A1 | 3/2008 | Wheeler et al. |
| 2008/0086087 A1* | 4/2008 | Spohn et al. .................. 604/151 |
| 2008/0086108 A1 | 4/2008 | Falkel et al. |
| 2008/0091104 A1 | 4/2008 | Abraham |
| 2008/0091109 A1 | 4/2008 | Abraham |
| 2008/0103564 A1 | 5/2008 | Burkinshaw |
| 2008/0140158 A1 | 6/2008 | Hamel |
| 2008/0154188 A1 | 6/2008 | Hochman |
| 2008/0213729 A1 | 9/2008 | Hochman |
| 2008/0249409 A1 | 10/2008 | Fraser et al. |
| 2008/0281265 A1* | 11/2008 | Hochman ..................... 604/110 |
| 2008/0306436 A1 | 12/2008 | Edwards et al. |
| 2009/0018485 A1 | 1/2009 | Krespi et al. |
| 2009/0030366 A1 | 1/2009 | Hochman |
| 2009/0103490 A1 | 4/2009 | Lakshmikanthan |
| 2009/0137956 A1 | 5/2009 | Souter |
| 2009/0163860 A1 | 6/2009 | Patrick |
| 2009/0171192 A1 | 7/2009 | Patrick et al. |
| 2009/0171193 A1 | 7/2009 | Patrick et al. |
| 2009/0326482 A1 | 12/2009 | Hochman |
| 2010/0204568 A1 | 8/2010 | Narouze |
| 2011/0306932 A1 | 12/2011 | Patrick et al. |
| 2012/0179036 A1 | 7/2012 | Patrick et al. |
| 2012/0259237 A1 | 10/2012 | Axelrod |
| 2013/0041258 A1 | 2/2013 | Patrick et al. |
| 2013/0079635 A1 | 3/2013 | Patrick et al. |

FOREIGN PATENT DOCUMENTS

| | | |
|---|---|---|
| EP | 0 538 241 | 2/1998 |
| EP | 0 814 860 | 11/1999 |
| EP | 1 013 269 | 6/2000 |
| EP | 1 072 283 | 1/2001 |
| EP | 0 781 150 | 11/2002 |
| EP | 0 660 714 | 7/2003 |
| EP | 0 814 719 | 10/2003 |

(56) References Cited

FOREIGN PATENT DOCUMENTS

| | | |
|---|---|---|
| EP | 1 370 321 | 12/2003 |
| EP | 0 950 373 | 3/2005 |
| EP | 1 568 324 | 8/2005 |
| EP | 1 119 389 | 12/2005 |
| EP | 1 707 231 | 10/2006 |
| EP | 1 504 713 | 7/2008 |
| GB | 2359756 | 9/2001 |
| JP | 10314166 A2 | 2/1998 |
| JP | 10314168 A2 | 2/1998 |
| JP | 10314171 A2 | 2/1998 |
| JP | 11267127 A2 | 5/1999 |
| JP | 2001/252272 A2 | 9/2001 |
| JP | 2004/154290 A2 | 3/2004 |
| WO | WO 97/10023 | 3/1997 |
| WO | WO 97/15232 | 5/1997 |
| WO | WO 97/18855 | 5/1997 |
| WO | WO 97/34656 | 9/1997 |
| WO | WO 97/40858 | 11/1997 |
| WO | WO 98/00194 | 1/1998 |
| WO | WO 98/02097 | 1/1998 |
| WO | WO 98/07367 | 2/1998 |
| WO | WO 98/23222 | 6/1998 |
| WO | WO 98/25655 | 6/1998 |
| WO | WO 98/55104 | 12/1998 |
| WO | WO 98/57696 | 12/1998 |
| WO | WO 99/11182 | 3/1999 |
| WO | WO 99/27981 | 6/1999 |
| WO | WO 99/49909 | 10/1999 |
| WO | WO 99/51295 | 10/1999 |
| WO | WO 99/51296 | 10/1999 |
| WO | WO 99/66980 | 12/1999 |
| WO | WO 00/02588 | 1/2000 |
| WO | WO 00/62858 | 10/2000 |
| WO | WO 01/01845 | 1/2001 |
| WO | WO 01/07110 | 2/2001 |
| WO | WO 02/07601 | 1/2002 |
| WO | WO 02/055131 | 7/2002 |
| WO | WO 02/058530 | 8/2002 |
| WO | WO 02/074175 | 9/2002 |
| WO | WO 02/076547 | 10/2002 |
| WO | WO 03/002189 | 1/2003 |
| WO | WO 03/011105 | 2/2003 |
| WO | WO 03/096255 | 11/2003 |
| WO | WO 03/105693 | 12/2003 |
| WO | WO 2004/004709 | 1/2004 |
| WO | WO 2004/073769 | 9/2004 |
| WO | WO 2004/082749 | 9/2004 |
| WO | WO 2005/014079 | 2/2005 |
| WO | WO 2005/055849 | 6/2005 |
| WO | WO 2005/056104 | 6/2005 |
| WO | WO 2006/129099 | 12/2006 |
| WO | WO 2007/002079 | 1/2007 |
| WO | WO 2007/039905 | 4/2007 |
| WO | WO 2007/064937 | 6/2007 |
| WO | WO 2007/082189 | 7/2007 |
| WO | WO 2007/094001 | 8/2007 |
| WO | WO 2007/106558 | 9/2007 |
| WO | WO 2007/110076 | 10/2007 |
| WO | WO 2007/127176 | 11/2007 |
| WO | WO 2012/138668 | 10/2012 |

OTHER PUBLICATIONS

Hien et al. "Articular Punctures and Injections Controlled by Ultrasound". Arbeitsgruppe Orthopadische Sonographie, Friedrichshafener Str. 11, D-8000 Munchen 60, Germany. [Includes English Summary], Aug. 8, 1990.

Knorre et al. "Comparative Study of Therapy: Ultrasound, Cryotherapy and Intra-Articulare Cortisonoids to Treat Alterations of the Shoulder Joint Due to Inflammation. with 2 Figures". Z. Physiother. Jg. Oct. 26, 1990, 42/4 (221-225) Rheumatologische Klinik, Bezirkskrankenhaus Magdeburg, Klinikbereich Vogelsang-Gommern, 3301, German Democratic Republic. [Includes English Summary].

Koski et al. "Verification of Palpation-Guided Intra-Articular Injections Using Glucocorticoid-Air-Saline Mixture and Ultrasound Imaging (GAS-Graphy)." Clin Exp Rheumatol. May-Jun. 2006;24(3):247-52. Mikkeli Central Hospital, Porrassalmenkatu 35-37, Mikkeli, Finland.

Koski. "Ultrasound Guided Injections in Rheumatology". J Rheumatol. Sep. 2000;27(9):2131-8. The Lea Hirvonen Library, Mikkeli Central Hospital, Finland.

Migliore et al. "Efficacy and Safety of Viscosupplementation by Ultrasound-Guided Intra-Articular Injection in Osteoarthritis of the Hip". Osteoarthritis Cartilage. Apr. 2003;11(4):305-6. Department of Internal Medicine, S.Pietro-Fatebenefratelli Hospital, Rome, Italy.

Migliore et al. "Intra-Articular Treatment with Hylan G-F 20 under Ultrasound Guidance in Hip Osteoarthritis. Clinical Results After 12 months Follow-up". Reumatismo, 2005; 57(1): 36-43. Department of Internal Medicine, S. Pietro-Fatebenefratelli Hospital, Rome, Italy.

Migliore et al. "18-Month Observational Study on Efficacy of Intraarticular Hyaluronic Acid (Hylan G-F 20) Injections under Ultrasound Guidance in Hip Osteoarthritis". Reumatismo 2006;58(1): 39-49. S. Pietro-Fatebenefratelli Hospital, Rome, Italy.

Qvistgaard et al. "Guidance by Ultrasound of Intra-Articular Injections in the Knee and Hip Joints". Osteoarthritis and Cartilage. Aug. 2001; 9(6):512-7. The Parker Institute, Department of Rheumatology, H:S Frederiksberg Hospital, Copenhagen, Denmark.

Raza et al. "Ultrasound Guidance Allows Accurate Needle Placement and Aspiration from Small Joints in Patients with Early Inflammatory Arthritis". Rheumatology, 2003, 42.

Rutten et al. "Injection of the Subacromial-Subdeltoid Bursa: Blind or Ultrasound-Guided?" Acta Orthop. Apr. 2007; 78(2):254-7. Department of Radiology, Jeroen Bosch Hospital's-Hertogenbosch, The Netherlands.

Smith et al. "Office-Based Ultrasound-Guided Intra-Articular Hip Injection: Technique for Physiatric Practice". Arch Phys Med Rehabil. Feb. 2006;87(2):296-8.Department of Physical Medicine and Rehabilitation, Mayo Clinic College of Medicine, Rochester, MN 55905, USA.

Sofka et al. "Ultrasound-Guided Interventions in the Foot and Ankle". RS. Semin Musculoskelet Radiol. Jun. 2002; 6(2):163-8. Review.

Valls, R. et al., "Sonographic Guidance of Needle Position for MR Arthrography of the Shoulder". American Journal of Roentgenology, Sep. 1997; 169(3): pp. 845-847.

Press Release in 2 pages by Milestone Scientific, Inc., dated Jul. 13, 2006 and entitled, "Milestone Scientific Receives 510(k) Premarket Notification Acceptance from FDA for CompuFlo™ Computer Controlled Infusion Pump; Company to Pursue Strategic Relationships with Marketing Leaders in Medical Field," retrieved from the website of Milestone Scientific, Inc. at www.milesci.com/press-releases/pr_milestone-compuflo-510k-notification_13jul06.html.

Press Release in 2 pages by Milestone Scientific, Inc., dated Jan. 18, 2005 and entitled, "Milestone Scientific (MS) Announces Second Successful Epidural Clinical Study Using Its CompuFlo™ Technology," retrieved from the website of BioSpace, Inc. at www.biospace.com/news_story.aspx?NewsEntityld=18728720.

Press Release in 3 pages by Milestone Scientific, Inc., dated Dec. 6, 2004 and entitled, "Milestone Scientific Inc. Announces Patent Protection on Two Critical Elements of Its CompuFlo™ Technology," retrieved from the website of the Free Library by Farlex at www.thefreelibrary.com/Milestone+Scientific+Inc.+Announces+Patent+Protection+on+Two+Critical . . .-a0132631635.

Helfer, A., "Profound Anesthesia Made Easy with the STA System". Endo Tribune, Nov. 2008, pp. 10-11.

Product Summary in 1 page related to, in part, Harvard 2 Dual Syringe Pump with Occlusion Detection, retrieved at www.cgs.com.br/H/A017.pdf (retrieved on or about Mar. 2010)—see footnote below.

(56) References Cited

OTHER PUBLICATIONS

Online Article entitled, "Harvard Clinical Technology Names Ohmeda Exclusive Worldwide Distributor of New Dual Syringe Infusion Pump," dated Apr. 3, 1997, retrieved from the website of AllBusiness.com at www.allbusiness.com/health-care/medical-practice-pediatrics/7036362-1.html.

Kinnealey, E. et al., "Infusion Pumps with 'Drug Libraries' at the Point of Care—A Solution for Safer Drug Delivery," dated Jan. 30, 2003, retrieved from the National Patient Safety Foundation website at www.npsforg/download/Kinnealey.pdf.

Product Brochure in 2 pages for Cardinal Health Alaris® Products Alaris® SE Single/Dual Channel Pumps (retrieved on or about Mar. 2010)—see footnote below.

* cited by examiner

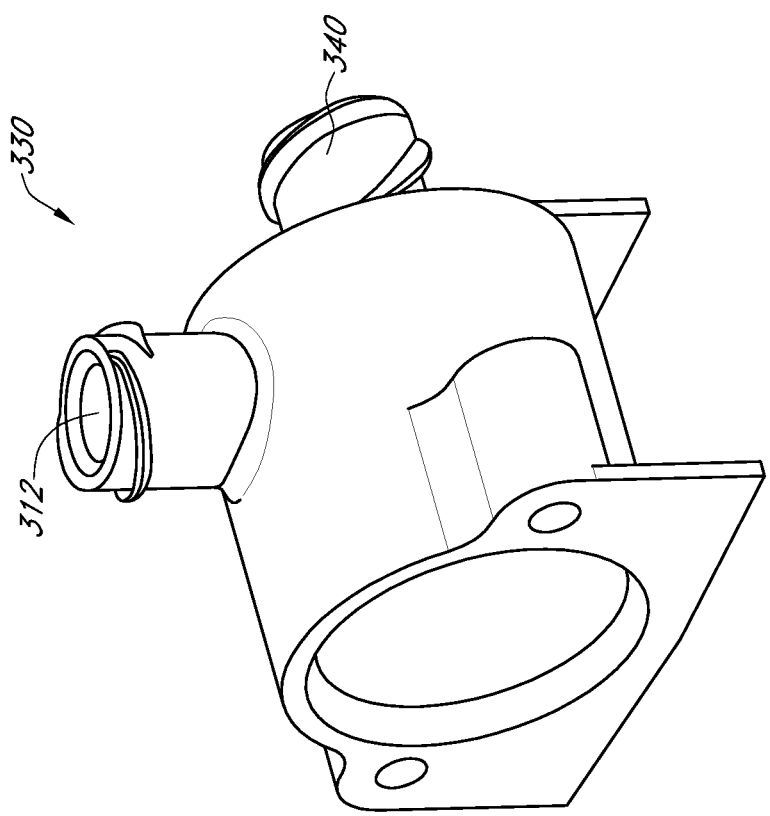

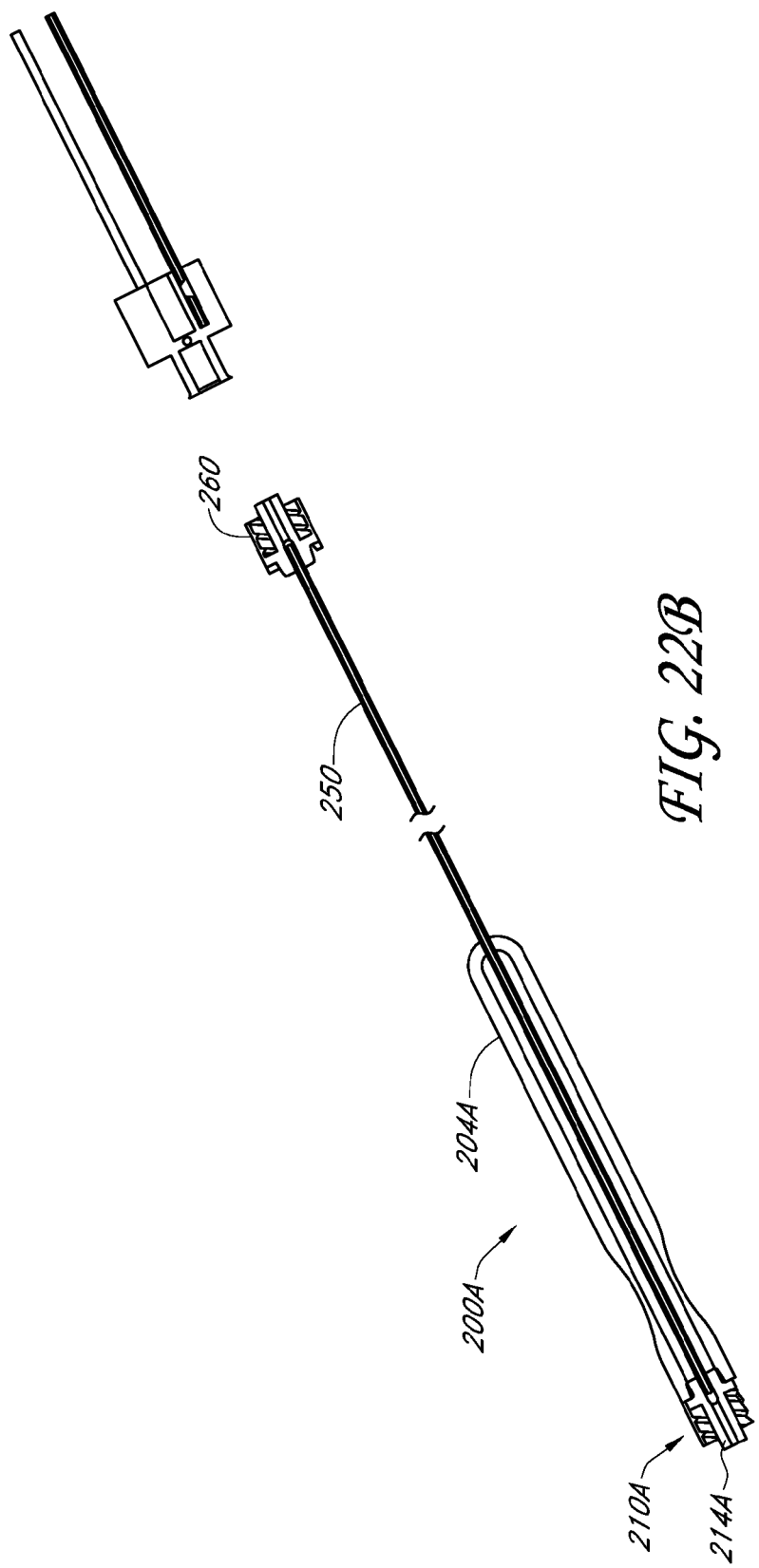

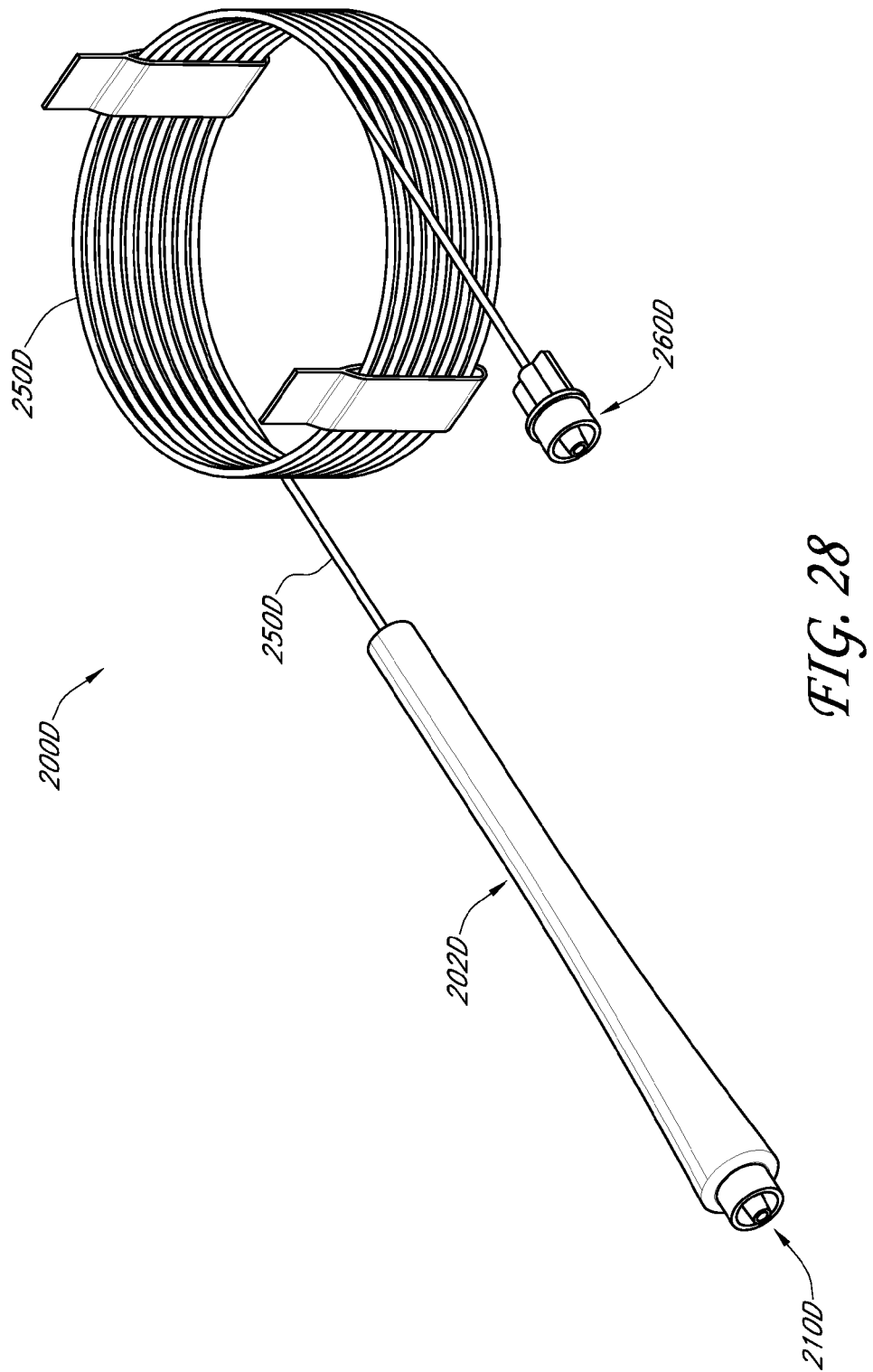

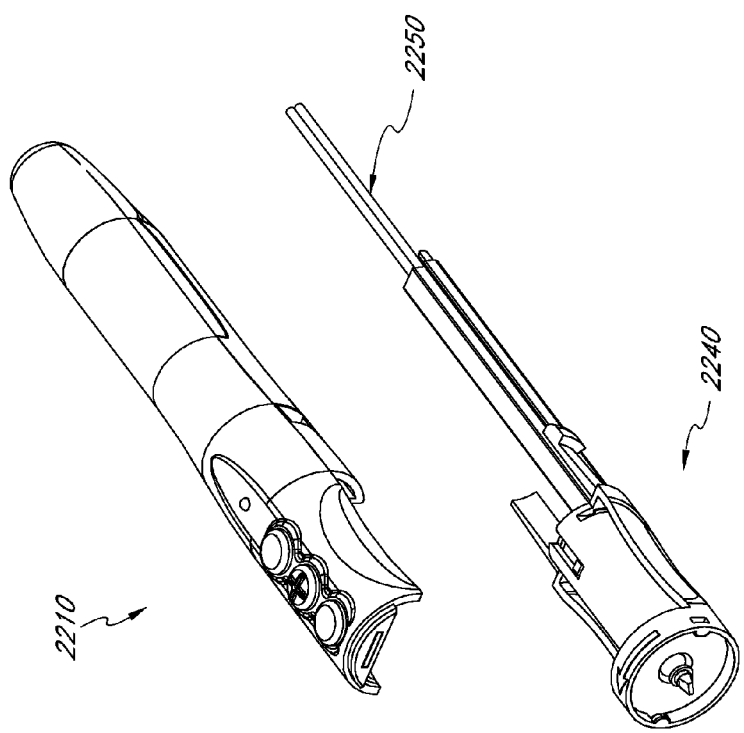
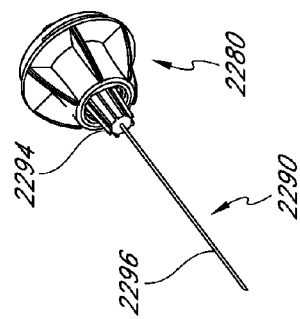
FIG. 29B

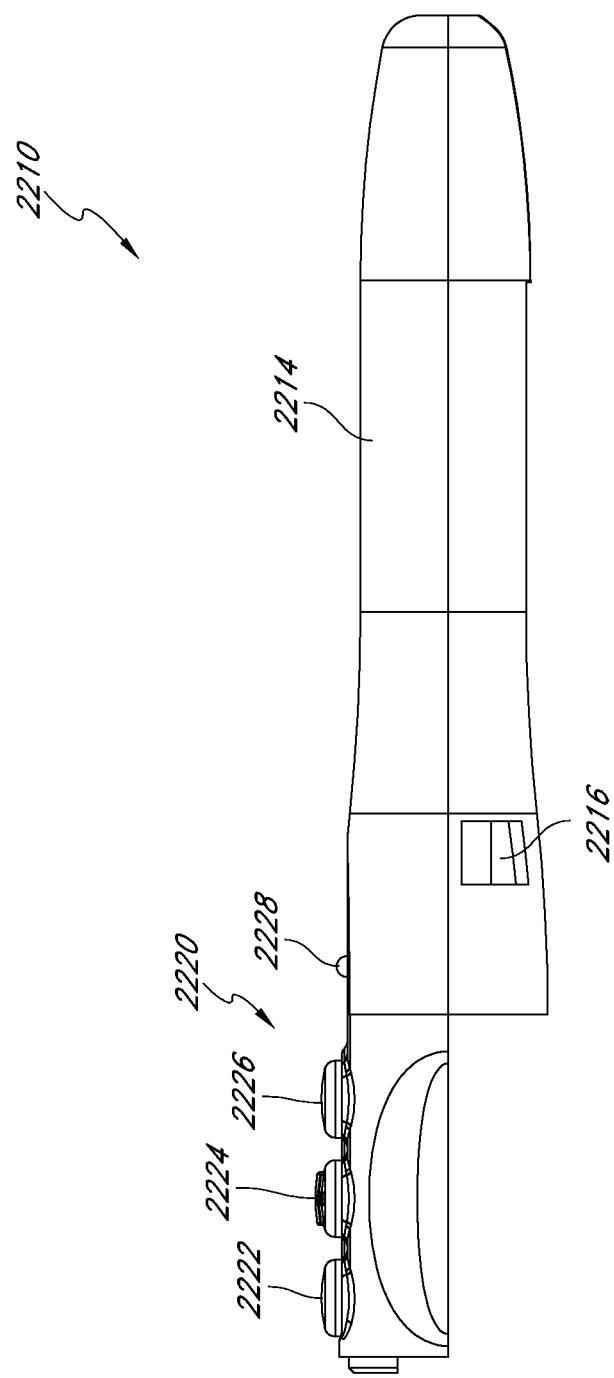

Treatment Summary

| | |
|---|---|
| Treating Clinician: | Drug, Strength & Dosage: |
| | Betamethasone Na PO / Ac - 6mg/mL - 1.5 mL |
| Patient Name / ID: | Aristospan - 20 mg/mL - 1.5 mL |
| | Lidocaine HCL - 1.0% - 1.5 mL |
| Treatment Initiation, Date / Time:<br>January 25, 2010 11:00 | Total Volume Delivered: 4.5 mL |
| Treatment Completion, Date / Time:<br>January 25, 2010 11:01 | |

Treating Clinician
Signature _____ Date _____

[PRINT]   [FINISH]

Ready

*FIG. 40S*

SYSTEM FOR INJECTING FLUIDS IN A SUBJECT

RELATED APPLICATIONS

This application is a continuation of U.S. patent application Ser. No. 12/823,004, filed Jun. 24, 2010, which claims the priority benefit under 35 U.S.C. §119(e) of U.S. Provisional Patent Application No. 61/220,175, filed Jun. 24, 2009, and which is a continuation-in-part of U.S. patent application Ser. No. 12/340,595, filed Dec. 19, 2008, and issued as U.S. Pat. No. 8,002,736 on Aug. 23, 2011, which claims the priority benefit under 35 U.S.C. §119(e) of U.S. Provisional Patent Application No. 61/016,395, filed Dec. 21, 2007. All of the aforementioned applications are hereby incorporated by reference and made a part of the present specification.

BACKGROUND

1. Field

This application relates generally to injection and/or aspiration devices, systems and methods, and more specifically, to devices, systems and methods of delivering pharmaceuticals, fluids and/or other substances to or near a joint or another anatomical location of a patient.

2. Description of the Related Art

Physicians, clinicians and/or other medical personnel often need to deliver a volume of medication, other fluid and/or other material to (or aspirate fluid from) an anatomical location, such as, for example a joint (e.g., toe, knee, wrist, shoulder, ankle, finger, spine, etc.). Accordingly, a needle can be inserted through a patient's skin and into the targeted location. A syringe or other fluid source that is in fluid communication with the needle can then be used to deliver the desired volume or other dosage of fluid and/or other material to the targeted joint or other anatomical location.

Current injection practice generally involves palpation by the physician of a bony prominence on the patient's anatomy to serve as a "landmark" to guide the injection into the targeted location. The injection is completed by advancing the needle, which is typically connected to a disposable glass or plastic syringe, into the target area. The syringe plunger is then advanced to deliver the fluid. In many cases, current treatment methods do not offer precise or accurate delivery.

SUMMARY

According to some embodiments, an injection system for delivering at least two different medicaments into a patient using a single needle penetration includes a fluid delivery module comprising a first loading area configured to receive a first container and a second loading area configured to receive a second container. The injection system further includes a handpiece assembly in fluid communication with the fluid delivery module. In one embodiment, the handpiece assembly is disposable. In some embodiments, the handpiece assembly is configured to removably receive a needle assembly at a distal end of the handpiece assembly. In one embodiment, the needle assembly comprises a needle. In several embodiments, the handpiece assembly comprises tubing that places the handpiece assembly and the needle assembly in fluid communication with the fluid delivery module. In some embodiments, the injection system further includes a control module comprising at least one controller configured to receive instructions for delivery of the first medicament and the second medicament to the patient. In some embodiments, the control module is configured to be removably secured to the handpiece assembly. In one embodiment, the first container comprises a first medicament, and the second container comprises a second medicament, wherein the second medicament is different than said first medicament. In some embodiments, the first loading area is configured to securely receive varying sizes and shapes of the first container, and the second loading area is configured to securely receive varying sizes and shapes of the second container. In one embodiment, the injection system is configured to receive instructions for delivering the first and second medicaments to the handpiece assembly. According to some embodiments, the fluid delivery module is configured to transfer at least a portion of the first medicament from the first container to a first reservoir of the fluid delivery module, and the fluid delivery module is configured to transfer at least a portion of the second medicament from the second container to a second reservoir of the fluid delivery module. In several embodiments, the handpiece assembly is maneuverable to position the needle within the patient to facilitate delivery of the first medicament and the second medicament into said patient with a single penetration of said needle. In some embodiments, the injection system further includes at least one motor housed within the fluid delivery module to mechanically transfer the first medicament and the second medicament to the patient.

According to some embodiments, an injection system for delivering at least two different medicaments into a patient using a single needle penetration comprises a fluid delivery module having a disposable cassette, which comprises a first loading area configured to receive a first container and a second loading area configured to receive a second container. In some embodiments, the first container comprises a first medicament, and the second container comprises a second medicament. In one embodiment, the first loading area is configured to securely receive varying sizes and shapes of the first container, and the second loading area is configured to securely receive varying sizes and shapes of the second container. In some embodiments, the injection system additionally comprises a handpiece assembly in fluid communication with the cassette. In one embodiment, the handpiece assembly is configured to removably receive a needle assembly at a distal end of the handpiece assembly, wherein the needle assembly includes a needle. In some embodiments, the handpiece assembly comprises tubing that places the handpiece assembly and the needle assembly in fluid communication with the cassette. In several embodiments, the injection system is configured to receive instructions for delivering the first and second medicaments to the handpiece assembly. In one embodiment, the fluid delivery module is configured to transfer at least a portion of the first medicament from the first container to a first reservoir of the fluid delivery module, and the fluid delivery module is configured to transfer at least a portion of the second medicament from the second container to a second reservoir of the fluid delivery module. In some embodiments, the first medicament exiting the first reservoir and the second medicament exiting the second reservoir are configured to be combined within the disposable cassette, upstream of the handpiece assembly. In some embodiments, the handpiece assembly is maneuverable to position the needle within the patient. In some embodiments, the fluid delivery module comprises at least one motor to mechanically deliver at least one of the first medicament and the second medicament to the patient.

According to some embodiments, a method for delivering at least two different medicaments into or near a joint of a patient using a single needle penetration includes providing a fluid delivery module comprising a first loading area configured to receive a first container and a second loading area configured to receive a second container. The method further includes providing a disposable handpiece assembly configured to be placed in fluid communication with the fluid delivery module. In some embodiments, the handpiece assembly is configured to removably receive a needle assembly at a distal end of the handpiece assembly, said needle assembly comprising a needle. In one embodiment, the handpiece assembly comprises tubing that places the handpiece assembly and the needle assembly in fluid communication with the fluid delivery module. In some embodiments, the method additionally comprises providing a control module having at least one controller configured to receive instructions for delivery of the first medicament and the second medicament to the patient. In some embodiments, the control module is configured to be removably secured to the handpiece assembly. In one embodiment, the first container comprises a first medicament, and the second container comprises a second medicament. In some embodiments, the second medicament is different (e.g., in type, concentration, etc.) than said first medicament. In some embodiments, the first loading area is configured to securely receive varying sizes and shapes of the first container, and the second loading area is configured to securely receive varying sizes and shapes of the second container.

According to some embodiments, the first medicament exiting the first reservoir and the second medicament exiting the second reservoir are configured to be combined within the disposable cassette, upstream of the handpiece assembly. In some embodiments, the method additionally comprises maneuvering the handpiece assembly to position the needle into or near a joint of the patient. In one embodiment, the method includes delivering a volume of at least one of the first medicament and the second medicament into a joint of the patient with a single needle penetration. In some embodiments, the fluid delivery module comprises at least one motor to mechanically facilitate the delivery of at least one of the first medicament and the second medicament to the patient.

According to some embodiments, the first loading area and the second loading area are configured to receive nonspecific fluid containers. In one embodiment, the first container and/or the second container is an original manufacturer's vial, ampoule or other container. In one embodiment, the first and second medicaments are delivered simultaneously to a target anatomical location of the patient. In other embodiments, the first and second medicaments are delivered sequentially to a target anatomical location of the patient. In some embodiments, the first and second loading areas and the first and second reservoirs are included in a disposable cassette, wherein the disposable cassette is removably positioned within a corresponding recess of the fluid delivery module. In one embodiment, the first and second medicaments exiting the first and second reservoirs, respectively, are configured to be combined within the disposable cassette, upstream of the handpiece assembly.

According to some embodiments, the fluid delivery module further comprises a third loading area configured to receive a third container containing a third medicament, wherein the injection system is configured to receive instructions for simultaneously or sequentially delivering the first, second and third medicaments through the handpiece assembly to a patient. In another embodiment, the controller comprises at least one button, dial, knob, switch, rollerball, rollerwheel and/or the like. In one embodiment, the fluid delivery module comprises a display (e.g., touchscreen) configured to provide status information of an injection procedure. In some embodiments, the status information comprises a volume of the first or second medicaments delivered through the handpiece assembly, a volume remaining in the first and second reservoirs of the fluid delivery module, the pressure against which the fluids are being delivered, an ultrasound or other imaging display showing the needle in relation to the patient's anatomy and/or any other data, images or information. In some embodiments, the fluid delivery module is in data communication with an imaging device (e.g., ultrasound device or system) configured to help locate a targeted anatomical location within the patient.

According to some embodiments, the first medicament comprises an anesthetic and the second medicament comprises a steroid. In some embodiments, the first medicament and the second medicament are different in type (e.g., formulation), strength (e.g., concentration) and/or other properties or characteristics. In one embodiment, the first medicament and the second medicament are similar in type but different in concentration or strength. In some embodiments, the motor comprises a stepper motor, a mechanical actuator and/or any other mechanically-driven device. In other embodiments, the motor is pneumatically operated.

According to some embodiments, the injection system further includes a control module having at least one controller, wherein the controller is configured to receive instructions for delivery of at least one of the first medicament and the second medicament to the patient. In some embodiments, the control module is configured to be removably secured to the handpiece assembly. In one embodiment, the control module is configured to be in data communication with the fluid delivery module using a wireless (e.g., radio frequency, Bluetooth, Wi-Fi, etc.) and/or a hardwired connection. In some embodiments, the control module is configured to be powered by one or more batteries (e.g., disposable, rechargeable, etc.). In one embodiment, the control module is configured to recharge in a docking station of the fluid delivery module and/or any other portion of the injection system. In some embodiments, the first loading area and the second loading area are configured to receive nonspecific fluid containers. In one embodiment, the first container and/or the second container includes an original manufacturer's vial, ampoule or other container. In one embodiment, such an original manufacturer's vial is as supplied by the original manufacturer or a supplier to the clinician using the injection system.

According to some embodiments, an injection system for delivering a fluid contained within a pre-filled syringe to a patient includes comprises a fluid delivery module comprising a receiving area configured to receive a pre-filled syringe and a handpiece assembly in fluid communication with the fluid delivery module. In some embodiments, the handpiece assembly is configured to removably receive a needle assembly at a distal end of the handpiece assembly, said needle assembly comprising a needle. In one embodiment, the handpiece assembly comprises tubing that places the handpiece assembly and the needle assembly in fluid communication with the fluid delivery module. In some embodiments, the injection system additionally comprises a control module having one or more controllers configured to receive instructions for delivery of the fluid contained within the pre-filled syringe to the patient. In some embodiments, the receiving area is configured to securely receive varying sizes and shapes of the pre-filled syringe. In one embodiment, the injection system is configured to receive instructions for delivering the fluid contained within the pre-filled syringe to the handpiece assembly. According to some embodiments, the fluid delivery module is configured to transfer at least a portion of the fluid from the pre-filled syringe to the handpiece assembly. In one embodiment, the handpiece assembly is maneuverable to position the needle within the patient to facilitate delivery of the fluid from the pre-filled syringe into the patient with a single penetration of the needle. In some embodiments, the injection system additionally includes at least one motor housed within the fluid delivery module to mechanically transfer the fluid to the patient. In some embodiments, the receiving area is included on a disposable cassette, said disposable cassette being removably positioned within a corresponding recess of the fluid delivery module.

According to some embodiments, the pre-filled syringe comprises hyaluronic acid. In one embodiment, the pre-filled syringe is configured to be placed within a centrifuge. In some embodiments, the pre-filled syringe comprises a centrifuged blood component (e.g., plasma, red blood cells, platelets, etc.). In some embodiments, the controller comprises at least one button, dial, knob, switch, rollerball, rollerwheel and/or the like. In some embodiments, the fluid delivery module comprises a display configured to provide status information of an injection procedure. In one embodiment, the status information comprises a volume of the fluid contained within the pre-filled syringe that has been delivered through the handpiece assembly, a volume of fluid remaining in the pre-filled syringe, a back-pressure reading, an ultrasound or other imaging device image and/or the like. In some embodiments, the fluid delivery module is in data communication with an ultrasound device or other imaging device configured to help locate a targeted anatomical location within the patient. In some embodiments, the motor comprises a stepper motor or another mechanically or pneumatically actuated device or system. In some embodiments, the pre-filled syringe comprises a first fitting along its distal end, wherein the proximal end of the tubing comprises a second fitting, said first fitting being configured to removably couple to said second fitting to place the handpiece assembly in fluid communication with the pre-filled syringe.

According to some embodiments, an injection system for delivering medicaments into a patient using a single needle penetration comprises a fluid delivery module configured to receive a first disposable cassette and a second disposable cassette. In one embodiment, the first disposable cassette comprises a first loading area configured to receive a first container, and a second loading area configured to receive a second container. In some embodiments, the first container comprises a first medicament, and the second container comprises a second medicament. In one embodiment, the first loading area is configured to securely receive varying sizes and shapes of the first container, and the second loading area is configured to securely receive varying sizes and shapes of the second container. In some embodiments, the second disposable cassette comprises a single receiving area for receiving a pre-syringe, which includes a pre-filled fluid (e.g., hyaluronic acid, blood plasma, blood cells, other blood component, anesthetic, steroid, other medicament, other centrifugable material, other fluids or materials, etc.). In some embodiments, the single receiving area is configured to securely receive varying sizes and shapes of the pre-filled syringe. In some embodiments, the injection system further includes a handpiece assembly in fluid communication with the fluid delivery module, regardless of whether the first disposable cassette or the second disposable cassette is secured to the fluid delivery module. In some embodiments, the handpiece assembly is configured to removably receive a needle assembly at a distal end of the handpiece assembly, said needle assembly comprising a needle. In one embodiment, the handpiece assembly comprises tubing that places the handpiece assembly and the needle assembly in fluid communication with the cassette. In several embodiments, the injection system is configured to receive instructions for delivering one of (i) the first and second medicaments and (ii) the pre-filled fluid to the handpiece assembly, depending on whether the first disposable cassette or the second disposable cassette is secured to the fluid delivery module. In one embodiment, the fluid delivery module is configured to transfer either (a) the first medicament and/or the second medicament or (b) the pre-filled fluid to the handpiece assembly. In some arrangements, the handpiece assembly is maneuverable to position the needle within the patient. In one embodiment, the fluid delivery module comprises at least one motor (e.g., stepper motor) to mechanically facilitate the delivery of at least one of the first medicament, the second medicament and the pre-filled fluid to the patient.

According to some embodiments, the first loading area and the second loading area are configured to receive nonspecific fluid containers. In some arrangements, the first container and/or the second container is an original manufacturer's vial, ampoule or other container. In some embodiments, the first and second medicaments are delivered simultaneously or sequentially to a target anatomical location of the patient. In one embodiment, the pre-filled syringe comprises hyaluronic acid. In some embodiments, the pre-filled syringe is configured to be placed within a centrifuge. In several embodiments, the fluid delivery module is in data communication with an imaging device (e.g., ultrasound device) configured to help locate a targeted anatomical location within the patient.

According to certain embodiments, systems for injecting fluids and/or other materials into a targeted anatomical location, in particular, an intra-articular space, include a handpiece assembly having a needle extending from its distal end, a fluid delivery module comprising a cassette and a fluid transfer device. A conduit is generally configured to place the fluid delivery module in fluid communication with the handpiece assembly. Medications, formulations and/or other fluids or materials contained within vials that are secured to the fluid delivery module can be selectively delivered into an anatomy through a needle located at the distal end of the handpiece assembly. In some embodiments, ultrasound or other imaging technologies can be used to locate a joint or other targeted anatomical location.

According to some embodiments, the handpiece assembly is disposable. In one embodiment, the handpiece assembly does not include a core or other controllers for regulating the flow of fluids and/or other materials therethrough. In some embodiments, the delivery of fluids and/or other materials from a fluid delivery module to the handpiece assembly is controlled using one or more foot pedals or other controllers. In one embodiment, such other controller is not positioned on the handpiece assembly. According to certain embodiments, vials or other containers containing medicaments, fluids and/or other substances are configured to be secured to a cassette of a fluid delivery module. In one embodiment, such vials or other containers are configured to be positioned within nests or loading areas having vented spikes. In some embodiments, such vented spikes do not include a needle or other sharps.

Several embodiments of the present application are particularly advantageous because they offer precise and accurate delivery of medications. For example, studies have shown that conventional needles miss the target location quite frequently. Many medications utilized for the treatment of arthritis, such as steroids and other medicaments can provide benefit to the patient only if they are injected directly into the patient's synovial fluid. Further, certain medications, such as steroids, break down connective tissue and cause other tissue damage. Therefore, when such medications or other formulations are not precisely delivered to the target intra-articular location, adverse tissue damage can occur to one or more anatomical locations of patients.

Moreover, in order to deliver a second medication, other fluid and/or other material to the same anatomical location, physicians or other medical personnel require multiple needle penetrations or leave the needle within the targeted intra-articular space, while unhooking the tubing or other conduit which is in fluid communication with the needle. Forceps or other tools are often used to disconnect and/or connect the tubing or other conduits to the needle in order to deliver a different medication or fluid to the patient. This can complicate the process for the physician or other person performing the procedure and breaks the sterile fluid path, thereby increasing the chance for infection. In addition, the process can prove to be uncomfortable and painful to the patient. Thus, several embodiments of the present inventions are directed to the delivery of two or more fluids or other medications to a patient with single needle penetration and/or without the use of tools to disconnect and/or connect the tubing or other conduits to the needle.

According to certain embodiments, a handpiece assembly for simultaneous or sequential delivery of multiple fluids into a joint comprises a core, a clip, a disposable tip, a needle, a first lumen and a second lumen. In any of the arrangements disclosed herein, a handpiece assembly can be configured to deliver medications, pharmaceutical compositions, drugs, cells, liquid and non-liquid fluids and flowable materials, nanoparticles, cement, microbeads and/or the like. In one embodiment, the handpiece assembly is configured to simultaneously or sequentially deliver an anesthetic and a steroid for treating a joint. In one embodiment, the core comprises at least one button, dial, knob, switch, rollerball, rollerwheel and/or other controller configured to control a rate of flow of at least one of a first fluid and a second fluid. In some configurations, the first fluid is adapted to flow through the first lumen and the second fluid is configured to flow through the second lumen. In other arrangements, the handpiece assembly can include three or more lumens for delivering three or more different fluids and/or other materials to a joint or other anatomical location. The controller can be configured to control whether the first and second fluids are delivered simultaneously or sequentially through the handpiece assembly and/or other components or portions (e.g., a tip, needle, etc.). In any of the embodiments described herein, two, three, four or more controllers are used.

In some arrangements, simultaneous delivery of said fluids is performed by combining the first and second fluids in the handpiece assembly. In one embodiment, the core of the handpiece assembly is in data communication with a fluid delivery module. In other configurations, the first and second lumens are adapted to direct said fluids from a fluid delivery module, through the clip, through the disposable tip and to the needle. In another embodiment, each of the lumens comprises a valve to prevent backflow of said fluids toward the fluid delivery module. The needle can be configured to be removably attached to the disposable tip and the disposable tip can be configured to be removably attached to the clip. In some embodiments, the needle is configured to be positioned within a joint to selectively deliver at least one said first fluid or said second fluid to said joint.

According to other arrangements, the first and second fluids are configured to be combined within the clip under a simultaneous delivery scheme. In one embodiment, the first and second fluids are configured to be combined at or near an interface between the clip and the disposable tip under a simultaneous delivery scheme. In another embodiment, the first and second fluids are configured to be combined at a distal end of the clip, near an interface between the clip and the disposable tip under a simultaneous delivery scheme. According to other arrangements, the first and second fluids are maintained separate until immediately upstream of the disposable tip. In some configurations, the handpiece assembly comprises one or more buttons and/or other controllers. In any of the embodiments disclosed herein, a handpiece assembly can include any type of controller, such as, multi-mode buttons, multi-depth buttons, rheostats, dials, knobs, switches, rollerballs, rollerwheels and/or combinations thereof.

According to certain arrangements, the one or more buttons and/or other controllers of the handpiece assembly are configured to control the rate of flow of at least one of the first fluid and the second fluid between a no flow condition, a first flowrate condition and at least a second flowrate condition. In any of the embodiments disclosed herein, the buttons and/or other controllers are configured to have additional modes and or functions. In addition, in some arrangements, the buttons and/or other controllers are configured to control or otherwise regulate the flow of one, two, three or more different fluid and/or other material streams through a handpiece assembly.

In certain embodiments, the handpiece assembly further comprises a third lumen, such that a third fluid is configured to be selectively conveyed therethrough. In one arrangement, the one or more buttons and/or other controllers are configured to control a rate of flow of the first fluid, the second fluid and/or the third fluid. The fluids being conveyed through the handpiece assembly can be configured to flow from the fluid delivery module to the needle either sequentially or simultaneously. For example, in one embodiment, two or more of the various fluid and/or other material streams can be delivered simultaneously through the handpiece assembly and the downstream needle.

According to certain arrangements, the core of the handpiece assembly includes a first controller configured to control the rate of flow of the first fluid, a second controller configured to control the rate of flow of the second fluid and a third controller configured to control the rate of flow of the third fluid. In any of the embodiments described herein, the buttons or other controllers on the core or other portions of the handpiece assembly can be used to control one or more other properties or aspects of the injection procedure. For example, in one embodiment, the buttons and/or other controllers control an ultrasound or other imaging device, regulate the sequence of delivery and/or the like. In another embodiment, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like.

In some embodiments, a handpiece device for use in an anatomical injection system comprises an outer housing enclosing a handpiece interior. The outer housing of the handpiece device or assembly can be configured to be grasped and manipulated by a user. In some arrangements, the handpiece device additionally includes a first and second conduit routed through the handpiece interior. In other arrangements, more or fewer conduits may be routed through the handpiece. According to one embodiment, the handpiece device further comprises a disposable tip having a first end and a second end, with the first end being adapted to removably receive a needle and the second end configured to secure to the outer housing.

In one embodiment, the first conduit is configured to place the needle in fluid communication with a first reservoir of a fluid delivery module and the second conduit is configured to place the needle in fluid communication with a second reservoir of the fluid delivery module. In alternative embodiments, additional conduits can place the needle in fluid communication with additional reservoirs of the fluid delivery module. In certain embodiments, the handpiece device includes at least one button or other controller positioned along the outer housing. Such a button or other controller can be adapted to selectively regulate a flow of fluids through at least one of the first conduit, the second conduit and/or any additional conduits that may be present. In some configurations, the handpiece device is adapted to deliver fluids and/or other materials through the first and second conduits to the needle simultaneously or sequentially. In one embodiment, each of the conduits comprises a check valve, a duckbill valve and/or any other type of valve to prevent fluid backflow toward the fluid delivery module. The needle positioned at the distal end of the handpiece device can be positioned within a joint to selectively deliver fluids thereto.

According to other arrangements, the one or more buttons and/or other controllers are in data communication with a fluid delivery module and/or any other portion of the injection system. The handpiece can additionally include a common chamber located upstream of the needle, wherein such a common chamber is configured to receive fluids and/or other materials from the first and second conduits. In any of the embodiments disclosed herein, the handpiece can include additional conduits configured to deliver fluids and/or other materials to a common chamber or other portion or area of the handpiece. In some configurations, the common chamber is located at or near a distal end of the outer housing of the handpiece device. However, in other embodiments, the common chamber is located at or near an interface between the outer housing and the disposable tip. In certain arrangements, the controller includes one or more buttons, dials, knobs, switches, rollerballs, rollerwheels, other controller and/or any other device configured to allow a user to regulate one or more aspects of an injection procedure.

According to some embodiments, an injection system configured for simultaneous or sequential delivery of different fluids into a patient includes a fluid delivery module adapted to receive a first container and at least a second container. In some arrangements, the fluid delivery module is configured to receive three or more vials or other containers. In one embodiment, the fluid delivery module comprises a first reservoir, a second reservoir and/or additional reservoirs that are configured to be placed in fluid communication with fluids and/or other materials contained within the containers secured to the fluid delivery module. In certain embodiments, the injection additionally includes a handpiece comprising a core, a clip, a disposable tip, a needle positioned at a distal end of said disposable tip, a first conduit and at least a second conduit. In some arrangements, the core comprises one or more buttons and/or other controllers configured to control a rate of flow of fluids through the first conduit and/or the second conduit. Such buttons and/or other controllers can be configured to control the flow of fluids through additional conduits that may be included in a handpiece assembly. In other embodiments, the buttons and/or other controllers can regulate one or more other aspects of the injection system and/or devices or systems operatively connected to the injection system, such as, an ultrasound or other imaging device. In certain arrangements, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like.

In some arrangements, the first fluid is configured to flow through the first conduit and the second fluid is configured to flow through the second conduit. In embodiments that include more than two conduits, additional fluids and/or other materials can be configured to be conveyed through such conduits. According to some arrangements, the first and second conduits are configured to direct fluids and/or other materials from the fluid delivery module, through the clip and the disposable tip and to the needle. The one or more buttons and/or other controllers of the handpiece assembly can be configured to control whether the first, second and/or additional fluids are delivered from the fluid delivery module to the needle simultaneously or sequentially. In one embodiment, the simultaneous delivery of fluids and/or other materials is performed by combining the fluids in the handpiece. According to certain arrangements, the core is in data communication with the fluid delivery module. Further, each of the conduits can include a valve or other feature or device to help prevent backflow of the fluids from the handpiece toward the fluid delivery module. In some embodiments, the disposable tip is configured to be removably attached to the clip. In any of the embodiments described herein, the needle is configured to be positioned within a target anatomical location to selectively deliver one or more medicaments, other fluids and/or other materials to a joint or other anatomical location of a patient.

In some embodiments, the controller comprises at least one button, dial, knob, switch, lever, rollerball, rollerwheel, other modulating device and/or the like. According to other arrangements, the handpiece assembly comprises a multi-function button configured to permit a user to select between a no flow condition and at least two flow conditions of varying speed. In one embodiment, such a button permits a user to selectively adjust the flowrate or any other flow property of one or more fluids and/or other materials being conveyed through the handpiece assembly. For example, the button and/or other controller can permit a user to choose between two, three or more distinct flowrates. Alternatively, the rheostat, button and/or other controller can permit a user to select between various non-distinct flowrates or other settings. In certain arrangements, the handpiece assembly includes one or more multi-depth buttons that are configured to be moved to one of two, three or more different depths. In one embodiment, each distinct or non-distinct depth corresponds to a different rate of flow for the first fluid, the second fluid and/or additional fluids and/or other materials being conveyed from the fluid delivery module to the needle. According to other embodiments, the core comprises a battery that is configured to be recharged using induction, simple charging (e.g., using a DC or AC connection), pulse charging and/or other charging methods or devices. In some arrangements, the battery of the core is configured to be inductively or otherwise recharged when the handpiece is positioned within a docking station of the fluid delivery module.

According to certain embodiments disclosed in the present application, a method of injecting two, three or more fluids into a joint or other anatomical location (e.g., organ, bone, etc.) of a patient using a handpiece assembly includes providing a handpiece assembly. In some arrangements, the handpiece assembly includes a core, a clip, a disposable tip, a needle, a first conduit and a second conduit. In other configurations, the handpiece assembly comprises three or more conduits. A first fluid or other material is configured to flow through the first conduit and a second fluid or other material is configured to flow through the second conduit. Other fluids or materials can be configured to flow through additional conduits of the handpiece assembly. In one embodiment, the core comprises at least one button or other controller adapted to control a rate of flow and/or other flow characteristics of the first fluid, second fluid and/or other fluids or materials being conveyed through the conduits of the handpiece assembly.

In certain embodiments, the core is configured to be in data and fluid communication with a fluid delivery module. The first, second and/or additional conduits are configured to convey fluids and/or other materials through the clip and the disposable tip, and to the needle. The conduits are routed through an interior of the handpiece assembly. In addition, the each conduit comprises a valve or other device to prevent backflow of fluids and/or materials flowing therethrough. In some embodiments, the needle is configured to be removably attached to the disposable tip, and the disposable tip is configured to be removably attached to the clip of the handpiece assembly. The needle is configured to be positioned within a joint or other anatomical location to selectively deliver a first fluid, a second fluid and/or additional fluids or materials to a target joint or other anatomical location.

The method additionally comprises positioning the needle into a joint or other target anatomical location of a patient, and delivering a volume of the first fluid, the second fluid and/or additional fluids or materials to the needle. In some arrangements, the one or more buttons and/or other controllers of the handpiece assembly are configured to control a rate of flow of the first fluid, second fluid and/or additional fluids or materials through the conduits. In one embodiment, the one or more controllers control whether the first and second fluids are delivered simultaneously or sequentially. In other arrangements, simultaneous delivery of fluids and/or other materials is performed by combining the first, second and/or additional fluids and/or other materials in the handpiece assembly. In some embodiments, the fluids are configured to be combined within the clip, at or near an interface between the clip and the disposable tip at a distal end of the clip, near an interface between the clip and the disposable tip and/or at any other location of the handpiece assembly. In one embodiment, the various fluids and/or other materials conveyed through the handpiece assembly are maintained separate until immediately upstream of the disposable tip.

According to certain arrangements, the controller comprises one or more buttons, dials, knobs, switches, rollerballs, rollerwheels and/or any other devices adapted to be modulated or adjusted. The buttons or other controllers are configured to regulate the rate of flow of the first fluid, the second fluid and/or any other fluids adapted to pass through the handpiece assembly. In some embodiments, such buttons or other controllers can permit a user to select between a no flow condition, a first flowrate condition and at least a second flowrate condition. In some arrangements, the handpiece assembly additionally includes a third conduit configured to convey a third fluid and/or other material therethrough. The buttons and/or other controllers can be configured to control a rate of flow of the first fluid, second fluid, third fluid and/or additional fluids or other materials. In one embodiment, the fluids are configured to sequentially or simultaneously flow through the clip and the disposable tip of the handpiece assembly to the needle. In other embodiments, the core comprises a first button or controller configured to control a rate of flow of the first fluid, a second button or controller configured to control a rate of flow of the second fluid and a third button or controller configured to control a rate of flow of the third fluid. Additional buttons or other controllers can be provided to regulate the flow of additional fluid or other material streams through the handpiece assembly. According to some configurations, the method additionally comprises monitoring a position of a distal end of the needle using an ultrasound, radio frequency, spectroscopy and/or other imaging device or system to accurately locate a target joint or other anatomical location of the patient. In some arrangements, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like.

In certain embodiments, a method of injecting two, three or more medicaments, fluids and/or other materials into an anatomy using a handpiece assembly includes providing a handpiece assembly that comprises a main body and needle removably positioned at a distal end of the main body. The handpiece assembly includes a first conduit and at least a second conduit that are positioned within an interior of the main body. In any of the embodiments described herein, the method can include the injection of three or more medicaments, fluids and/or other materials. A first fluid or other material is configured to flow through a first conduit, and a second fluid or other material is configured to flow through the second conduit. In one embodiment, the main body comprises at least one button and/or other controller configured to regulate a rate of flow of the first fluid, the second fluid and/or additional fluids or materials through the various conduits of the handpiece assembly. The handpiece assembly is configured to be in data and fluid communication with a fluid delivery module. In certain arrangements, the first and second conduits are configured to convey fluids and/or other materials to the needle. Each of the conduits can include a valve and/or other retrograde flow devices to prevent backflow of the fluids and/or other materials toward a proximal end of the main body. According to some embodiments, the needle is configured to be positioned within a target anatomical location to selectively deliver a volume of the first fluid, the second fluid and/or additional fluids or materials to a target anatomical location. The method further comprises positioning the needle into an anatomy and delivering a volume of the first fluid, the second fluid and/or additional fluids or materials through the conduits to the needle. In some embodiments, positioning the needle into an anatomy comprises using an ultrasound, radio frequency, spectroscopy and/or other imaging device or system to accurately locate the target anatomical location. The one or more buttons and/or other controllers are configured to control a rate of flow of the first fluid, the second fluid and/or additional fluid or other material streams conveyed through the conduits of the handpiece assembly. Simultaneous delivery of the various fluids and/or other materials can be performed by combining such fluids in the handpiece assembly.

According to certain embodiments, under a simultaneous delivery scheme, the first, second and/or other fluids are configured to be combined within the main body, at a distal end of the main body, immediately upstream of a proximal end of the needle and/or at any other location. In other arrangements, different fluid and/or other material streams are maintained separate until immediately upstream of the needle. In other arrangements, the controller includes one or more push buttons, dials, knobs, switches, rollerballs, rollerwheels, rheostats and/or the like. In one embodiment, a button or other controller is configured to control the rate of flow of one or more various fluid streams passing through the conduits of the handpiece between a no flow condition, a first flowrate condition and at least a second flowrate condition. The buttons or other controllers can be configured to provide additional flowrate settings.

In certain embodiments, a method of injecting two or more different medicaments or other materials contained in non-specific fluid containers into a patient using a single needle penetration comprises providing an injection system. The injection system includes a fluid delivery module and a handpiece assembly. According to one embodiment, the fluid delivery module comprises a first loading area configured to receive a first container and a second loading area configured to receive a second container. A fluid delivery module can include additional loading areas to receive additional containers. In some configurations, the first container comprises a first medicament and the second container comprises a second medicament. In certain embodiments, the loading areas are configured to securely receive vials or other containers of varying type, size, shape and/or one or more other characteristics. In one embodiment, such containers comprise standard or non-standard vials. In another embodiment, the vials are supplied to a clinician or other user of an injection system by a manufacturer or supplier of such medicaments, fluids and/or other materials.

According to certain arrangements, the injection system is configured to receive instructions for delivering the first, second and/or additional medicaments. The medicaments can include medications, pharmaceutical compositions, drugs, cells, liquid and non-liquid fluids and flowable materials, nanoparticles, cement, microbeads and/or the like. In one embodiment, the injection system is configured to simultaneously or sequentially deliver an anesthetic and a steroid for treating a joint. In one embodiment, the fluid delivery module is configured to transfer at least a portion of the first medicament from the first container to a first reservoir of the fluid delivery module and at least a portion of the second medicament from the second container to a second reservoir of the fluid delivery module.

In certain arrangements, the handpiece assembly is configured to receive a needle. The handpiece assembly is adapted to selectively be in fluid communication with the first, second and/or additional reservoirs of the fluid delivery module. In one embodiment, the handpiece assembly is maneuverable to position the needle within the patient. In another arrangement, based at least in part on instructions entered by a user, the injection system is configured to combine the first, second and/or additional medicaments or other materials prior to their delivery to the patient. In an alternative embodiment, the injection system is configured to administer the first, second and/or additional medicaments and/or other materials sequentially. The method further comprises delivering a volume of the first medicament from the fluid delivery module to the patient through the needle of the handpiece assembly based at least in part on instructions provided to the injection system, and delivering a volume of the second medicament from the fluid delivery module to the patient through the needle of the handpiece assembly based at least in part on instructions provided to the injection system. In other embodiments, additional medicaments and/or other materials are selectively delivered from the fluid delivery module to the patient through the needle of the handpiece assembly.

In certain arrangements, the handpiece assembly comprises at least one button and/or other controller configured to receive instructions for delivery of the first, second and/or additional medicaments and/or other materials. In one embodiment, the fluid delivery module is configured to transfer a predetermined volume of the first medicament and the second medicament to the patient. In another arrangement, the fluid delivery module comprises a motor to facilitate the delivery of the various medicaments and/or other materials to the patient. According to some embodiments, the first medicament comprises an anesthetic and the second medicament comprises a steroid.

In another configuration, the fluid delivery module further comprises a third loading area adapted to receive a third container comprising a third medicament or other material. The injection system is configured to receive instructions for simultaneously or sequentially delivering the first, second and third medicaments through the handpiece assembly to a patient. In certain embodiments, the first, second, third and/or additional medicaments are delivered either simultaneously or sequentially to a joint or other target anatomical location of a patient. In one embodiment, the fluid delivery module comprises a display configured to provide status information about an injection procedure, such as, the volume of the first or second medicaments delivered through the handpiece assembly or remaining in the first and second reservoirs of the fluid delivery module. In some arrangements, one or more of the containers secured to the loading areas of the fluid delivery module are original manufacturer's vials. In another embodiment, the needle is secured to a removable tip of the handpiece assembly. The method can additionally include monitoring a position of a distal end of the needle using an ultrasound, radio frequency, spectroscopy and/or other imaging device or system to accurately locate a target anatomical location (e.g., joint, organ, etc.). In any of the embodiments disclosed herein, the imaging device or system can be configured to cooperate with the injection system. In some embodiments, the imaging device or system is in data communication with the handpiece assembly, the fluid delivery module and/or another portion of the injection system. In some embodiments, one or more buttons or other controllers of the handpiece assembly are configured to control one or more aspects of the imaging device or system (e.g., capturing an image, zoom, etc.).

According to certain embodiments, a method of treating a joint of a patient by selectively delivering at least two different fluids through a single needle penetration includes providing an injection system. The injection system comprises a fluid delivery module and a handpiece assembly. In one embodiment, the handpiece assembly comprises a disposable tip with a needle positioned at a distal end of the tip. In certain arrangements, the handpiece assembly comprises one or more buttons or other controllers configured to be operated while a user grasps the handpiece assembly. In some embodiments, a user can handle, manipulate and/or otherwise operate one or more of these buttons or other controllers without having to let go of the handpiece assembly. In certain configurations, the fluid delivery module comprises a first loading area adapted to receive a first container and a second loading area adapted to receive a second container. The first container comprises a first fluid, and the second container comprises a second fluid. A fluid delivery module can include additional loading areas for securing additional containers thereto. In some arrangements, the first fluid or other material is configured to be selectively placed in fluid communication with a first reservoir of the fluid delivery module and a first conduit of the handpiece assembly after the first container is secured to the first loading area. In addition, the second fluid or other material is configured to be selectively placed in fluid communication with a second reservoir of the fluid delivery module and a second conduit of the handpiece assembly after the second container is secured to the second loading area. In one embodiment, the first and second conduits are routed through an interior of the handpiece assembly.

In any of the arrangements disclosed herein, the first loading area and second loading area are configured to securely receive vials or other containers of various types, designs, sizes and shapes. In some embodiments, such containers comprise medications, pharmaceutical compositions, drugs, cells, liquid and non-liquid fluids and flowable materials, nanoparticles, cement, microbeads and/or the like. In one embodiment, the first fluid comprises an anesthetic and the second fluid comprises a steroid. In some embodiments, such containers comprise standard or non-standard vials. In one embodiment, the vials are supplied, either directly or indirectly, to a clinician or other user of an injection system by a manufacturer or supplier of such medicaments, fluids and/or other materials. The injection system is configured to receive instructions for delivering the first, second and/or additional fluids or other materials to the needle of the handpiece assembly. In one arrangement, the fluid delivery module is configured to simultaneously or sequentially transfer a volume of the first fluid, the second fluid and/or additional fluids or materials to the needle through the first, second and/or additional conduits. In one embodiment, the handpiece assembly is configured to be in data communication with the fluid delivery module of the injection system. The handpiece assembly is maneuverable to position the needle within the patient.

According to some arrangements, under a simultaneous injection mode, the first, second and/or additional fluids or materials are combined within the handpiece assembly at a location upstream of the needle. The method additionally comprises delivering a volume of the first fluid from the fluid delivery module to the patient through the needle and through the first conduit based at least in part on instructions provided to one or more of the buttons and/or other controllers of the handpiece assembly. In some embodiments, the method comprises delivering a volume of the second fluid from the fluid delivery module to the patient through the needle and through the second conduit based at least in part on instructions provided to one or more of the buttons and/or other controllers of the handpiece assembly. In one embodiment, the controller comprises at least one button, knob, dial, switch, lever, rheostat, rollerball, rollerwheel and/or the like. In some embodiments, each of the conduits comprises a valve or other device to prevent backflow of fluids and/or other materials toward the fluid delivery module. In some arrangements, the method additionally includes monitoring a position of the distal end of the needle using an ultrasound, radio frequency, spectroscopy and/or other imaging device or system to accurately locate a joint or other target anatomical area of the patient.

In accordance with other embodiments disclosed in the present application, a system for injecting two, three or more different medicaments into a patient through a single needle penetration using nonspecific fluid containers includes a fluid delivery module and a handpiece. The fluid delivery module comprises a first loading area configured to secure a first fluid container and a second loading area configured to secure a second fluid container. In some embodiments, the first fluid container comprises a first medicament and/or other fluid or material, and the second fluid container comprises a second medicament and/or other fluid or material. The first loading area and the second loading area are configured to securely receive containers of various types, sizes and shapes. In some embodiments, such containers comprise standard or non-standard vials, ampoules and/or the like. In one embodiment, the vials are supplied to a clinician or other user of an injection system by a manufacturer or supplier of such medicaments, fluids and/or other materials.

In one embodiment, a disposable needle is configured to removably attach to a distal end of said handpiece. The needle is configured to be positioned within or near a joint or another portion of a patient's anatomy. In certain configurations, the fluid delivery module is adapted to receive instructions for delivering the first and second medicaments and/or other materials to the needle through an interior portion of the handpiece. In any of the embodiments disclosed herein, the fluid delivery module may be adapted to receive and subsequently deliver through the handpiece additional medicaments and/or other fluids. In some arrangements, first and second reservoirs are positioned within an interior of the fluid delivery module. The fluid delivery module can be configured to transfer at least a portion of the first medicament from the first fluid container to the first reservoir, and at least a portion of the second medicament from the second fluid container to the second reservoir. According to some arrangements, a first conduit is configured to selectively place the handpiece in fluid communication with the first reservoir of the fluid delivery module and a second conduit is configured to selectively place the handpiece in fluid communication with the second reservoir of the fluid delivery module. The injection system can include additional conduits for placing the handpiece in fluid communication with additional reservoirs of the fluid delivery module. In one embodiment, the first and second conduits are positioned within an interior portion of said handpiece. In certain embodiments, the fluid delivery module is configured to combine the first and second fluids prior to delivery to the patient. Alternatively, the fluid delivery module can be configured to administer the first and second fluids sequentially, depending on the instructions received by the fluid delivery module, the handpiece and/or any other component or portion of the injection system. In one arrangement, each of the conduits comprises a valve to prevent backflow of fluids toward the fluid delivery module.

According to other embodiments, the handpiece comprises at least one button or other controller configured to receive at least one instruction related to an injection procedure. In some configurations, the controller comprises at least one button, dial, knob, rheostat, rollerball, rollerwheel, switch and/or the like. In another arrangement, the fluid delivery module comprises a motor to facilitate delivery of the first, second and/or additional fluids and/or other materials from the reservoirs to the conduits and needle. In one embodiment, the fluid delivery module additionally comprises a display configured to receive at least one instruction related to an injection procedure and/or configured to provide status information regarding a particular injection procedure. In some embodiments, the first, second and/or additional fluids are delivered either simultaneously or sequentially to a joint or other anatomical location of a patient. In certain configurations, the status information provided by the display of the fluid delivery module comprises the volume of the first or second fluids already delivered through the handpiece assembly or remaining in the first and second reservoirs of the fluid delivery module. In other arrangements, at least one of the first fluid container and the second fluid container is a nonspecific fluid container. In one embodiment, the first and/or second fluid container comprises an original manufacturer's vial (e.g., having a capacity of 5 ml, 10 ml, 50 ml, 100 ml, less than 5 ml, greater than 100 ml, ranges between these values and/or the like). In one embodiment, the fluid delivery module is in data communication with an ultrasound, radio frequency, spectroscopy and/or other imaging device or system configured to locate a targeted joint or other anatomical location within the patient.

According to certain embodiments, a system for injecting two or more different fluids into a patient using a single needle penetration includes a fluid delivery module having a base and a disposable portion. The disposable portion comprises a first loading area and at least a second loading area, such that each of the loading areas is configured to securely receive a container thereon. The system further comprises a first reservoir configured to be placed in fluid communication with an interior of a first container securely positioned within the first loading area, and a second reservoir configured to be placed in fluid communication with an interior of a second container securely positioned with the second loading area. In other embodiments, the system comprises additional loading areas and corresponding reservoirs to accommodate additional fluids and/or other materials. In some embodiments, the first reservoir comprises a first outlet, and the second reservoir comprises a second outlet. The base of the fluid delivery module comprises a fluid transfer device adapted to selectively transfer fluids from the first reservoir to the first outlet and from the second reservoir to the second outlet. In one embodiment, the disposable portion is configured to be removably positioned within a recess of the base.

The injection system additionally includes a handpiece assembly comprising a handle portion configured to be grasped and manipulated by a user and a tip having at least one internal passage. The handle portion includes an interior and a chamber. The tip additionally includes a proximal end and a distal end. In one embodiment, the proximal end of the tip is secured to the handle portion. In another arrangement, the internal passage is in fluid communication with the chamber when the tip is secured to the handle portion. The injection system further comprises a needle extending from the distal end of the tip. According to certain configurations, the needle is adapted to be positioned within an anatomy of a patient. In one embodiment, the system further includes a first conduit placing the first outlet in fluid communication with the chamber of the handpiece assembly, and a second conduit placing the second outlet in fluid communication with the chamber. In certain arrangements, the handpiece assembly comprises at least one controller configured to at least partially control the delivery of fluids from at least one of the first and second reservoirs through the chamber and to the needle. In some arrangements, fluids and/or other materials conveyed within the first and second conduits are maintained separate upstream of the chamber. In some embodiments, each of the conduits comprises a valve to prevent backflow of said fluids toward the fluid delivery module.

In certain arrangements, the chamber is located at or near an interface between the handle portion and the tip of the handpiece assembly, upstream of an interface between the handle portion and the tip of the handpiece assembly or at any other location. In another embodiment, one or more of the loading areas are configured to receive a nonspecific container. The nonspecific container can include a vial as originally supplied by a drug manufacturer. In one embodiment, the controller comprises at least one button, dial, knob, switch, rheostat, lever, rollerball, rollerwheel and/or the like positioned along an exterior surface of the handle portion of the handpiece assembly. In one embodiment, the button comprises a multi-mode and/or multi-depth button that permits a user to vary a flowrate and/or other flow characteristic of the fluids through the handpiece assembly based on the depth or other position of the button. In another arrangement, the injection system is operatively connected to an ultrasound, radio frequency, spectroscopy and/or other imaging device or system configured to assist a user in advancing the needle to a desired anatomical position within the patient. In any of the embodiments described or otherwise disclosed herein, one or more of the loading areas is adapted to continuously or intermittently rotate a fluid container positioned thereon in order to mix the contents of a vial or other container positioned within the loading area.

According to certain embodiments disclosed in the present application, a method of injecting a plurality of fluids into multiple patients using nonspecific fluid containers includes providing an injection system. The injection system includes a fluid delivery module and a handpiece. The handpiece comprises a clip, a disposable tip, a reusable core and at least one button or other controller. In addition, the fluid delivery module comprises a first loading area configured to secure a first container, and a second loading area configured to secure a second container. In some embodiments, a fluid delivery module can comprise three or more loading areas to receive additional containers. In some embodiments, the loading areas are configured to securely receive vials or other containers of various types, designs, shapes and/or sizes. In some arrangements, the fluid delivery module is configured to receive instructions for delivering the first, second and/or additional fluids or materials for a first patient. Further, the fluid delivery module is configured to receive instructions for delivering the first, second and/or additional fluids or materials for a second patient. In some arrangements, the instructions are modifiable between patients. According to some embodiments, the fluid delivery module is configured to transfer at least a portion of the first fluid from the first container to a first reservoir and at least a portion of the second fluid from the second container to a second reservoir. In one embodiment, the first and second reservoirs are positioned within an interior of the fluid delivery module. In certain configurations, a distal end of the disposable tip of the handpiece is adapted to receive a first disposable needle for use with a first patient and a second disposable needle for use with a second patient. In one embodiment, the tip is configured to be disposed between patients. The disposable tip can comprise a valve to prevent reverse flow of the first, second and/or additional fluids from the needle into the clip of the handpiece. In certain embodiments, the handpiece is configured to be in fluid communication with the first and second reservoirs of the fluid delivery module. In certain arrangements, the handpiece is maneuverable to position the needle within the patient. In one embodiment, the fluid delivery module and handpiece are configured to combine the first and second fluids and/or other materials prior to delivery to the patient. In an alternative embodiment, the fluid delivery module and handpiece are configured to administer the first and second fluids and/or other materials sequentially, depending on the instructions received by the fluid delivery module and/or the handpiece.

In some arrangements, the controller of the handpiece comprises at least one button, knob, dial, switch, rheostat, rollerball, rollerwheel and/or other device configured to receive instructions for controlling at least one aspect of an injection procedure. According to another embodiment, the fluid delivery module is configured to simultaneously or sequentially transfer a predetermined volume of the first fluid and the second fluid to a patient. In one arrangement, the fluid delivery module comprises a motor to facilitate the delivery of the fluids to a patient. In other arrangements, the first fluid comprises an anesthetic and the second fluid comprises a steroid. In certain configurations, the first and second fluids are delivered either simultaneously or sequentially to a joint in a patient. In another embodiment, the injection system further comprises a display adapted to provide information regarding the delivery of the first and second fluids into a patient. In some arrangements, the first and/or the second containers comprise vials as supplied by a drug manufacturer or another nonspecific container. According to other embodiments, the method further includes monitoring a position of the distal tip of the needle using an ultrasound, radio frequency, spectroscopy and/or other imaging device or system operatively connected to the injection system to accurately locate a target anatomical location of a patient.

In some embodiments, a method of locating a target anatomical location of a patient and injecting at least two different medicaments into the target anatomical location using a single needle penetration includes providing an injection system. The injection system comprises a fluid delivery module and a handpiece having at least one controller. The fluid delivery module comprises a first loading area configured to secure a first container and a second loading area configured to secure a second container. In other embodiments, a fluid delivery module includes additional loading areas configured to secure additional containers. The first container comprises a first medicament or other material and the second container comprises a second medicament or other material. In one embodiment, the handpiece is configured to be in fluid and data communication with the fluid delivery module. In other arrangements, the fluid delivery module is configured to selectively transfer a portion of the first medicament, the second medicament and/or additional medicaments or other materials to the handpiece. In one embodiment, a distal end of said handpiece is configured to receive a needle. The handpiece is maneuverable to position the needle within the patient. The method further comprises locating the needle at or near the target anatomical location using an imaging device that is in data communication with the injection system. In certain embodiments, the injection system is configured to combine the first and second medicaments prior to delivery to the patient. Alternatively, the injection system is configured to administer the first and second medicaments sequentially, depending on the instructions received by the injection system. In addition, the method comprises delivering a volume of the first medicament, the second medicament and/or additional medicaments or other materials to the patient through the needle based on instructions received by the injection system.

According to some embodiments, the fluid delivery module is configured to receive instructions for delivering the first and second medicaments using one or more buttons or other controllers positioned on the handpiece. In one embodiment, the imaging device is operatively connected to the injection system using a hardwired or a wireless connection. In another configuration, at least one function of the imaging device or system is configured to be selectively controlled by an imaging controller and/or another portion or component of the handpiece. In some arrangements, the imaging controller of the handpiece comprises a button, dial, switch, knob, rollerball, rollerwheel and/or the like. In another embodiment, the fluid delivery module comprises a motor to facilitate the delivery of the medicaments and/or other materials to the handpiece. In one embodiment, the first and second medicaments are delivered either simultaneously or sequentially through the handpiece to the patient. In another arrangement, the fluid delivery module comprises a display configured to display or otherwise provide the volume of the first and/or second medicaments already delivered to the patient or remaining within the fluid delivery module or other status information regarding the injection procedure. In one embodiment, the display comprises a touchscreen that is configured to receive instructions that help control an injection procedure. In certain embodiments, the first and/or second containers are standard or non-standard vials supplied by a manufacturer or some other nonspecific container.

According to other embodiments, a system for injecting at least two fluids into an anatomy of a patient includes a handpiece assembly having a proximal end and a distal end. The handpiece assembly comprises at least one controller and a needle extending from the distal end of the handpiece assembly. The system further includes a fluid delivery module configured to securely receive at least a first container comprising a first fluid and a second container comprising a second fluid. The fluid delivery module is configured to selectively transfer a volume of the first fluid and/or the second fluid into the patient. According to some embodiments, the system further includes a first conduit configured to convey the first fluid from the fluid delivery module to the needle and a second conduit configured to convey the second fluid from the fluid delivery module to the needle. In one embodiment, the first and second conduits are routed through an interior of the handpiece assembly. In another embodiment, the system further includes an imaging device operatively connected to the fluid delivery module, the handpiece assembly and/or any other portion of the injection system. The imaging device is configured to help a user advance the needle to a joint or another target location of the patient's anatomy. In one embodiment, the transfer of the first, second and/or additional fluids or other materials from the fluid delivery module to the needle is at least partially controlled using the at least one button or other controller of the handpiece assembly. In one embodiment, the imaging device comprises an ultrasound device.

In several embodiments, the injection systems, devices and methods described herein are configured to use nonspecific containers. As used herein, nonspecific containers shall be given its ordinary meaning and shall include, without limitation, containers that vary in size or shape, such as original vial from a drug manufacturer, formulator and/or supplier. Thus, a nonspecific container may include, without limitation, a standard or non-standard vial or other container that includes one or more medications, formulations and/or other active or non-active ingredients. The size (e.g., diameter, height, etc.), capacity, shape, material of construction, closure type and/or other details can vary between different nonspecific containers. For example, the nonspecific container used by a first drug manufacturer or supplier may comprise a relatively small or wide vial, while the nonspecific container used by a second drug manufacturer or supplier may comprise a relatively large or narrow vial.

According to one preferred embodiment, an injection system is configured to selectively deliver two or more medications, formulations and/or other fluids or substances into or near a joint of a patient (or another target anatomical location) using a single needle penetration. The injection system includes a fluid delivery module that is adapted to receive vials or other containers comprising the medicaments and/or other materials to be transferred to the patient through a needle positioned along the distal end of a downstream handpiece assembly. In some embodiments, vials or other containers comprising the desired medicaments and/or other substances to be used in a particular injection procedure are nonspecific containers that are secured to corresponding loading areas of the fluid delivery module or other portion of the system with the assistance of adapter.

According to a second preferred embodiment, the injection system comprises a handpiece assembly that includes a removable tip, needle and one or more other components or portions. Nonspecific containers (e.g., vials) containing one, two or more different medicaments and/or other substances can be secured onto a fluid delivery module and be subsequently placed in fluid communication with the handpiece assembly. The various types of medicaments and/or other substances can be administered, in sequential injection procedures, to a plurality of patients in a manner that permits the clinician or other user to selectively modify and customize the manner in which the various substances loaded onto the fluid delivery module are administered to each patient (e.g., modifying the sequence of delivery, the volume or other amount of each medication and/or other substance delivered, etc.).

Such systems, devices and methods can be adapted to allow a clinician to quickly and efficiently treat one or more joints of multiple patients. Moreover, the system permits a clinician to customize the injection protocol according to the patient being treated or as otherwise desired or required. In addition, pain and discomfort to the patient being treated is generally reduced by the various embodiments of the injection system disclosed herein. The various medicaments and/or other materials can be delivered simultaneously or according to a desired sequence. A clinician or other user can advantageously regulate the delivery of the medicaments and/or other materials into the patient using buttons or other controllers conveniently positioned on the handpiece assembly or another component of the injection system.

In some arrangements, an injection system is configured to be in data communication with and operate concurrently with an ultrasound wand and/or other imaging or intra-anatomical location systems or technologies.

According to some embodiments of the present inventions, a system for injecting two or more fluids into a targeted anatomical location includes a handpiece assembly having a proximal end and a distal end, a needle extending from the distal end of the handpiece assembly, a fluid delivery module comprising a fluid transfer device and at least two openings for inserting fluid containers and a conduit being at least partially routed through an interior of the handpiece assembly, the conduit being configured to place the fluid delivery module in fluid communication with the needle. According to some embodiments, the fluid transfer device is configured to transfer fluid from fluid containers placed within the openings of the fluid delivery module to the targeted anatomical location. In some embodiments, the targeted anatomical location comprises a bone, organ, muscle tissue, other tissue, a bodily cavity or any other portion of the anatomy. In other embodiments, the anatomical location comprises an intra-articular space (e.g., ankle, wrist, hand joint, knee, foot joint, spine joint, shoulder joint, any other joint or space, etc.), bone, muscle tissue, other tissue, an organ and/or the like.

According to other embodiments, a method for injecting at least two fluids into a targeted anatomical location comprises inserting a needle into the targeted anatomical location, the needle being in fluid communication with a handpiece assembly and a fluid delivery module, loading at least a first and second fluid into the fluid delivery module, instructing the fluid delivery module to deliver the first fluid through the handpiece assembly and the needle, instructing the fluid delivery module to deliver the second fluid through the handpiece assembly and the needle and removing the needle from the anatomical location.

In one embodiment, a method for aspirating and injecting fluids into a targeted anatomical location is provided. In one embodiment, the method comprises inserting a needle into the targeted anatomical location, the needle being in fluid communication with a handpiece assembly and a fluid delivery module, aspirating a first fluid through the handpiece assembly and the needle, loading at least a second fluid into the fluid delivery module, delivering the second fluid through the handpiece assembly and the needle, and removing the needle from the anatomical location. The first fluid can comprise one or more endogenous and/or exogenous fluids (e.g., naturally occurring fluids, such as synovial fluid, lavage fluids, serum, etc.). The second fluid can comprise one or more endogenous and/or exogenous fluids. In some embodiments, endogenous fluids include fluids that were pre-existing in the target area prior to delivery of the needle and/or a second fluid. For example, an endogenous fluid may include a diagnostic fluid, a visualization fluid, an anesthetic, or a lavage fluid such as saline, for which aspiration prior to delivery of the exogenous fluid may be desirable or any other fluid. Exogenous fluids include, but are not limited to, medications, pharmaceutical compositions, drugs, cells, liquid and non-liquid fluids and flowable materials, nanoparticles, cement, microbeads, therapeutics or diagnostic fluids, imaging fluids, lavage fluids and/or the like, and any combinations thereof. In one embodiment, the system for dual aspiration and fluid delivery comprises a single conduit for both aspiration and delivery. In another embodiment, the system comprises separate aspiration and delivery conduits.

In several embodiments, an imaging device is used to guide the insertion of the needle, the aspiration of fluid, and/or the delivery of fluid to the target. In one embodiment, the imaging device comprises an ultrasound device.

In some embodiments, a method of transferring a volume of fluid to an anatomical location comprises providing a module having an imaging component and an injection component, with the injection component being configured to receive and selectively deliver a volume of fluid to a needle. The method further includes inserting the needle into an anatomy, positioning the needle in a targeted anatomical location using the imaging component and injecting a volume of fluid into the targeted anatomical location using the injection component.

BRIEF DESCRIPTION OF THE DRAWINGS

These and other features, aspects and advantages of the present application are described with reference to drawings of certain embodiments, which are intended to illustrate, but not to limit, the various inventions disclosed herein. It is to be understood that the attached drawings are for the purpose of illustrating concepts and embodiments of the present application and may not be to scale.

FIGS. 9A-9E illustrate various views of a manifold of a cassette according to another embodiment;

FIGS. 22A and 22B illustrate views of a handpiece assembly configured for use with an injection system according to another embodiment;

FIG. 28 illustrates a perspective view of a handpiece assembly according to one embodiment;

FIG. 29B illustrates an exploded perspective view of the handpiece assembly of FIG. 29A;

FIG. 30B illustrates a side view of the core of FIG. 30A;

DETAILED DESCRIPTION

The discussion and the figures illustrated and referenced herein describe various embodiments of an injection device and system, as well as methods related thereto. A number of these embodiments of injection systems, devices and methods are particularly well suited to transfer a volume of one or more fluids and/or other materials to or near (and/or from) an intra-articular or joint space, a bone, an organ, cavity or other location of the human anatomy (e.g., toe, foot, ankle, knee, hand, finger, etc.). Such devices, systems and methods are well-suited for treating osteoarthritis, rheumatoid arthritis, other inflammatory diseases and/or other joint diseases or conditions. However, the various devices, systems, methods and other features of the embodiments disclosed herein may be utilized or applied to other types of apparatuses, systems, procedures and/or methods, regardless of whether they are medically-related or not.

As discussed in greater detail herein, this application discloses devices, systems and methods of locating a target joint (e.g., knee, ankle, elbow, shoulder, wrist, finger, toe, hip, facet joint, vertebra, other spinal joints or spaces, etc.) or other anatomical location and delivering and/or withdrawing fluids and/or other materials (e.g., medications, pharmaceutical compositions, drugs, cells, liquid and non-liquid fluids and flowable materials, nanoparticles, cement, microbeads, etc.) thereto and/or therefrom. According to some embodiments, the devices, systems and methods disclosed herein facilitate the delivery and/or aspiration of fluids and/or other materials to and/or from an intra-articular space (e.g., joint) or other anatomical location by advantageously using a single needle penetration. The fluids and/or other materials can vary in type (e.g., formulation), strength (e.g., concentration) and/or in any other manner. The delivery of fluids and/or other materials to or near joints and/or other anatomical locations using the embodiments disclosed herein can help decrease pain and discomfort to patients during treatment procedures. Such systems, devices and methods can be especially useful for the treatment of smaller joints, such as, for example, toes, thumbs, other fingers and/or the like that are highly innervated. In addition, such devices and methods can simplify the execution of related procedures by physicians and other medical personnel. Accurately locating an intra-articular space is typically a very difficult task, especially when the targeted joints (e.g., fingers, toes, etc.) or other anatomical locations are relatively small. According to some embodiments, the devices, systems and methods disclosed herein help a clinician or other user to locate targeted joints or other anatomical spaces for the subsequent accurate delivery of fluids and/or other materials thereto.

Figure 1:
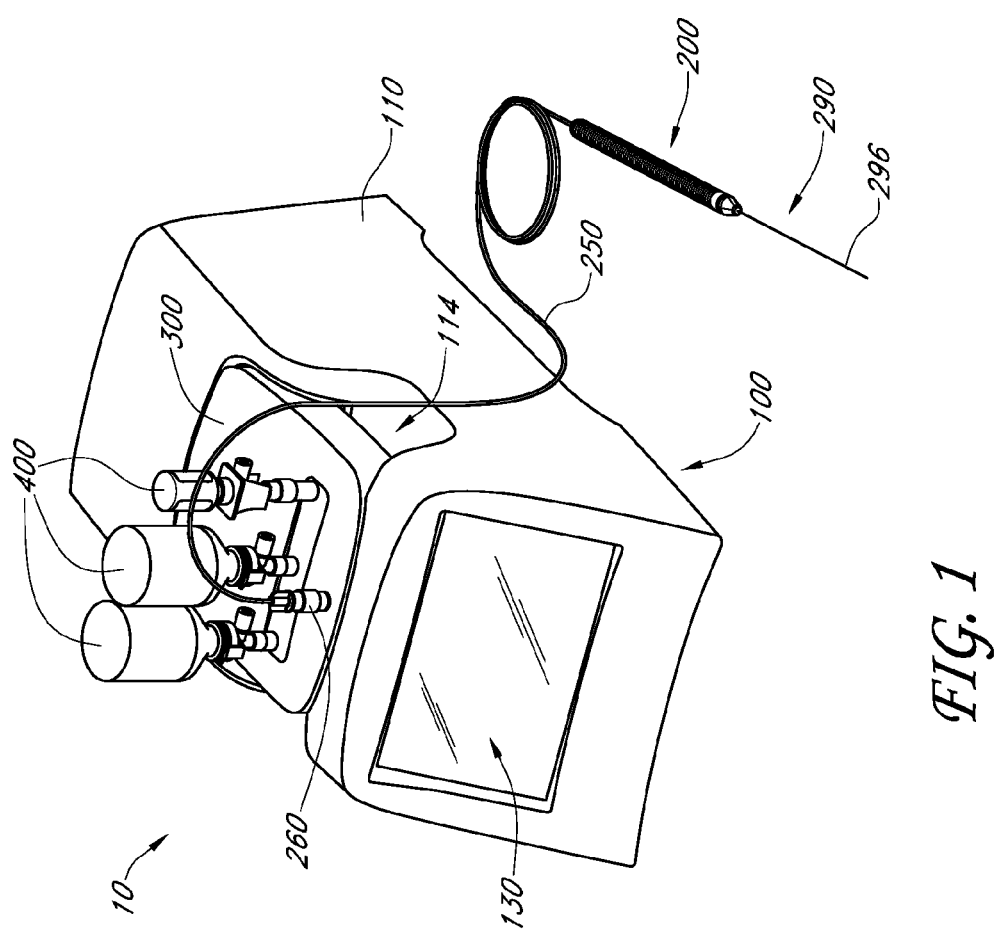
FIG. 1 illustrates a perspective view of an injection system according to one embodiment.

FIG. 1 illustrates a perspective view of one embodiment of an injection system 10. The injection system 10 can include a handpiece assembly 200 having a needle assembly 290 positioned along its distal end. In the illustrated embodiment, a delivery conduit 250 (e.g., flexible tubing) or other some other conduit can be used to deliver one or more fluids and/or other materials to and/or from a targeted area or region of the anatomy (e.g., a joint, an organ, etc.) via the handpiece assembly 200. In some embodiments, the materials delivered to the target anatomical location include one or more medications or medicaments (e.g., anesthetics, steroids, hyaluronic acid, etc.), other formulations, other fluids or substances, such as, for example, pharmaceutical compositions, drugs, cells, liquid and non-liquid fluids and flowable materials, nanoparticles, cement, microbeads, therapeutics or diagnostic fluids, imaging fluids, lavage fluids, other endogenous or exogenous fluids or materials and/or the like.

As illustrated in FIG. 1, the delivery conduit 250, and thus, the handpiece assembly 200, can be placed in fluid communication with a fluid delivery module 100. As discussed in greater detail herein, the fluid delivery module 100 can be advantageously configured to accurately deliver one, two or more different fluids, compositions, other substances or materials and/or the like to the handpiece assembly 200 in accordance with a desired delivery protocol. In some embodiments, the fluid delivery module 100 is an electromechanical software-controlled device that uses motors, pumps and/or other mechanical, pneumatic, electrical or other types of devices to transfer fluids and/or other materials from multi-dose vials or other containers to a downstream handpiece assembly via a cassette 300 or other component or device. IN one embodiment, the system comprises one or more stepper motors and/or other mechanically-operated actuators or devices to accomplish the accurate delivery of fluids from the fluid delivery module to and through the handpiece assembly. Further, in some embodiments, a needle positioned at the distal end of the handpiece assembly 200 is placed in fluid communication with an aspiration source in order to selectively remove fluids and/or other materials or substances from a targeted anatomical location (e.g., a joint, an organ, a cyst, another body cavity, etc.), as desired or required. The terms "handpiece," "handpiece assembly" and "handpiece device" are used interchangeably herein.

According to some embodiments, the fluid delivery module 100 of the injection system 10 includes one or more motors, pumps, other fluid transfer devices (e.g., syringes operated by a motor, actuator and/or other mechanical device) to help transfer one or more medicaments, fluids and/or other substances or materials to a targeted anatomical location (e.g., toe, knee, other joint, etc.). Such fluids, substances and/or materials can be included in vials 400, ampoules and/or other containers that may be conveniently secured to the fluid delivery module 100. In some embodiments, the motor comprises a stepper motor or any other type of motor that is configured to accurately transfer a volume of fluid and/or other material from the injection system to or near a joint or another targeted anatomical location. Stepper motors or other mechanically-driven motors or devices can be especially helpful in intra-articular injections (e.g., due to, in part, the relatively high backpressure associated with injecting fluids and/or other materials into small joint, the innervated nature of such joints, the need to deliver very accurate volumes of fluids and/or other materials to such joints and/or other factors or reasons). In addition, the execution of such injections can be facilitated and enhanced by the systems and devices disclosed herein, as the need for two or more different needle penetrations to access a joint or other targeted anatomical area is advantageously eliminated.

According to other embodiments, the fluid transfer device comprises one or more peristaltic pumps, syringe pumps, gear pumps, bladder pumps, diaphragm pumps, metering pumps and/or any other type of pump (e.g., mechanical, pneumatic, etc.). Such a fluid transfer device can be adapted to deliver liquids, gases, other fluids, solids, non-Newtonian fluids, other non-flowable materials, combinations thereof and/or the like to a desired anatomical location.

The general arrangement of the systems, systems and methods illustrated and discussed herein permits one or more fluids, substances or other materials to be delivered to and/or removed from an intra-articular space with a single needle penetration. Therefore, pain and/or discomfort to a patient can be advantageously reduced. This may be especially helpful when transferring fluids to and/or from the intra-articular space of a small joint, such as, for example, a toe, thumb, other finger and/or the like. Such small joints are typically highly innervated, making them more sensitive to pain. Further, the complexity and other difficulties associated with executing such procedures can be reduced for physicians or other clinicians. In addition, as discussed in greater detail herein, such systems can be configured to easily and accurately deliver a desired quantity of one or more medicaments (e.g., pharmaceuticals, drugs, medications, etc.) and/or other fluids, substances or materials, or a combination thereof, to a desired anatomical location. In some embodiments, an injection system can comprise and/or can be operatively coupled to an imaging device (e.g., ultrasound device) to assist a user in accurately positioning the needle within a patient's anatomy (e.g., joint) prior to delivering the desired pharmaceuticals and/or other fluids or materials.

According to some embodiments, as part of a desired treatment protocol, one or more anesthetics are initially delivered into the patient using the injection system. For example, a desired volume of Lidocaine and/or any other short-acting and/or long-acting anesthetic can be delivered within the anatomy to reduce the pain and discomfort to the patient. Such anesthetics can be delivered before and/or while the needle located at the distal end of a handpiece assembly is being advanced through the skin and other anatomical tissues and portions of the patient. Alternatively, a short or long acting anesthetic can be delivered into the patient after the needle has been accurately positioned at or near the target anatomical location (e.g., joint, organ, etc.). Further, in some embodiments, the delivery of an anesthetic is followed by the delivery of a second anesthetic (e.g., a slow-acting anesthetic), a steroid (e.g., Depo-Medrol®) and/or any other pharmaceutical or other material (e.g., hyaluronic acid, saline, pain-relieving medications, pharmaceutical compositions, other medications or drugs, cells, liquid and non-liquid fluids and flowable materials, nanoparticles, cement, microbeads, etc.) in accordance with a desired treatment protocol. For example, a physician or other clinician can use particular injection protocols for treating certain joints, diseases, conditions and/or patients. As discussed in greater detail herein, various medications, formulations and/or other fluids and/or other materials can be delivered into a patient simultaneously and/or sequentially.

With continued reference to the injection system illustrated in FIG. 1 the fluid delivery module 100 can be configured to receive a cassette 300, cartridge or other member, which in some arrangements, is configured to be removably secured to the fluid delivery module 100. The injection system 10 can be configured so that one or more vials 400, ampoules or other containers comprising medications and/or other fluids, substances or materials can be easily loaded onto (and subsequently removed from) the cassette 300 or other portion of the fluid delivery module 100. In some embodiments, a cassette or other portion of the fluid delivery module is configured to receive off-the-shelf medication and/or fluid packages in multi-dose vials or ampoules. Further, in certain arrangements, a cassette or other portion of the fluid delivery module is configured to receive one or more nonspecific fluid containers. In alternative embodiments, the fluid delivery module 100 does not include a cassette or other removable member on which vials or other containers can be loaded.

Medications, fluids, materials and/or substances included within vials or other containers that are loaded onto the cassette 300 can be accurately and conveniently administered to a targeted joint or other anatomical location. The injection system 10 can be configured to selectively transfer such fluids and/or other materials from the respective vials, through the cassette 300, to a needle assembly 290 located at the distal end of the handpiece 200. In some embodiments, the handpiece assembly 200 is configured to be in fluid communication with the fluids and/or other materials contained within the vials 400 or other containers. In some arrangements, the system 10 is additionally configured to selectively aspirate fluids and/or other substances from an intra-articular space or other portion of the anatomy, either in lieu of or in addition to delivering one or more fluids and/or other substances within the anatomy.

In some embodiments, the needle assembly 290 secured to the distal end of the handpiece assembly 200 includes a needle 240 that can be advanced through the skin and other tissues of a patient so as to adequately reach a targeted joint (e.g., toe, ankle, knee, spine, hand, finger, neck, etc.) or other anatomical location (e.g., organ, cyst, cavity, etc.). In several embodiments, the needle has a gauge of 18 G-30 G and a length of about 0.5 to 5.0 inches (e.g., 1.0 to 1.5 inches). However, in other arrangements, the gauge, length and/or other details of the needle can be greater or smaller than the range indicated herein, as desired or required by a particular application. Further, the needle can comprise surgical-grade stainless steel and/or any other suitable material (e.g., other metals, alloys, etc.).

With continued reference to FIG. 1, the intra-articular injection or delivery system 10 can include one or more displays 130 or other user interfaces along one or more of its outer surfaces. As discussed in greater detail herein, the display 130 can be configured to provide various data and/or other information to the user. In some embodiments, the fluid delivery module 100 comprises a data input device (e.g., touchscreen, keyboard, keypad, dials, buttons, etc.) to permit a user to enter data and/or other information regarding a particular procedure. For example, in one arrangement, the display 130 comprises a touchscreen configured to both provide information to and receive information and instructions from a user.

In some embodiments, the handpiece assembly includes one or more electrical components, such as, for example, an electrically-operated controller. Thus, the fluid delivery module 100 can include one or more charging receptacles or other docking stations that are sized, shaped and otherwise configured to receive a handpiece assembly. However, in other arrangements, as illustrated in FIG. 1 and discussed in greater detail herein, the handpiece assembly 200 does not comprise any electrical components. As a result, the need for a docking or recharging station on or near the fluid delivery module 100 can be advantageously eliminated.

In addition, the fluid delivery module 100 can include one or more other components or features to enhance the function, aesthetic appearance and/or other aspect of the system 10. For example, in FIG. 1, the fluid delivery module 100 comprises a recess or groove 114 along its upper end that facilitates positioning the cassette 300 into and/or out of the top of the module 100. The quantity, location, shape, size and/or other details of such recesses or grooves 114 can be different than depicted in FIG. 1. Moreover, an intra-articular injection system 10 can include one or more other components or features, as desired or required by a particular application.

As shown in the embodiment of FIG. 1, the housing 110 or outer chassis of the fluid delivery module 100 can include generally rounded corners. Alternatively, however, the housing 110 can comprise any other shape, size, configuration and/or feature. Further, the fluid delivery module 100 can include generally smooth or glossy surfaces that are configured to withstand frequent cleaning. In some arrangements, the fluid delivery module 100 is waterproof or water-resistant or substantially waterproof or water-resistant. In some embodiments, generally smooth exterior surfaces of the module 100 can facilitate cleaning and prevent residual contamination from remaining on the housing. Further, the fluid delivery module 100 can be configured to maintain vials and/or other containers secured thereon at a particular thermal setting or temperature range. For example, the module 100 can include a temperature control system (e.g., cooling/heating device, temperature sensor, regulator, etc.) that permits the module 100 to maintain a pharmaceutical or other material to be delivered into a patient within a desired temperature range. This can be particularly useful and beneficial for the delivery of formulations or other substances that degrade or otherwise become disadvantageously transformed when not adequately temperature-controlled (e.g., cooled or otherwise refrigerated, heated, etc.).

In some embodiments, as illustrated in FIG. 1, a touchscreen display 130 of a fluid delivery module 100 is generally rectangular. In certain arrangements, the display 130 comprises a flat panel touchscreen having a 7-inch color TFT LCD. The resolution of the display 130 can be approximately 800×600 with a total of about 480,000 pixels and a brightness rating of approximately 300 cd/m$^3$. In addition, the touchscreen display 130 can use restive technology for sending touch input. In some embodiments, the touchscreen is compatible with and/or without the use of gloves (e.g., latex gloves). However, the type, size, resolution, brightness, compatibility and/or other details about the display 130 can vary, as desired or required.

In some embodiments, the touchscreen display 130 can comprise a 16 to 9 aspect ratio. However, as noted above, the type, shape, size, aspect ratio, resolution and/or other characteristics of the display 130 can vary, as desired or required. As discussed in greater detail herein, the touchscreen display 130 can be adapted to identify one or more characteristics regarding the vials and/or other containers (e.g., syringe, etc.) secured to the module 100. In addition, the touchscreen display 130 can be configured to display status information, patient information (e.g., name, vital signs, known allergies, etc.), imaging information, injection procedure programming and/or status information and/or any other information. Further, the touchscreen display 130 and/or another data entry device can permit a physician, other clinician or other user to control the operation of the procedure (e.g., verify patient, verify fluids or other materials to be delivered, locate target joint, start, stop, reduce/increase flowrate or other rate of delivery, etc.) and/or to enter other data within the system 10.

According to some arrangements, the touchscreen display 130 is configured to illustrate text and/or images (e.g., icons). The use of icons can facilitate the physician or other user in performing the required injection and/or aspiration procedure. For example, the touchscreen display 130 can be configured to display a list of various body parts (e.g., foot, hand, spine, knee, other body parts or organs, etc.) into which a desired injection is to occur. Once a user selects the general anatomical area targeted by the procedure, the touchscreen display 130 can provide a more detailed selection list of available target sites within that general area. For example, if a foot is selected, the touchscreen display 130 can provide a more detailed list of joints associated with the foot (e.g., ankle, toe, etc.). Alternatively, the display 130 can provide a list of various treatment procedures or injection protocols from which to choose. In other embodiments, as illustrated in FIGS. 39A-39J and 40A-40T, the touchscreen display 130 can include "UP" and "DOWN" softkeys, arrows, other icons, text and/or other images that facilitate the user during the execution of the corresponding procedure.

In some embodiments, the selected icon or other portion of the display 130 can be configured to change color, shade, shape and/or the like when a user selects it. Further, the fluid delivery module 100 can be configured to provide visual and/or audible verification that a selection was made (e.g., tone, beep, etc.). In some embodiments, a touchscreen display 130 and/or any other component of the fluid delivery module 100 includes one or more other features, as required or desired by a particular application. As discussed, an injection system can also include a voice command/notification system that permits a user to receive audile updates from the system (e.g., volume dispensed, volume remaining, etc.) and/or to control the operation of the system using audible instructions (e.g., "START," "STOP," "DECREASE DELIVERY RATE," "INCREASE DELIVERY RATE," "PAUSE," "TERMINATE" and/or the like). The disclosure included herein regarding the display 130 (e.g., touchscreen device) and other features of the injection system can be applied to any other embodiment of a fluid delivery module disclosed herein or equivalents thereof.

The fluid delivery module 100 and/or any other components of the injection system 10 can be electrically energized by one or more power sources. For example, in some embodiments, the fluid delivery module 100 is configured to connect to an AC power supply (e.g., via a cord or other connection). In such arrangements, an AC transformer can be situated either within or outside of the module housing 110. Thus, in some embodiments, a fluid delivery module includes an external power supply. In other embodiments, however, the fluid delivery module is powered by one or more batteries (e.g., rechargeable lithium batteries, disposable batteries, etc.) or another DC power source, either in addition to or in lieu of an AC power supply. This can provide an extra measure of protection to ensure that an injection procedure is not interrupted because of a power outage or other disruption. In addition, the use of batteries and/or an external AC power transformer can advantageously enhance the portability of the injection system and/or help to reduce its overall size and/or weight. However, in alternative embodiments, one or more other types of devices and/or methods are used to provide electrical power to the fluid delivery module 110 and/or other components of the injection system 10.

According to some embodiments, a fluid delivery module 100 includes one or more other ports, slots and/or other connection sites configured to operatively connect the module 100 to one or more other devices, processors and/or the like (e.g., ultrasound or other imaging device, personal computer, internet, other local or non-local network, etc.). Such ports or slots can be standard (e.g., USB, mini-B, parallel, etc.) or non-standard, as desired or required.

Further, a fluid delivery module 100 can comprise one or more memory, communication and/or other types of slots or connections. Thus, the module 100 can be upgraded with additional programs, functions and/or other capabilities in accordance with a desired protocol. In some embodiments, a fluid delivery module 100 comprises a USB or other port that is configured to communicate with a personal computer, a PDA, a Smartphone and/or any other device (e.g., the hospital's computing network, an internet connection, a monitoring device, an ultrasound device, another medical device, etc.). In yet other arrangements, the fluid delivery module 100 includes one or more wireless connections or communication systems (e.g., modem, Wi-Fi, RFID, Bluetooth, etc.) that advantageously permit the module to selectively communicate with other components of the injection system (e.g., handpiece assembly) and/or one or more other computing systems or devices. These types of communication devices and/or systems can permit a user to transfer data (e.g., continuously or intermittently) to and/or from the module 100, as desired or required. For example, new software or software patches can be periodically installed onto the module 100, either automatically or manually. In other embodiments, information about a particular treatment procedure (e.g., patient information, date and time, drug types, dosages and volumes injected, other injection protocol details, etc.) is selectively transmitted from the fluid delivery module 100 to an external source (e.g., network, computer, etc.).

The fluid delivery module 100 can comprise and/or can be in communication with one or more processors, control devices and/or the like. This can permit the module 100 to adequately process data and control the operation of the various components of the fluid injection/aspiration system. In some embodiments, the processor and/or control unit are included within the housing 112 of the fluid delivery module 110. Alternatively, such components can be external to the module 100. In such arrangements, the fluid delivery module 100 can be placed in data communication with an external processor and/or control unit using one or more hardwired and/or wireless communications.

Figure 2:
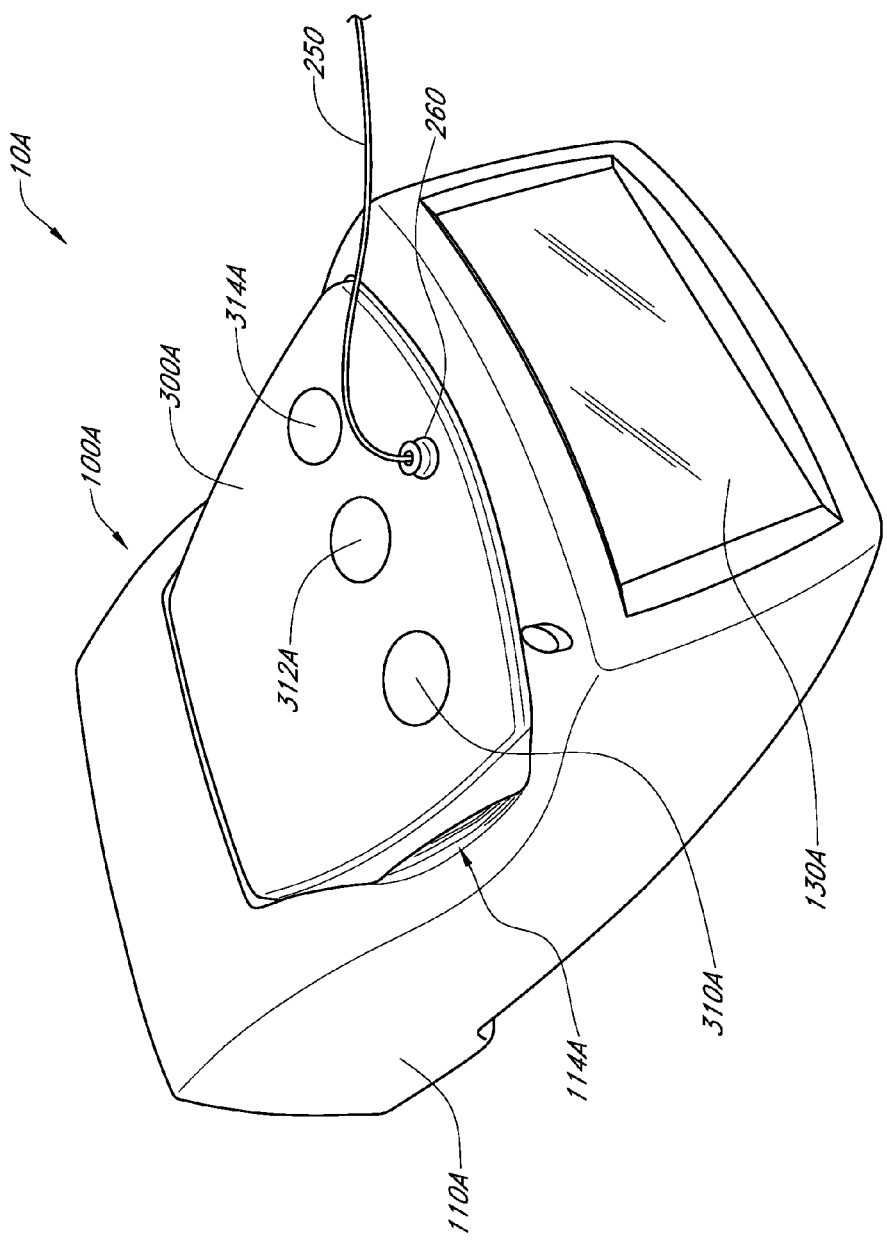
FIG. 2 illustrates a perspective view of an injection system according to another embodiment.

FIG. 2 illustrates another embodiment of a fluid delivery module 100A configured for use in an articular injection system 10A. As shown in FIG. 2, the fluid delivery module 100A can include a cassette 300A configured to be selectively positioned within and removed from the module housing 110A. The cassette 300A can comprise an outer housing that is configured to enclose one or more internal components (e.g., manifolds, syringes or other reservoirs, etc.). As shown in FIG. 2, the cassette 300A can include a generally contoured rectangular shape. In other embodiments, the cassette 300A is permanently or semi-permanently secured to the fluid delivery module 100A, or the cassette 300A forms a generally unitary structure with the fluid delivery module 100A. Further, in some embodiments, the cassette 300A and/or any of its components or portions comprise one or more materials, such as, for example, plastic or other polymers, rubber, other elastomers, metals, alloys and/or any other synthetic or natural materials, or combinations thereof. However, the shape, size, materials of construction and/or other characteristics of the cassette 300A can vary, as desired or required for a particular application or use. In addition, the cassette 300A can comprise one or more finger wells, grooves and/or other recessed areas or features that facilitate placement of the cassette 300A into and/or out of the corresponding area of a fluid delivery module 100A.

According to some embodiments, the cassette 300A is a disposable item that is configured to be replaced according to a desired or required protocol or schedule (e.g., once, twice or more often per day, less often than once a day, etc.). As discussed in greater detail herein, the cassette 300A can be configured to be removed and replaced together with the downstream delivery line 250 (e.g., tubing, other conduit, etc.) and/or handpiece assembly 200 (FIG. 1) once a day, whenever a treatment scheme is varied or modified and/or according to any other protocol. In other embodiments, the cassette 300A may be configured to be replaced more or less often than indicated herein, as desired or required. Alternatively, the cassette 300A can be removed and replaced when one or more medications or other fluids or substances being delivered through the injection system are changed (e.g., types of fluids, dosages or concentrations, etc.). This can help prevent cross-contamination between different types of substances, different dosages of substances and/or the like.

In the embodiment depicted in FIG. 2, up to three vials (not shown) or other containers may be secured to receiving sites 310A, 312A, 314A located along the top surface of the cassette 300A. In some embodiments, each receiving site comprises a nest or loading area that is adapted to accept a standard or non-standard vial or other container. The cassette 300A can include more or fewer receiving sites 310A, 312A, 314A, as desired or required. In addition, the location, spacing and other details of the receiving sites 310A, 312A, 314A can be different than illustrated in FIG. 2. As discussed in greater detail herein, once the vials 400 (FIG. 1) or other containers are secured to the cassette 300A, the injection system can be configured to selectively transfer the contents of such vials or other containers within the fluid delivery module 100, 100A (e.g., within one or more syringes or other reservoirs of a removable cassette secured to the fluid delivery module), and subsequently, accurately deliver the interior contents of one or more of such vials to a targeted anatomical location in a precise and accurate manner, in accordance with a desired protocol. According to some embodiments, one or more of the vials can be configured to be continuously or intermittently mixed, either automatically or manually, while they are secured to the cassette and/or during the execution of an injection procedure. Such mixing may be desired or required for certain medicaments, substances and/or other materials, such as, for example, steroids or other solutions or mixtures having solids or other components that have a tendency to settle or that require mixing. In certain arrangements, the receiving sites of the cassette are configured to receive a variety of different vials or other containers, including off-the-shelf vials and/or customized vials or containers.

Figure 3:
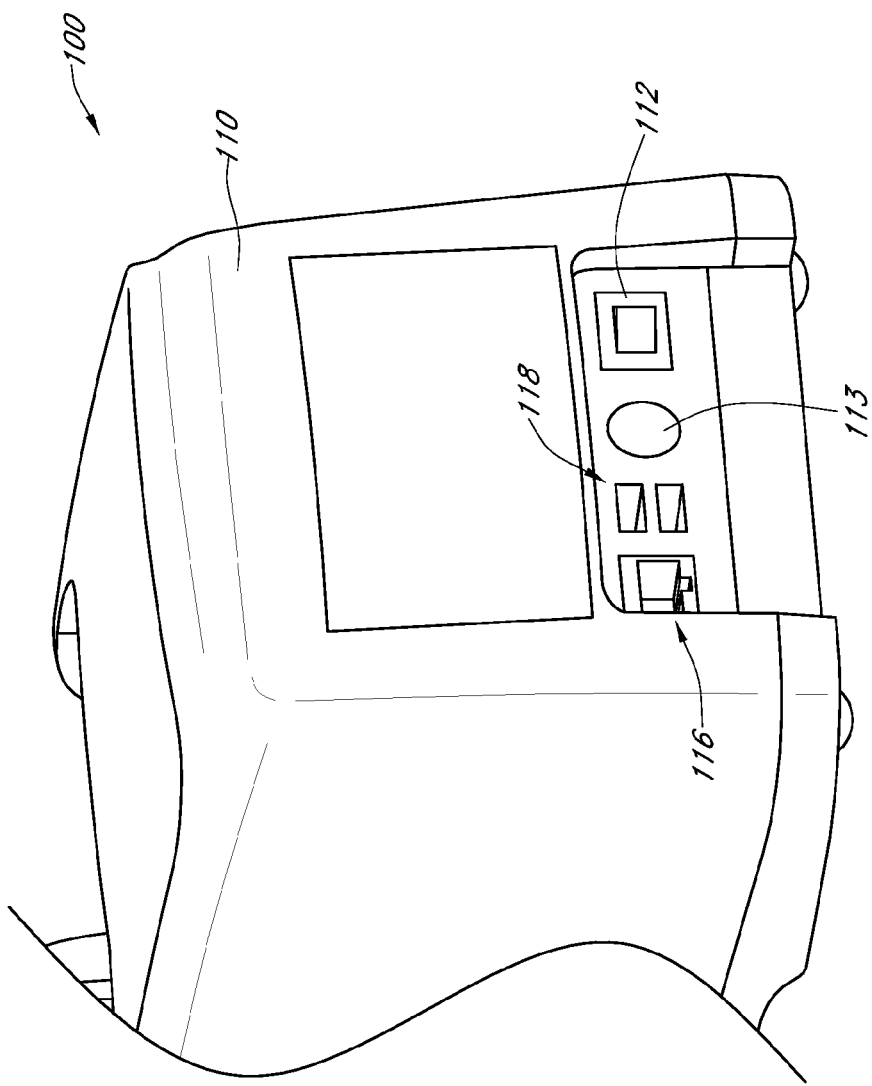
FIG. 3 illustrates a rear perspective view of an injection system according to one embodiment.

FIG. 3 illustrates a rear portion of one embodiment of a fluid delivery module 100. One or more buttons, ports or other connection points and/or the like can be included along one or more portions of the module's housing 110. In the depicted embodiment, the fluid delivery module 100 comprises an On/Off button 112, switch or other controller, a power port 113, one or more electrical fuses, one or more USB ports 118, an Ethernet or other network port 116 and/or the like. As discussed in greater detail herein, such ports and/or other connection points can help place the fluid delivery module in data communication with an external device (e.g., a computer, an imaging device, etc.), system, network (e.g., a facility's main network, the Internet, etc.) and/or the like.

Figure 4:
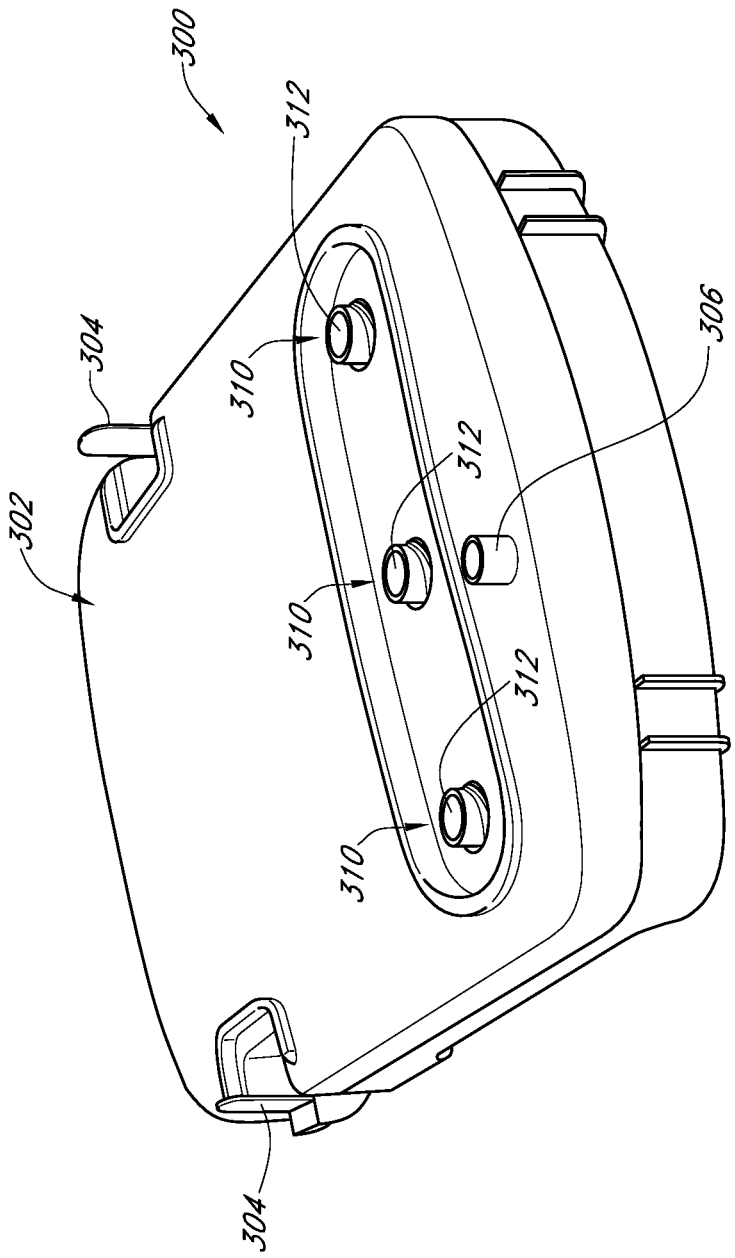
FIG. 4 illustrates a perspective view of a cassette configured for placement within a fluid delivery module of an injection system, according to one embodiment.

FIG. 4 illustrates one embodiment of a cassette 300 adapted for placement within a fluid delivery module of an injection system. The cassette 300 can be configured to receive up to three different vials and/or other containers (not shown in FIG. 4). However, in other embodiments, the cassette 300 is adapted to receive fewer (e.g., one or two) or more (e.g., four, five, more than five, etc.) vials or other containers, as desired or required.

Figure 5A:
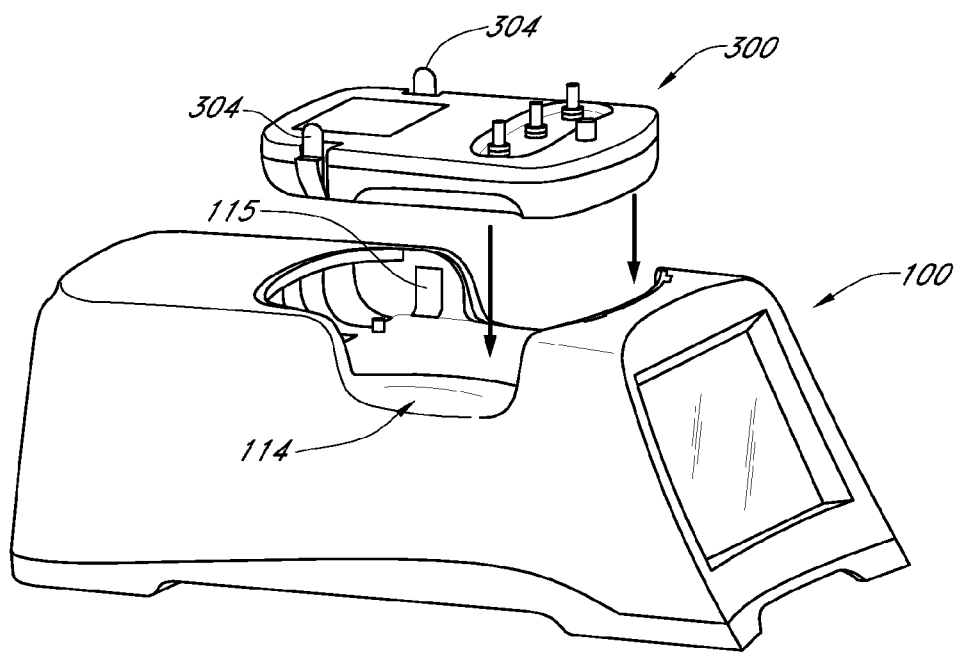
FIGS. 5A and 5B illustrate side perspective views of a cassette being inserted within and removed from a fluid delivery module, according to one embodiment.
Figure 5B:
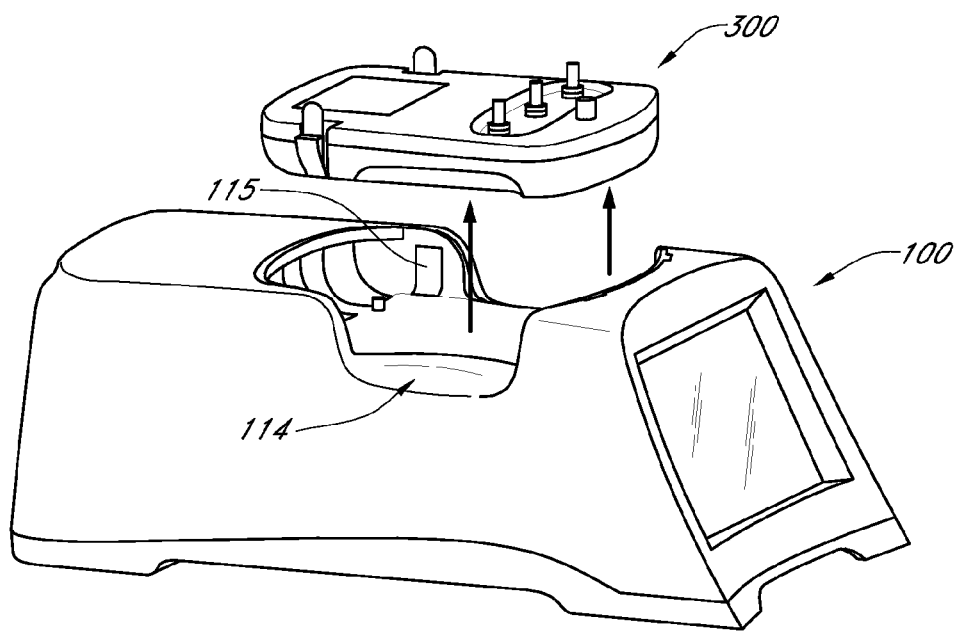

With continued reference to FIG. 4, the cassette 300 can include an outer housing 302 that encloses one or more of its internal components, such as, for example, reservoirs, syringes, tubing, manifolds and/or the like. As shown in FIG. 4, the cassette 300 can comprise one or more resilient tabs 304, clips, recesses and/or other features that are configured to engage corresponding members, recesses or features 115 on the fluid delivery module 100 (FIGS. 5A and 5B). For example, in some embodiments, as illustrated in FIG. 5A, the cassette 300 is secured to the fluid delivery module 100 by urging it within a corresponding recess 114 along the top of the module 100. Tabs 304 on either side of the cassette 300 can engage corresponding recesses 115 or other features of the fluid delivery module. As a result, in some embodiments, the cassette 300 is releasably locked to the fluid delivery module 100.

In one embodiment, in order to release the cassette 300 from the fluid delivery module 100, the tabs 304 are urged toward one another. Accordingly, the interlocking features between the cassette 300 and the module 100 can disengage, permitting the cassette 300 to be lifted or otherwise removed, as illustrated in FIG. 5B. When lockingly engaged to the fluid delivery module 100, the cassette 300 can be properly connected to the motors (e.g., stepper motors) and/or other devices or components that help control the internal components of the cassette (e.g., the plungers or other movable members) to selectively deliver one or more fluids and/or other substances from the vials (or other containers) to the handpiece assembly.

The cassette 300 can include one or more receiving sites 310 located along the top surface of the cassette 300. For example, the arrangement illustrated in FIG. 4 includes a total of three receiving sites 310. Alternatively, however, a cassette can include more or fewer receiving sites 310, as desired or required. In some embodiments, a nest (or loading device or area) is configured to removably or permanently attach to one or more of the receiving sites 310. As discussed in greater detail herein, such nests or loading devices (not shown in FIG. 4) are adapted to receive a standard or non-standard vial, ampoule, syringe and/or other container. The location, spacing and other details of the receiving sites 310 can be different than illustrated in FIG. 4.

Regardless of their exact design and configuration, the nests or loading devices are adapted to attach to the cassette 300 using a luer lock or other standard or non-standard connection (e.g., threaded, friction fit, flanged, clipped, etc.). As illustrated in FIG. 4, the cassette can include, at each receiving site 310, a female or male luer lock fitting 312 that is sized, shaped and otherwise configured to removably attach to a corresponding fitting of a nest or other loading device. Additional details regarding certain embodiments of nests or other devices adapted to secure to a cassette's receiving sites 310 are provided below.

Once the desired vials or other containers are secured to the cassette's nests or loading areas, the injection system can be configured to transfer the contents of such vials or other containers within the fluid delivery module 100 and subsequently deliver them to a targeted anatomical location in a precise and accurate manner. In some embodiments, the cassette 300 comprises one or more rigid and/or semi-rigid materials, such as, for example, plastic, metal, elastomer, ceramic, composite, any other natural or synthetic material and/or the like. The housing 302 of the cassette 300 can be manufactured in two or more pieces (e.g., upper and lower portions) that are subsequently secured to each other using screws or other fasteners, adhesives, welds and/or any other connection device or method. Alternatively, the cassette housing 302 can comprise a generally unitary structure.

Figure 6A:
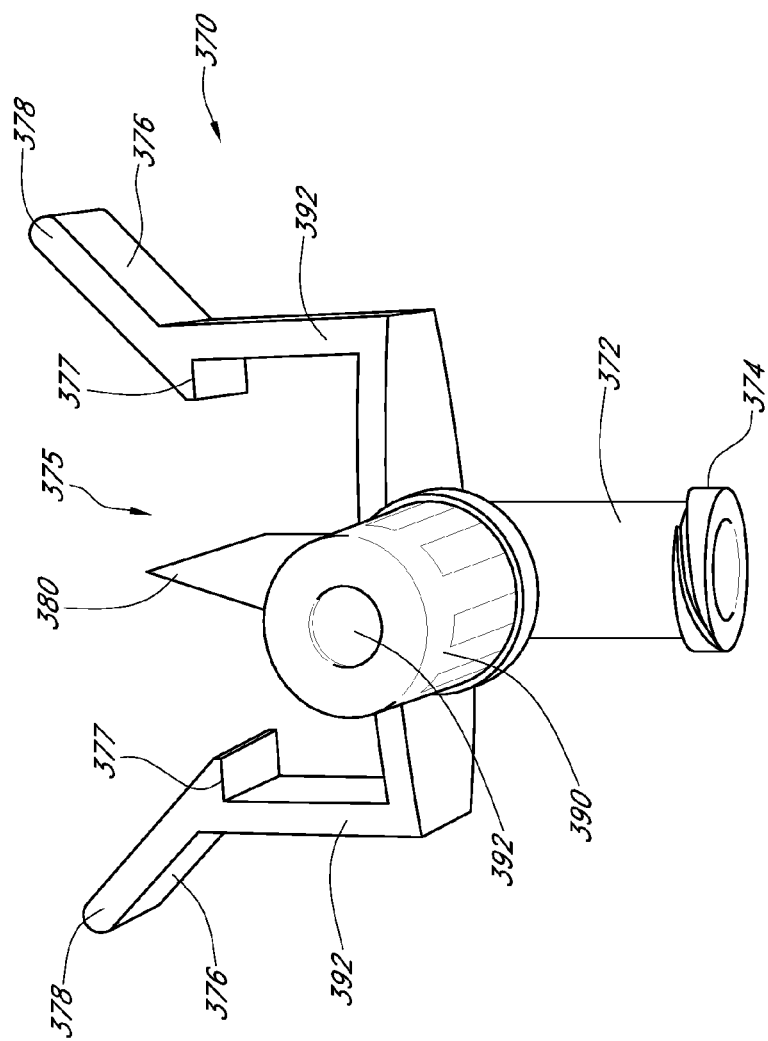
FIG. 6A illustrates a front perspective view of one embodiment of a nest or loading area configured to be secured to a cassette of a fluid delivery module.

According to some arrangements, each receiving site of a cassette 300 comprises a nest, loading area or other component, region or portion to which a vial, ampoule, syringe and/or other container may be secured. One embodiment of such a nest or loading area 370 is illustrated in FIG. 6A. The loading area 370 or nest can be a separate member that is permanently or removably joined to the housing or other portion of the cassette 300 using one or more attachment devices or methods (e.g., luer lock fitting, other standard or non-standard fittings or connections, etc.). Alternatively, as noted herein, the loading areas 370 or nests (or equivalents thereof) can form a unitary structure with the cassette 300 (e.g., the loading area or nest can be molded or manufactured as a single piece or unit with the housing or other portion of the cassette 300 or fluid delivery module). As used herein, the term loading area is a broad term and includes, without limitation, a nest, docketing port or station, an opening, a slot and/or any other component, area or portion configured to receive a vial or other container. Accordingly, the terms loading area, loading device, nest and the like are used interchangeably herein.

A nest or loading area or device 370 can be sized, shaped and otherwise adapted to securely receive the top portion (e.g., neck area) and/or any other feature or portion of various vials or other containers. Accordingly, a clinician or other user of the injection system can easily, quickly and conveniently position multi-dose vials (e.g., standard or non-standard vials as supplied to the clinician by a manufacturer or other supplier) onto the fluid delivery module (e.g., cassette). Such vials or other containers can vary in size, shape, closure member design and/or any other characteristic. Thus, the need to transfer liquids, other fluids and/or other substances from such vials to other reservoirs or containers of an injection system (e.g., to a separate reservoir, syringe, other container and/or the like, either within or outside of the injection system, etc.) can be advantageously reduced or eliminated. This can result in one or more benefits or other advantages. For example, potentially time-consuming efforts to transfer the medicaments, fluids and/or other substances from vials or other containers in which they are initially supplied to the injection system can be eliminated. Relatedly, the use of such nests or other loading areas can make the injection procedure safer, as the likelihood of contamination of the various fluids or other substances (e.g., with the outside environment, by the clinician, between the various medicament streams, etc.) can be reduced. In some embodiments, this is the case because, among other things, the need to manually transfer the contents of vials and other containers is eliminated or reduced. Further, the volume or other amount of wasted fluids and/or other materials that would otherwise remain as unused and discarded residual within the vials or other containers can be advantageously reduced or eliminated. This can provide one or more environmental, cost-saving and/or other benefits.

FIG. 6A illustrates one embodiment of a nest 370 or loading area, which is configured to be attached to a cassette and which is adapted to securely receive a vial or other container. As noted above, the nest 370 (or loading area) and the cassette 300 can be separate items that are attached to one another using one or more connection devices or methods. For example, in the depicted embodiment, the nest 370 comprises a bottom portion 372 (e.g., tube) that is configured to removably secure to the cassette 300. In some embodiments, as illustrated in FIG. 6A, the bottom portion or tube 372 comprises a luer lock or any other standard or non-standard connection or fitting 374 that is adapted to fit within a corresponding coupling or feature of the cassette 300. However, in other arrangements, other types of standard or non-standard fittings or connection devices, features or methods are used to help secure (e.g., either removably or permanently) the nest 370 or loading area to the cassette 300, such as, for example, threaded connections, press-fit connections, snap or clip connections and/or the like. Alternatively, as noted herein, the cassette 300 and the nest 370 can be integrally formed with one another.

With continued reference to FIG. 6A, the nest 370 or loading area can include an interior region 375 into which a vial or other container may be positioned. In the illustrated arrangement, the nest 370 comprises wings 376 that are positioned opposite of one another. In some embodiments, as illustrated in FIG. 6A, the nest 370 or loading area includes two wings 376 or other flexible members that are adapted to releasably secure a vial or other container to the nest. Each wing 376 can include a vertical portion 392 that helps to define the interior region 375 of the nest 370 or loading area. In other embodiments, the nest 370 includes more (e.g., three, four, five, six, more than six, etc.) or fewer than two wings 376 or other flexible members. Further, the shape, size, design and/or other characteristics of the wings 376 can be different than discussed and illustrated herein.

An upper portion of each wing 376 can include an inwardly-facing locking portion or member 377 that is configured to engage and maintain the neck or other closure portion of a vial or other container within the interior region of the nest 370 or loading area or device. In some arrangements, each locking portion 377 comprises one or more sloped portions. In addition, an upper region of each wing 376 can include a handle member 378 that can facilitate moving the wing 376 away from the interior region of the nest 370 or loading area (e.g., to place a vial or other container within the interior region 375 of the nest). According to some embodiments, the wings 376 or other flexible members are configured to maintain the position illustrated in FIG. 6A. Thus, after the wings 376 are pulled apart (e.g., to insert or remove a vial within the nest 370), the wings 376 resiliently return to their inward (e.g., static) position upon their release by the user.

According to some embodiments, as illustrated in FIG. 6A, the nest 370 or loading area comprises a ventilated spike 380. Thus, when a vial or other container is properly secured to the nest or loading area or device 370, the ventilated spike 380 can place the internal contents of the vial (e.g., anesthetic, steroid, other drug or medicament, other fluid, material or substance, etc.) in fluid communication with one or more subcomponents of the cassette 300 (e.g., manifold, syringe or other reservoir, etc.) and/or other components of the injection system. The ventilated spike 380 can be sized, shaped and otherwise configured to penetrate a septum or other membrane of a vial or other container secured to the cassette. A ventilation member 390 of the loading area 370 can selectively permit air to pass into the vial or other container when fluids or other substances are being transferred from the vial or other container to one or more other components of the cassette 300. The ventilation member can be incorporated into the ventilated spike design. In some embodiments, the ventilation member 390 comprises or is operatively connected to a filter to reduce the likelihood of contaminants from the surrounding environment (e.g., ambient air) entering the vial. The filter can include pores having a cross-sectional dimension of approximately 0.05 μm, 0.1 μm, 0.2 μm, 0.3 μm, 0.4 μm, 0.5 μm, less than 0.05 μm, greater than 0.5 μm and/or ranges between such values.

As noted above, the use of a nest 370 or other loading area or device with a ventilated spike can provide one or more advantages. For example, by eliminating needles (e.g., a main needle, a vent needle, etc.) or other sharps from the interior of the nest 370, the likelihood of puncture or other sharps-related injuries to a user of the injection system can be advantageously reduced or eliminated. Relatedly, this provides a safer environment for a physician, nurse or other clinician or user associated with the execution of an injection procedure. For example, such a configuration can make it easier for a clinician to load or remove one or more vials or other containers to or from the cassette in order to manually shake, agitate or otherwise mix the contents thereof (e.g., hyaluronic acid, steroid, cells, bone cement, beads, etc.). In some embodiments, a clinician or other user can manually remove and shake such vials or other containers one or more times (e.g., before loading the vial to the cassette, immediately prior to the transfer of fluids from the vial or other container to the fluid delivery module, at any other time), as desired or required. Thus, the contents of the vial or other container can be maintained in a mixed state and thereby reducing the likelihood of settling, stratification and/or any other undesirable occurrences. In other embodiments, the internal contents of a vial or other container can be automatically mixed (e.g., continuously or intermittently). Additional details regarding such embodiments are provided in U.S. patent application Ser. No. 12/340,595, filed Dec. 19, 2008 and published as U.S. Publication No. 2009/0163860, the entirely of which is hereby incorporated by reference herein.

In some embodiments, the nest or loading area 370 can be removed from the cassette 300, thereby allowing a syringe or another container to be secured directly to the cassette. This can be facilitated by the use of standard connections or fittings on the cassette 300, such as, for example, a universal luer lock connection 312 (FIG. 4), a threaded connection and/or the like. Thus, a syringe or other container having a similar connection can be directly secured to the cassette 300. Consequently, as with the internal contents of a vial or other container secured within a nest or loading area, the contents of a syringe or other container that is secured to the cassette (e.g., without the nest or loading area) can be subsequently transferred within one or more subcomponents of the cassette (e.g., reservoir, manifold, etc.) and other downstream components and portions of the injection system (e.g., handpiece assembly) for selective delivery into a joint or other target anatomical location.

With continued reference to FIG. 6A, in order to secure a vial or other container to the nest 370, a clinician or other user can align the closure member or other portion of the vial within the interior region 375 defined by the wings 376. In some embodiments, during this alignment and loading process, the closure member or other leading surface of the vial initially contacts the sloped or slanted surfaces 377 of the wings 376. As the vial is urged downwardly (e.g., into the interior region of the nest 370), the closure member of the vial or other container can slide against the sloped surfaces 377, thereby causing the wings 376 to separate outwardly (e.g., away from each other). The presence of the wings 376 can help center or properly align the vial or other container within the nest 370. If the vial is urged far enough into the interior area 375, the ends of the slanted surfaces can move above the closure member of the vial so that the wings 376 resiliently move inwardly (e.g., toward each other) within the neck of the vial. Thus, in some embodiments, once properly positioned within a nest 370, the vial or other container cannot be removed, at least temporarily, from the interior region of the nest 370, because the wings 376 engage the adjacent surfaces of the closure member or other portion of the vial. Consequently, the vial or other container can "snap" or "lock" into the nest 370 or loading area to removably secure it thereto.

In any of the embodiments disclosed herein, the nest 370 or other loading area or device can be adapted to receive vials or other containers of different shapes, sizes, designs, configurations and/or the like. According to some embodiments, the loading area 370 can accommodate containers (e.g., standard or non-standard vials, ampoules or other vessels having a capacity of 5 ml, 10 ml, 50 ml, 100 ml, smaller than 5 ml, larger than 100 ml, ranges between these ranges and/or the like) as provided, either directly or indirectly, to the clinician or other user by a pharmaceutical manufacturer or supplier. In other arrangements, the nest 370 or loading area is configured to receive vials or containers of various types and/or sizes. As discussed, once a vial or other container is positioned within the loading area 370, the ventilated spike 380 can penetrate a septum or other portion of the vial's closure member to access the interior of such vial or other container. Thus, the internal contents of the vial (e.g., medicaments, other fluids or materials, etc.) can be placed in fluid communication with other portions of the cassette and fluid delivery module (e.g., internal reservoirs, tubing, handpiece assembly, etc.).

In order to remove a vial or other container from the nest 370, the clinician or other user can pull the handles 378 outwardly so the wings 376 move far enough apart from one another to permit the closure member of the vial to be lifted out of the interior region 375. In some embodiments, the handles 378 are configured so that they may be selectively grasped and separated using a single hand. This can permit a user to conveniently separate the wings 376 of the loading area 370 with one hand while removing the vial or other container with the other. In other arrangements, one or more other ways of securing a vial to a nest 370 or loading area (and/or removing it therefrom) can be used.

As discussed herein, one or more of the cassette's nests or loading areas can be configured to continuously or intermittently mix the contents (e.g., steroids, other pharmaceuticals or medicaments, other fluids, solids or other mixtures, etc.) of a vial or other container secured thereto. Such mixing can be performed manually (e.g., by the user) or automatically (e.g., by one or more features or components of the fluid delivery module). In some arrangements, it is desirable to maintain the internal contents of a vial or other container at least partially mixed while such vial or other container is positioned on the cassette. For example, certain types of formulations (e.g., steroids) that include a relatively high solids concentration may need to be mixed to ensure that a generally consistent and homogeneous dose is drawn into the injection system and delivered to the patient during an injection procedure. It may be desirable for other types of fluids, materials and/or other mixtures to be continuously or intermittently mixed to mitigate or eliminate problems other than settling in relation to an injection or other treatment procedure. Thus, one or more devices or methods of agitating the internal contents of a vial or other container can be advantageously provided. As discussed above, in any of the embodiments disclosed herein, such vials or other containers can be easily removed from the cassette or other portion of the fluid delivery module, manually mixed (e.g., by shaking or otherwise moving the vial or other container) and re-securing it to the cassette.

In any of the arrangements disclosed herein, or variations thereof, the nests or loading areas and/or other components of the cassette comprise one or more plastic, metal and/or other rigid, semi-rigid and/or flexible materials. The materials can be selected to withstand the various elements and potentially damaging conditions to which they may become exposed, including, for example, forces, moments, temperature and pH variations, other physical or chemical factors and/or the like.

Figure 6B:
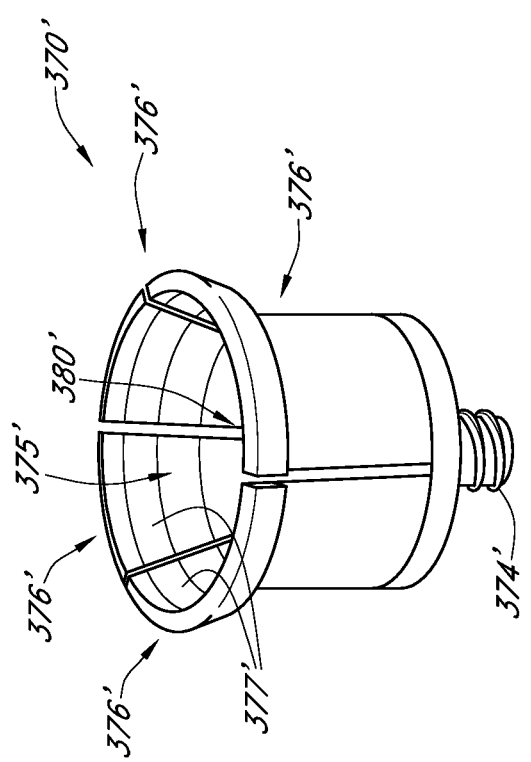
FIG. 6B illustrates a perspective view of another embodiment of a nest or loading area configured to be secured to a cassette of a fluid delivery module.

FIG. 6B illustrates another embodiment of a nest or loading device 370' configured to receive a vial, ampoule and/or another standard or non-standard container. As discussed herein with reference to the nest of FIG. 6A, the nest 370' can be configured to accommodate vials and/or other containers of different or varying sizes, shapes, designs and/or configurations, as desired or required. The nest 370' can include a plurality of resilient wings 376' that help define an interior area 375' into which a vial (not shown) or other container can be selectively inserted and secured. In some embodiments, the wings 376' define a generally cylindrical shape with relatively small spaces between adjacent wings. However, in other arrangements, the spaces between adjacent wings 376' can be larger or smaller than illustrated in FIG. 6B. Further, the overall shape formed by the wings 376' can be different than cylindrical.

With continued reference to FIG. 6B, the wings 376' can be configured to be resilient so that they move outwardly (e.g., away from the interior area 375') when a vial or other container is inserted therein. As with the nest described herein with reference to FIG. 6A, one or more of the wings 376' can comprise an inwardly-facing locking portion or member 377' that is adapted to engage and maintain the neck or other closure portion of a vial or other container within the interior region of the nest 370' or loading area or device. In some embodiments, the wings 376' are moved radially outwardly in order to disengage the vial or other container from the corresponding locking portion(s) or member(s) 377' and remove it from the nest 370' or other loading area or device.

In some embodiments, when a vial or other container is properly secured to the nest or loading area or device 370', a ventilated spike 380' contained therein can place the internal contents of the vial (e.g., anesthetic, steroid, other drug or medicament, other fluid, other material or substance, etc.) in fluid communication with one or more subcomponents of the cassette 300 (e.g., manifold, syringe or other reservoir, etc.) and/or other components of the injection system. As discussed above with reference to the nest of FIG. 6A, the ventilated spike 380' can be sized, shaped and otherwise configured to penetrate a septum or other membrane of a vial or other container secured to the cassette. Further, one or more ventilation members (not shown in FIG. 6B) of the loading area 370' can selectively permit air to pass into the vial or other container when fluids or other substances are being transferred from the vial or other container to one or more other components of the cassette 300. In some embodiments, the ventilation member comprises or is operatively connected to a filter to reduce the likelihood that one or more contaminants will enter the vial or other container from the surrounding environment (e.g., ambient air).

Figure 7:
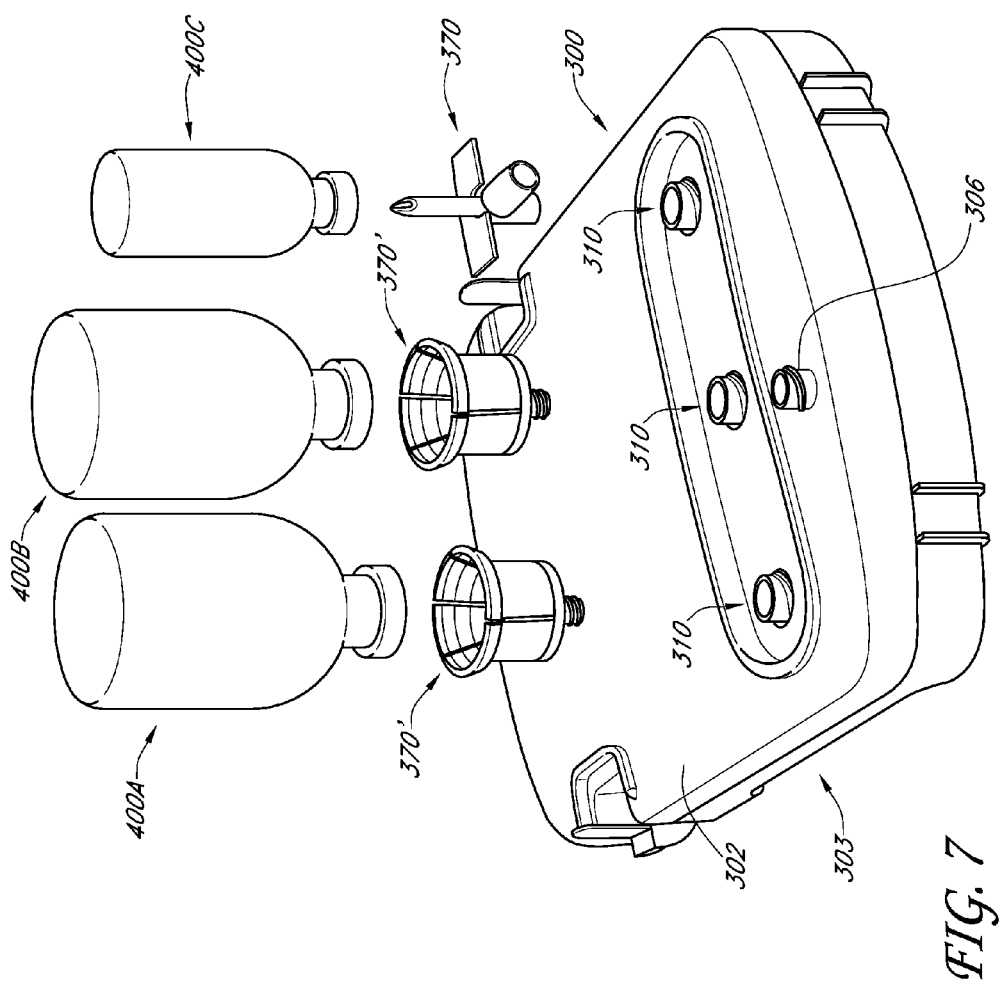
FIG. 7 illustrates an exploded perspective view of a cassette and corresponding nests or loading areas and vials or other containers configured to be positioned thereon, in accordance with one embodiment.

FIG. 7 illustrates an exploded view of one embodiment of a cassette 300 configured to be positioned within a fluid delivery module of an injection system. As discussed and illustrated in greater detail herein, the cassette 300 can comprise an outer housing 302 that is configured to enclose one or more internal components (e.g., manifolds, syringes or other reservoirs, etc.). The depicted cassette 300 has a generally rectangular shape with contoured, smooth edges or corners. The cassette 300 can be removably secured to the fluid delivery module, as illustrated, for example, in FIGS. 5A and 5B. Alternatively, the cassette 300 can form a generally unitary structure with the fluid delivery module. Further, in some embodiments, the cassette 300 and/or any of its components or portions comprise one or more plastic, other polymeric, metal and/or other synthetic or natural materials, or combinations thereof. However, the shape, size, materials of construction and/or other characteristics of the cassette 300 can vary, as desired or required for a particular application or use. In addition, the cassette 300 can comprise one or more finger wells 303, grooves, recessed areas and/or other features that facilitate placement of the cassette 300 into and/or out of the corresponding area of a fluid delivery module. Such finger wells 303 can be located on one or both sides of the cassette 300.

As discussed in greater detail herein, the cassette 300 can be a disposable item that is replaced periodically (e.g., once, twice or more often per day). In other embodiments, the cassette 300 is configured to be replaced more or less often than indicated herein, as desired or required. Alternatively, the cassette 300 can be removed and replaced when one or more medications or other fluids or substances being delivered using the injection system are modified or otherwise changed (e.g., formulation or type, strength, etc.). This can help prevent cross-contamination between different types of substances, different dosages of substances and/or the like. According to some arrangements, the cassette 300 is replaced along with one or more other components of the injection system, such as, for example, the handpiece assembly and the corresponding delivery line (e.g., tubing) that places the handpiece assembly in fluid communication with the cassette 300 and/or the like. In other embodiments, the cassette is replaced less or more often that the handpiece assembly and/or any other component of the injection system.

In the embodiment depicted in FIG. 7, up to three vials 400A-400C or other containers may be secured to receiving sites 310 located along the top surface of the cassette 300. In some embodiments, each receiving site comprises a nest or loading device that is adapted to accept a standard or non-standard vial or other container 400A-400C. As illustrated in FIG. 7, the nests 370, 370' can be identical or similar to the embodiments of FIG. 6A and/or FIG. 6B. However, any other nest design can be used (e.g., to accommodate a particular vial, ampoule and/or other anticipated container). Additional embodiments and details of nest designs or loading area are provided in U.S. patent application Ser. No. 12/340,595, filed Dec. 19, 2008 and published as U.S. Publication No. 2009/0163860, the entirely of which is hereby incorporated by reference herein. In addition, the cassette 300 can include more or fewer receiving sites 310, as desired or required. In addition, the location, spacing and other details of the receiving sites 310 (and thus, the corresponding nests or other loading devices) can be different than illustrated in FIG. 7. As discussed in greater detail herein, once the vials 400A-400C or other containers are secured to the cassette 300, the injection system can be configured to transfer the contents of such vials or other containers within the fluid delivery module 100 and accurately deliver the interior contents of one or more of such vials 400A-400C to a targeted anatomical location in a precise and accurate manner.

In the illustrated embodiment, larger vials 400A, 400B (e.g., 50 ml capacity) are secured to two receiving sites of the cassette, while a smaller vial 400C (e.g., 5 ml capacity) is secured to one receiving site. The type of nest or other loading device used at each receiving site 310 can be selected according to the vial or other container that will be attached thereto. In some embodiments, one or more vials or other containers can be secured to a nest or loading area of the cassette 300 that is configured to keep the internal contents of such vial mixed. Thus, as discussed in greater detail herein, such mixing may be desired or required for certain medicaments or other materials, such as, for example, steroids or other solutions or mixtures that have a tendency to settle or that require mixing. In certain arrangements, the receiving sites of the cassette are configured to receive a variety of different vials or other containers (e.g., varying in size, shape, design, closure member and/or the like).

Figure 8:
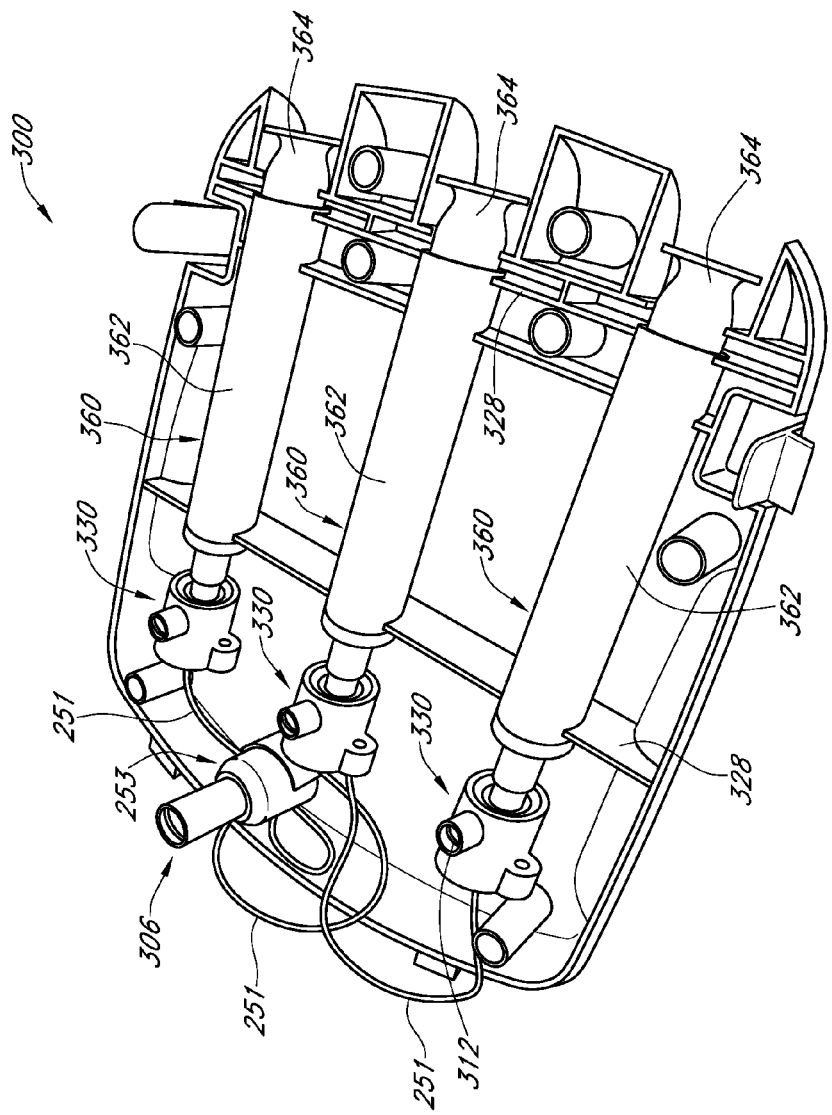
FIG. 8 illustrates one embodiment of a cassette (with a portion of its housing removed to show the internal components) configured for placement within a fluid delivery module.
Figure 9C:
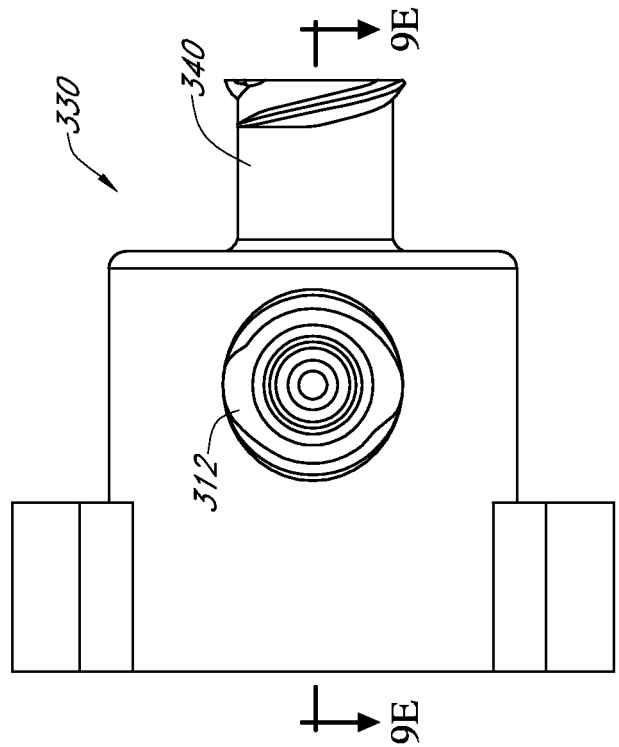
Figure 9B:
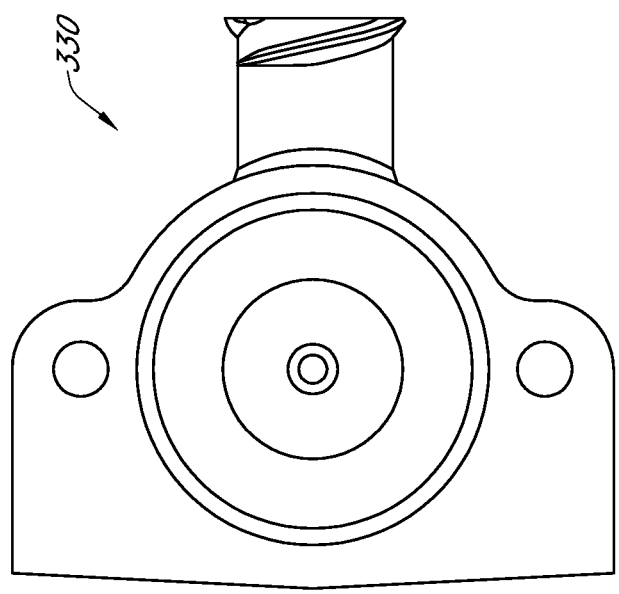
Figure 9E:
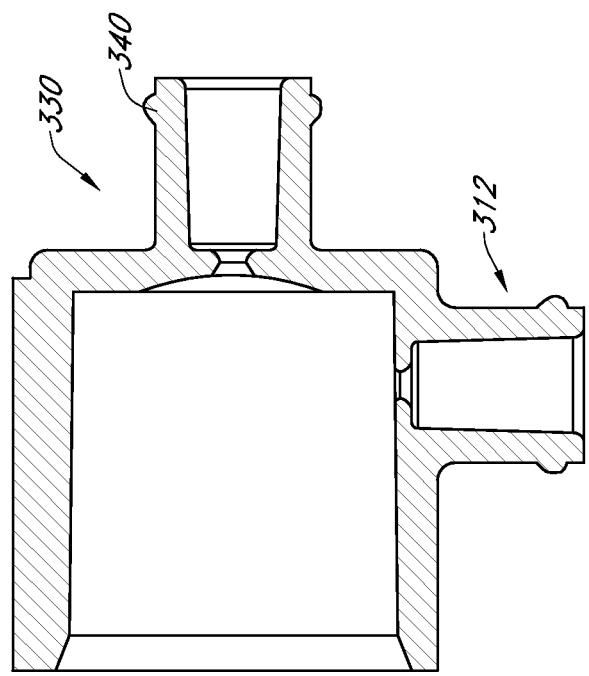
Figure 9D:
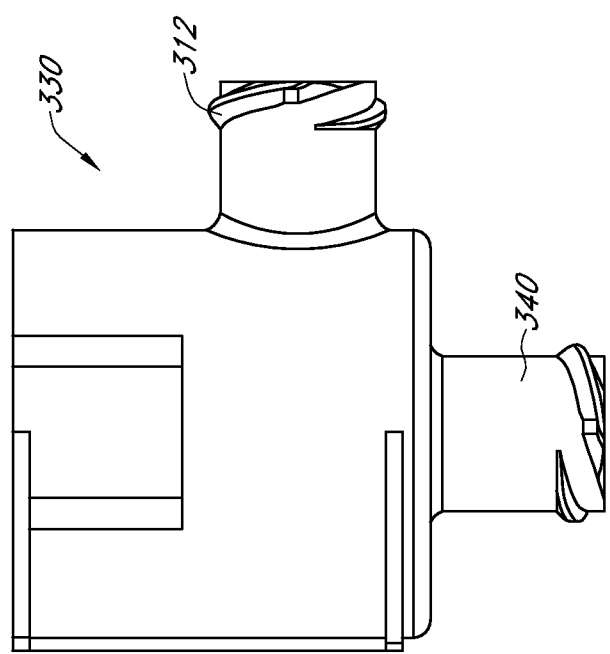

In the embodiment illustrated in FIG. 8, the top portion of a cassette housing has been removed to reveal the interior of the cassette 300. As shown, the cassette 300 can comprise one manifold 330 and one syringe 360 for each receiving station 310 (FIGS. 4 and 7). In the illustrated embodiment, the interior of the cassette 300 includes grooves and other recesses into which the various components of the cassette 300 can be positioned. For example, one or more interior surfaces (e.g., bottom, top, etc) of the cassette 300 can comprise recesses and/or other features that are sized, shaped and otherwise configured to receive the manifolds 330. In addition, the cassette 300 can include one or more other positioning baffles 328 or other members that are configured to support and securely maintain the position of the syringes 360, other reservoirs and/or any other component of the cassette 300. In the depicted arrangement, the positioning baffles 328 include slots that are sized, sized and otherwise adapted to receive one or more portions of the syringes 360. However, the manifolds 330, syringes 360 and/or any other component or feature can be secured to the cassette 300 using one or more other attachment methods or devices (e.g., adhesives, fasteners, etc.), either in addition to or in lieu of the recesses, positioning baffles 328 and other features illustrated in FIG. 8.

With continued reference to FIG. 8, each syringe 360 or other reservoir positioned within the cassette 300 can include an inner plunger 364 that is slidably movable within an outer barrel 362. In some embodiments, the syringes 360 are standard plastic, sterile syringes. Alternatively, the syringes 360 can be non-standard syringes that are specifically designed for use with a cassette 300. In some embodiments, as illustrated in FIGS. 15A-17B, the reservoirs, plungers and/or other internal components of the cassette can include one or more unitary structures or components. In addition, the syringes 360 can comprise one or more other materials (e.g., glass), as desired or required. As discussed and illustrated in greater detail herein, movement of the inner plunger 364 away from the outer barrel 362 (e.g., in a direction generally away from the manifold 330), can cause fluids and/or other materials from the respective vial 400A-400C (FIG. 7) to be drawn into the interior of the syringe 360 or other reservoir. Once one or more fluids and/or other materials have been loaded into the syringe 360 or other reservoir, a stepper motor, a pump, another mechanically-driven (e.g., mechanical motor), pneumatically-driven device and/or the like can be used to selectively move the inner plunger 364 toward the manifold 330, thereby delivering a desired volume of such fluids and/or other materials to the handpiece assembly of the injection system. As discussed in greater detail herein, a stepper motor or other mechanical device can be used to initially move the inner plunger 364 away from the manifold 330 in order to transfer fluids and/or other materials from a vial into the corresponding syringe 360 or other reservoir.

According to some arrangements, in part for patient safety, the motor, pump or other fluid transfer device incorporated into the fluid delivery module is configured to accurately measure and regulate the flowrate and/or pressure of a medication, fluid and/or other material being delivered to a patient. Thus, the system can comprise pressure and/or flow measurement devices (e.g., pressure transducers, flowmeters, etc.). Pressure sensing devices can be used to ensure that the pressure or vacuum created by the discharge of the medication, fluid or other material within the anatomy does not exceed a particular threshold level. This can help prevent or reduce the likelihood of harm or other damage occurring to the patient being treated using the injection system. In some embodiments, such an internal force measurement system is configured to automatically shut off the pump or other transfer device when the discharge pressure exceeds a maximum level (e.g., 3 psi, levels lower or higher than 3 psi, etc.). In other arrangements, the fluid delivery module and/or any other portion of the injection system (e.g., handpiece assembly) includes a visual and/or audible alarm or other feature to alert the user than a threshold pressure has been attained, either in lieu of or in addition to any automatic shut-off mechanism. Such safety features can be incorporated in any of the embodiments of the modules or systems disclosed herein.

With continued reference to the embodiment illustrated in FIG. 8, the cassette 300 includes a plurality of slots or other openings adjacent to the syringe plunger 364 (e.g., generally along the lower end of the cassette). Thus, an arm, lever or other actuation device mechanically or otherwise connected to a mechanical (or other type of) motor or other movement device can be used to slidably move the inner plunger 364 relative to the outer barrel 362 of the syringe 360 or other reservoir to selectively transfer fluids and/or other materials into or out of the syringes 360. As medicaments, other fluids and/or other materials are selectively expelled through a syringe 360, they are directed through an interior portion of the downstream manifold 330 to an outlet 390. In some embodiments, the outlet 390 places the syringe 360 and manifold 330 in fluid communication with a corresponding outlet conduit 251. As shown in FIG. 8, the conduits 251 at the downstream end of each manifold 330 can be connected to a downstream hub or junction 253 configured to combine the flow streams from one or more of the individual conduits 251. In some embodiments, one or more one-way valves (e.g., duckbill or other check valve) can be positioned immediately upstream of the hub 253 to reduce the likelihood of cross-contamination of various medicaments, other fluids and/or other substances (e.g., through retrograde flow) included in the various vials or other containers loaded onto the cassette.

With continued reference to FIG. 8, the hub or junction 253 can include a luer fitting 306 or any other standard or non-standard connection. In some embodiments, as illustrated in FIGS. 4 and 7, such a fitting 306 or other connection can extend through a corresponding opening of the cassette housing 302. A corresponding connector can be secured to the luer lock fitting 306 or other coupling in order to place a handpiece assembly and/or any other component of the injection system in fluid communication with the cassette 300. For example, as illustrated herein, a handpiece assembly 200, which includes corresponding tubing (e.g., single lumen, multi-lumen, etc.) and a luer fitting (or other type of standard or non-standard connection) at the proximal end thereof, can be sized, shaped and otherwise configured to removably connect to the fitting 306 of the cassette 300. In some embodiments, such a handpiece assembly 200 is disposable so that it can be replaced after use. Thus, one or more of the medicaments, other fluids and/or any other materials provided in the vials or other containers loaded onto the cassette 300 can be selectively delivered to or near a target joint (e.g., toe, ankle, knee, other joints, etc.) and/or other anatomical location (e.g., organ, cavity, etc.).

FIGS. 9A-9E illustrate various views of a manifold 330 configured to be positioned within a cassette 300 of an injection system. As shown, the manifold 300 can include one or more standard or non-standard inlet and outlet fittings 312, 390 or other connections, such as, for example, universal luer lock fittings, threaded connections and/or the like. As discussed in greater detail herein, the use of such fittings, couplings or other connections can facilitate the connection of the manifolds to the other hydraulic components of the cassette and injection system (e.g., syringes, other reservoirs, nests or loading areas, etc.). As shown, the manifold 330 can include an inlet 340 into which the distal end of a syringe or other reservoir attaches. In some embodiments, the receiving site 312, the inlet 340 (and/or the outlet) and/or any other port or connection of the manifold 330 is adapted to receive a standard or non-standard fitting or corresponding mating portion (e.g., a luer lock, a threaded connection, another type of coupling 390, etc.). As discussed herein, an outlet coupling 390 can be used to place the manifold 330 in fluid communication with a downstream discharge conduit 251. In some embodiments, a ventilated spike 380 (FIGS. 6A and 6B), needle and/or another type of conduit is used to place one or more of the internal fluid passages of the manifold 330 in fluid communication with a vial or other container removably secured to a cassette. Such ventilated spikes, needles or other connectors can be included in a nest or other loading device that attaches to the manifold 330 (e.g., to the receiving site 312). Alternatively, the spike, needle or other conduit can directly attach to a loading area or any other component or portion of the cassette 300 or fluid delivery module.

Figure 10:
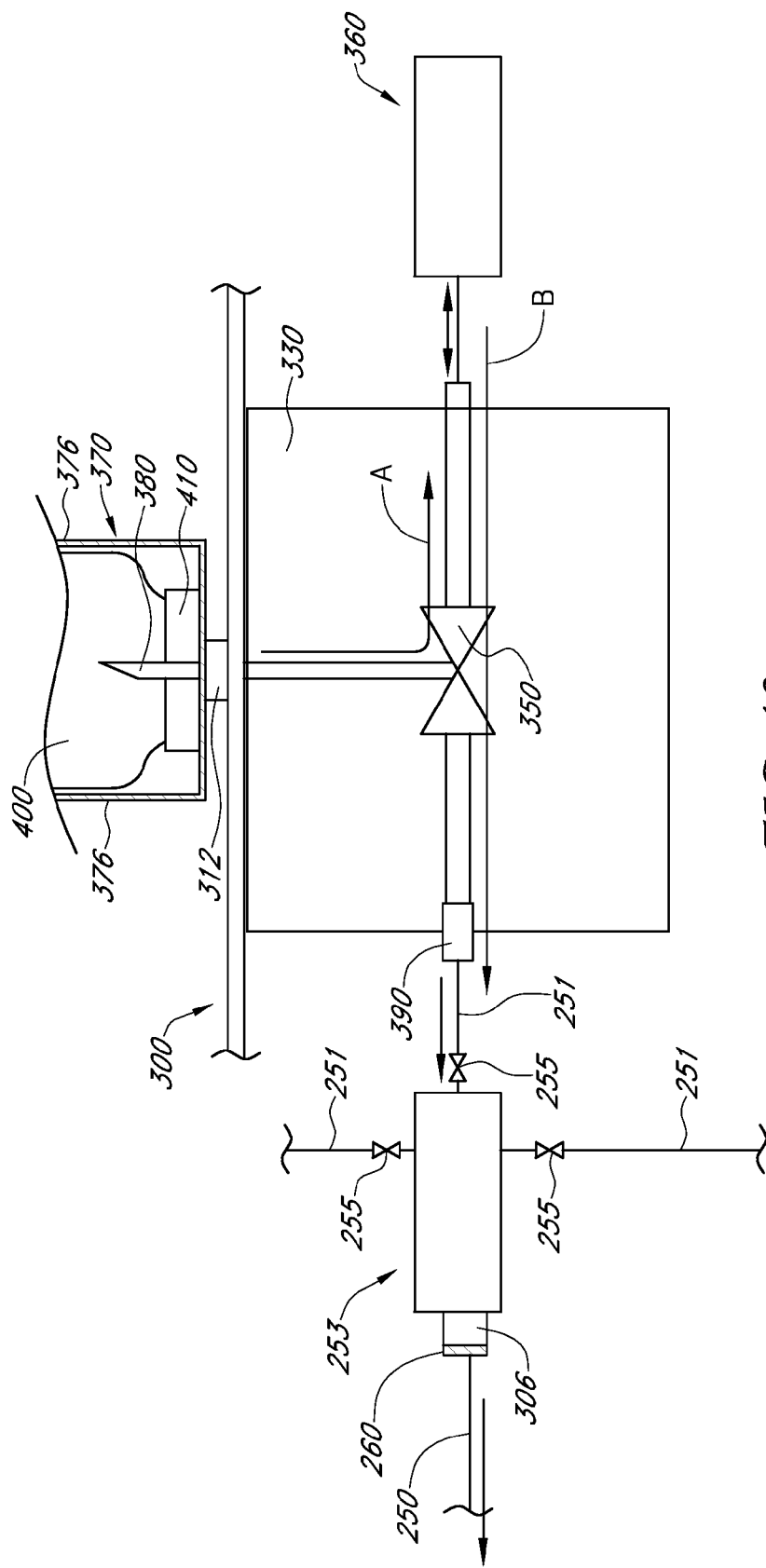
FIG. 10 schematically illustrates a cross-sectional view of the interior of a manifold according to embodiment.

FIG. 10 illustrates one embodiment of a schematic generally representing the movement of fluids and/or other materials within and between various components (e.g., separate, unitary, etc.) of an injection system, such as, for example, a vial 400, a manifold 330, a syringe 360 or other reservoir, other components or portions of a cassette 300 and/or the like. As shown, once a vial 400 has been properly secured to a nest 370, other loading area or other device of a cassette 300 (e.g., between opposing wings 376), a ventilated spike 380 or other portion of the nest 370 can be configured to extend into the interior of the vial 400. In some embodiments, the closure member 410 of the vial 400 comprises a septum or other pierceable membrane or member (not shown) through which the spike 380 may pass. As a result, the medicament, other fluid and/or other material contained within the vial 400 can be advantageously placed in fluid communication with the ventilated spike 380 of the nest 370. As discussed in greater detail herein, the nest 370 can be attached to a receiving site of the cassette 300 using a luer lock connector or other standard or non-standard fitting 312.

Next, in order to load the syringe 360 with the internal contents of the vial 400, the inner plunger of the syringe 360 can be retracted relative to the outer barrel of the syringe or other reservoir 360. As discussed in greater detail herein, a mechanical motor, other type of motor, actuator or other device within the fluid delivery module can be used to selectively move the inner plunger relative to the outer barrel. Thus, in some embodiments, the fluids and/or other materials contained within a vial or other container are transferred through the injection system mechanically (e.g., not pneumatically). In some embodiments, this provides a more accurate and controlled delivery of fluids and/or other materials. In addition, mechanically-driven injections can allow a clinician to overcome the relatively high back pressures associated with injecting fluids and/or other materials into small joints (e.g., toes, fingers, etc.).

The suction created within the syringe 360 or other reservoir of the cassette can cause the fluid and/or other materials contained within the vial 400 to be drawn into the syringe 360 in the direction generally represented by arrow A in FIG. 10. Thus, fluids and/or other materials can be delivered from the vial 400 to the syringe 360 through a valve 350 or other flow-control device. In some embodiments, the valve 350 comprises a combination duckbill-umbrella valve that is configured to permit flow in the direction generally represented by arrow A when suction is created within the syringe or other reservoir 360. This can help ensure that fluids and/or other materials are not inadvertently transferred toward the discharge conduit 251, the collection hub or junction 253 or any other component of the injection system located downstream of the manifold 330. Alternatively, one or more other types of valves and/or flow schemes can be used.

With continued reference to the schematic of FIG. 10, once fluids and/or other materials have been transferred from the vial 400 to the syringe 360 or other reservoir within the cassette, the fluid delivery module can selectively transfer a desired volume of fluids and/or other materials through the injection system to the downstream handpiece assembly. In one embodiment, the syringe 360 or other reservoir is configured to draw out the entire contents of a vial 400 during the initial loading stage. Alternatively, only a portion of the internal contents of the vial 400 or other container are transferred to the syringe 360 or other reservoir before such contents are selectively delivered to the handpiece assembly 200 and/or other downstream components of the injection system.

Once a syringe 360 or other reservoir has been properly loaded with fluids and/or other materials, a desired volume of such fluids and/or other materials can be selectively transferred through the manifold 330. The transfer of fluids and/or materials from the syringe 360 or other reservoir to downstream components of the injection system (e.g., discharge conduit 251, hub 253, handpiece assembly, etc.) can be accomplished with the help of a mechanical motor (e.g., stepper motor), hydraulic pump and/or other device. For example, a stepper motor or other mechanically-driven actuator can be configured to operate the syringe 360 or other reservoir of the cassette (e.g., move the inner plunger relative to the outer barrel) in order to selectively transfer fluids and/or other materials from the syringe 360 or other reservoir to the manifold 330. In the depicted embodiment, fluids and/or other materials are transferred from the syringe or other reservoir toward the discharge line or conduit 251 in a direction generally represented by arrow B. Thus, fluids and/or other materials can be routed through the same valve 350 that is used to control the transfer of fluids and/or other materials from the vial 400 (or other container) to the syringe 360 or other reservoir. For example, the valve 350 or other flow control device can be configured to allow fluid flow in a direction generally represented by arrow B when a sufficiently high positive pressure is created within the syringe 360 or other reservoir. This can be accomplished by using a valve 350 (e.g., a combination duckbill-umbrella valve, other direction valve, etc.) that regulates flow of fluids and/or other materials in certain desired directions depending on the type of forces and pressures exerted within the syringe 360 or other reservoir (e.g., negative or suction, positive, etc.). Additional details regarding flow through such a combination duckbill-umbrella valve 350 are provided herein in reference to the discussion of FIGS. 11A-11C.

In other embodiments, the quantity, type, orientation, general configuration and other details of the passages, valves and/or other components of the manifold 330 and/or other components of a cassette 300 can vary, as desired or required. Further, the general manner in which the syringes or other reservoirs 360 of a cassette are filled (e.g., with the internal contents of the vials or other containers) can be different than discussed and illustrated herein. For example, in some embodiments, the contents of the vials 400, ampoules or other containers can be configured to gravity flow into desired portion (e.g., syringe 360, other reservoir, etc.) of the cassette 300. In other arrangements, the vials 400 or other containers can be directly secured within an interior of the cassette 300 or other portion of the fluid delivery module. Moreover, a cassette 300 need not include a syringe 360 or other reservoir, a manifold 330 and/or any other component or feature illustrated and discussed herein. Other methods or devices can be utilized to load a fluid and/or other substance into the cassette 300 for later delivery to a downstream handpiece assembly 200 or other component of an injection system.

With continued reference to the schematic of FIG. 10, a fluid or other material exiting an outlet fitting 390 (e.g., luer lock, threaded, flanged and/or any other coupling or connector, etc.) of the manifold 330 can be routed to a discharge conduit or line 251. Discharge conduits 251 from two or more manifolds 330 of a cassette 300 can connect to a common hub or other junction 253. A one-way valve 255 (e.g., a duckbill valve, a check valve, etc.) can be located immediately upstream of the hub 253 to prevent cross-contamination of fluids and/or other materials flowing within the various discharge lines 251. As shown, the hub or junction 253 can include a luer connection 306 or other fitting or coupling. In some embodiments, the luer lock 306 or other fitting is configured to removably attach to a corresponding coupling 260 of a fluid delivery line 250 that places the cassette 300 and other portion of the fluid delivery module in fluid communication with a handpiece assembly. With reference back to FIGS. 4, 7 and 8, the luer or other coupling 306 can extend through an opening of the cassette housing 302 (e.g., along the top, side or any other surface). Thus, a user can easily attach and detach a handpiece assembly to a fluid delivery module of the injection system.

Figure 11A:
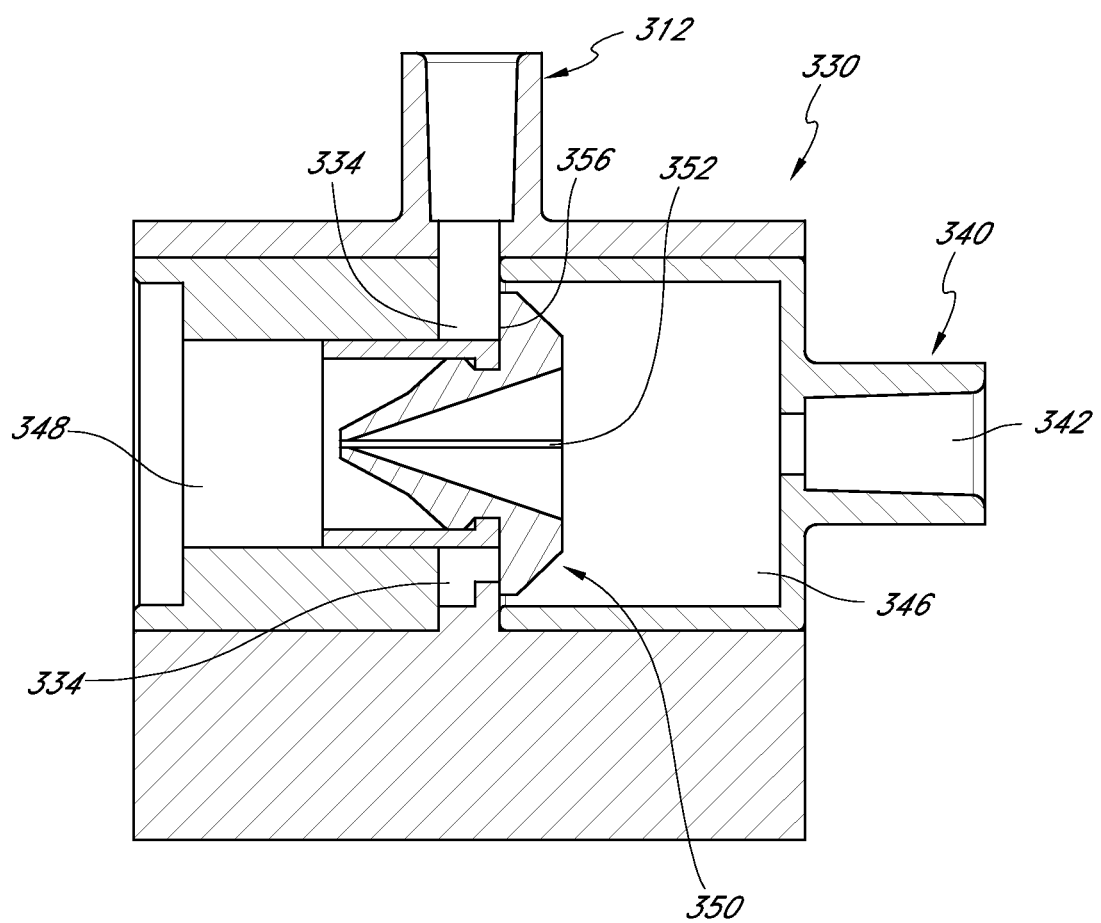
FIG. 11A illustrates a schematic cross-sectional view of the interior of a manifold according to another embodiment.

The schematic cross-sectional view of FIG. 11A illustrates the internal configuration of a manifold 330 according to one embodiment. As discussed, a ventilated spike of a nest (not shown) can be used to place the manifold 330 in fluid communication with a vial or other container (not shown) loaded onto a cassette or other portion of a fluid delivery module. In FIG. 11A, such a ventilated spike (not shown), needle or other conduit directly or indirectly attaches to the luer fitting 312 or other connection site of the manifold 330. Thus, the spike, needle or other conduit can be placed in fluid communication with one or more voids 334 located within an interior of the manifold 330. In some arrangements, the void 334 comprises an annular area that completely or partially surrounds a valve 350 (e.g., combination duckbill-umbrella valve). However, the type, shape, size and/or other details of the void 334, valve 350, general fluid scheme and other components or features of the manifold can be different than illustrated and discussed herein, as desired or required.

With continued reference to FIG. 11A, the manifold 330 can be configured so that the void 334 is selectively placed in fluid communication with an upstream cavity 346 to permit fluids and/or other materials to be advantageously transferred through the ventilated spike or other portion of the nest (not shown) to the inlet 340 of the manifold 330. As discussed, such a step can be performed in order to fill the syringe 360 or other reservoir of the cassette that is positioned upstream of the inlet 340. Such a syringe 360 or other reservoir can be a separate item from the manifold or can form a generally unitary structure with it. Regardless of the exact interior design of the cassette, some or all of the contents of a vial or other container with which the main needle 332 is in fluid communication (e.g., medication, formulation, other fluids or substances, etc.) can be delivered to the syringe, other reservoir and/or any other portion of the fluid delivery module.

Figure 11B:
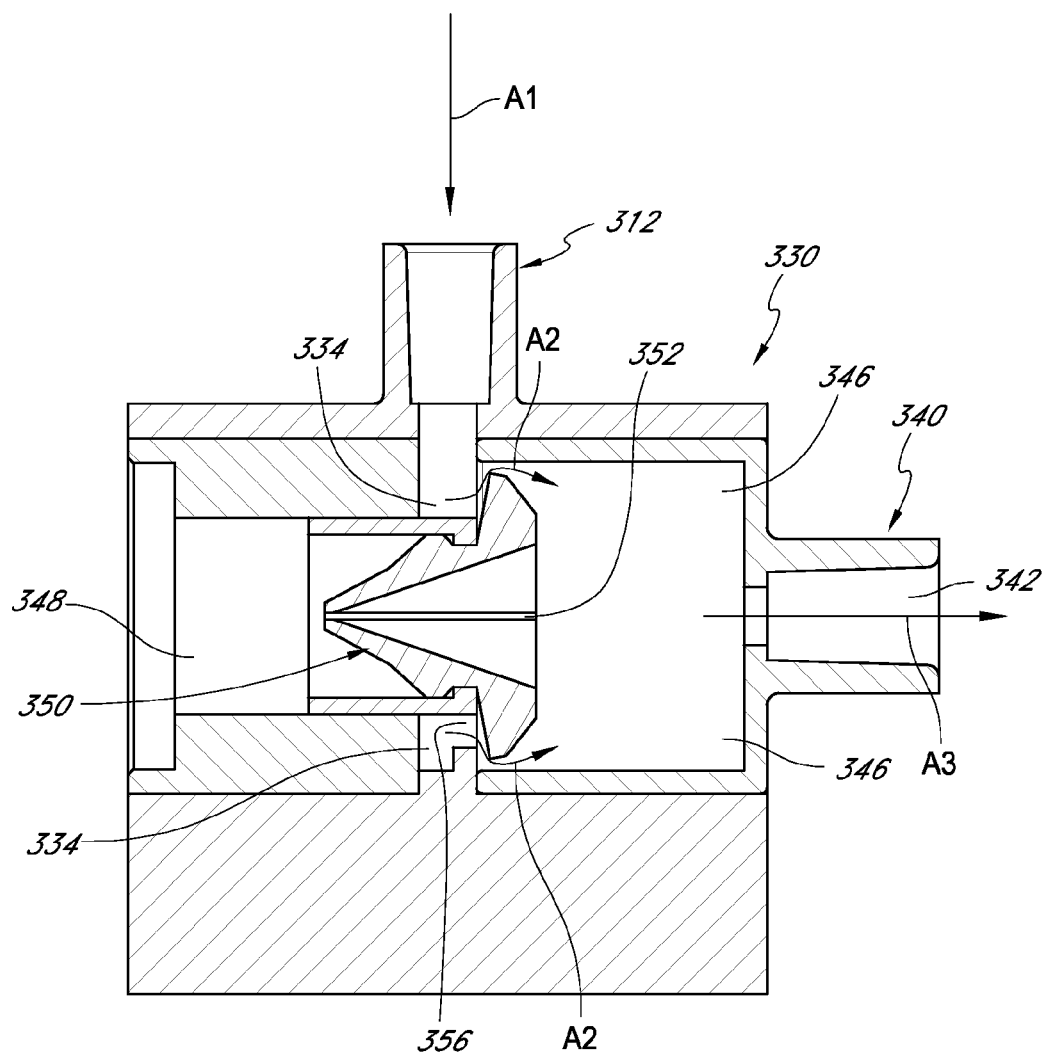
FIG. 11B illustrates a schematic cross-sectional view of the manifold of FIG. 11A when fluids and/or other materials are being transferred from a vial to the syringe or other reservoir according to one embodiment.

FIG. 11B schematically illustrates the manifold of FIG. 11A while fluids and/or other materials are being transferred through the receiving site 312 (e.g., from a ventilated spike or other portion of the nest or loading area attached to the receiving site) to the inlet 340 of the manifold 330. In some embodiments, a suction force can be applied to the upstream cavity 346 of the manifold (e.g., by moving the inner plunger away from the outer barrel of a syringe). Thus, if the tip of the syringe or other reservoir is attached to, inserted into or otherwise placed in fluid communication with the inlet 340 of the manifold 330, a corresponding suction force can be created within the upstream cavity 346.

As shown in FIG. 11B, if the vacuum force is sufficiently high, the umbrella portion 356 of the combination valve 350 can move away from the void 334, thereby allowing fluids and/or other materials to be delivered from the main needle 332 to the upstream cavity 346 in a direction generally represented by arrows $A_1$ and $A_2$ in FIG. 11B. From the upstream cavity 346, the fluids and/or other contents of a vial or other container can be routed to a syringe or other reservoir (not shown) attached to, constructed together with or placed in fluid communication with the inlet 340 of the manifold 330. For example, in the depicted embodiment, fluids and/or other materials can be delivered into a syringe or other reservoir that is positioned within the inlet nozzle 342 in a direction generally represented by arrow $A_3$. Once the suction force is terminated or sufficiently reduced (e.g., by stopping the movement of the inner plunger relative to the outer barrel of the syringe or other reservoir), the umbrella portion 356 of the valve 350 can seat against the void 334, thereby preventing the flow of materials from the ventilated spike, needle or other conduit of the nest (not shown), through the luer or other fitting of the receiving site 312 and to the upstream cavity 346.

Figure 11C:
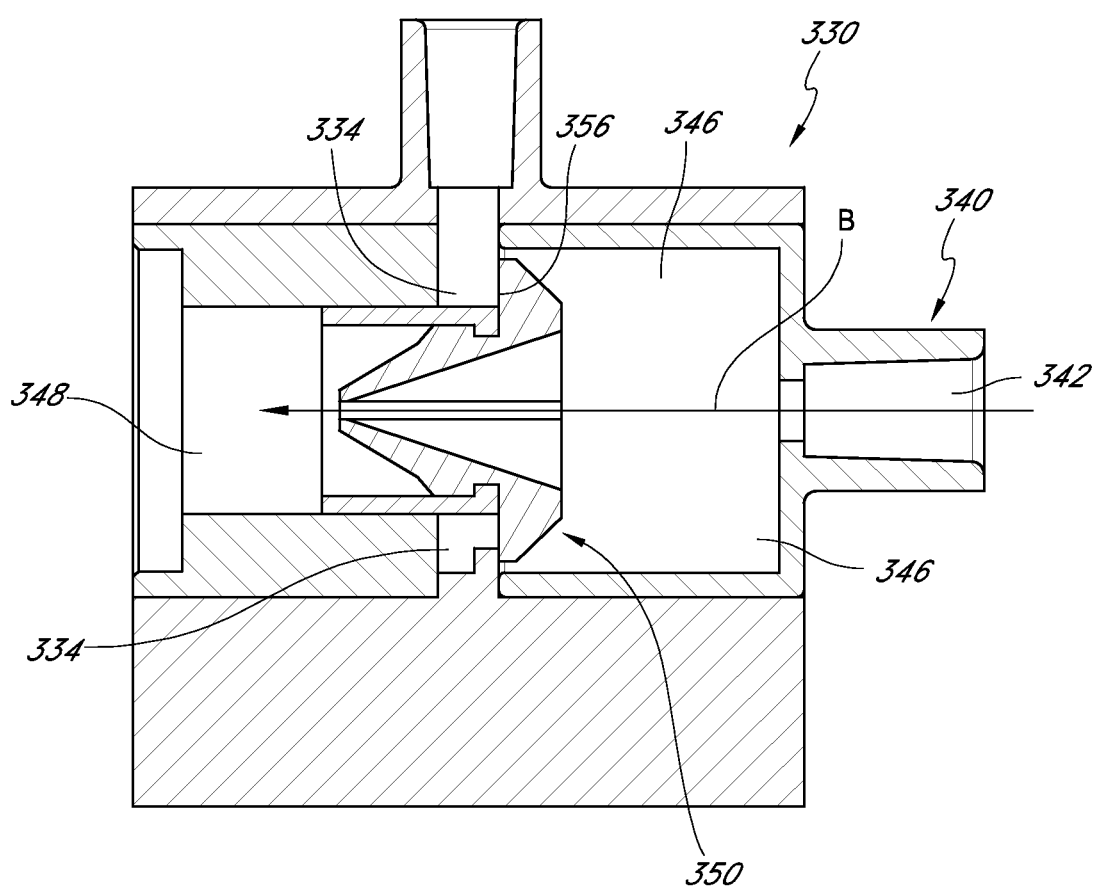
FIG. 11C illustrates a schematic cross-sectional view of the manifold of FIG. 11A when fluids and/or other materials are being transferred from the syringe or other reservoir to the outlet of the manifold according to one embodiment.

FIG. 11C schematically illustrates the manifold 330 of FIG. 11A as fluids and/or other materials are being delivered through the combination duckbill-umbrella valve 350 to the downstream cavity 348. As shown, if sufficient positive backpressure is applied to the upstream cavity 348, fluids and/or other materials may be transferred through the duckbill portion 352 of the combination valve 350 in a direction generally represented by arrow B. As discussed, in some embodiments, the necessary backpressure may be generated by moving the inner plunger within the outer barrel of the syringe or other reservoir positioned along the inlet 340 of the manifold 330 in order to expel the fluids and/or other materials contained within the syringe or other reservoir. As a result, such fluids and/or other materials can pass through the duckbill portion 352 of the valve 350 to the downstream cavity 348. At the same time, the positive backpressure within the upstream cavity 348 can cause the umbrella portion 356 of the valve to seat against the void 334, thereby ensuring that no fluids and/or other materials enter the void 334, toward the receiving site 312, the ventilated spike or other portion of the nest (not shown) and/or any other components. Consequently, as discussed herein with reference to, inter alia, FIGS. 8 and 10, a desired volume of fluids and/or other materials exiting the manifold 330 can be delivered to a discharge conduit 251 and a collection hub or junction 253. According to some embodiments, from the collection hub 253, one or more fluid and/or other material streams can be directed through a downstream fluid conduit and handpiece assembly.

Figure 12A:
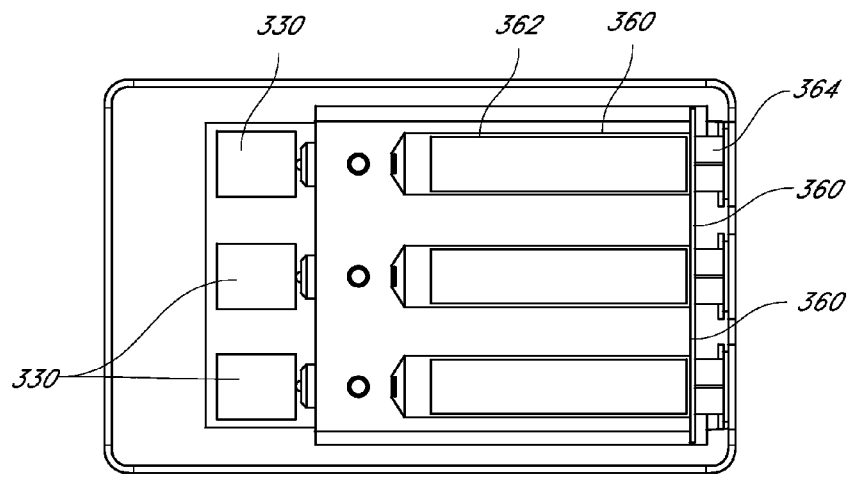
FIG. 12A illustrates a top view of the syringes or other reservoirs of a cassette in a first position.
Figure 12B:
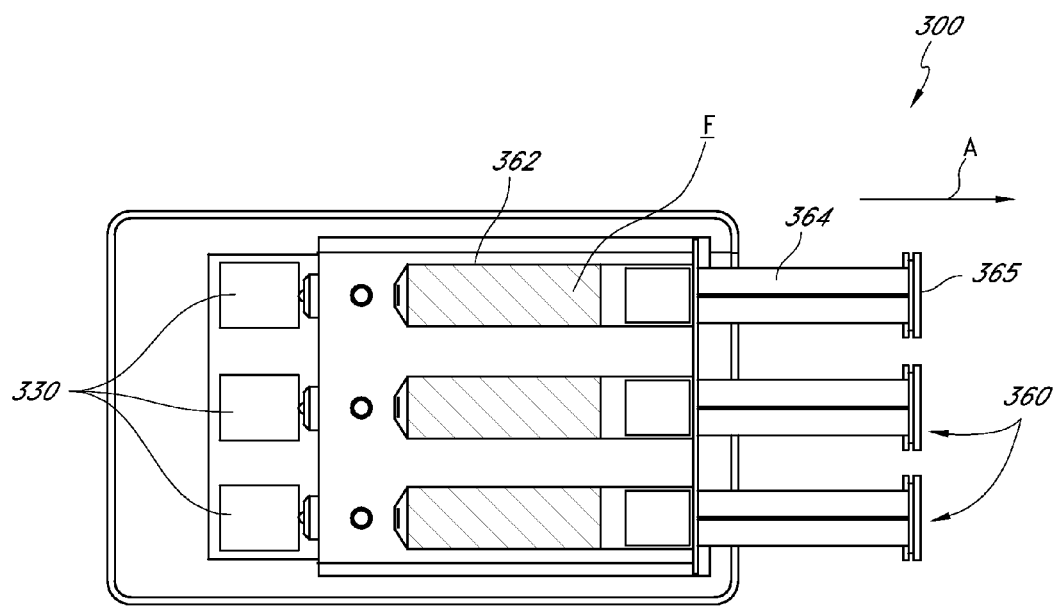
FIG. 12B illustrates a top view of the syringes or other reservoirs of a cassette in a second position.

FIGS. 12A and 12B schematically illustrate the filling of the syringes 360 or other reservoirs positioned within a cassette 300. As discussed in greater detail herein, the syringes or other reservoirs can be separate items or can be incorporated into a unitary structure with one another and/or other internal components of a cassette 300 (e.g., manifolds). In FIG. 12A, each of the three syringes 360 is empty or substantially empty, as the inner plunger 364 is positioned completely within the outer barrel 362. As the inner plungers 364 are drawn rearwardly away from the respective manifolds 330 (e.g., in a direction generally represented by arrow A), fluids F and/or other substances from the vials or other containers secured to the cassette (e.g., nests, loading areas or devices, other receiving areas, etc.) can be drawn through the manifolds 330 and into the syringes 360 or other reservoirs. As discussed, such fluids F and/or other substances can be subsequently delivered to a downstream handpiece assembly from one or more of the syringes 360 (e.g., through individual discharge conduits 251 downstream of each manifold, a hub or junction, a fluid delivery line, etc.). Accordingly, one, two or more different drugs, pharmaceuticals or medicaments, formulations, mixtures, other fluids and/or other materials can be accurately delivered into a patient's anatomy through a single needle positioned at the distal end of the handpiece assembly. Once a syringe 360 has been partially or fully emptied, the inner plunger 364 can once again be moved to fill the interior of the syringe 360 or other reservoir with additional fluids and/or other materials from the corresponding vial or other container positioned on the cassette. For example, once a spent vial positioned on the cassette is replaced with the a filled vial, a motor, actuator and/or other device within the fluid delivery module can mechanically move the inner plunger 364 relative to the outer barrel 362 of the syringe 360 or other reservoir in order to refill the syringe or other reservoir of the cassette 300.

According to some embodiments, the syringes 360 (or other reservoirs positioned within a cassette) are filled and emptied with the assistance of a stepper motor or other mechanical or pneumatic device. For example, such a device can be configured to slidably move the inner plunger 364 of each syringe 360 relative to the outer barrel 362. As discussed in greater detail herein with reference to FIGS. 8 and 11A-12B, fluids and/or other materials contained within a vial or other container can be selectively loaded into the syringe 360 or discharged from the syringe 360 toward a needle at the distal end of a handpiece assembly. Preferably, such a motor or other mechanical device, pneumatic device and/or the like can be configured to precisely move the inner plunger 364 into or out of the outer barrel 362 (or otherwise fill and/or empty the syringe 360 or other reservoir) to help ensure that a desired volume of fluids and/or other materials is accurately delivered to the anatomy.

Figure 13A:
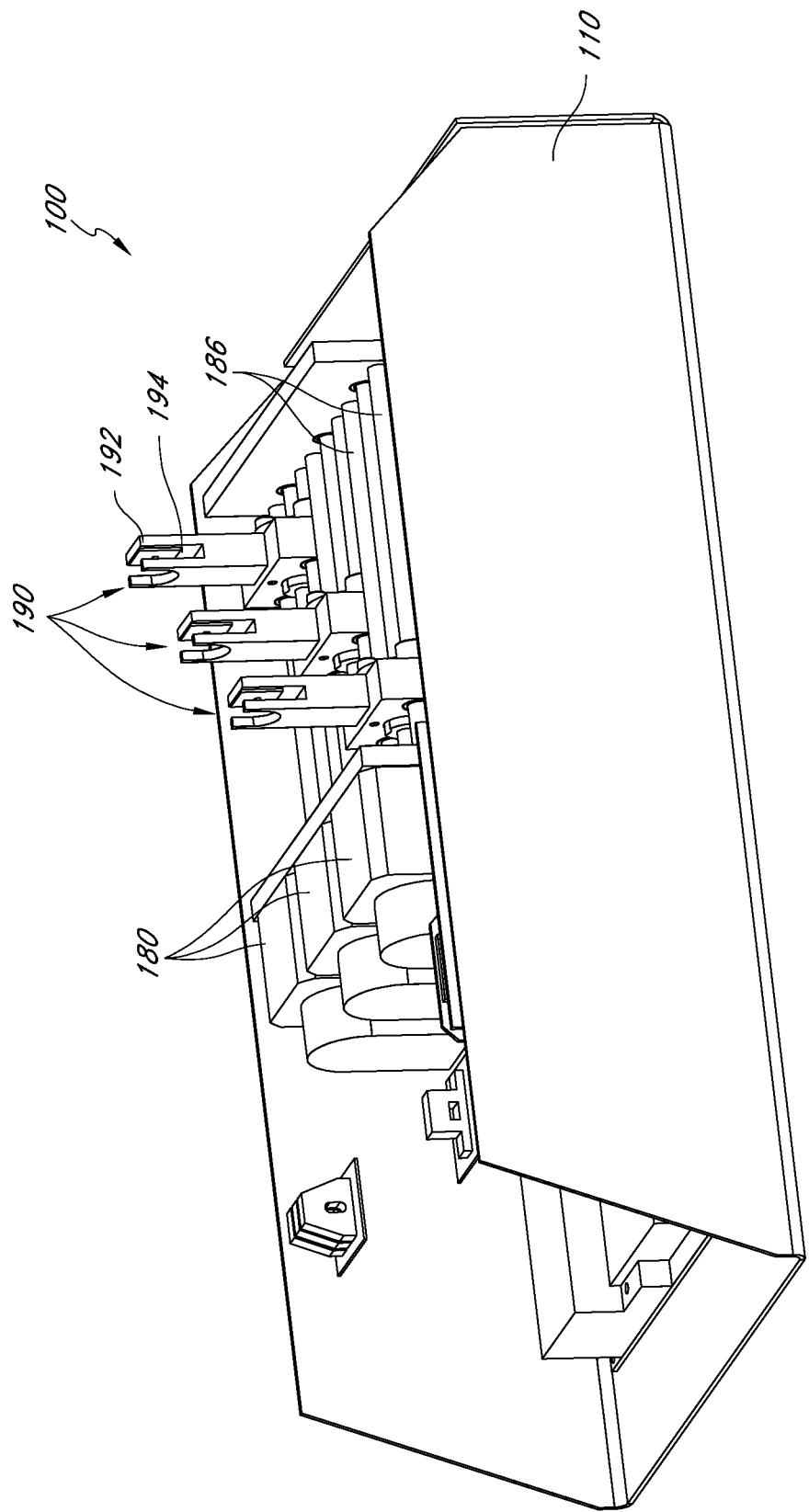
FIG. 13A illustrates a perspective view of a motor and accompanying components of a fluid delivery module according to one embodiment.
Figure 13B:
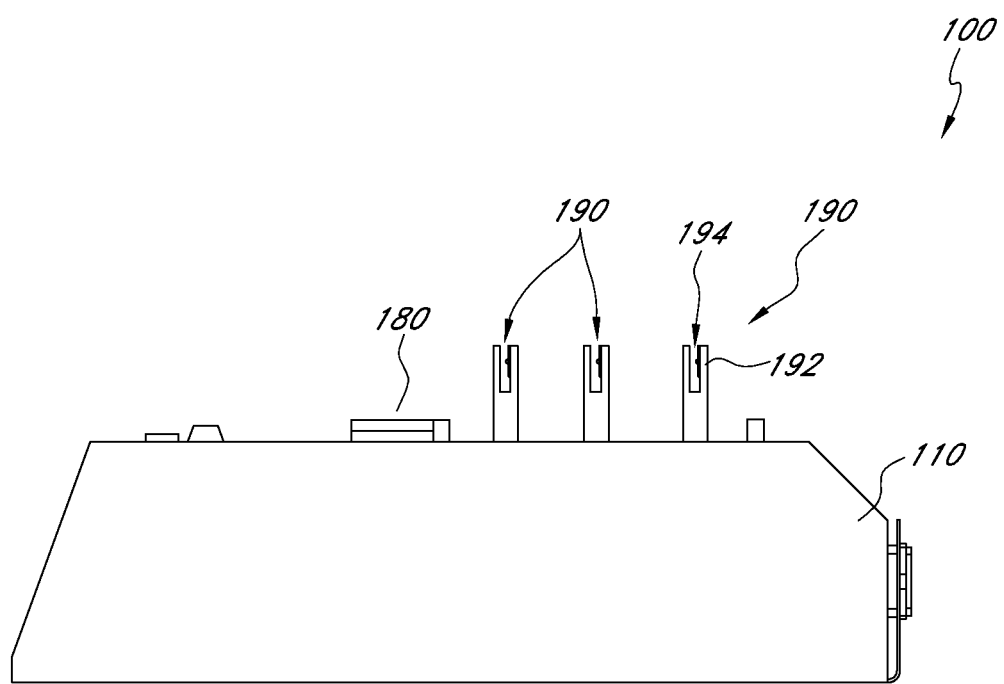
FIG. 13B illustrates a side view of the fluid delivery module of FIG. 13A.

One embodiment of a fluid delivery module 100 configured to accurately adjust the position of the inner plungers 364 relative to their respective outer barrels 362 or other portion of a syringe or other reservoir is illustrated in FIGS. 13A and 13B. As shown, an interior of the fluid delivery module 100 can comprise one or more stepper motors 180 or other devices (e.g., pumps, another mechanical or pneumatic device, etc.) configured to move fluids and/or other materials between vials (or other containers), syringes 360 or other reservoirs, a handpiece assembly and/or other components of an injection system.

With continued reference to FIGS. 13A and 13B, the fluid delivery module 100 can comprise a stepper motor 180 or other device for each syringe or other reservoir positioned within a cassette (not shown). Alternatively, a stepper motor or other device can be configured to control two or more syringes or other reservoirs. As shown, each stepper motor 180 can be adapted to selectively move a corresponding pusher block 190 along one or more guide rails 186. In the depicted embodiment, each pusher block 190 is configured to move linearly relative to two guide rails 186. However, in other embodiments, a pusher block 190 is configured to move in two or more directions, along more or fewer guide rails and/or in a completely different manner, as desired or required.

In the illustrated embodiment, each pusher block 190 includes a vertical portion 192 that is sized, shaped and otherwise adapted to engage the end portion 365 of a syringe's or other reservoir's inner plunger 364 (FIG. 12B). As discussed herein with reference to, inter alia, FIG. 8, a cassette 300 can include one or more openings 324 adjacent to the syringes 360 or other reservoirs (e.g., along the bottom of the cassette housing, along any other surface or portion of the cassette, etc.). Accordingly, the vertical portion 192 of each pusher block 190 can be configured to extend through such an opening 324 of the cassette 300 in order to engage a movable portion of the syringe 360 or other reservoir (e.g., the end portion 365 of the inner plunger 364).

In FIG. 13A, the vertical portion 192 of the pusher block 190 comprises a slot 194 that is sized, shaped, positioned and otherwise configured to securely receive the end portion 365 of the inner plunger 364 or other movable member of a reservoir. Thus, as the pusher block 190 is moved along the guide rails 186, the position of the inner plunger 364 relative to the outer barrel 362 of the syringe or other reservoir can be selectively modified. As discussed in greater detail herein, this permits fluids and/or other materials to be loaded into the cassette and/or to be accurately delivered to a targeted anatomical location (e.g., a joint, an organ, a cavity, etc.) using a handpiece assembly. In order to ensure that the position of the pusher blocks 190 is being accurately controlled, the fluid delivery module 100 can comprise one or more sensors (e.g., optical sensors), other position detection devices and/or the like. In some embodiments, one or more other methods and/or devices for controlling the loading of vials or other containers and/or the subsequent delivery of fluids and/or other substances can are used.

Medicaments and/or other fluids or materials to be delivered to a targeted anatomical location (e.g., a toe, ankle, knee, other joint, organ, etc.) are typically provided to clinicians and other users of an articular injection system in standard or non-standard drug vials. The size or capacity (e.g., 5 ml, 10 ml, 50 ml, less than 5 ml, more than 50 ml, etc.), shape, material type (e.g., glass, plastic, acrylic, etc.) and/or characteristics of such vials can vary, depending on the physician or other clinician performing the procedure, the specific protocol, the pharmaceutical manufacturer or distributor and/or other factors. As discussed herein with reference to various embodiments of a cassette, it may be desirable to secure a vial, ampoule and/or other container to a nest, loading area or device and/or any other portion of the cassette or fluid delivery module. This can facilitate delivery of the internal contents of the vials to the anatomy using an injection system. Accordingly, as illustrated in FIG. 7, a nest 370, 370' or other loading area or device can be configured to receive one or more nonspecific containers (e.g., vials of varying sizes, shapes, capacities, etc.) 400A-400C.

Figure 14:
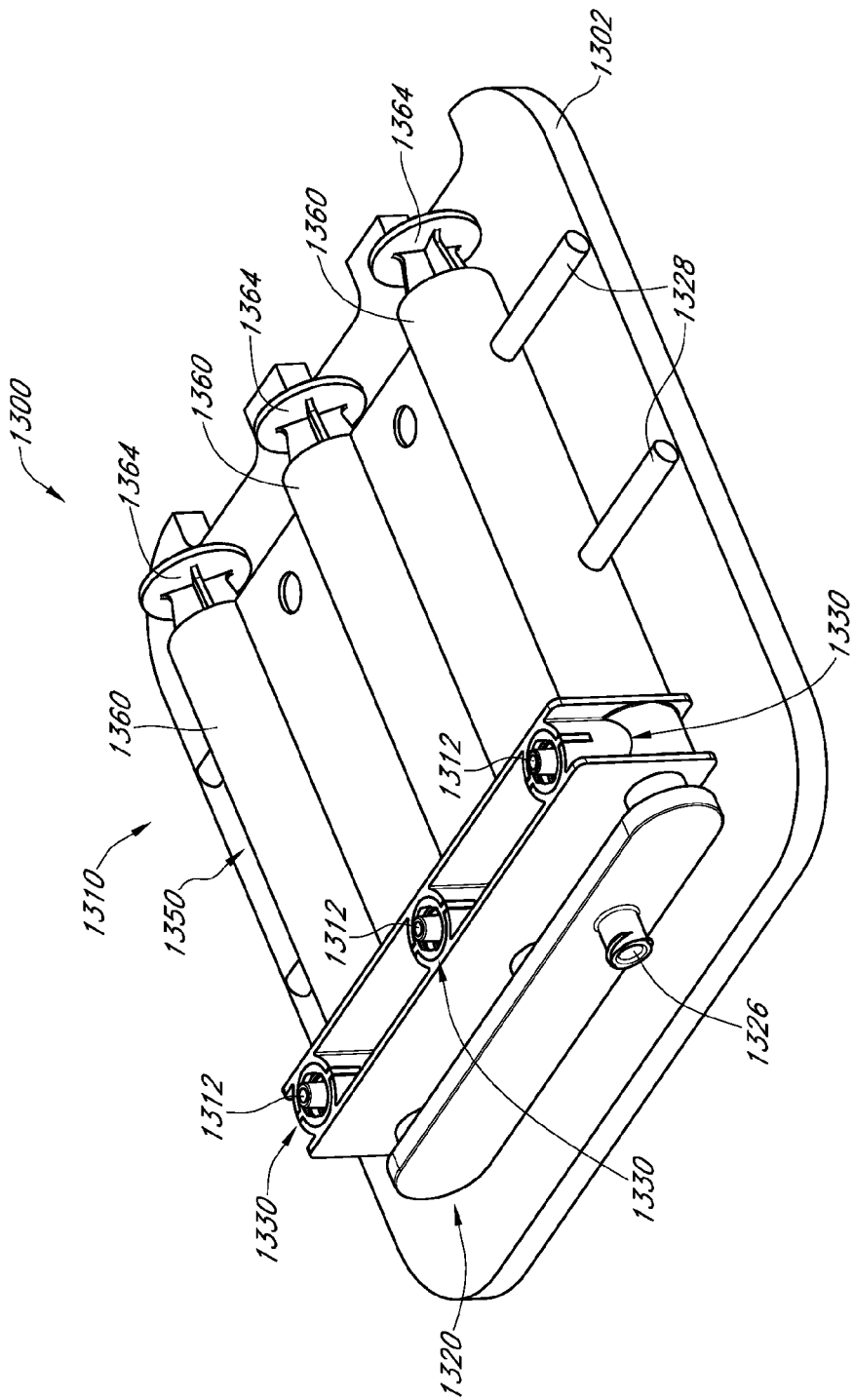
FIG. 14 illustrates another embodiment of a cassette (with a portion of its housing removed to show the internal components) configured for placement within a fluid delivery module.

FIGS. 14-17B illustrate another embodiment of a cassette 1300 configured for use with an injection system. In FIG. 14, the top portion of the cassette housing 1302 has been removed to reveal the cassette interior. In the depicted embodiment, the individual syringes or reservoirs, manifolds and other separate components (for example, as described herein with reference to FIG. 8) are replaced with one or more portions that can connect into a unitary structure 1310. For example, in FIG. 14, the syringes are replaced by a single reservoir portion 1350 that includes three individual reservoirs 1360. In other embodiments, the reservoir portion 1350 comprises fewer (e.g., one or two) or more (e.g., four, five, six, more than six, etc.) reservoirs 1360, as desired or required. Each reservoir 1360 can include a generally cylindrical shape configured to slidably receive a plunger member 1364 therein. As discussed herein with reference to other embodiments (e.g., FIGS. 7-13B), movement of the plunger members 1364 within the reservoirs 1360 can cause fluids and/or other materials from corresponding vials to be loaded therein and/or to be subsequently discharged to one or more downstream components (e.g., handpiece assembly, tubing, needle assembly, etc.)

With continued reference to FIGS. 14-17B, manifolds 1330 can be incorporated into the distal end of the reservoir portion 1350. Alternatively, the manifolds 1330 can be separate items that are removably attached to the reservoir portion 1350. As discussed herein with reference to FIGS. 7-13B, for example, the manifolds 1330 in the depicted embodiment can be configured to selectively direct fluids and/or other materials from a vial or other container attached to a nest of the cassette to the reservoirs 1360. Subsequently, such fluids and/or other materials can be directed from the reservoirs 1360 to a collection member 1320 positioned downstream of the reservoir portion 1350.

Figure 15A:
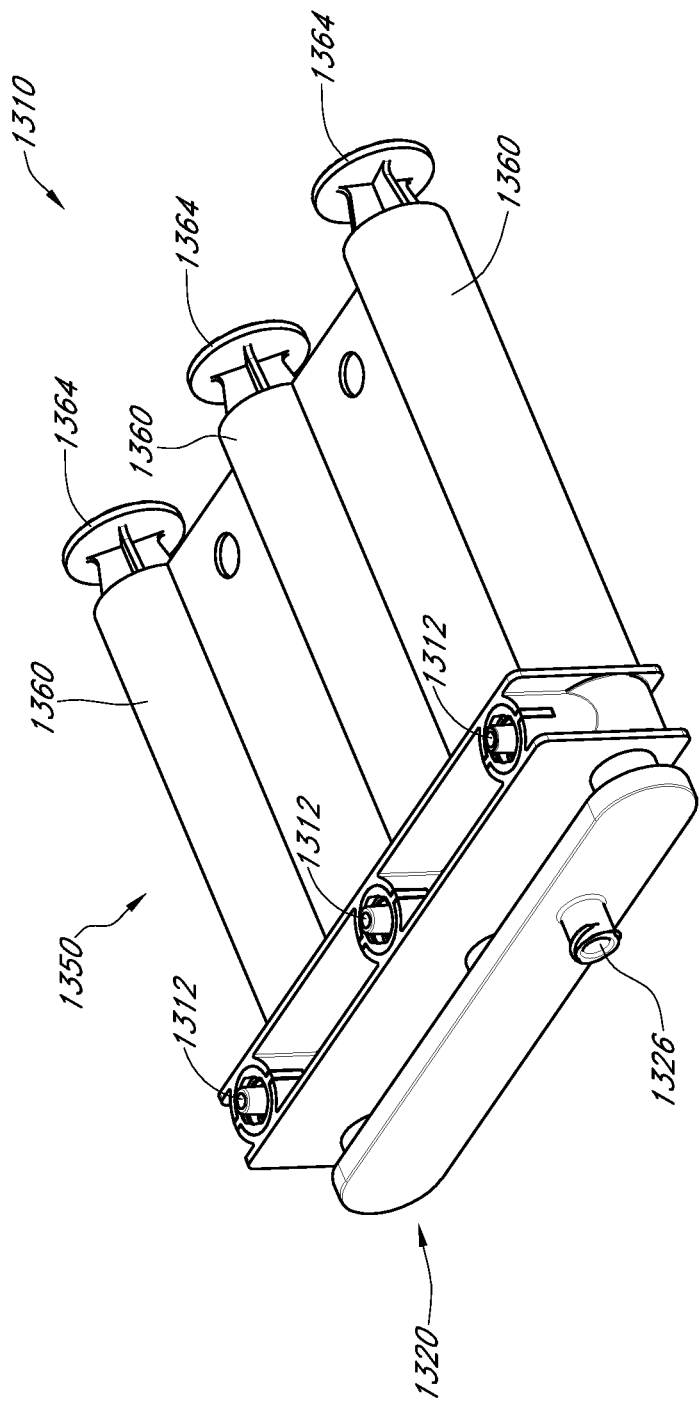
FIG. 15A illustrates a perspective view of the internal components of the cassette of FIG. 14.
Figure 15B:
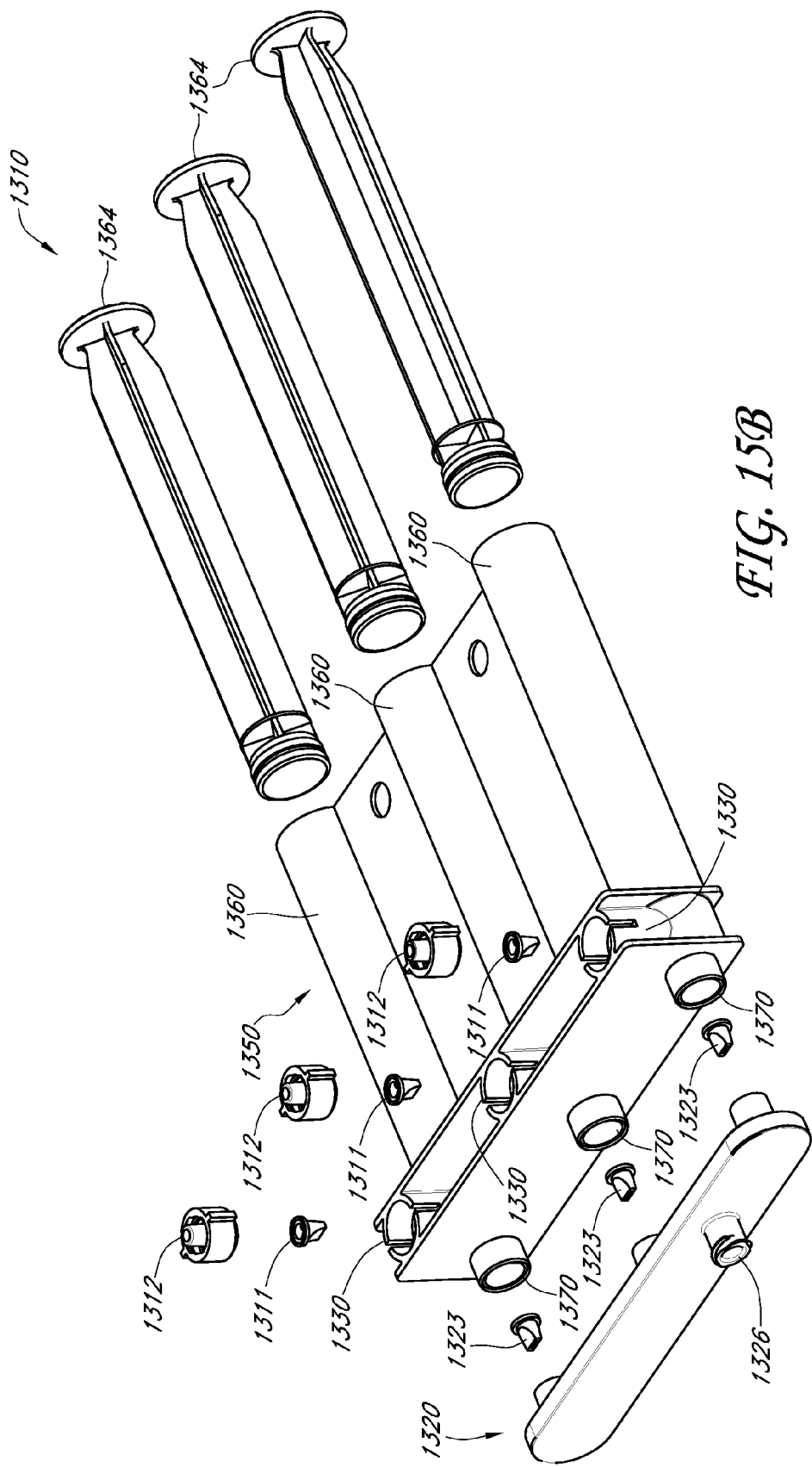
FIG. 15B illustrates an exploded perspective view of the internal components of the cassette of FIG. 14.

As illustrated in FIGS. 15A and 15B, a luer or other standard or non-standard fitting 1312 can be attached to the top of each reservoir 1330. Such luers, other fittings and/or other receiving sites 1312 can be configured to extend through corresponding openings of the cassette housing (e.g., as illustrated in FIG. 4). Thus, nests or other loading devices can be secured to one or more of the receiving sites 1312, allowing vials, ampoules and/or other containers positioned within the nests or other loading device to be advantageously placed in fluid communication with the reservoir portion 1350.

Figure 17A:
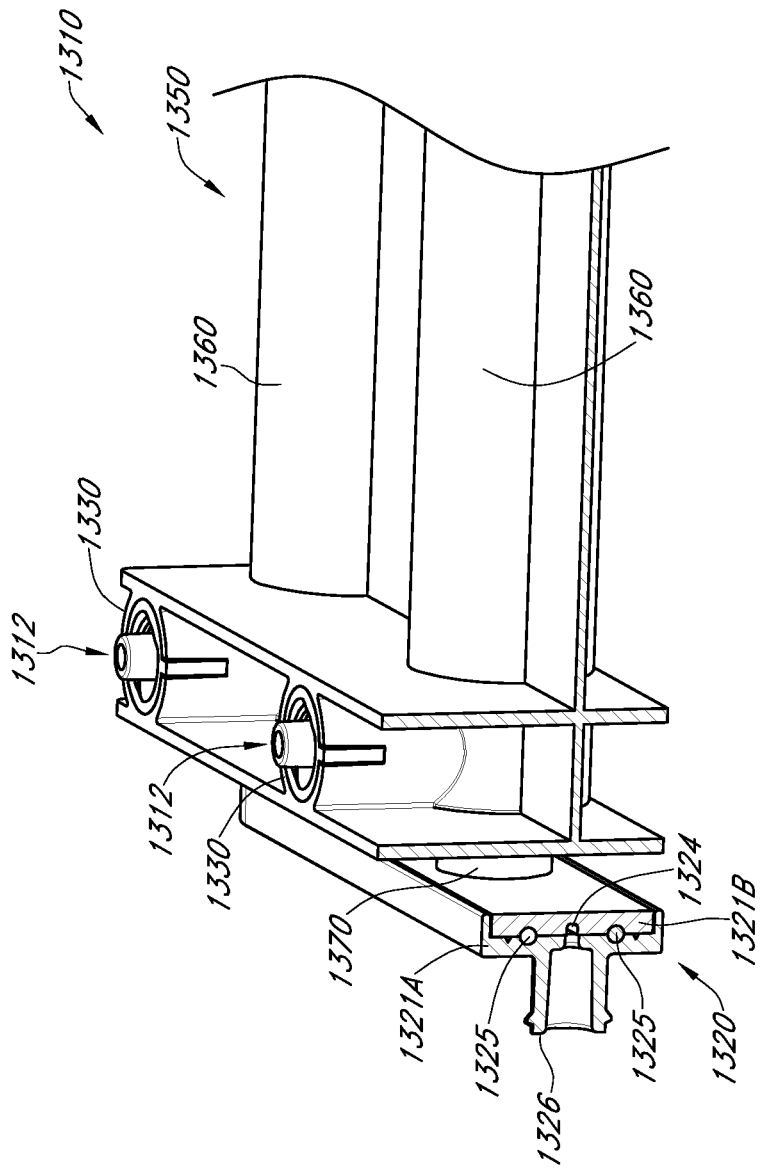
FIG. 17A illustrates a side view of the internal components of the cassette of FIG. 14.
Figure 17B:
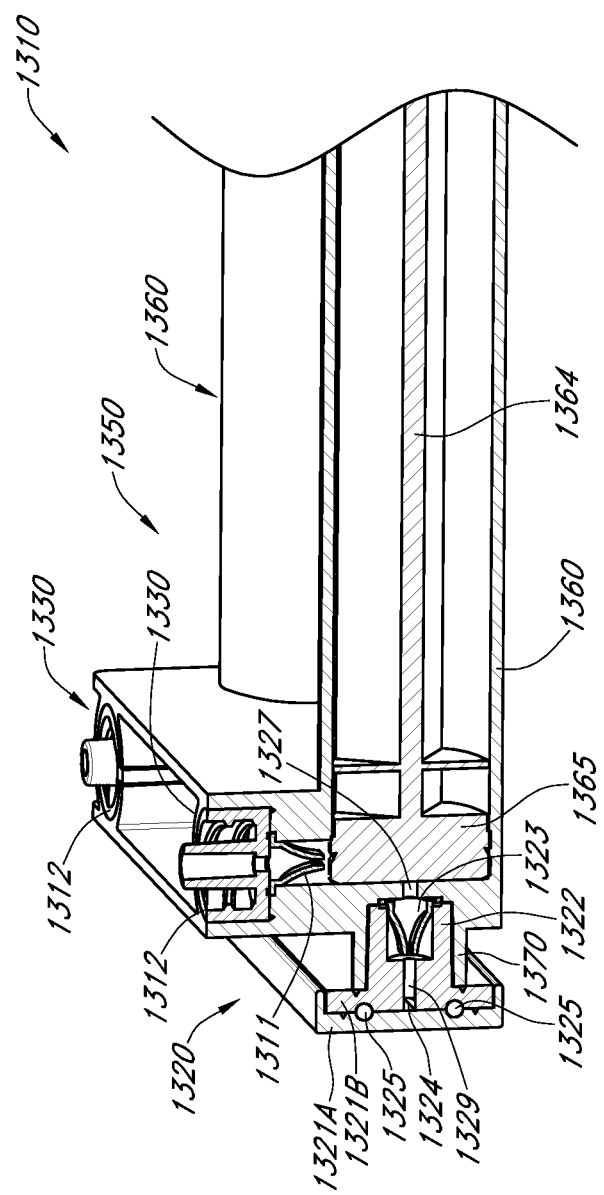
FIG. 17B illustrates a cross-sectional side view of the internal components of the cassette of FIG. 14.

According to some embodiments, as illustrated in FIGS. 15B and 17B, the manifold reservoir portion design can be advantageously configured to simplify the manner in which fluids are moved therein (e.g., into or out of the manifold reservoir portion). For example, as illustrated in the cross-sectional view of FIG. 17B, a one-way valve 1311 (e.g., a duckbill valve, other check valve, etc.) can be positioned immediately beneath the luer fittings or other receiving sites 1312 within an interior of the reservoir portion 1350. In the depicted embodiment, the plunger member 1364 is positioned completely or substantially completely within the interior of the corresponding reservoir 1360 such that the stopper or end portion 1365 of the plunger member contacts the distal end of the reservoir interior. As the plunger member 1364 is retracted (e.g., generally away from the one-way valve), a vacuum or negative pressure is created within the reservoir 1360, causing fluids and/or other materials to flow from a vial or other container (not shown), through the receiving site 1312 and the one-way valve 1311 and into the reservoir 1360. As a result, the reservoir can be completely or partially filled or loaded in preparation for a subsequent injection process. As discussed with reference to other embodiments herein, the plunger member 1364 can be slidably moved into and/or out of the interior of the reservoir mechanically (e.g., using a stepper motor, other types of motors, actuator or other mechanical device), pneumatically (e.g., using a pump) and/or in any other manner.

With continued reference to FIG. 17B, the one-way valve 1311 can include a flange, other radially extending portion and/or any other feature to help maintain a desired position of the valve 1311 within the unitary structure 1310. For example, in FIG. 17B, a flange located along the upper portion of the one-way valve 1311 is generally sized, shaped and configured to fit within a corresponding recess of the manifold 1330 (e.g., below the luer lock fitting 1312, other receiving site, etc.).

With continued reference to the embodiment illustrated in FIGS. 15B and 17B, the distal end of the reservoir portion 1350 comprises outlet nozzles 1370 through which fluids and/or other materials can exit the corresponding manifolds 1330. In some embodiments, the outlet nozzles 1370 have a generally cylindrical shape and extend outwardly from the distal end of the reservoir portion 1350. However, in other embodiments, the shape, size and/or configuration of the outlet nozzles 1370 can vary, as desired or required. As best depicted in FIG. 17B, fluids and/or materials that have been loaded into the interior of a reservoir 1360, can exit the reservoir and enter into an interior of the nozzle 1370 through one or more outlet openings 1327. In some embodiments, the outlet nozzle 1370 is configured to receive an inlet nozzle 1322 of the downstream collection member 1320. As discussed in greater detail below, fluids and/or other materials from one or more of the reservoirs 1360 can be directed into the collected member 1320 and combined therein.

According to some embodiments, the collection member 1320 is secured to the unitary reservoir portion 1350 using a friction fit or press fit connection between the corresponding nozzles 1370, 1322. However, any other connection device, feature and/or method can be used to removably or permanently attach the collection member 1320 to the reservoir portion 1350, as desired or required.

Figure 16A:
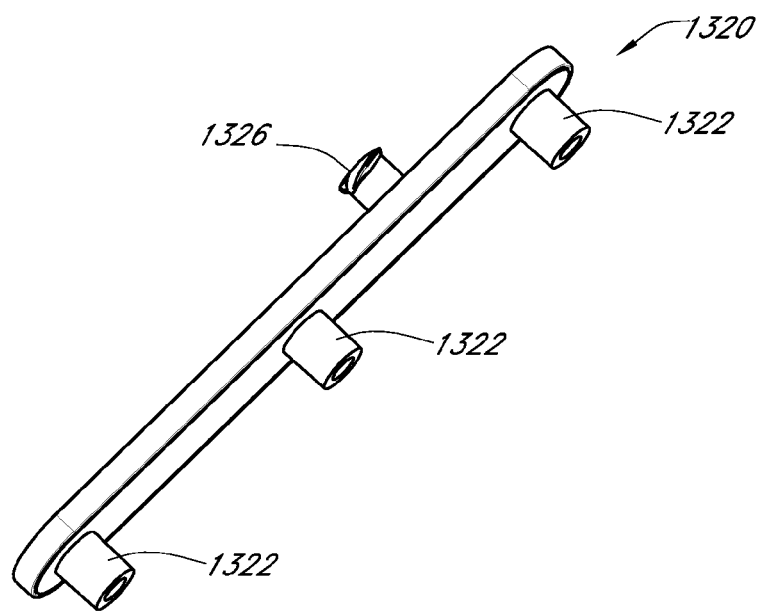
FIG. 16A illustrates a perspective view of the collection member of the cassette of FIG. 14.
Figure 16B:
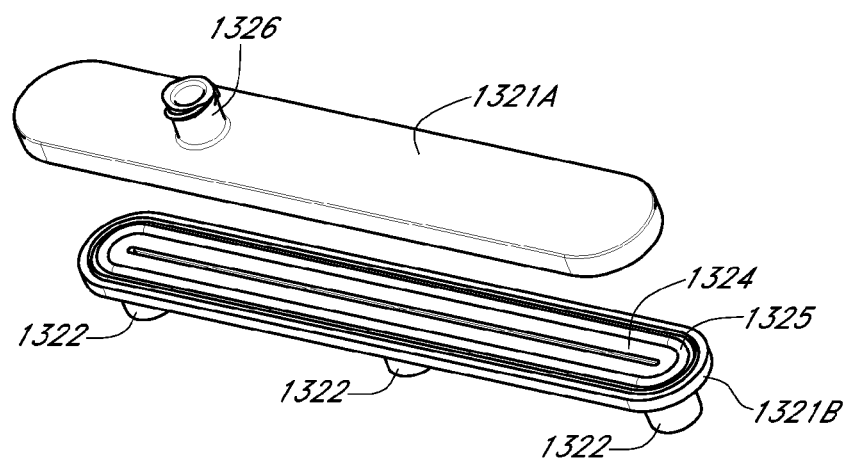
FIG. 16B illustrates an exploded perspective view of the collection member of the cassette of FIG. 14.

With reference to FIGS. 16A and 16B, the collection member 1320 can include an inlet nozzle 1322 corresponding to each outlet nozzle 1370 of the reservoir portion 1350. In some embodiments, the collection member 1320 additionally comprises an outlet port 1326. In the depicted arrangement, the outlet port 1326 extends from a first side or surface of the collection member 1320 that is generally opposite of the side or surface from which the inlet nozzles 1322 extend. However, the location, spacing, orientation, shape, size and/or other details regarding the nozzles, ports and/or other connection points 1322, 1326 of the collection member 1320 can vary.

According to some embodiments, as illustrated in the exploded perspective view of FIG. 16B, the collection member 1320 can comprise two or more portions 1321A, 1321B that are configured to removably or permanently attach to one another. In such arrangements, the separate portions 1321A, 1321B can attach to one another using adhesives, welds, hot melt connections, press-fit or snap-fit connections, friction fit connections, screws, bolts, rivets or other fasteners and/or the like. As illustrated in FIG. 16B, one or more gaskets 1325 or other sealing members can be positioned between the separate portions 1321A, 1321B of the collection member 1320 in order to prevent or reduce the likelihood of undesirable leaks. The gasket 1325 or other sealing member can include an O-ring, another elastomeric or polymeric member and/or the like.

In some embodiments, the collection member 1320 comprises an internal chamber 1324 that is in fluid communication with one or more of the inlet nozzles 1322, and thus, one or more of the reservoirs 1360. For example, with continued reference to FIG. 17B, the internal chamber 1324 can be in fluid communication with a channel 1329 that extends, at least partially, within an inlet nozzle 1322 of the collection member 1320. In some embodiments, another one-way valve 1323 (e.g., duckbill valve, another check valve, etc.) is positioned between the channel 1329 of the collection member 1320 and the corresponding outlet opening 1327 of the reservoir portion's outlet nozzle 1370. As with the valve 1311 located between the receiving site 1312 (e.g., luer lock fitting) and the reservoir 1360, the position of this additional one-way valve 1323 can be properly maintained using one or more securement devices or methods, such as, for example, press-fit or friction-fit connections, clasps, clamps or other fasteners and/or the like.

As illustrated in the cross-sectional view of FIG. 17B, the one-way valve 1323 can be configured to only allow fluids to flow from the upstream reservoir 1360 and the outlet opening 1327 to the downstream channel 1329 and chamber 1324 of the collection member 1320. Consequently, the one-way valve 1323 can advantageously prevent fluids and/or other materials from being transferred from the collection member 1320 into the upstream reservoirs 1360 (e.g., in a retrograde direction). This can help prevent or reduce the likelihood of cross-contamination between the various fluids and/or other materials loaded onto a cartridge of the injection system.

Once fluids and/or other materials from one or more of the reservoirs 1360 have passed through the respective backflow prevention valve(s) 1323, they can pass into the main chamber 1324 of the collection member. In the chamber 1324, the fluids and/or other materials can be mixed and combined (e.g., if originating from two or more different reservoirs 1360). Ultimately, as illustrated in FIGS. 15A-17A, such fluids and/or other materials will exit the collection member 1320 through an outlet port 1326. In some embodiments, the outlet port 1326 comprises a standard or non-standard fitting or connection, such as, for example, a luer lock fitting, a threaded fitting, a flanged fitting and/or the like. Thus, as discussed in greater detail herein, a handpiece assembly comprising proximal tubing can easily attach or otherwise mate to the outlet port 1326 using a corresponding standard or non-standard fitting or connection. In some embodiments, the outlet port 1326 is configured to extend along an exterior surface of the cassette to further facilitate connecting to or disconnecting from a corresponding component or system (e.g., handpiece assembly).

As noted herein, the reservoir portion 1350, collection member 1320 and/or one or more other internal components or features of the cassette can be manufactured using an injection molding or any other molding method (e.g., thermoforming, compression molding, etc.). Thus, the number of separate components used in a particular cassette can be reduced and the overall design of the cassette can be advantageously simplified. In other embodiments, however, the methods of manufacture, the number of separate components and/or other details or features of a cassette and its design can vary, as desired or required.

One embodiment of how fluids are transferred from a vial, ampoule or other container 400 through the internal components of a cassette is schematically illustrated in FIGS. 18A-18D. For example, once a vial or other container 400 has been properly secured to a nest 377 or other loading device or area of the cassette, a ventilated spike 380 or other conduit can be configured to place the internal contents of the container 400 (e.g., anesthetic, steroid, other medicament, any other fluid or substance, etc.) in fluid communication with a corresponding reservoir 1360. In some embodiments, the nest 370 is adapted to removably couple to an adjacent receiving site 1312 (e.g., luer fitting, other standard or non-standard fitting, etc.). Thus, as noted in greater detail herein, the nest can be easily and promptly attached and/or removed from the cassette or other portion of the fluid delivery module.

Figure 18A:
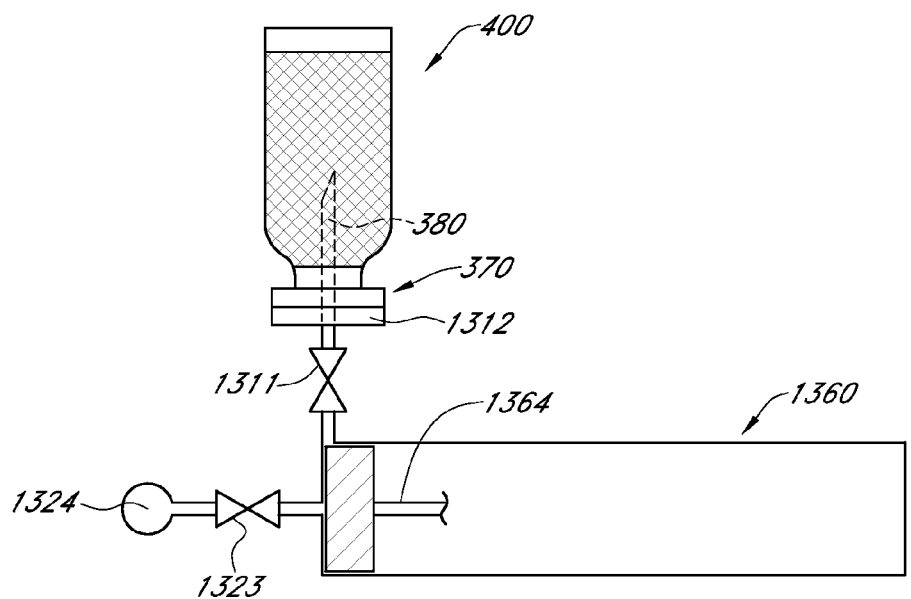
FIGS. 18A-18D schematically illustrate, in time-sequential steps, the transfer of fluids and/or other materials from a vial to and through a corresponding reservoir, according to one embodiment.
Figure 18B:
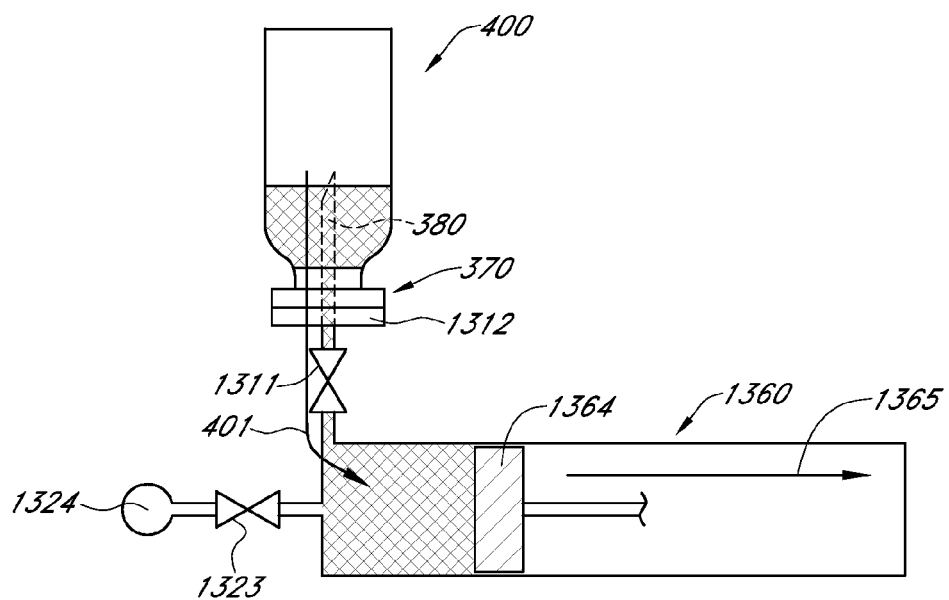

According to some embodiments, as illustrated in FIG. 18A, before fluids and/or other materials are transferred from the vial 400 to the corresponding reservoir 1360 of the cassette, the plunger member 1364 is positioned completely or substantially completely (e.g., distally) within the reservoir interior. As the plunger member 1364 is slidably retracted away from the receiving site 1312 (e.g., in a direction generally represented by arrow 1365 in FIG. 18B), a vacuum or negative pressure is created within the interior of the reservoir 1360. Consequently, fluids and/or other materials from the vial or other container 400 can be drawn into the reservoir 1360, through the one-way valve 1311, as generally represented by arrow 401 in FIG. 18B. As discussed in greater detail herein, the one-way valve 1311 can comprise a duckbill valve or any other type of check or retrograde prevention valve. Further, due to the negative pressure created within the reservoir, fluids and/or other materials are generally not permitted to pass through the other valve 1323. Thus, in some embodiments, fluids and/or other materials will pass from the vial 400 only to the interior of the reservoir 1360 as a result of retracting the plunger member 1364.

Once a desired volume of fluids and/or other materials have been loaded into the interior of the reservoir 1360, the retraction of the plunger member 1364 can be stopped. In some embodiments, all or substantially all of the fluids and/or other materials from a vial or other container 400 are transferred into the corresponding reservoir 1360. Alternatively, however, only a portion of the vial's contents may be delivered to the corresponding reservoir during this initial loading step, as desired or required. For example, the plunger member 1364 can slidably retract just far enough to load the volume of fluids and/or other materials into the reservoir that will be delivered through a handpiece assembly in a subsequent injection stage.

Figure 18C:
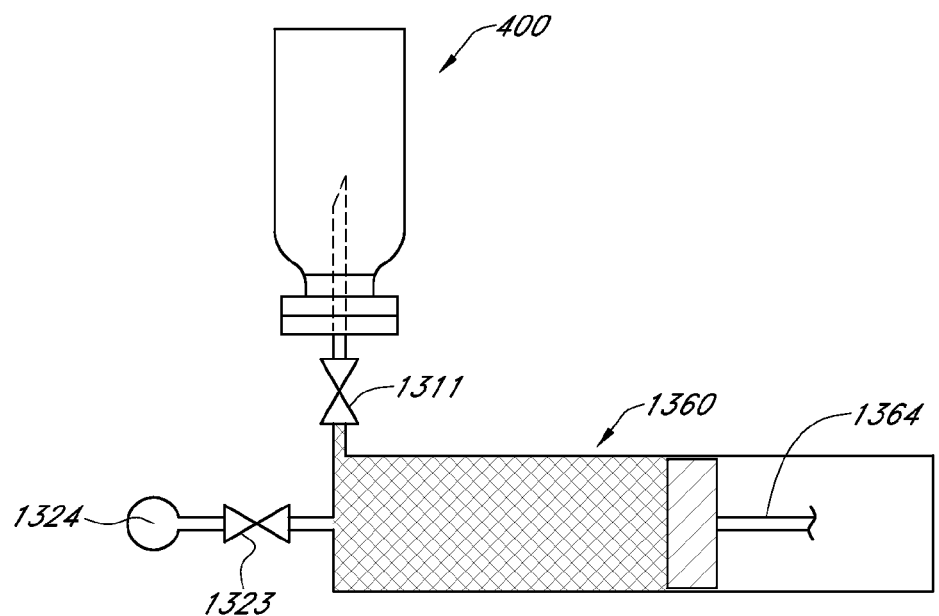

FIG. 18C schematically illustrates one embodiment in which all or substantially all of the fluids and/or other materials have been transferred or loaded from the vial 400 to the corresponding reservoir 1360. If the two or more other fluids and/or materials are to be delivered into a patient's anatomy in a particular injection protocol, the above steps can be repeated to load such fluids and/or other materials from other vials or containers into corresponding reservoirs of the cassette. Once the various fluids and/or other materials have been properly loaded into their respective reservoirs, the subsequent injection into the anatomy can be initiated by a user. As discussed in greater detail herein, the various fluid or other material streams can be delivered to the downstream handpiece assembly either sequentially and/or simultaneously, in accordance with a desired protocol or procedure.

Figure 18D:
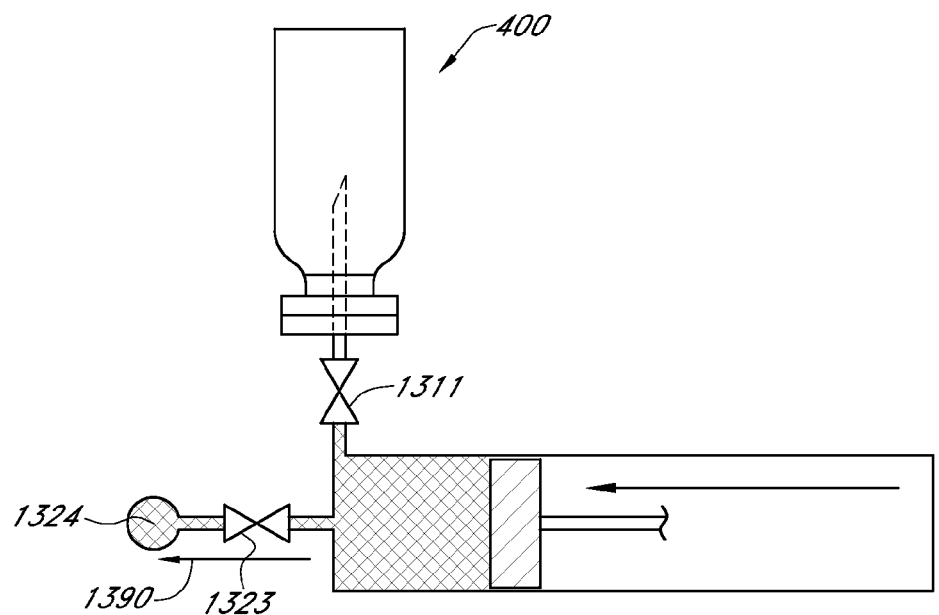

In some embodiments, as schematically depicted in FIG. 18D, in order to evacuate the fluids and/or other materials from the interior of the reservoir 1360, the plunger member 1364 is slidably moved toward the distal end of the reservoir (e.g., in a direction generally represented by arrow 1390). As a result, the fluids and/or other materials will be forced out through one or more openings along the distal end of the reservoir and a downstream one-way valve 1323. In some embodiments, in to order to purge any entrapped gasses (e.g., air bubbles), the injection system can be configured to expel a certain volume of "waste" fluid prior to initiating the injection of fluids and/or other materials into the anatomy.

As discussed in greater detail herein, the one-way valve (e.g., duckbill valve, umbrella valve, other check valve or retrograde-prevention valve, etc.) can help ensure that fluids and/or other materials only pass from the reservoirs 1360 to the collection member, thereby eliminating or reducing the likelihood of undesirable cross-contamination of fluids and/or other materials. Fluids and/or other materials passing through the valve 1323 can be directed into an internal chamber 1324 of a downstream collection member. In some embodiments, the collection member is configured to receive and combine fluids and/or materials from two, three or more different reservoirs 1360. The internal chamber 1324 can be placed in fluid communication with a downstream handpiece assembly (e.g., tubing, handpiece, etc.), in order to allow the fluids and/or other materials entering the internal chamber 1324 to be selectively injected into a patient's anatomy.

Figure 18E:
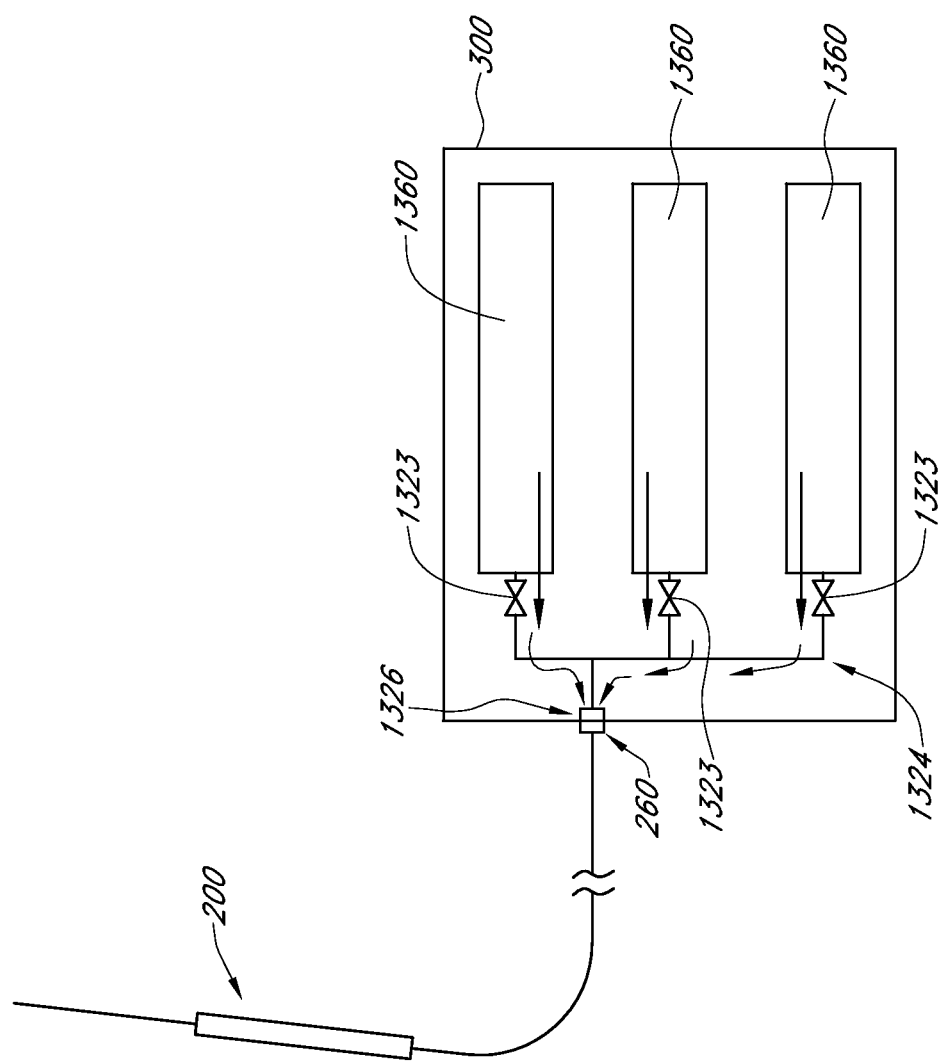
FIG. 18E schematically illustrates a top view of a cassette configured for placement within a fluid delivery module according to one embodiment.

FIG. 18E schematically illustrates one embodiment of a cassette 300 configured for placement within a fluid delivery module of an injection system. As shown, the cassette 300 can include three reservoirs 1360, each of which is configured to receive a medicament (e.g., slow acting and/or fast acting anesthetic, steroid, other pharmaceutical, etc.), other fluid and/or any other materials. In alternative embodiments, the cassette 300 comprises more or fewer reservoirs 1360, as desired or required. As discussed herein with reference to FIGS. 14-18D, fluids and/or other materials from each of the reservoirs 1360 can be selectively transferred through a downstream valve 1323 and into a common internal chamber 1323 of a collection member. Once in the collection member, the various fluids and/or other materials can be mixed, combined and exit through an outlet 1326. In some embodiments, the outlet 1326 (e.g., luer lock fitting, nozzle, port, other standard or non-standard connection, etc.) can be selectively coupled or otherwise attached to a corresponding connection 260 of a handpiece assembly 200. For example, the connection 260 of the handpiece assembly 200 can include a luer fitting that is adapted to mate with, and thus, selectively attach to and detach from, the outlet 1326 of the collection member. Consequently, fluids and/or other materials can be transferred from one or more of the reservoirs 1360, through the downstream collection member and handpiece assembly 200, ultimately into a patient's anatomy (e.g., a targeted joint).

As discussed herein, in some embodiments, fluids and/or other materials are transferred into and out of the reservoirs 1360 by mechanically moving plunger members 1364 within the corresponding reservoirs 1360. The plunger members 1364 can be moved with the help of a mechanically-operated actuator or motor (e.g., stepper motor, other type of motor, etc.) and/or any other mechanical device capable of accurately delivering fluids and/or other materials into relatively small spaces (e.g., small joints) under relatively high back pressure. In other embodiments, the plunger members are moved using pneumatic and/or other methods or devices. In yet other embodiments, fluids and/or other materials are selectively transferred through an injection system without the use of plunger members. For example, one or more pumps can be used to transfer one or more fluid and/or other material streams from a vial or other container into a patient's anatomy (e.g., a joint, an organ, a cavity, etc.) using an injection system.

Figure 19A:
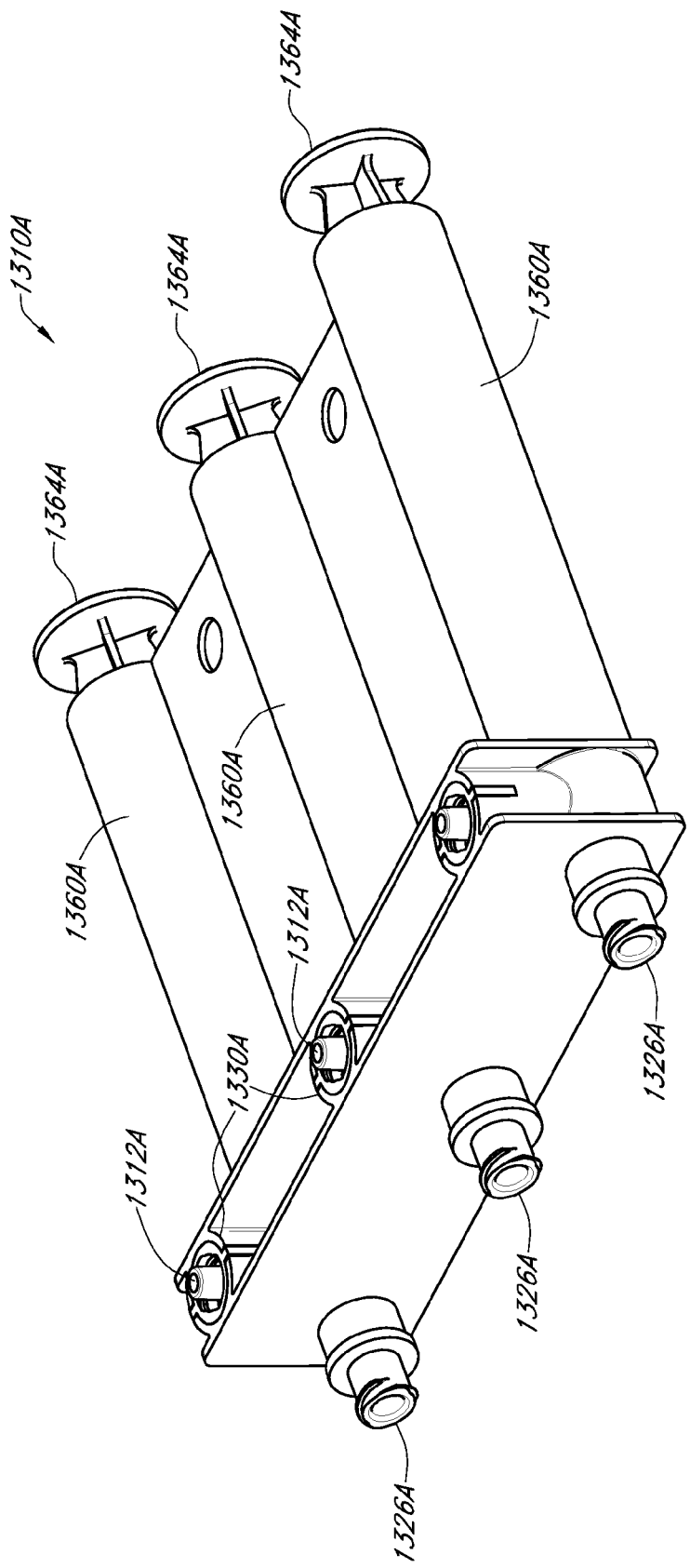
FIGS. 19A and 19B illustrate different views of the internal components of a cassette according to another embodiment.
Figure 19B:
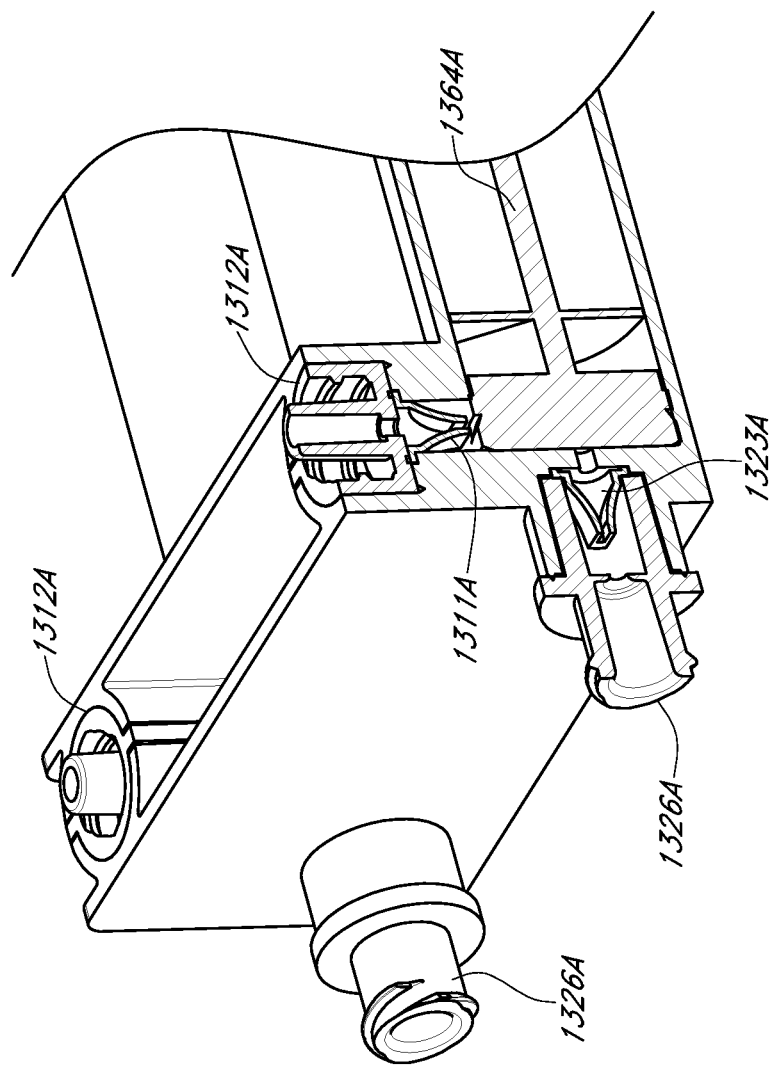

Another embodiment of the internal hydraulic components 1310A and structure of a cassette is illustrated in FIGS. 19A and 19B. The depicted arrangement is similar to the one discussed above with reference to FIGS. 18A-18E. As discussed above, the embodiment of FIGS. 18A-18E is configured to combine the fluids and/or materials exiting each reservoir in a collection member positioned immediately downstream of the reservoir portion. In contrast, the structure 1310A of FIGS. 19A and 19B includes a separate outlet 1326A for each reservoir 1360A. Therefore, the various fluids and/or other materials can be maintained separate from each other until a location that is further downstream. For example, individual conduits or other lines (not shown) can place each of the outlets 1326A in fluid communication with a handpiece assembly that is similar or identical to the one discussed herein with reference to FIGS. 29A-34C. In such arrangements, the various fluid and/or other material streams can be combined within the handpiece assembly (e.g., immediately upstream of the tip or needle assembly).

Figure 19C:
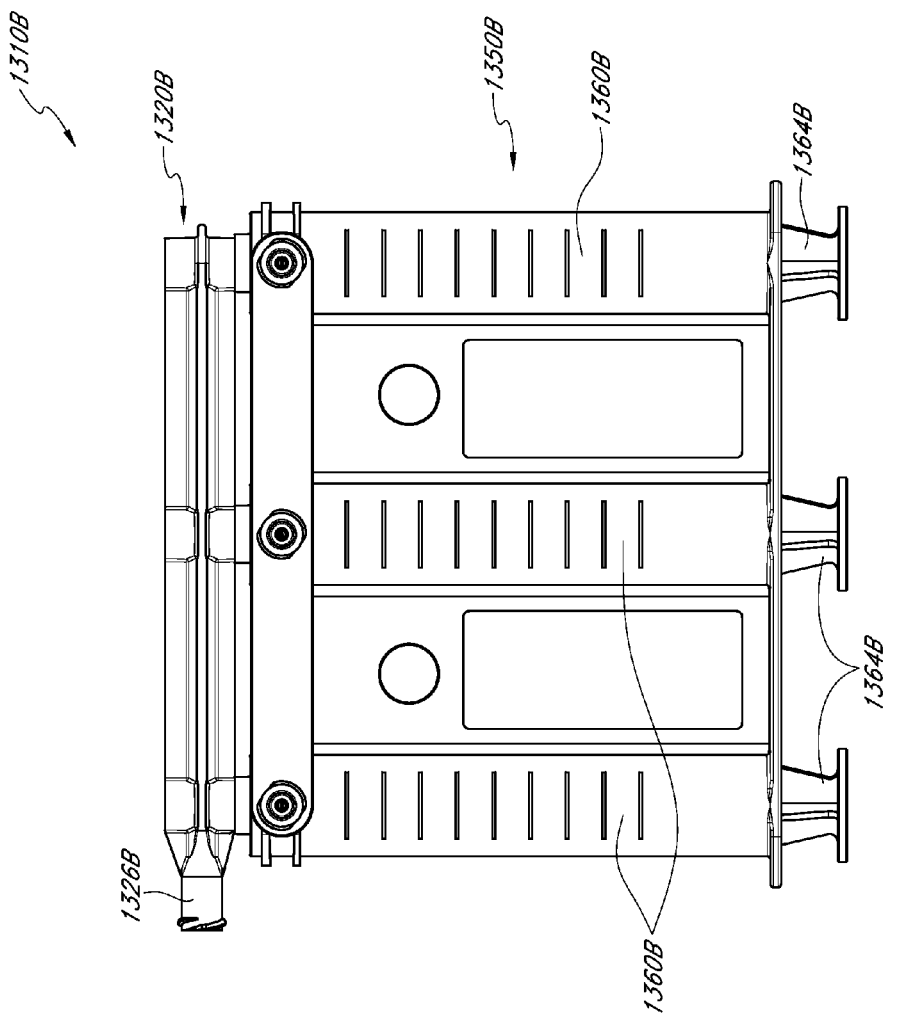
FIG. 19C illustrates a top view of the internal components of a cassette according to yet another embodiment.

As noted herein, the collection member 1320B located at the downstream end of the cassette's internal hydraulic components can be manufactured as a unitary structure (e.g., as a single piece, thereby eliminating the need to subsequently attach two or more portions to each other). A top view of one such embodiment is illustrated in FIG. 19C. In addition, the outlet port 1326B of the collection member 1320B can be orientated along the side of the collection member 1320B (FIG. 19C), along the front (FIG. 14), along the top or at any other location, as desired or required.

As discussed in greater detail herein, a cassette, another portion of a fluid delivery module and/or any other component of an injection system can be configured to receive (and selectively deliver within a patient's anatomy) fluids and/or other materials contained in any one of a variety of containers. For example, in any of the embodiments disclosed herein, or equivalents thereof, a cassette can be adapted to receive standard or non-standard vials, ampoules and/or any other container. In some arrangements, such containers are in the form supplied by a pharmaceutical manufacturer or distributor. However, in other embodiments, the containers are re-packaged, either prior to or after being provided to the users of the injection system.

Figure 20A:
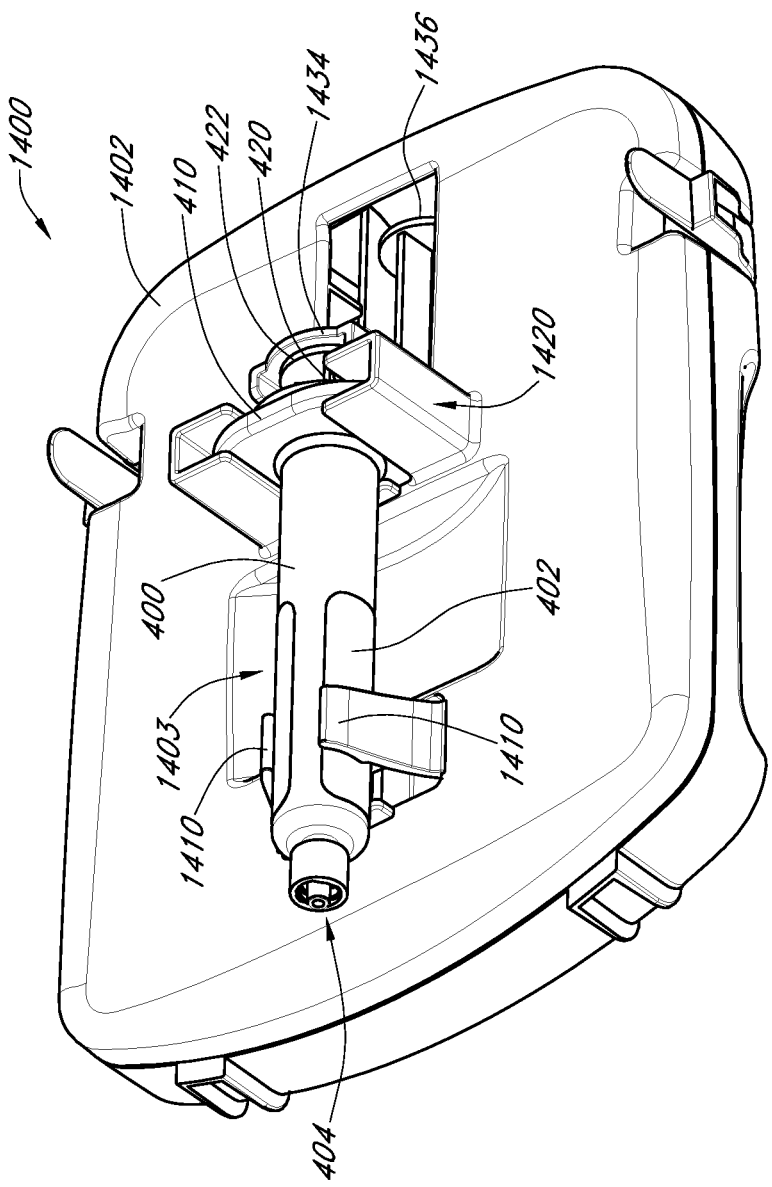
FIG. 20A illustrates a perspective view of one embodiment of a cassette configured for placement within a fluid delivery module and adapted to receive a prefilled syringe or other container.

With reference to the embodiment illustrated in FIG. 20A, a cassette 1400 adapted for placement within a fluid delivery module or other portion of an injection system can be configured to receive a pre-filled syringe 400 or other container. The cassette 1400 can be sized, shaped and otherwise configured to replace a cassette having multiple (e.g., two, three, four, etc.) receiving sites on which vials, ampoules and/or other containers can be loaded, such as, for example, the cassettes depicted and discussed herein with reference to FIGS. 1, 2, 4, 5A, 5B, 7, 8 and 14-19B. Thus, the various cassette embodiments disclosed herein can be used interchangeably with one another in one or more injection systems. As a result, the cassette can include a housing 1402, tabs, recesses and/or other features that are similar, substantially similar or identical to those in the multiple receiving site cassettes disclosed herein. According to some embodiments, the pre-filled syringe 400 comprises hyaluronic acid, plasma, red blood cells, other separated or centrifuged blood components and/or the like. In some embodiments, the pre-filled syringe, vial or other container intended to be secured to the cassette 1400 can be configured for placement in a centrifuge or other apparatus (e.g., before and/or after being secured to the cassette 1400). Thus, once a fluid has been centrifuged, the syringe 400 can be loaded onto the cassette 1400. Accordingly, one or more of the separated layers and/or portions of the fluid (e.g., blood) and/or other materials contained within the syringe 400 can be selectively delivered to a target anatomical location (e.g., vessel, joint, etc.) using the injection system.

With continued reference to FIG. 20A, a pre-filled syringe 400 or other container can be secured to the top of the cassette 1400 using one or more clips, guides and/or other devices or features 1410, 1420. For example, the cassette 1400 can include a pair of tabs or clips 1410 that are sized, shaped and otherwise configured to receive the barrel 402 or other exterior surface or portion of the syringe 400. In some embodiments, the tabs 1410 include two adjacent members that are configured to resiliently move apart in order to maintain a syringe 400 therebetween. The inside surfaces of the tabs 1410 can be contoured (e.g., rounded, curved, etc.) in order to accommodate the outer shape of the syringe barrel 402. The tabs 1410 can be sized, shaped, resiliently-designed and otherwise adapted to receive pre-filled syringes 400 (or other containers) of varying sizes (e.g., both standard and non-standard), shapes and/or other configurations. Thus, the cassette 1400 can be used to load and subsequently deliver fluids and/or other materials from a number of different types and sizes of syringes and other containers.

In some embodiments, the flange portion 410 at the proximal end of the syringe barrel 402 is configured to be secured within a recess 1420 or similar feature of the cassette 1400. For example, as illustrated in FIG. 20A, the recess 1420 can include two channel members forming a slot that is sized, shaped and otherwise configured to receive the syringe's flange portion 410. In alternative embodiments, one or more other features or members can be used to retain the flange portion 410 and/or otherwise help retain maintain the position of the syringe 400 relative to the cassette 1400. As illustrated in FIG. 20A, the top surface of the cassette housing 1402 can include one or more recessed areas 1403 underneath or near the loading area of the syringe. Such recessed areas 1403 can facilitate loading and unloading of a pre-filled syringe or other container to or from the cassette 1400.

Figure 20B:
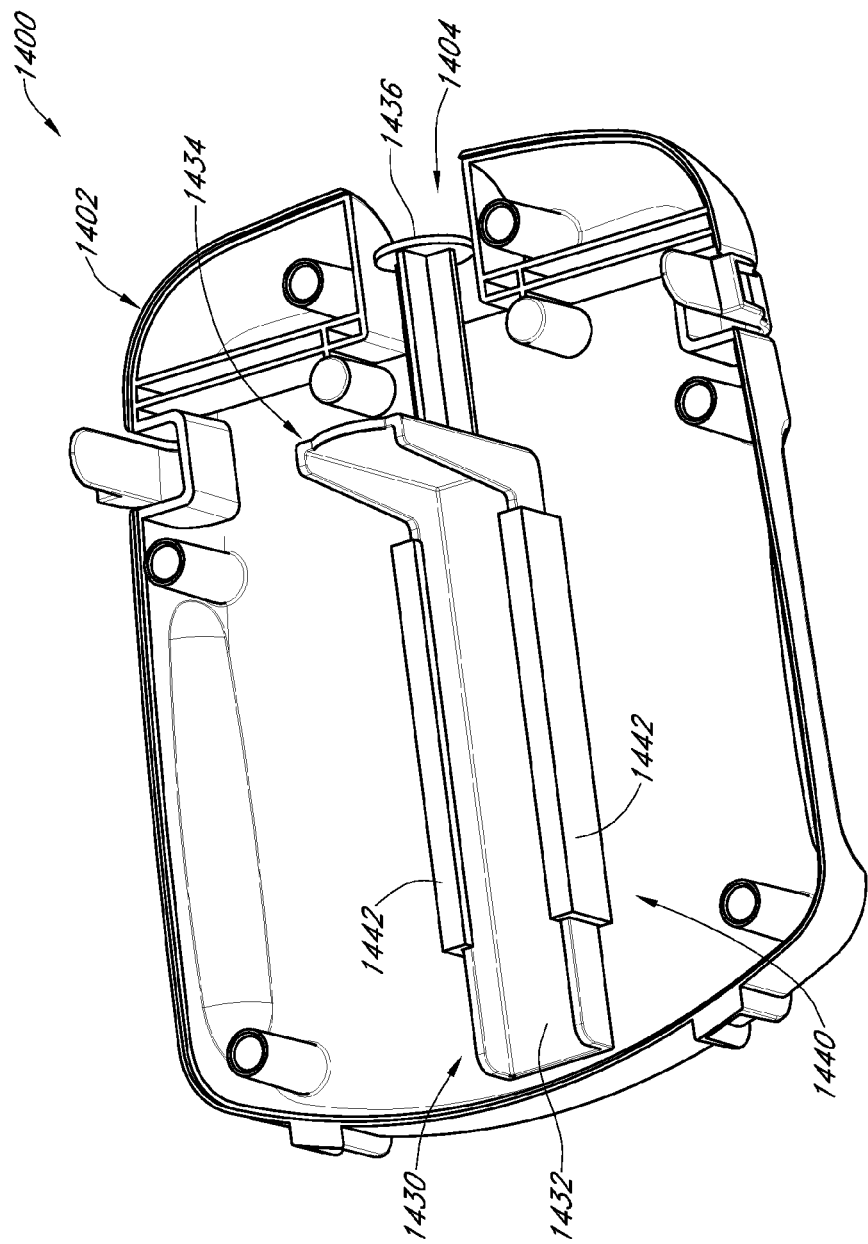
FIGS. 20B and 20C illustrate different views of the cassette of FIG. 20A.

With reference to FIGS. 20A and 20B, the plunger portion 420 of the pre-loaded or pre-filled syringe 400 or other container can be configured to be slidably moved within the interior of the barrel portion 402 to discharge fluids and/or other materials contained therein through the outlet 404 at the syringe's distal end. In some embodiments, the cassette 1400 comprises an actuator member 1430 that is adapted to retain and selectively move the plunger portion 420 of the pre-filled syringe 400. As illustrated in FIG. 20B, the actuator member 1430 can include a main portion 1432 that is adapted to slidably move within a rail system 1440 located along the bottom surface of the cassette interior. In some embodiments, the rail system 1440 comprises two channels 1442 that are shaped, sized and otherwise configured to create a space through which the main portion 1432 of the actuator member 1430 can slide.

As illustrated in FIG. 20A, the actuator member 1430 can comprise a riser 1434 that extends generally vertically from the main portion 1432. In some embodiments, the riser 1434 includes a channel or other retaining portion or shape to help secure the plunger member 420 of the pre-filled syringe 400 or other container loaded onto the cassette 1400. For example, as illustrated in FIG. 20A, the riser 1434 can be adapted to retain the handle or flange portion 422 of the syringe's plunger member 420. Accordingly, movement of the actuator member 1430 relative to the cassette housing 1402 (e.g., within the rail system 1440) can cause the plunger member 420 to move relative to the adjacent barrel portion 402 of the pre-filled syringe 400 or other container.

Figure 20C:
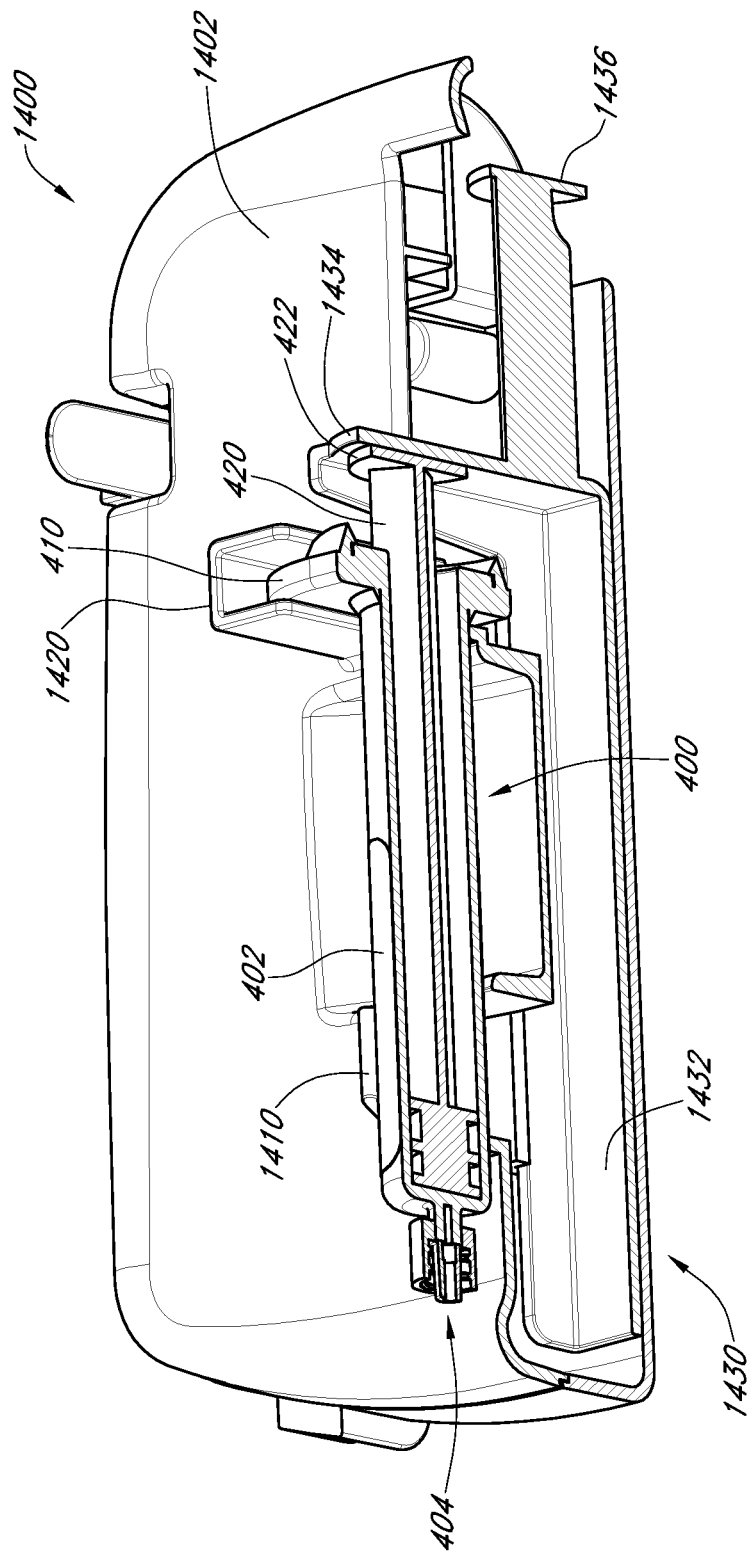

With continued reference to FIG. 20B, the actuator member 1430 can include a stem 1436 or other member that extends from the main portion 1432 and the riser 1434, toward the rear of the cassette 1400. In some embodiments, the stem 1436 is generally aligned with a slot or opening 1404 along the bottom surface of the cassette housing 1402. Accordingly, as with the cassette embodiments discussed herein with reference to, inter alia, FIGS. 4, 8, 12A, 12B and 14, the stem 1436 can be secured within a pusher block of the fluid delivery module. For example, the stem 1436 can be sized, shaped and otherwise configured to replace a plunger member is such other cassette designs. As a result, a motor (e.g., stepper motor), other mechanically-operated movement system and/or any other device or system of the fluid delivery module, can advantageously manipulate the stem 1436 to selectively move the syringe's plunger member 420 relative to its barrel portion 402. As noted above, urging the plunger member 420 within the interior of the barrel portion 402 helps to discharge fluids and/or other materials contained within the pre-filled syringe 400 through its distal outlet 404. Thus, the same motors can be used to discharge fluids out of both the reservoirs (e.g., in a design similar to those illustrated in, inter alia, FIGS. 8 and 14) and a pre-filled syringe (e.g., FIGS. 20A-20C).

According to some embodiments, the outlet 404 of the syringe 400 or other container can include a luer lock fitting and/or any other standard or non-standard connection. For example, the outlet 404 can include a threaded connection, a flanged connection, a snap-fit, pressure-fit or friction-fit connection and/or the like. Thus, a handpiece assembly can be easily and quickly connected to and/or disconnected from the outlet 404 of the pre-filled syringe 400. As discussed with other embodiments herein, the handpiece assembly can include tubing with a fitting 260 configured to mate with a corresponding fitting of the syringe outlet 404 (FIG. 21A-21E).

According to some embodiments, the fluids and/or other materials being delivered from the vials, ampoules and/or other containers to the handpiece assembly 200 are configured to be combined prior to exiting a cassette 300. For example, the contents of two, three or more of the vials or other containers secured to a cassette 300 can mix with one another within a collection member, a hub (or other junction) and/or the like, immediately or substantially immediately downstream of the manifolds positioned within a cassette or at any other location within the injection system. Therefore, in some embodiments, a single-lumen tubing or any other conduit 250 can be used to place the cassette in fluid communication with the downstream handpiece assembly 200 (see, for example, FIGS. 1 and 2).

With continued reference to FIGS. 1 and 2, the tubing 250 or other conduit can include a fitting 260 that is sized, shaped and otherwise configured to mate and connect with a corresponding fitting along a surface of the cassette. For example, in some embodiments, the fitting 260 comprises a standard or non-standard luer lock fitting, a threaded connection and/or the like. In such arrangements, the process by which the tubing 250 is connected to the cassette (or disconnected from it) can be advantageously facilitated (e.g., by allowing a user to quickly, securely and conveniently attach to and detach from the cassette).

Further, since in some embodiments the fluids and/or materials contained within the different vials or other containers are mixed inside the cassette (e.g., before being transferred to the tubing 250), the design of the handpiece assembly 200 can be advantageously simplified. For example, in such arrangements, the need for a core or similar component of the handpiece assembly 200 can be eliminated, as the flow control of the various fluid or other material streams does not occur within the handpiece assembly 200. Relatedly, the need to provide electronic components (e.g., electrical power, buttons or other controllers, other control features, etc.) in the handpiece assembly 200 can be eliminated. Consequently, such a configuration permits the handpiece assembly to have a simpler design, allowing it to be manufactured more inexpensively. Due to such a relatively simplified design, the handpiece assembly 200 can be adapted to be replaced together with the tubing 250 and/or the cassette 300 in accordance with a desired or required protocol (e.g., once a day, every time the type or concentration of the medicaments loaded onto a cassette are altered, etc.). Thus, according to some embodiments, the handpiece assembly is disposable. This can generally facilitate the use and maintenance of the injection system and can help improve the hygienic and safety aspects of the treatment procedures performed using the injection system embodiments disclosed herein.

One embodiment of tubing 250 or other conduit configured to place a handpiece assembly 200 in fluid communication with a cassette or other component of a fluid delivery module is illustrated in FIGS. 21A-21E. In some arrangements, the handpiece assembly 200 and the tubing 250 comprises a unitary structure. For example, the handpiece assembly 200 can be integrally formed with the tubing 250. In one embodiment, the handpiece assembly 200 and the tubing 250 are coextruded, molded or otherwise formed during a single manufacturing procedure. In other configurations, however, the handpiece assembly 200 is separate and distinct from the tubing 250 or other conduit. Thus, one or more attachment devices or methods (e.g., standard or non-standard couplings, other fasteners, adhesives, welds, etc.) can be used to secure the tubing 250 to the handpiece assembly 200, as desired or required.

In any of the embodiments disclosed herein, a handpiece assembly can be partially or completely disposable, either alone or together with the proximal tubing or other conduit that places it in fluid communication with a fluid delivery module. Such disposable embodiments can provide one or more benefits to the clinician and/or the patient. For example, by discarding the entire handpiece assembly, which may include the needle assembly and the tubing connecting the handpiece to an upstream fluid delivery module, the transition between procedures can be improved (e.g., simplified, expedited, etc.). In addition, the risk of infection, cross-contamination and/or the like can be reduced as the need to reuse, clean and/or otherwise prepare the handpiece assembly for a subsequent procedure is eliminated.

As illustrated in FIGS. 21A-21E, the proximal end of the tubing 250 can include a luer lock connection or another standard or non-standard coupling 260 or fitting (e.g., a threaded connection, snap fitting, friction fit fitting, etc.). Regardless of its exact design, such a coupling 260 or fitting can be configured to quickly and easily connect to and disconnect from a corresponding coupling or fitting located on the cassette 300 or other portion of the fluid delivery module 100. For example, as depicted in the detailed view of FIG. 21D, the coupling 260 can comprise a universal luer fitting that may be selectively secured to a cassette. Thus, the connection of the tubing (and any other downstream components, e.g., handpiece assembly 200) to the fluid delivery module can be simplified. For example, according to certain embodiments, the coupling 260 can be detached from a corresponding coupling or fitting (e.g., luer fitting, threaded fitting, etc.) of the cassette 300. In addition, the coupling 260 can be selectively swabbed between patients or as otherwise required or desired. In other embodiments, one or more other cleaning or maintenance protocols can be used to help ensure that a required or desired level of hygiene and safety is maintained.

As noted above, in some embodiments, the different fluid and/or other material streams being delivered from the fluid delivery module to the handpiece assembly 200 can be mixed within the cassette, prior entering the downstream tubing 250 and the handpiece assembly 200. For instance, the fluids and/or other materials can be combined in a hub, a collection member and/or the like, depending on the particular cassette design. However, in other arrangements, the various streams can be mixed within the downstream handpiece assembly 200, the tubing 250 that places the handpiece in fluid communication with the cassette and/or any other portion or component of the fluid delivery module or the injection system, as desired or required. In such configurations, the tubing 250 can have two or more lumens for at least part of its length.

In embodiments where the separate fluids and/or other materials loaded onto a fluid delivery module are mixed prior to exiting the cassette (e.g., immediately downstream of the manifolds), backflow prevention valves can be positioned within each individual line immediately upstream of the mixing location. This can help ensure that fluids and/or other materials do not inadvertently flow backwards through the system, thereby helping to eliminate or reduce the likelihood of undesirable cross-contamination.

Figure 21A:
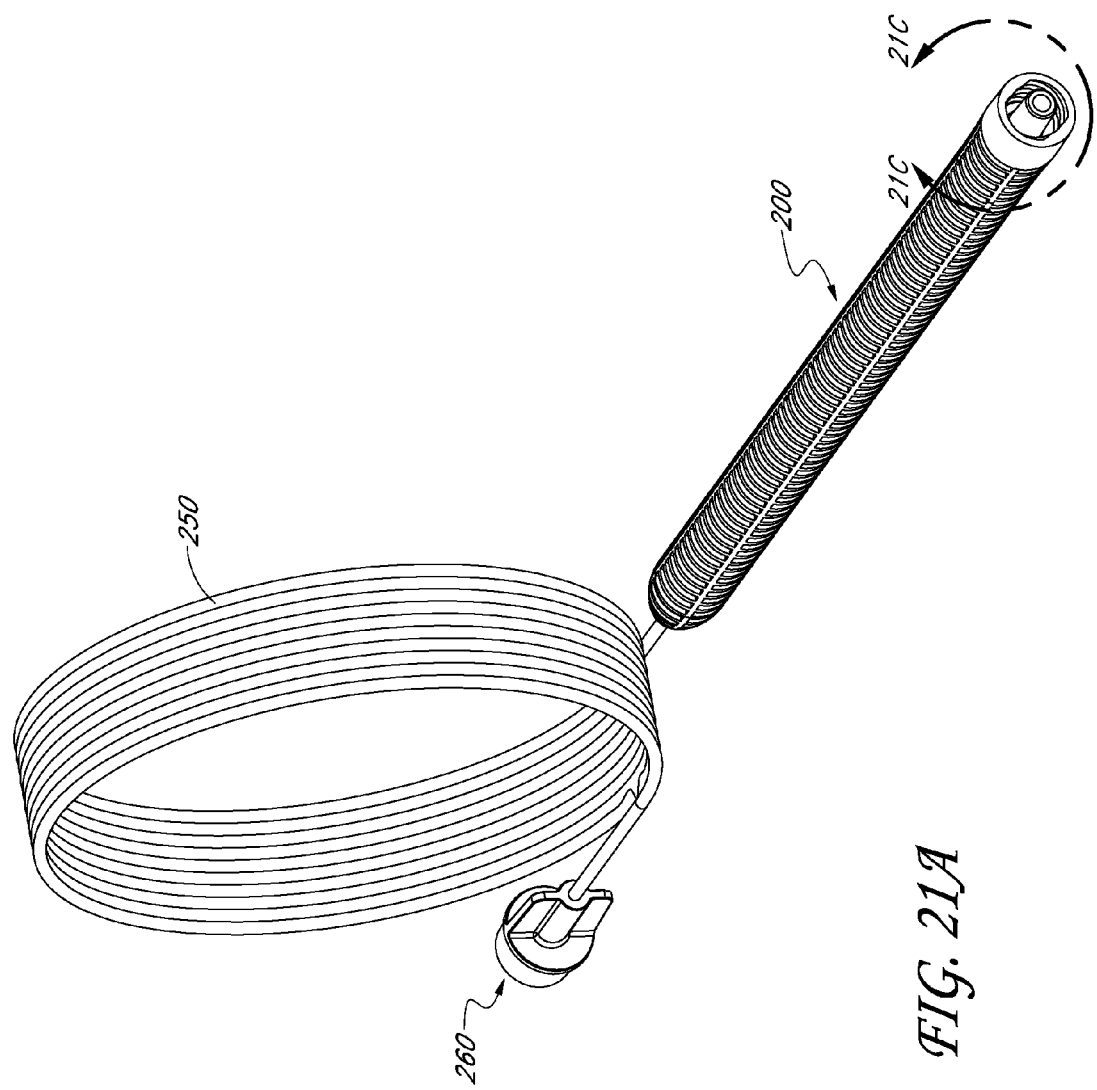
FIGS. 21A-21E illustrate various views of a fluid conduit and a handpiece assembly configured for use with an injection system according to one embodiment.
Figure 21B:
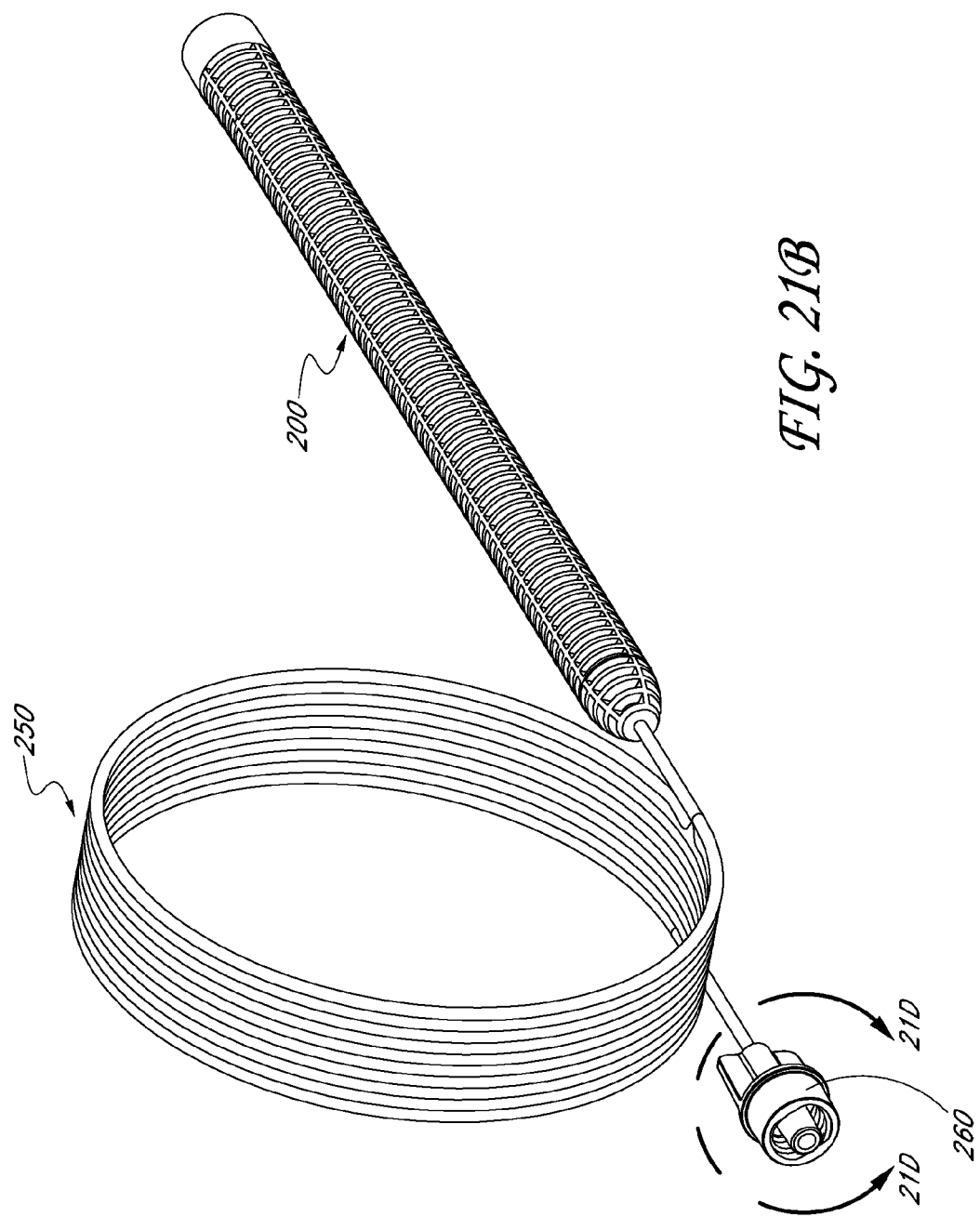
Figure 21C:
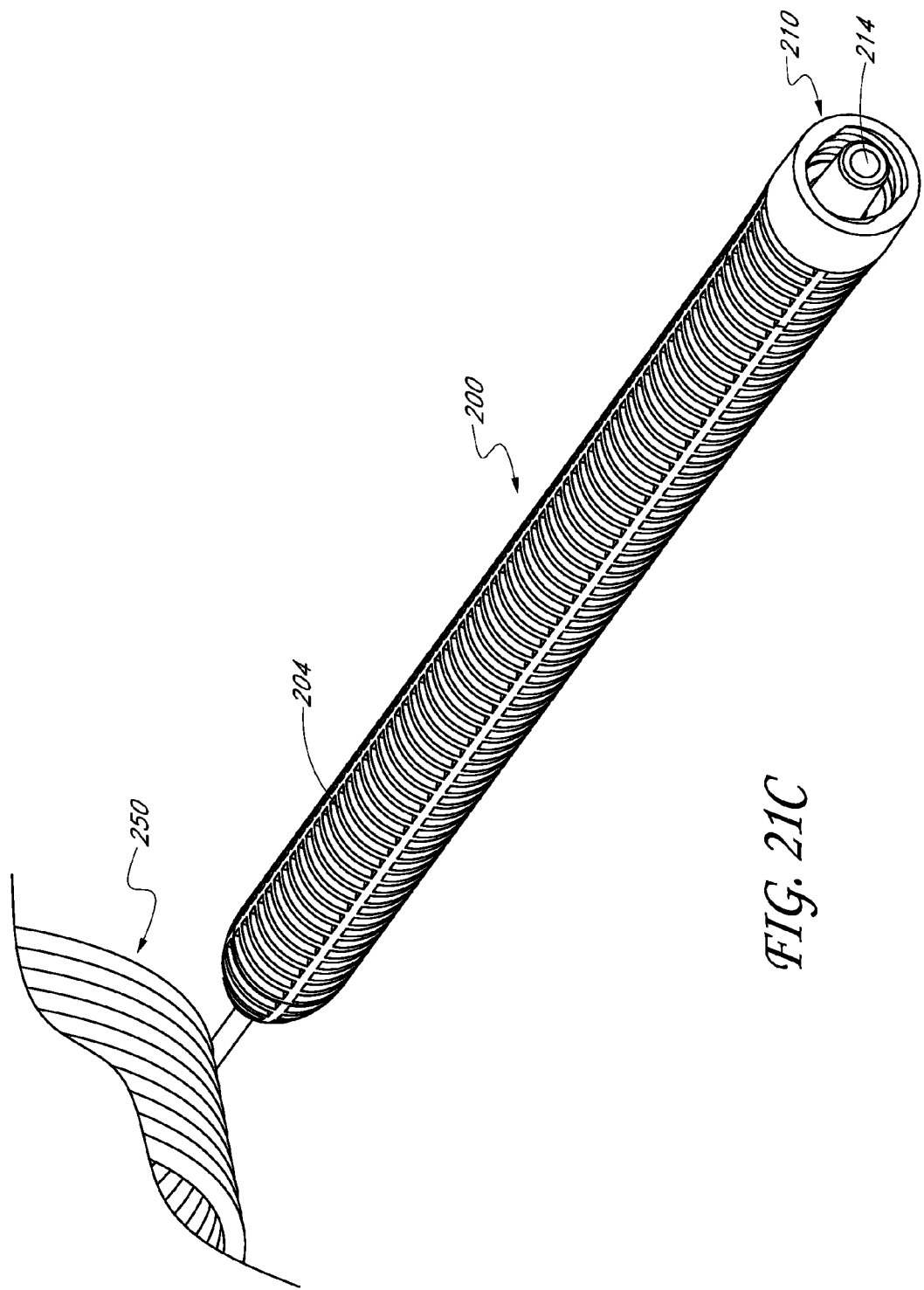
Figure 21D:
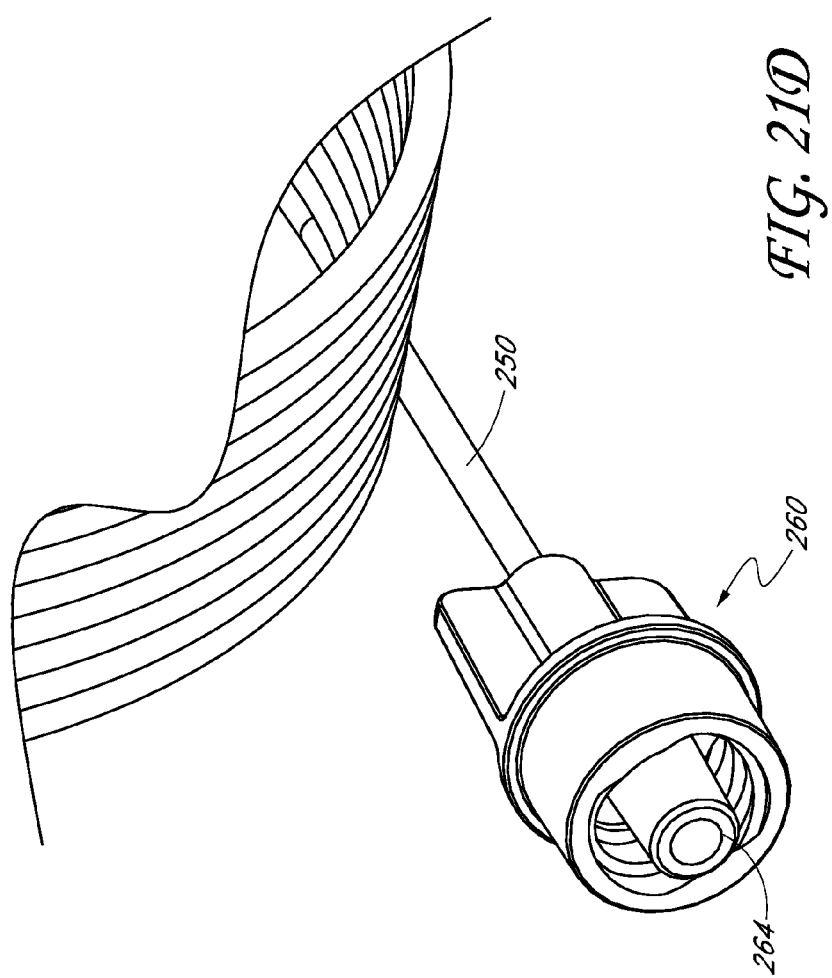
Figure 21E:
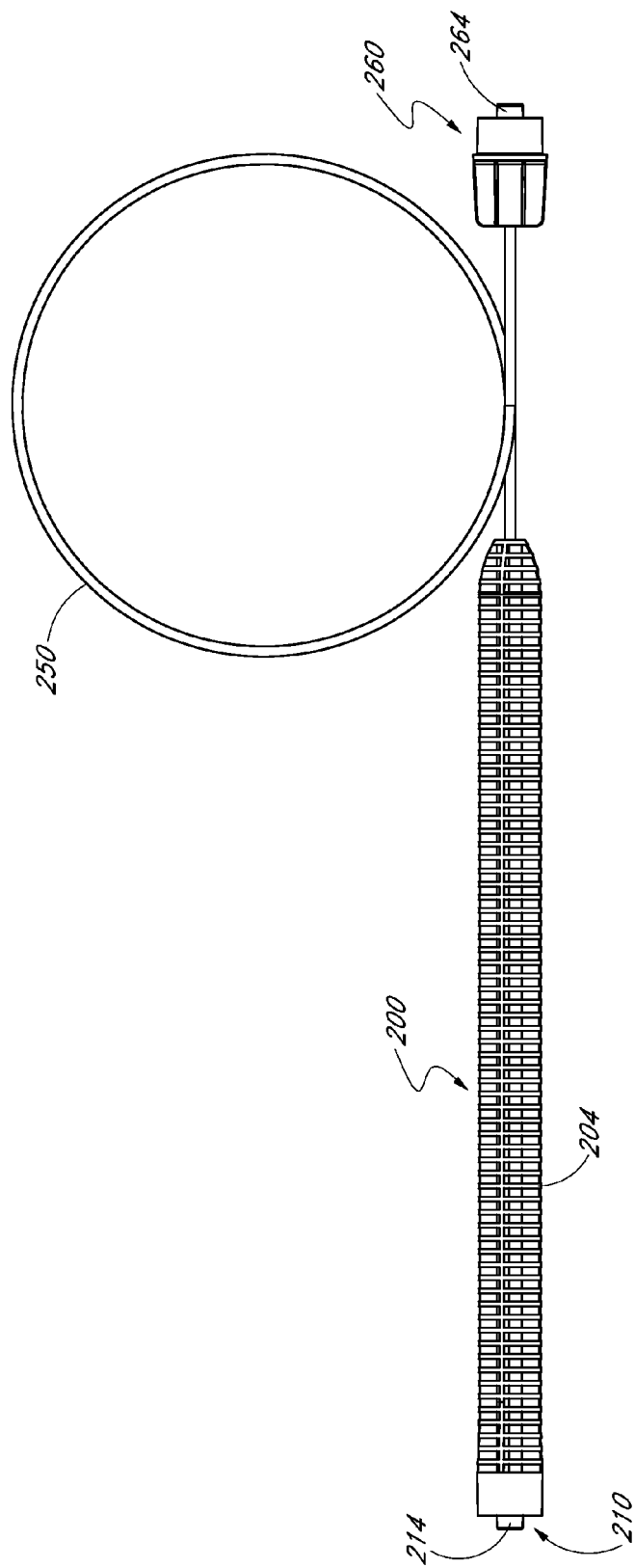

With continued reference to FIGS. 21B and 21C, a distal end 210 of the handpiece assembly 200 can include interior threads that are adapted to engage a corresponding thread pattern (e.g., standard or non-standard) of a needle hub. For example, the needle hub can be attached to the opening using a luer lock connection 214 and/or any other type of standard or non-standard coupling. Thus, a needle can be easily secured to and removed from the distal end of the handpiece assembly 200. This can further facilitate the execution of an injection protocol and the required maintenance between procedures.

The type, size (e.g., gauge), length and/or other details of the needle that may be attached to the distal end 210 of the handpiece assembly 200 can be selected according to the particular application. For example, in some embodiments, the needle has a gauge of approximately 18 G-30 G and a length of approximately 0.5 to 5.0 inches (e.g., 1.0 to 1.5 inches). However, that the gauge, length and/or other details of the needle can be greater or smaller than the range indicated herein, as desired or required by a particular application.

Figure 22A:
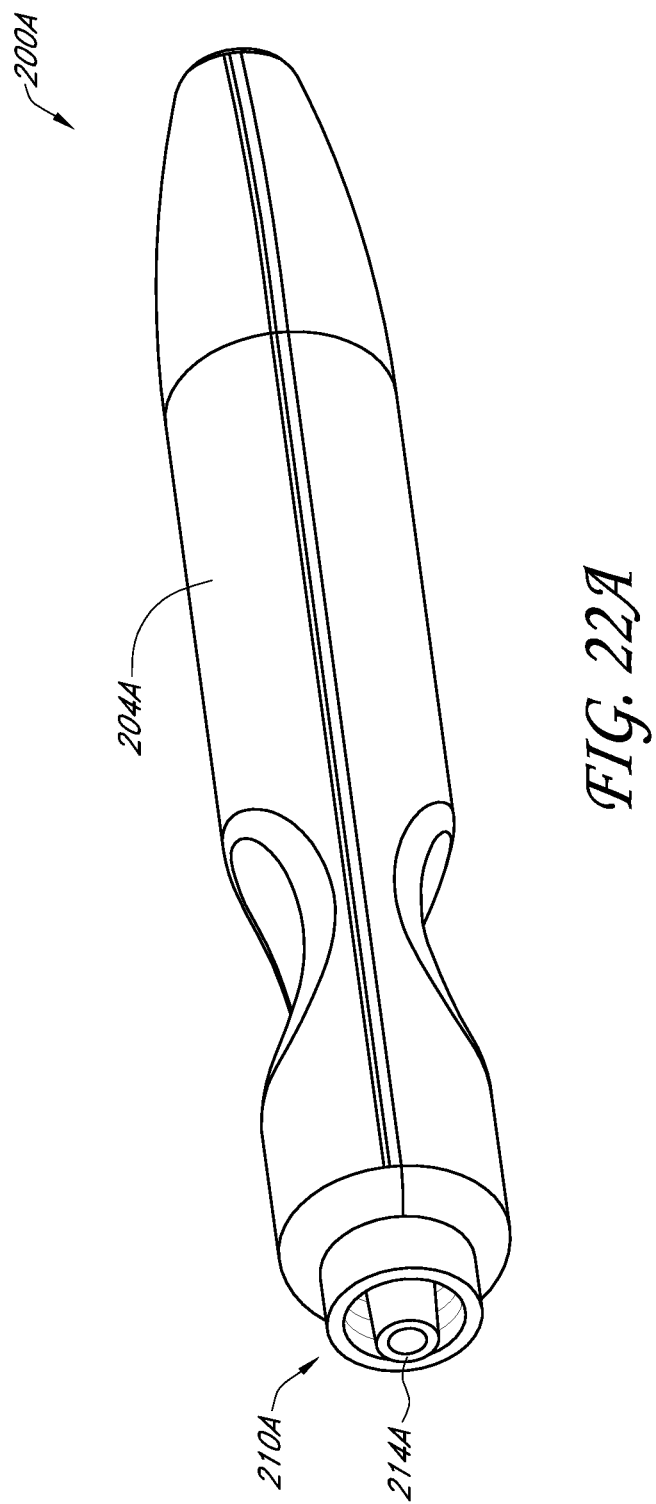

Another embodiment of a handpiece assembly 200A configured for use with an injection system is illustrated in FIGS. 22A and 22B. As shown, the handpiece assembly 200A can include an outer housing 204A that is configured to surround the fluid conduit 250 passing therethrough. As discussed herein with reference to other arrangements, the fluid conduit 250 can be adapted to selectively place a tip 210A (and downstream needle) or other distal portion of the handpiece assembly 200A in fluid communication with the cassette or other portion of the fluid delivery module. According to certain embodiments, as illustrated in FIGS. 22A and 22B, the handpiece assembly 200A is a separate item from the fluid conduit 250. However, in other embodiments, the handpiece assembly 200A and the fluid conduit 250 are coextruded, molded or otherwise manufactured as a unitary structure.

Figure 23A:
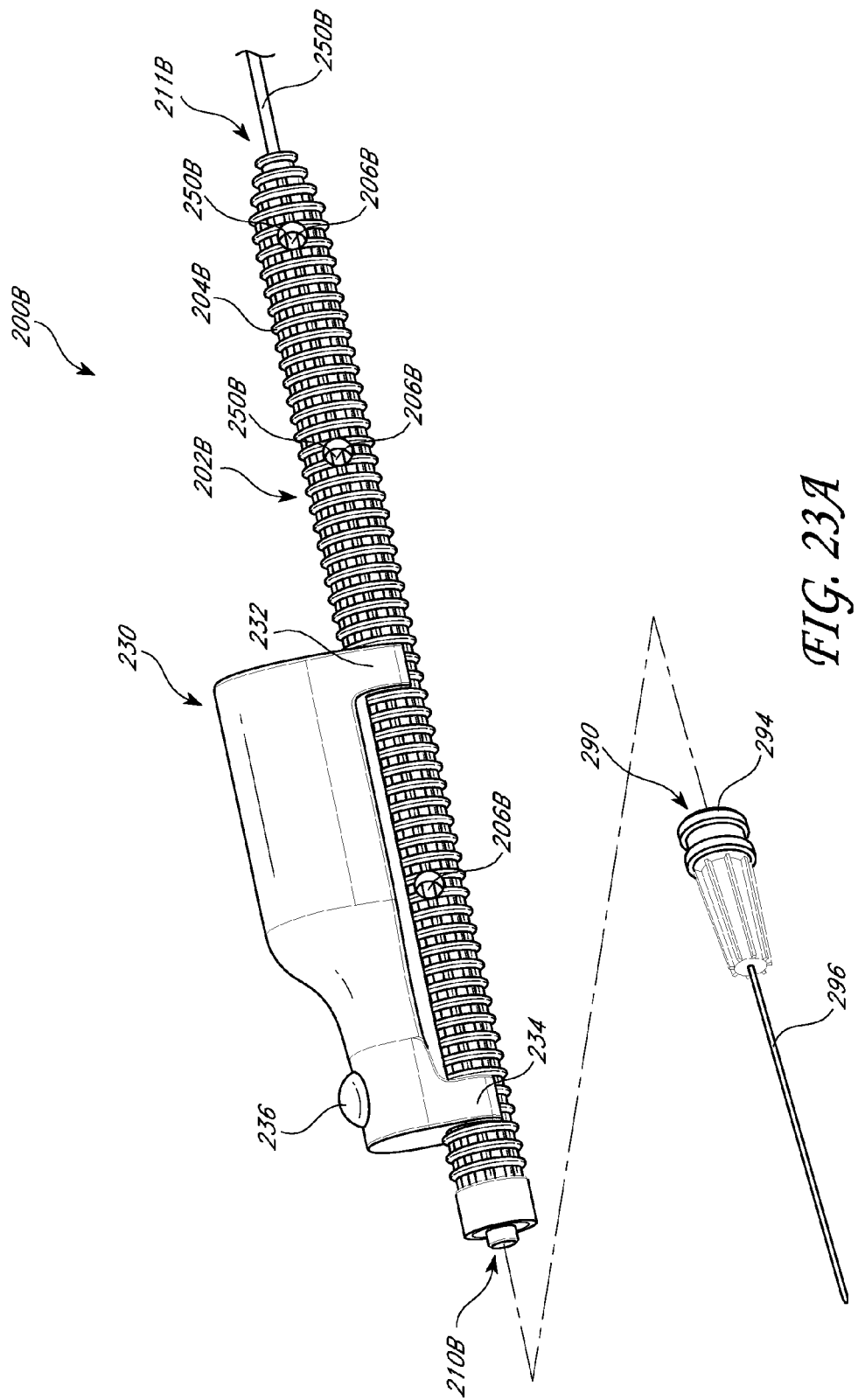
FIG. 23A illustrates a perspective view of a handpiece assembly configured to receive a removable control module.
Figure 23B:
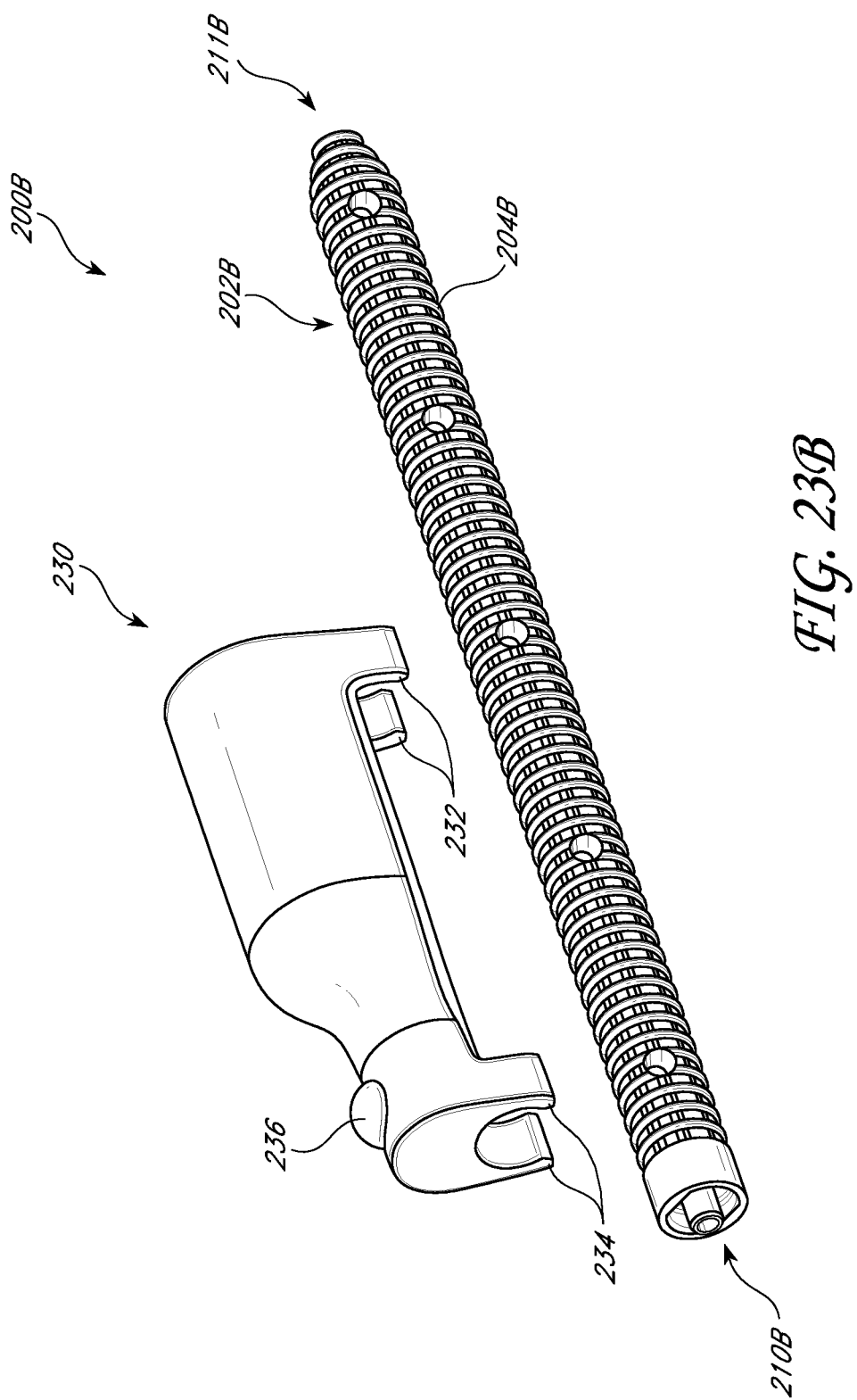
FIG. 23B illustrates an exploded view of the handpiece assembly and control module of FIG. 23A.

Another embodiment of a handpiece assembly 200B is illustrated in FIGS. 23A and 23B. As shown, the handpiece assembly 200B can include a handpiece portion 202B having an outer housing 204B. In some embodiments, the handpiece portion 202B is manufactured using a molding process (e.g., injection molding, compression molding, etc.), extrusion process, thermoforming, casting and/or other process. The handpiece assembly can comprise one or more materials, such as, for example, thermoplastics, elastomers, metals and/or the like. As illustrated in FIGS. 23A and 23B, the handpiece portion 202B can include a corrugated, ribbed and/or other textured design. In some embodiments, such a configuration can serve one or more purposes and/or provide one or more benefits. For example, a textured design can improve the ability of a user to grasp and manipulate the handpiece assembly, provide an enhanced surface for attachment of control module 230 or other device and/or the like.

With continued reference to FIGS. 23A and 23B, the handpiece 202B can include one or more holes or other openings 206B along the outer housing 204B. Such holes 206B can extend partially or completely through the body of the handpiece portion 202B. In some embodiments, the holes or openings 206B are sized, shaped, oriented and otherwise configured to receive corresponding protrusions or other portions or features of a control module 230. Accordingly, the openings 206B can provide a way to more securely attach a control module 230 and/or other device or item to the handpiece 202B. In other embodiments, a handpiece portion includes openings having a different size, shape (e.g., oval, rectangular, irregular, etc.), orientation and/or other characteristics, as desired or required. Alternatively, a handpiece can include one or more other features configured to secure a control module or other item thereto, either in addition to or in lieu of holes or openings 206B. For example, the handpiece 202B can comprise couplings, tabs, fittings and/or the like. In yet other arrangements, a handpiece portion includes no openings and no other securement features or items at all.

With continued reference to FIGS. 23A and 23B, the assembly 200B can include tubing 250B that places the handpiece portion 202B in fluid communication with a cassette or other portion of a fluid delivery module. Thus, one or more fluids and/or other materials discharged from the fluid delivery module can be advantageously delivered within a person's anatomy (e.g., joint, organ, cavity, etc.) through a needle (not shown) secured to the distal end 210B of the handpiece 202B. As depicted in FIGS. 23A and 23B, the tubing 250B can enter the proximal end 211B of the handpiece portion 202B and pass through an interior thereof. In embodiments of the handpiece that comprise holes or other openings 206B, the tubing 250B can be visible from the exterior of the handpiece assembly.

As discussed in greater detail herein, the tubing 250B can include one or more flexible materials, such as, for example, plastics, elastomers and/or the like. In other arrangements, the tubing comprises a rigid and/or semi-rigid material (e.g., plastic, metal, glass, other natural or synthetic materials, etc.), as desired or required. Depending on the number of fluid and/or other material streams that an injection system is configured to handle, the particular cassette design being used and/or any other factors, the tubing can include a single lumen or a multi-lumen design. For example, for the cassette embodiments discussed herein with reference to FIGS. 8 and 14, single-lumen tubing can be used to place the handpiece in fluid communication with the fluid delivery module. A single-lumen tubing configuration can also be utilized when a cassette is configured to receive the contents from a single pre-filled syringe (e.g., FIGS. 20A-20C), vial, ampoule or other container. However, in arrangements where multiple fluid and/or other material streams are configured to be combined downstream of the cassette or other portion of the fluid delivery module, tubing can include two, three or more lumens, as desired or required.

As discussed above and illustrated in FIGS. 23A and 23B, in some embodiments, a handpiece assembly 200B comprises a control module 230 that can be removably attached to the handpiece portion 202B. The control module 230 can include one or more clips 232, 234, tabs and/or other securement members that are adapted to facilitate attachment to and detachment from the handpiece portion 202B. For example, a securement member 232, 234 can include a protruding portion or feature that is sized, shaped and otherwise configured to mate with a corresponding opening 206B along the handpiece housing 204B. In the depicted embodiment, the control module 230 includes two proximal clips or tabs 232 and two distal clips or tabs 234. However, in other arrangements, a control module or other removable portion or component includes more or fewer (and/or different) securement members. Any other device and/or method of securing the control module to the handpiece can be used.

According to some embodiments, the control module 230 comprises one or more buttons 236 controllers and/or other adjustment devices (e.g., knobs, dials, switches, etc.). Such buttons or other controllers 236 can help regulate the delivery of various fluids and/or other materials through the handpiece assembly 200. For example, the button 236 illustrated in FIGS. 23A and 23B can be used to activate or deactivate (e.g., ON/OFF) the delivery of one or more fluids and/or other substances to a patient's anatomical location (e.g., joint, organ, cavity, etc.). In certain embodiments, the buttons or other controllers are manipulated to regulate the rate of delivery (e.g., flowrate) of one or more medicaments and/or other materials being transferred through the handpiece assembly 200. As discussed in greater detail herein, in embodiments where the fluid delivery module is in data communication with one or more other components or devices (e.g., ultrasound devices, radio frequency spectroscopy devices, other imaging devices or systems, etc.), one or more buttons 236 or other controllers on the control module 230 and/or other portions of the injection system can be used to help regulate the operation of such systems. For example, one or more buttons or other controllers of a control module can be used to capture an ultrasound image or video while a target anatomical space (e.g., joint, organ, etc.) is being located and/or while one or more fluids or other materials are being injected into a target anatomical location. Alternatively, the buttons or other controllers can be used to vary one or more other aspects of an imaging system, such as, for example, zoom, resolution, contrast, brightness and/or the like. In some embodiments, a control module 230 includes additional, fewer and/or different buttons, knobs, levers and/or other control devices that permit a user to control one or more aspects of the injection system.

With continued reference to FIGS. 23A and 23B, the buttons 236 or other controllers of the control module 230 can be used to initiate and/or terminate a particular injection procedure. Thus, once a particular injection protocol has been selected by a user (e.g., through the display or other interface of the fluid delivery module), pressing the button 236 and/or otherwise manipulating another controller can regulate one or more aspects of the delivery of fluids and/or other materials through the handpiece assembly. For example, by pressing or manipulating the button 236 once, the injection procedure can be initiated. In some embodiments, additional manipulation of the button 236 can terminate or temporarily pause the procedure. In yet other embodiments, manipulation of the button or other controller can alter the flowrate, sequence and/or any other aspect of an injection procedure.

According to certain embodiments, a control module 230 and/or any other portion of a handpiece assembly or injection system comprises one or more two-mode or other multi-mode buttons and/or other controllers. Pressing or otherwise manipulating such a button can commence or terminate (e.g., in an alternating pattern) the delivery of one or more fluids and/or other materials through the assembly. Alternatively, the handpiece assembly 200B can include one or more other types of buttons or controllers. In some arrangements, the buttons 236 are configured to permit the user to select between two, three or more different settings. In other embodiments, a button is of the multi-depth type (e.g., dual-depth, tri-depth, etc.), enabling a user to selectively press the button to two or more distinct depths or other levels. Each distinct depth or level can correspond to a particular setting (e.g., flowrate, selection of which fluids or other materials to deliver, etc.). For example, pressing the button to the first level can cause the desired fluid and/or other material to be conveyed at the maximum or minimum rate. Further, continuing to press the button to subsequent lower levels can cause the rate of delivery to increase, decrease or terminate. In other embodiments, the handpiece assembly comprises multi-depth buttons that do not include distinct depths, such as, for example, a rheostat. Thus, a particular setting (e.g., flowrate) can be varied based on the depth to which a button is depressed.

In other arrangements, the control module 230 comprises one or more buttons 236 that have only two positions, but which are configured to permit a user to select between three or more different settings. For example, an injection system can be adapted to sequentially move between different flowrate settings (e.g., high-medium-low-off, vice versa, etc.) every time such a button is pressed.

In addition, a control module 230 and/or another portion of a handpiece assembly 200B can comprise other types of controllers, either in lieu of or in addition to buttons. For example, the handpiece assembly can include a roller ball, a roller wheel, a dial, a knob, a modulating switch or other device and/or the like. Regardless of their exact configuration and design, such control devices can enable a clinician or other user to regulate the delivery of fluids and/or other materials from the fluid delivery module to a patient. As discussed, the various fluids and/or other materials loaded onto a cassette or other portion of a fluid delivery module can be delivered through the handpiece assembly 200B simultaneously and/or sequentially, as desired or required. For example, a user can pre-select a desired injection protocol, which includes the rate of delivery, the sequence of delivery, the volume or other amount to be delivered and/or other details for each medicament, other fluid and/or other substance used in a particular treatment. Thus, a user simply has to press, release or otherwise manipulate the button 236 (or other controller) of the control module 230 in order to initiate, terminate, pause or otherwise alter the preselected protocol.

In relation to any of the embodiments disclosed herein, an injection system can be configured to transfer two or more fluids and/or other materials from a fluid delivery module to a joint or other targeted anatomical location sequentially and/or simultaneously, in accordance with a specific delivery protocol. For example, a protocol can require that, for some time period, fluids A and B (e.g., loaded in separate loading areas of a cassette or other portion of a fluid delivery module) be delivered to a joint simultaneously. Further, during a separate sequential delivery stage, which may occur either before or after the simultaneous delivery, the injection protocol can cause fluid A to be delivered to the patient before fluid B. Fluids A and B can differ from one another in a variety of ways, including in the formulation or type of drug or other material, in strength, concentration or dosage (e.g., thus, fluids A and B can comprise the same formulation but a different concentration) and/or the like. Thus, an injection system can be configured to deliver two or more drugs, medicaments and/or other fluids or materials sequentially, simultaneously or both sequentially and simultaneously, depending on the specific injection protocol being used by the clinician.

In other embodiments, such buttons and/or other controllers 236 can be used to select which fluids or other materials, or combinations thereof, are to be directed through the handpiece assembly 200B. In other embodiments, the controllers are configured to control the rate of delivery (e.g., flowrate) of such fluids and/or other substances to a patient. In still other arrangements, the buttons control one or more other aspects of the injection procedure (e.g., the sequence of delivery, an ultrasound or other imaging device that is in data communication with the injection system, etc.).

In other embodiments, one or more buttons 236 of the control module 230 are adapted to guide the user through one or more user-interface screens on the display or graphic user interface (GUI) 130, 130A (FIGS. 1 and 2) on the fluid delivery module. Thus, the buttons 236 and/or other controllers located on the control module 230 or otherwise associated within a handpiece assembly 200B can be used to make selections through one or more menus or the like.

In any of the embodiments disclosed herein, a control module can be connected to the fluid delivery module of the injection system using a radio frequency (RF) or other wireless connection (e.g., Bluetooth, Wi-Fi, etc.). However, the control module 230 can be configured to communicate with the fluid delivery module and/or any other component of the injection system using a hardwired connection, either in addition to or in lieu of a wireless connection. The control module 230 can comprise one or more disposable or rechargeable batteries (e.g., standard or non-standard batteries, battery packs, etc.). In some embodiments, the batteries of the control module are configured to be recharged when the control module 230 is placed within or near a docking station or other recharging location (e.g., of the fluid delivery module, other portion or component of the injection system, etc.). In some embodiments, batteries (e.g., standard or non-standard batteries, battery packs, etc.) configured to power the control module 230 can be removed from the control module before being recharged (e.g., by placement in or near a recharging device or location). Such batteries (not shown) can be positioned within an interior portion of the control module 230. In some embodiments, the fluid delivery module or another component of the injection system comprises a docking station that is adapted to recharge a battery using electromagnetic induction, simple charging (e.g., using a DC or AC connection), pulse charging and/or any other charging method or device. Thus, in some arrangements, the batteries within the control module 230 can be permitted to recharge when the handpiece assembly is not in use. Alternatively, the control module 230 can be configured to draw its power from one or more other sources, such as, for example, a DC or AC hardwired connection and/or the like. In yet other embodiments, an injection system comprises two or more control modules 230, allowing one or more modules to be recharged while the handpiece assembly 200B is being utilized.

In addition to batteries, an interior portion of the control module 230 can include circuitry, indicator lights (e.g., LEDs) and/or any other component or feature. For example, the control module 230 can include one or more indicator lights that provide information to the clinician or other user of the assembly prior to, during and/or following an injection procedure. For example, an LED or other indicator light can be configured to light up when the battery power of the module is above or below a particular threshold level (e.g., adequately charged, in need of charging, etc.). Alternatively, the brightness, color and/or other characteristics of the indicator light can be configured to change in response to certain conditions. For instance, the properties of the light can vary based on the strength of the battery, on the signal strength of the wireless connection (e.g., RF, Bluetooth, etc.) between the control module 230 and the fluid delivery module and/or another component of the injection system and/or any other aspect associated with the injection system.

With continued reference to FIG. 23A, the distal end 210B of the handpiece 202B can be configured to removably receive a needle assembly 290. As shown, a luer lock connection or other standard or non-standard fitting at the distal end 210B of the handpiece 202B can be adapted to receive a corresponding hub or base portion 294 of the needle assembly 290. The needle 296, which distally extends past the hub 294, can include a gauge of 18 G-30 G and a length of about 0.5 to 5.0 inches (e.g., 1.0 to 1.5 inches). However, in other embodiments, the gauge, length and/or other details of the needle can be greater or smaller than the range indicated above, as desired or required by a particular application. Further, the needle can comprise surgical-grade stainless steel and/or any other suitable material (e.g., other metals, alloys, etc.).

Following an injection procedure, if a user wishes to discard the handpiece assembly 200B, he or she can easily and conveniently remove the control module 230 from the handpiece portion 202B. The control module 230 can be subsequently attached to another (e.g., new, sterile, etc.) handpiece assembly before initiating a new treatment protocol. However, in any of the embodiments disclosed herein, or equivalents thereof, the transfer of fluids and/or other materials from a fluid delivery module (e.g., cassette) to and through the handpiece assembly need not include a control module that attaches to the handpiece portion. For example, a clinician or other user of the injection system can control the flow of fluids and/or other materials through the injection system using a foot pedal, buttons or controllers located along or near the fluid delivery module or on another component or portion of the system and/or the like. Alternatively, such button or controllers are directly incorporated into a unitary handpiece design. In other embodiments, the injection procedure is controlled using a separate device that is in data communication with the injection system (e.g., a separate computer, handheld device, Smartphone, etc.), using audible commands and/or the like, as desired or required. In some embodiments, such a separate device is not located in close proximity to one or more components of the injection system.

Figure 24:
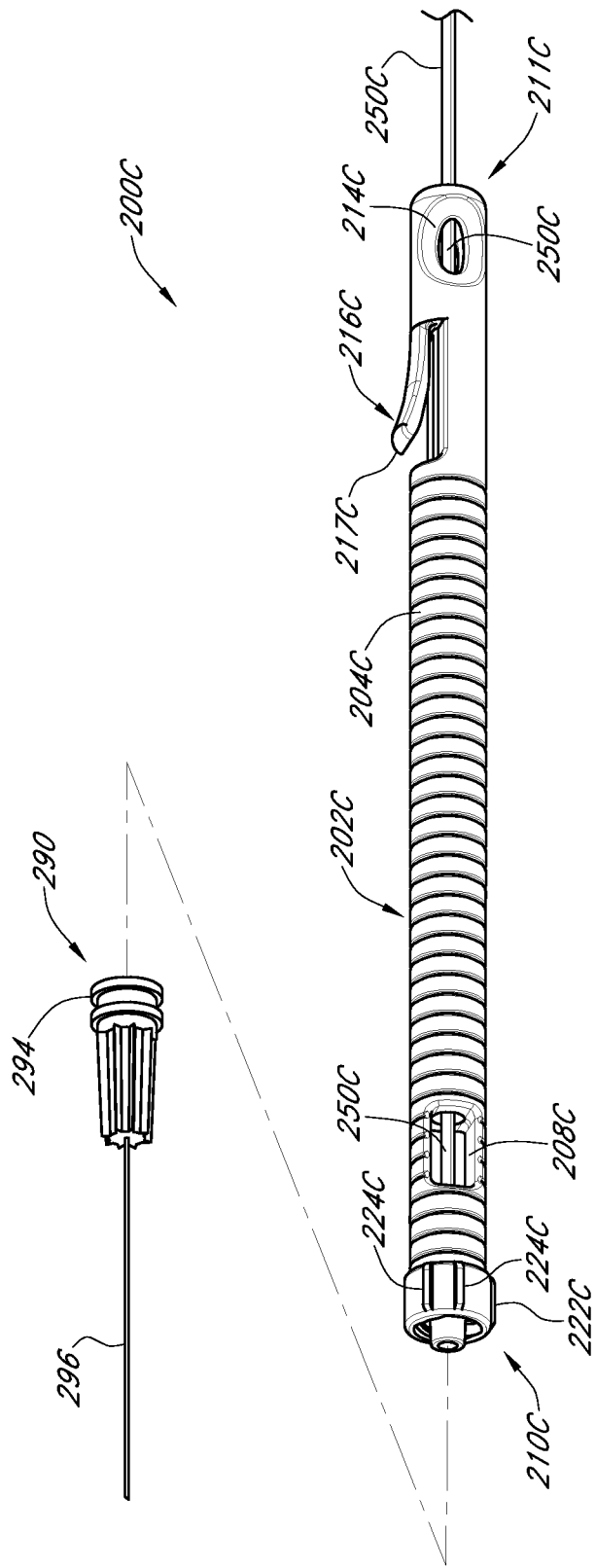
FIG. 24 illustrates a perspective side view of another embodiment of a handpiece assembly.

Another embodiment of a disposable handpiece assembly 200C configured for use with an injection system is illustrated in FIG. 24. As shown in FIGS. 26A-27C and discussed in greater detail herein, the handpiece assembly 200C can be sized, shaped and otherwise adapted to removably receive a control module 230' along its handpiece portion 202C.

With reference to FIG. 24, the handpiece 202C can comprise one or more rigid, semi-rigid and/or flexible materials, such as, for example, plastics, elastomers, metals, other natural or synthetic materials and/or the like. In addition, the handpiece can be manufactured using a molding process (e.g., injection molding, compression molding, etc.), an extrusion process, thermoforming, casting and/or other method. As discussed herein with reference to other embodiments, the handpiece assembly 200C can be configured to attach to and disconnect from a fluid delivery module (e.g., a cassette) and/or another component of the injection system using a luer lock connection or another quick-connect fitting or coupling (e.g., threaded connection, snap-fit connection, friction-fit connection, flanged connection, etc.). Thus, in disposable arrangements, the handpiece assembly 200C can be attached and/or removed from the rest of the injection system with relative ease and quickness. This can advantageously permit a clinician to complete a treatment procedure in less time, and thus, to perform more procedures and treat more patients during a particular time period. As noted herein, in some embodiments, the handpiece portion 202C, the tubing 250C and other portions of the assembly 200C are disposable, allowing a clinician or other user to discard and replace the handpiece assembly 200C between patients and injection procedures.

With continued reference to FIG. 24, the handpiece assembly 200C can include tubing 250C that places the handpiece portion 202C (and thus, the needle assembly 290 that is configured to removably attach to the distal end 210C thereof) in fluid communication with a fluid delivery module (e.g., cassette) and/or other portion of the injection system. As shown in FIG. 24 and discussed with reference to other embodiments herein, the distal end 210C of the handpiece 200C can include a luer connection or another standard or non-standard coupling (e.g., having a threaded, snap-fit, friction-fit, flanged, clipped and/or other type of connection). Accordingly, the hub 294 or other proximal portion of the needle assembly 290 can include a corresponding fitting or connection, allowing the needle assembly 290 to be quickly attached to and/or removed from the handpiece portion 202C.

Figure 25B:
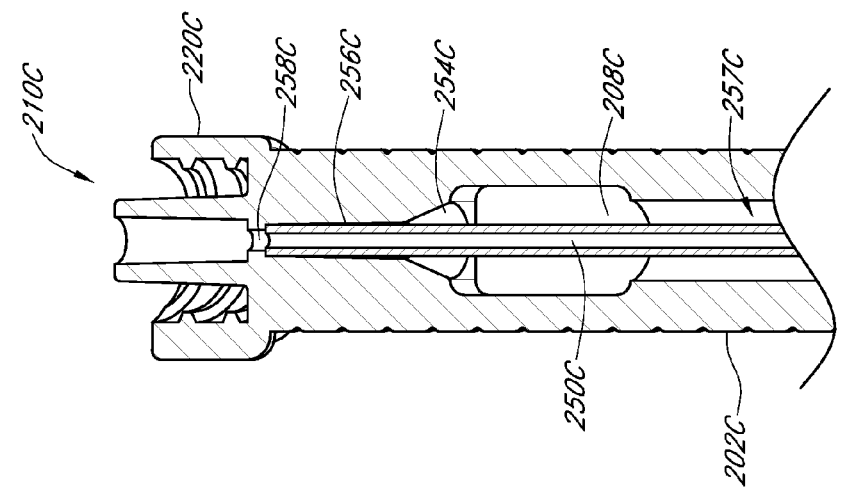
FIG. 25B illustrates a cross-sectional view of the handpiece assembly of FIG. 24.
Figure 25A:
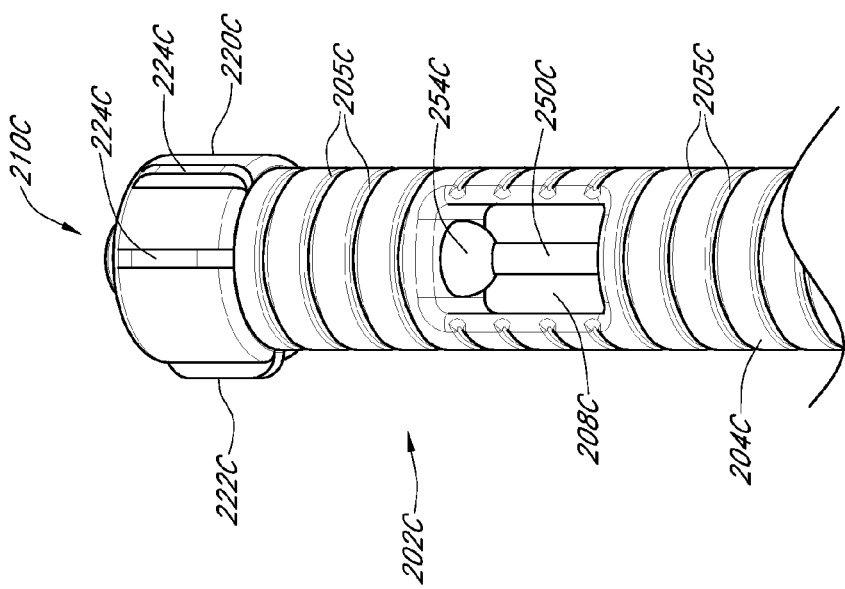
FIG. 25A illustrates a detailed side perspective view of the handpiece assembly of FIG. 24.

As illustrated in FIGS. 24, 25A and 25B, the tubing 250C (e.g., single lumen, multi-lumen, etc.) can pass through an opening along the proximal end 211C, at least partially through an interior of the handpiece portion 202C. In some embodiments, the tubing 250C is routed along or near a centerline of the handpiece interior. Alternatively, however, the tubing 250C is not routed along or near the centerline of the handpiece interior. For example, the tubing 250C can be oriented along or near the handpiece housing 204C or any other surface or area. One or more supports, guides or other members can be used to maintain the desired position of the tubing 250C relative to the handpiece interior.

With continued reference to FIGS. 25A and 25B, the tubing 250C can be maintained within the handpiece 202C using, among other things, one or more tight-fit connections 256C. For example, in the illustrated embodiment, the tubing 250C is secured to the interior of the handpiece 202C using a single tight-fit connection 256C along the distal portion of the handpiece. Alternatively, the tubing 250C can be secured to the handpiece using additional tight-fit connections and/or any other type of attachment method or device (e.g., tabs, fasteners, welds, adhesives, hot melt connections, etc.). As depicted in FIGS. 25A and 25B, the tubing 250C can be attached to the handpiece 202C using an adhesive 254C. In some embodiments, the adhesive 254C comprises a UV adhesive and/or another type of adhesive selected to be compatible with both the tubing 250C and handpiece 202C materials. For example, UV adhesive 254C can be used to bond the tubing 250C to a handpiece portion 202C comprising polycarbonate. In some embodiments, the tubing 250C can be attached to adjacent interior surfaces of the handpiece 202C at two or more locations, as desired or required. Further, as illustrated in FIG. 25B, in one or more portions of the handpiece, a clearance fit 257C can exist between the outside of the tubing 250C and the interior surfaces of the handpiece.

In other embodiments, the handpiece comprises a different type of thermoplastic and/or another material (e.g., metal, alloy, elastomeric material, a composite, other synthetic or natural material, etc.), either in lieu of or in addition to polycarbonate. For example, one or more portions of the handpiece portion 202C can include polyethylene, polypropylene and/or other plastics. According to some embodiments, all or some of the handpiece portion 202C is overmolded on the tubing 250C. Alternatively, as discussed in greater detail herein, one or more other manufacturing methods can be used to make the tubing 250C, the handpiece 202C and the other components and portions of the handpiece assembly 200C, such as, for example, extrusion, thermoforming, injection molding, other molding methods, casting and/or the like.

With continued reference to FIGS. 25A and 25B, the handpiece 202C can include one or more windows 208C or other openings along its outer housing 204C. As shown, such openings 208C can provide access to the tubing 250C routed through the handpiece and/or any other interior components or portions of the handpiece. In some embodiments, the windows or openings 208C can facilitate manufacturing and/or assembly of the handpiece assembly 200C. For example, the opening 208C can provide an access point for supplying an adhesive 254C (e.g. a UV adhesive) to the tubing/handpiece interface. In some embodiments, such openings 208C can provide a location to which a removable control module or other device can be secured to the handpiece portion 202C.

As shown in FIGS. 25A and 25B, the distal end 210C of the handpiece 202C can include a coupling 220C that includes a luer lock or other fitting (e.g., configured to selectively receive and mate with a corresponding feature of a needle assembly). As discussed in greater detail below with reference to FIGS. 27A and 27B, the distal coupling 220C can include one or more orientation rails 222C, 224C, protrusions and/or other features adapted to generally align with and engage corresponding recesses or other features of a control module or other device designed to removably secure to the handpiece portion 202C.

Figure 26A:
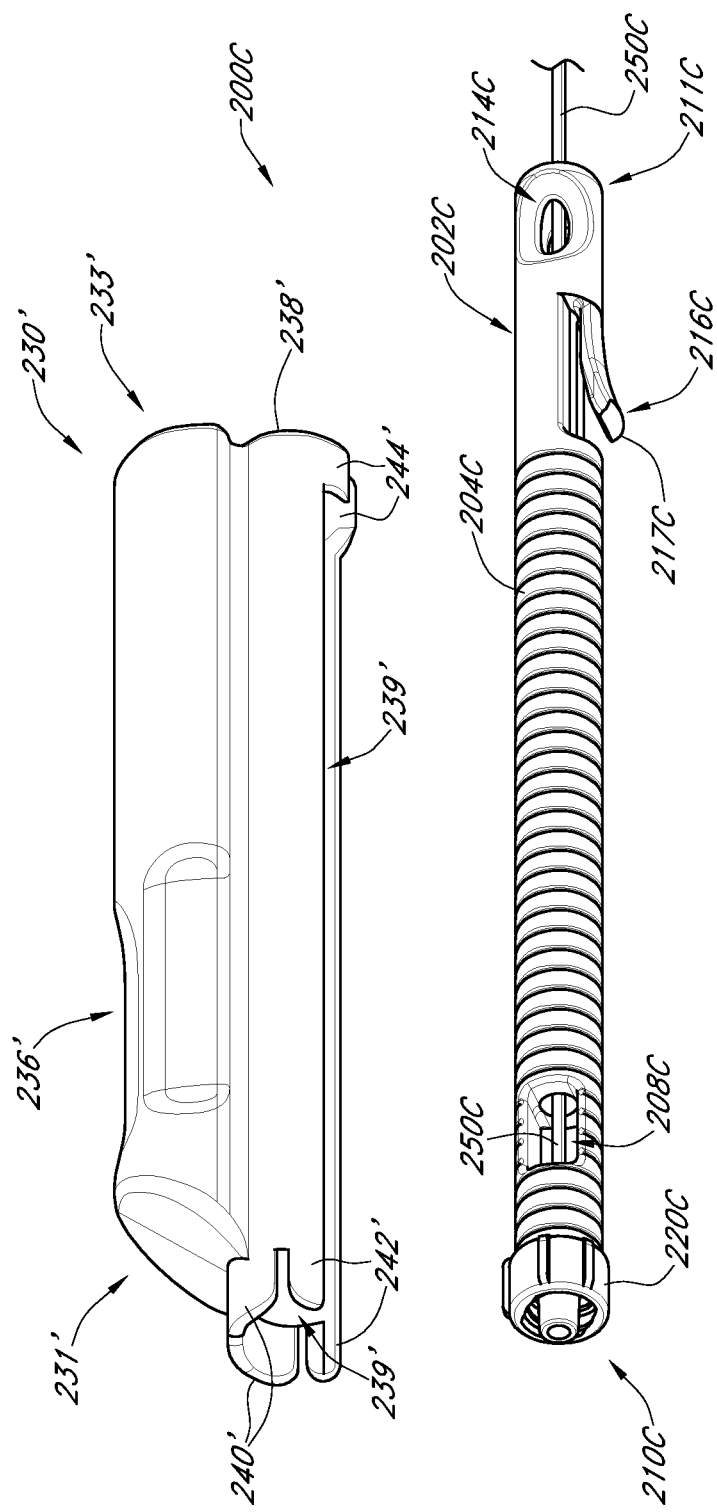
FIGS. 26A and 26B illustrate different views of the handpiece assembly of FIG. 24 and a control module configured to attach thereto.

With reference to FIG. 26A, a control module 230' can be sized, shaped and otherwise configured to secure to the outside of the handpiece 202C. As discussed with reference to other arrangements herein, the control module 230' can include one or more buttons 236' and/or other controllers that allow a clinician or other user to regulate the delivery of fluids and/or other materials from the fluid delivery module (e.g., cassette) into a target location within a patient's anatomy (e.g., joint, organ, cavity, etc.). For example, the buttons and/or other controllers 236' can selectively initiate, terminate, pause or otherwise alter the delivery of fluids and/or other materials during an injection procedure.

According to some embodiments, in order to properly secure it to the handpiece 202C, the control module 230' is adapted to slide over the handpiece (e.g., from the handpiece's proximal end 211C). As illustrated in FIG. 26A, the bottom surface of the control module's main portion 238' can comprise a concave, contoured or generally curved shape that defines a partially-circular open channel or space 239'. In some embodiments, the shape of the curved bottom surface of the control module 230' matches or substantially matches the exterior curved shape of the handpiece portion 202C. Thus, the distal end 231' of the control module 230' can be positioned along the proximal end 211C of the handpiece 202C and can be slidably moved along the handpiece 202C toward its distal end 210C. In some embodiments, the proximal end 211C of the handpiece portion 202C can include a tapered portion 214C to facilitate insertion of the control module 230' over the proximal end of the handpiece portion 202C. In addition, as discussed with reference to FIGS. 25A and 25B, the tapered portion 214C and/or any other portion of the handpiece 202C can include one or more windows or openings to permit access to the interior of the handpiece 202C. Such access openings can facilitate the manufacturing or assembly of the handpiece (e.g., insertion of UV or other adhesives to bond the tubing 250C to the handpiece), to examine the tubing 250C and/or for any other purpose.

As illustrated in FIGS. 24 and 26A, the handpiece assembly 200C can include one or more clips 216C or other members or features that extend along the exterior surface of the handpiece portion 202C. In some embodiments, such a clip 216C can form a unitary structure with adjacent portions of the handpiece 202C. Alternatively, the clip 216C or other member or feature can be a separate item that is attached to the handpiece using one or more connection devices or methods (e.g., adhesives, fasteners, hot melt connections, welds, etc.). As shown in FIGS. 24 and 26A, the clip 216C can extend outwardly along its detached end 217C. In some embodiments, the clip 216C is ordinarily (e.g., when not subjected to any forces) resiliently biased in such an outward position. However, the clip 216C can be configured to move inwardly (e.g., to generally align with adjacent surfaces of the handpiece exterior housing 204C) when subjected to a sufficiently large inwardly-directed radial force. As discussed in greater detail below, the clip 216C can help securely maintain the position of a control module and/or other device relative to the handpiece.

Figure 26B:
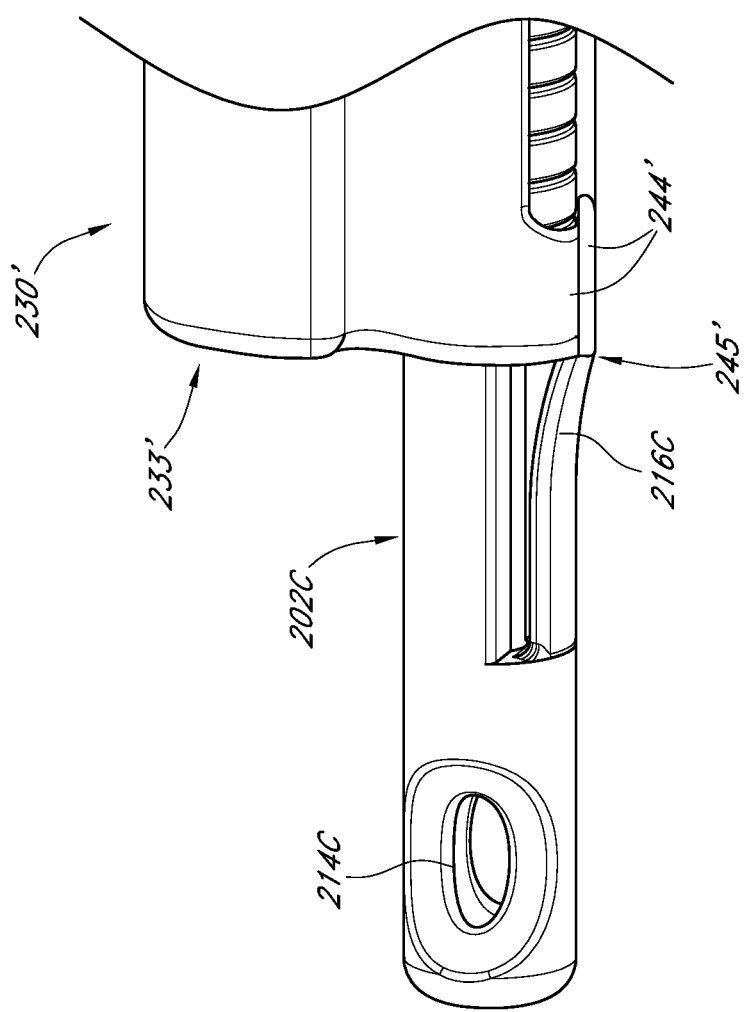

With reference to FIGS. 26A and 26B, as the control module 230' is slidably advanced over the handpiece portion 202C, one or more proximal engagement members 244' of the control module 230' can exert a force on the clip 216C. In some embodiments, the engagement member 244' will contact and move the clip 216C (e.g., against an external resilient or biasing force). Consequently, the clip 216C can be urged inwardly, in the direction of the handpiece interior and toward the adjacent surfaces of the handpiece exterior surface or housing 204C. If the control module 230' is advanced sufficiently far relative to the handpiece 202C, the engagement members 244' of the control module will move past the clip 216C, as illustrated in FIG. 26B. As a result, the clip 216C can resiliently return to its normal, radially-extended position, which, in some embodiments, causes the clip 216C to abut against a distal end surface of the control module's engagement members 244'. Such a configuration can help maintain the control module 230' to the handpiece portion 202C, as the contact between the clip 216C and control module 230' (e.g., the engagement members 244' and/or another portion or member) generally prevents the control module 230' from retracting relative to the handpiece.

Figure 27A:
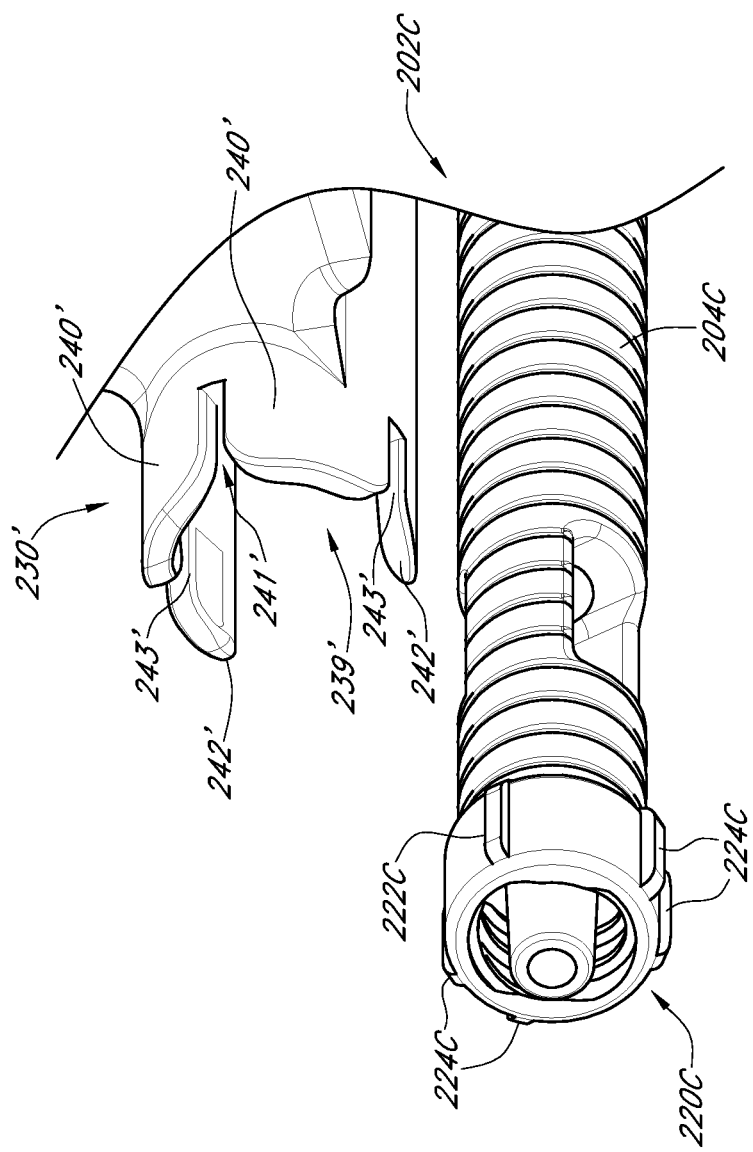
FIGS. 27A and 27B illustrate different perspective view of another embodiment of a control module configured to removably attach to a handpiece assembly.
Figure 27B:
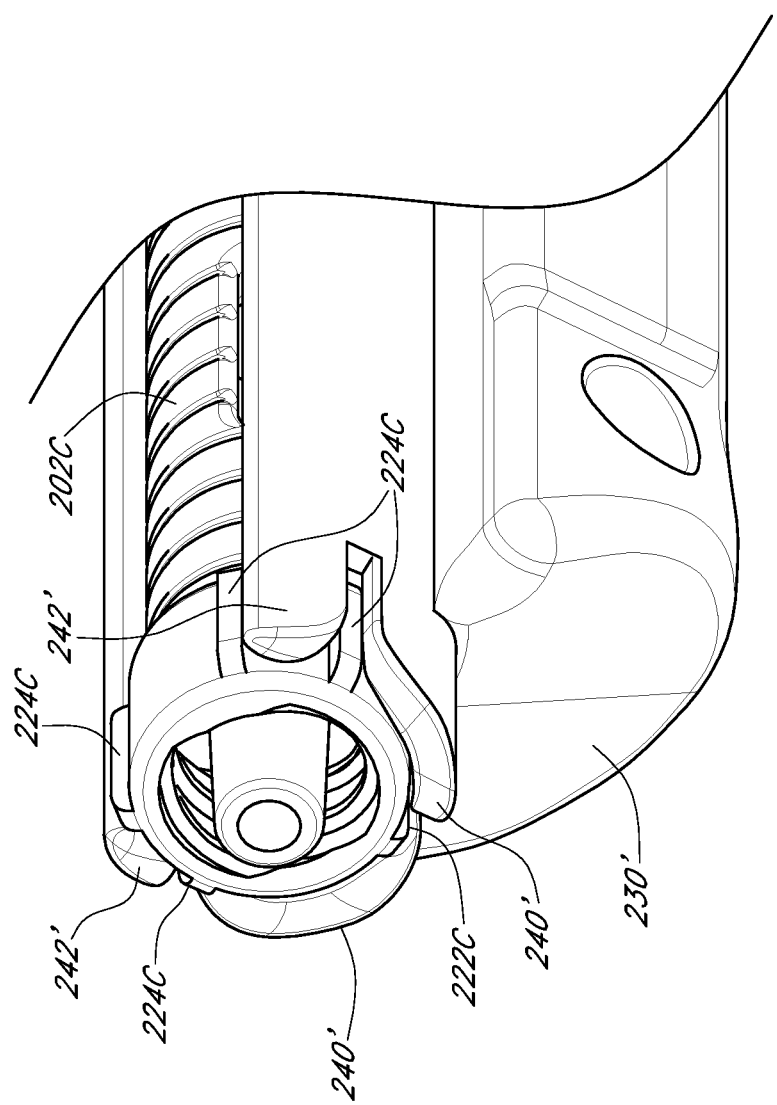

In addition, the control module 230' can be aligned with and secured to the handpiece 202C using one or more other members or features. For example, as illustrated in FIGS. 27A and 27B, the distal coupling 220C of the handpiece 202C can comprise one or more orientation rails 222C, 224C, protrusions and/or other features adapted to generally align with and engage corresponding recesses 241', 243' or other features of a control module (and/or any other device configured to removably secure to the handpiece assembly). In the illustrated embodiment, the coupling 220C comprises a main or central orientation rail 222C and a pair of adjacent rails 224C positioned on either side of the main rail 222C. In other arrangements, however, the quantity, shape, size, spacing, orientation and/or other details regarding the orientation rails 222C, 224C or other alignment or securement protrusions or features can vary. As best illustrated in FIG. 27B, the distal end of the control module 230' can include slots or recesses 241', 243' that are sized, shaped and otherwise configured to receive the corresponding rails 222C, 224C of the coupling 220C. The various slots or recesses 241', 243' can separate the distal end of the control module 230' into two or more wings, tabs or other portions 240', 242'. Accordingly, with the use of the distal orientation rails 222C, 224C and the proximal clip 216C (as well as corresponding features of the control module), the handpiece 202C can help ensure that the control module 230' is both properly aligned with and secured to the handpiece assembly 200C. In alternative embodiments, one or more other devices and/or methods of removably or permanently securing the control module to (and/or aligning it with) the handpiece can be used, as desired or required.

Figure 27C:
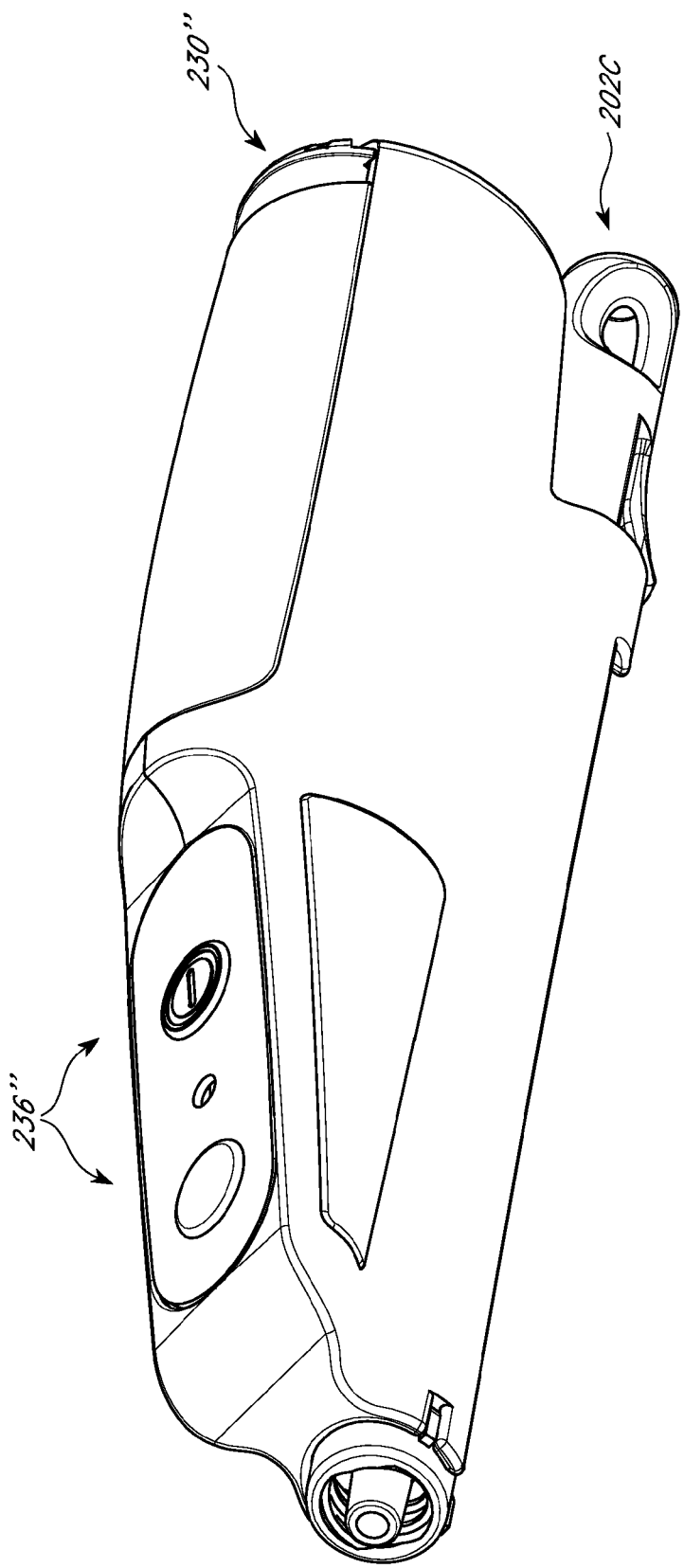
FIG. 27C illustrates a perspective view of yet another embodiment of a control module configured to removably attach to a handpiece assembly.

FIG. 27C illustrates a perspective view of yet another embodiment of a control module 230" that is sized, shaped and otherwise configured to secure to the outside of the handpiece 202C. As shown, the control module 230" can be relatively large so that it extends across most or all of the length of the handpiece 202C. In addition, the control module 230" can comprise a thickness (e.g., diameter or other cross sectional dimension) that facilitates grasping and maneuvering of the handpiece assembly. As with other arrangements disclosed herein, the control module 230" can include one or more buttons 236" and/or other controllers that allow a clinician or other user to regulate the delivery of fluids and/or other materials from the fluid delivery module (e.g., cassette) into a target location within a patient's anatomy (e.g., joint, organ, cavity, etc.).

Another embodiment of a handpiece assembly 200D configured to be removably secured to a fluid delivery module or another component or portion of an injection system is illustrated in FIG. 28. As discussed with reference to other arrangements disclosed and discussed herein, the assembly 200D can include a handpiece portion 202D and tubing 250D configured to place the handpiece portion in fluid communication with an upstream fluid delivery module (not shown). The proximal end of the tubing 250D can comprise a luer lock or other standard or non-standard fitting 260D that is sized, shaped and otherwise adapted to selectively mate and attach to a corresponding fitting or coupling of the fluid delivery module (e.g., cassette) or other component or portion of the injection system. Further, the distal end 210D of the handpiece 202D can include a standard or non-standard fitting or coupling (e.g., luer lock) configured to removably receive a needle assembly (not shown).

As discussed with reference to various embodiments herein, a handpiece assembly of an injection system can allow a user to selectively deliver one, two or more different medicaments, other fluids and/or other materials into a patient's anatomy through a single needle. In some embodiments, a clinician uses one or more buttons and/or other controllers positioned on the handpiece assembly to control the delivery of the various fluids and/or other materials through the assembly. A user can manipulate such buttons or other controllers to modify one or more aspects of the injection procedure (e.g., initiating or terminating an injection procedure, which fluids are being delivered, sequence of delivery, flowrate, etc.) while continuing to grasp and manipulate the handpiece assembly. Accordingly, in some embodiments, a user executes a desired procedure without taking his or her hands off the handpiece assembly.

As discussed herein, two or more different fluid and/or other material streams can be combined within a cassette and/or any other location upstream of a handpiece assembly. Alternatively, however, a handpiece assembly can be configured to permit two or more different fluids and/or other materials to be transferred to or near a needle without prior mixing or cross-contamination of the various streams. Thus, in some embodiments, the different fluids and/or other substances are mixed just prior to entering the needle assembly at the distal end of a handpiece. As discussed in greater detail herein, the various fluid or other material streams can be mixed at a distal end of the clip (e.g., a common or collection area), at or near the interface between the clip and the disposable tip and/or at any other location. In certain situations, the effectiveness of an injection may be enhanced if the contact time between the various fluids and/or other substances being delivered into a patient is reduced or minimized (e.g., for various chemical, biological and/or other reasons). Relatedly, the handpiece assembly can be adapted to prevent backflow of fluids and/or other materials being transferred therethrough. This can help reduce the likelihood of cross-contamination or inadvertent mixing of the various medicaments and other substances. For example, as discussed, the handpiece can include various valves (e.g., duckbill valves, combination duckbill/umbrella valves, other check valves, etc.) and/or other backflow prevention devices.

In some embodiments, the handpiece assembly includes buttons and/or other controllers that are used to operate another device, such as, for example, an ultrasound device or another imaging system. Such buttons or other controllers can be included either in lieu of or in addition to the buttons and controllers on the handpiece (or a removable control module) for the operation of the injection system itself. Thus, a clinician or other user can advantageously control the operation of an ultrasound or other imaging device and/or any other system using only the handpiece assembly. As a result, the clinician can control and complete an injection procedure while continuing to hold the handpiece assembly (e.g., without the use of any other device or system). Accordingly, this can help improve the safety and accuracy of a procedure as the user is permitted to operate various systems during an injection while continuing to hold and manipulate the handpiece assembly.

In addition, as discussed in greater detail herein, configuring different devices and systems to interface with one another during an injection procedure can provide additional benefits. For example, information about the delivery of fluids and/or other substances (e.g., the volume of each medicament delivered, the volume of each medicament remaining, the flowrate of medicament through the handpiece, etc.) can be incorporated into the same visual display with the graphics of an ultrasound or other imaging technology. As discussed in greater detail herein, this can further facilitate the execution of an injection procedure. In addition, such a configuration can improve record-keeping, billing and other functions that are related to the administration of a medical procedure.

Figure 29A:
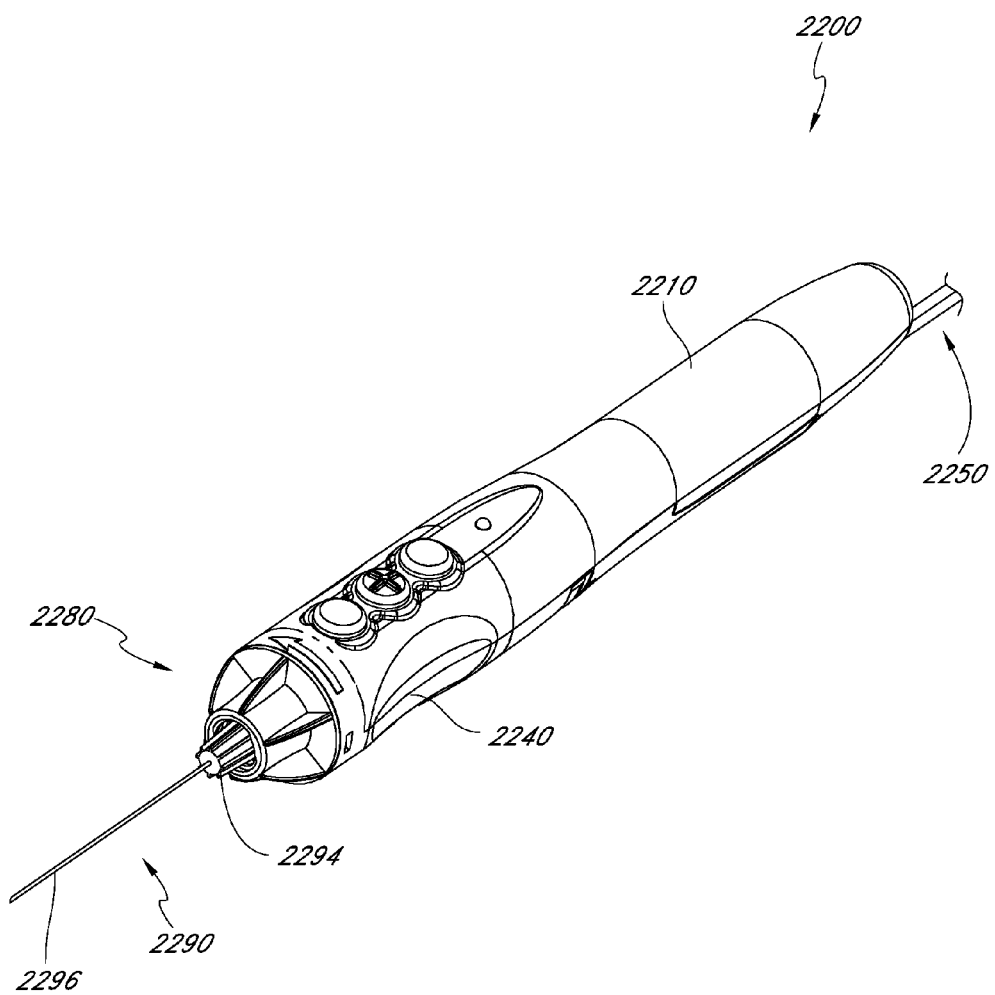
FIG. 29A illustrates a perspective view of a handpiece assembly configured for use with an injection system according to one embodiment.

Another embodiment of a handpiece assembly 2200 configured for use with an injection system is illustrated in FIG. 29A. As shown, the handpiece assembly 2200 can comprise a core 2210, a clip assembly 2240 and a tip 2280 having a needle 2290 along its distal end. A delivery line 2250 comprising one or more different conduits 2251 can be used to place the handpiece assembly 2200 in fluid communication with the cassette 300 and/or another portion of the fluid delivery module 100. In one embodiment, the tip 2280 is replaced after each injection (e.g., immediately following removal of the needle 2290 from the anatomy). Further, the clip assembly 2240 can be replaced when the type and/or dosage of the medications, formulations and/or other materials being delivered through the handpiece assembly 2200 are modified. As discussed, in some embodiments, the clip assembly 2240, the delivery line 2250 and the cassette 300 can be supplied and replaced as a single system or kit as desired or required.

The handpiece assembly 2200 can be adapted to allow a clinician or other user to easily grasp and manipulate it during an injection procedure. As such, the diameter, length, other dimensions and/or other characteristics of the handpiece assembly 2200 can be advantageously selected to achieve the desired functional and/or aesthetic goals. Further, the handpiece assembly 2200 can include a shape, other features (e.g., finger grooves, tactile members or outer surface, etc.) and/or the like to further enhance its ergonomic and/or other properties. According to some arrangements, the approximate diameter and total length (e.g., not including the needle 2290) of the handpiece assembly 2200 are approximately 5 to 6 inches and approximately 0.5 to 0.7 inches, respectively. In addition, the various components of the handpiece assembly 2200, including the core 2210, clip 2240, tip 2280 and the like, can be manufactured using one or more materials that are durable and otherwise suitable to withstand the forces and wear and tear to which the handpiece assembly 2200 may be exposed. For example, in several embodiments, the handpiece assembly 2200 comprises plastics, other polymeric materials, metals, alloys and/or any other synthetic or natural materials.

In some embodiments, the clip assembly 2240 is replaced according to a particular schedule or protocol. For instance, the clip assembly 2240 (and, in certain arrangements, the delivery line and the cassette together with the clip assembly) can be replaced following a predetermined number of injection procedures, following a predetermined volumetric amount of fluids and other materials passing through the clip assembly 2240, based on a predetermined time frequency (e.g., once a day, once every four hours, etc.) and/or according to some other set of rules, as desired or required by the particular application or use. In some arrangements, the core 2210 is advantageously configured to not contact any fluids and/or other materials being conveyed through the handpiece assembly 2200. As a result, the same core 2210 can be used repeatedly without the need to replace or clean it. However, it will be appreciated that even such a core 2210 may need to undergo frequent cleaning (e.g., sterilization), calibration and/or other maintenance procedures. Each component of such a handpiece assembly 2200 is discussed in greater detail herein.

Figure 30A:
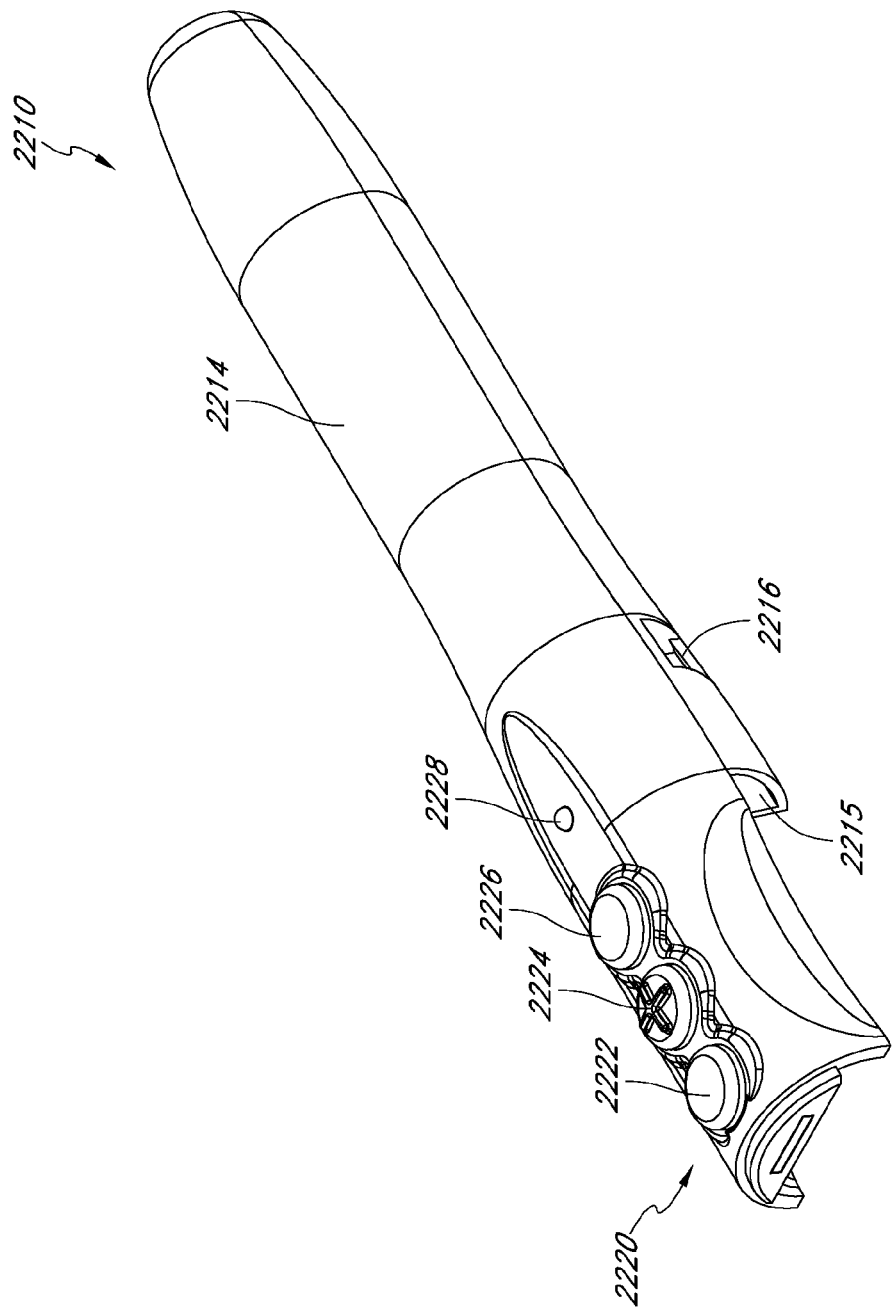
FIG. 30A illustrates a perspective view of a core of a handpiece assembly according to one embodiment.

FIGS. 30A and 30B illustrate different views of the core 2210 included in the handpiece assembly 2200 of FIGS. 29A and 29B. As shown, the core 2210 can comprise a control portion 2220 having one or more buttons 2222, 2224, 2226, controllers and/or other adjusting devices (e.g., knobs, dials, switches, etc.). In addition, the control portion 2220 can include one or more indicator lights 2228 and/or any other feature that provides information to the user regarding the operation of the assembly 2200 and/or the injection system.

The buttons 2222, 2224, 2226 and/or other control features of the core 2210 can help regulate the delivery of various fluids and/or other materials through the handpiece assembly 2200. For example, such buttons 2222, 2224, 2226 can be used to activate or deactivate (e.g., ON/OFF) the supply (and/or withdrawal) of fluid or other substances to or from an intra-articular space or other anatomical location. In certain arrangements, the buttons or other controllers are manipulated to regulate the rate of delivery (e.g., flowrate) of one or more medicaments and/or other materials being transferred through the handpiece assembly. As discussed, in other embodiments where the fluid delivery module is in data communication with one or more other components or devices (e.g., ultrasound devices, radio frequency spectroscopy devices, other imaging devices or systems, etc.), buttons or other controllers can be used to also regulate the operation of such systems. For example, as discussed in greater detail herein, the buttons or other controllers of a handpiece assembly can be used to capture an ultrasound image or video while a target anatomical space (e.g., a joint, organ, etc.) is being located and/or while one or more fluids or other materials are being injected into a target anatomical location. Alternatively, the buttons or other controllers can be used to vary one or more other aspects of an imaging system, such as, for example, zoom, resolution, contrast, brightness and/or the like. In some embodiments, a handpiece assembly includes additional, fewer and/or different buttons, knobs, levers and/or other control devices that permit a user to control one or more aspects of the system.

With continued reference to FIG. 30A, each of the buttons 2222, 2224, 2226 along the outside of the core 2210 can be configured to correspond to one of the medications and/or other materials which are loaded onto the fluid delivery module 100 and which can be selectively delivered from to the handpiece assembly 2200. For instance, each such medication, other fluid or the like can be associated with a particular color, shape, pattern, design, scheme, texture, other identifying feature and/or the like. Thus, in some embodiments, the color, shape or pattern of the buttons 2222, 2224, 2226 is configured to match a corresponding characteristic of the medications and/or other materials that are loaded onto the fluid delivery module (e.g., positioned on the nests or loading areas of the cassette). By way of example, one of the buttons 2222 on the core can be yellow. In addition, the user may have selected yellow to also correspond to a particular type of therapeutic agent (e.g., steroid) which is loaded onto the cassette and which may be selectively delivered from the fluid delivery module to the handpiece assembly 2200. In another embodiment, the buttons are textured in a manner that permits a clinician or other user who handles the handpiece assembly to identify the various buttons without having to look at them. For example, the buttons can include a raised or recessed pattern (e.g., a "plus" or "minus" sign, dots, a rectangle, circle, other geometric design, other discernable pattern and/or the like). Thus, by pressing the appropriate button 2222, the user can commence, terminate, speed up, slow down and/or otherwise adjust the delivery of a therapeutic agent and/or other fluid or substance to the patient.

According to certain embodiments, a handpiece assembly 2200 comprises one or more two-mode or other multi-mode buttons and/or other controllers. Pressing or otherwise manipulating such a button can alternately commence or terminate the delivery of one or more fluids and/or other materials through the assembly. Alternatively, the handpiece assembly 2200 can include one or more other types of buttons or controllers. In some arrangements, the buttons are configured to permit the user to select between two, three or more different settings. In other embodiments, a button is of the multi-depth type (e.g., dual-depth, tri-depth, etc.), enabling a user to selectively press the button to two or more distinct depths or other levels. Each distinct depth or level can correspond to a particular setting (e.g., flowrate, selection of which fluids or other materials to deliver, etc.). For example, pressing the button to the first level can cause the desired fluid and/or other material to be conveyed at the maximum or minimum rate. Further, continuing to press the button to subsequent lower levels can cause the rate of delivery to increase, decrease or terminate. In other embodiments, the handpiece assembly comprises multi-depth buttons that do not include distinct depths, such as, for example, a rheostat. Thus, a particular setting (e.g., flowrate) can be varied based on the depth to which a button is depressed.

In other arrangements, the core 2210 of the handpiece assembly comprises one or more buttons that have only two positions, but which are configured to permit a user to select between three or more different settings. For example, an injection system can be adapted to sequentially move between different flowrate settings (e.g., high-medium-low-off, vice versa, etc.) every time such a button is pressed.

As discussed, a core 2210 or other portion of a handpiece assembly can comprise other types of controllers, either in lieu of or in addition to the buttons. For example, the handpiece assembly 2200 can include a roller ball, a roller wheel, a dial, a knob, a modulating switch or other device and/or the like. Regardless of their exact configuration and design, such control devices can enable a clinician or other user to regulate the delivery of fluids and/or other materials from the fluid delivery module to a patient. As discussed, the various fluids and/or other materials can be delivered through the handpiece assembly simultaneously or sequentially, as desired or required. For example, the buttons and/or other controllers can be used to select which fluids or other materials, or combinations thereof, are to be directed through the handpiece assembly. In other embodiments, the controllers are configured to control the rate of delivery (e.g., flowrate) of such fluids and/or other substances to a patient. In still other arrangements, the buttons control one or more other aspects of the injection procedure (e.g., the sequence of delivery, an ultrasound or other imaging device that is in data communication with the injection system, etc.).

In other arrangements, the buttons 2222, 2224, 2226 on the handpiece assembly 2200 are adapted to guide the user through one or more user-interface screens on the display or graphic user interface (GUI) on the fluid delivery module. Thus, the buttons 2222, 2224, 2226 can be used to make selections through one or more menus or the like.

According to some embodiments, the handpiece assembly 2200 is connected to the fluid delivery module of the injection system using one or more hardwired connections. However, the handpiece assembly 2200 can be configured to communicate with the fluid delivery module and/or any other component of the injection system using a wireless connection, such as, for example, radio frequency (RF), Wi-Fi, Bluetooth and/or like, either in addition to or in lieu of a hardwired connection. As discussed herein, the handpiece assembly 2200 can comprise a battery that is configured to be recharged when the handpiece assembly is positioned within a corresponding docking station of the fluid delivery module. Such a battery (not shown) can be positioned within an interior portion of the core 2210. The docking station can be adapted to recharge the battery using electromagnetic induction, simple charging (e.g., using a DC or AC connection), pulse charging and/or any other charging method or device. Thus, in some arrangements, the battery within the core is permitted to recharge when the handpiece assembly is positioned within a docking station of the fluid delivery module. Alternatively, the handpiece assembly 2200 may draw its power from one or more other sources, such as, for example, a DC or AC hardwired connection and/or the like.

As discussed, an interior portion of the core 2210 can include a battery, circuitry, indicator light 2228 (e.g., LED) and/or any other component or feature. As illustrated in FIGS. 30A and 30B, the core 2210 can include one or more indicator lights 2228 that provide information to the clinician or other user of the assembly prior to, during and/or following an injection procedure. For example, the light 2228 can be configured to light up when the battery of the assembly is above or below a particular threshold level (e.g., adequately charged, in need of charging, etc.). Alternatively, the brightness, color and/or other characteristics of the indicator light 2228 can be configured to change in response to certain conditions. For instance, the properties of the light 2228 can vary based on the strength of the battery, on the signal strength of the wireless connection (e.g., radio frequency, RF, Bluetooth, etc.) between the handpiece assembly and the fluid delivery module or other component of the system and/or the like.

In other embodiments, an indicator light 2228 is activated (e.g., lights up, begins to flash, changes color, etc.) as a warning to the user. For example, the triggering event for such an activation can include a low battery level, the presence of air or other gas within a fluid delivery conduit, excessive back-pressure encountered during the delivery of a fluid or other material within the anatomy, low fluid level within a reservoir of the fluid delivery module, some other breach and/or the like. According to certain embodiments, the core 2210 or other portions of the handpiece assembly 2200 includes a small display (e.g., LCD) that is configured to provide information to the user in the form of text, graphics and/or the like, either in addition to or in lieu of one or more indicator lights 2228.

Consequently, the inclusion of the various electronic and/or other components and features within a single core 2210 or other portion of the handpiece assembly 2200 provides a number of benefits. As discussed, such configurations can permit a clinician or other user to control some or all aspects of an injection procedure without having to take his or her hands off the handpiece assembly 2200. In addition, a single handpiece assembly 2200 can be adapted to control one or more other devices or systems which are used during the execution of injection procedures. For example, the buttons or other controllers of the handpiece assembly can be used to advantageously regulate an ultrasound device or other imaging system. Although the inclusion of electrical and control components within the relatively limited space of a core 2210 is challenging, the convenience and other benefits associated with using a single handpiece to control some, most or all aspects of an injection procedure can be beneficial.

As described in greater detail herein, a touchscreen display or other graphic user interface which is either attached to the fluid delivery module or operatively connected to it can be used to regulate, at least in part, the function of the handpiece assembly 2200 and/or other components of the articular injection system. In other embodiments, a separate handheld device, instrument and/or other device or system can be used to control the handpiece assembly 2200 and/or other components of the injection system. For example, such a control device or other instrument can include separate power, control and/or instrumentation wires that are molded within or otherwise positioned relative to the separate device. In some embodiments, the separate control device is configured to attach to (e.g., snap or otherwise mount to) or otherwise secure to the handpiece assembly 2200 using one or more types of connection devices and/or methods.

Moreover, other devices and methods of controlling one or more aspects or components of the injection system can be used, either in addition to or in lieu of the devices and methods specifically disclosed herein. In some embodiments, the injection system includes a foot pedal or other user-actuated lever or control. Alternatively, the injection system can comprise control features that are configured to respond to a clinician's or other user's voice commands or prompts, such as, for example, "START," "STOP," "INJECT/DELIVER," "ASPIRATE," "INCREASE FLOWRATE," "DECREASE FLOWRATE," "CHANGE MODE/SEQUENCE" and/or the like. It will be appreciated that an articular injection system can include any combination of controls or other features described herein, as desired by the user or required by a particular application.

In some embodiments, the shape of the core housing 2214 and other graspable portions of the handpiece assembly 2200 are configured to be ergonomically correct or are otherwise designed to facilitate the handling and manipulation of the handpiece assembly 2200. Further, as discussed in greater detail herein, the core 2210 can be configured to quickly and easily attach to and detach from one or more other subcomponents of the handpiece assembly 2200, such as, for example, the clip assembly 2240 and the tip 2280.

FIGS. 31A-31D illustrate various views of one embodiment of a clip assembly 2240 configured to be used in a handpiece assembly 2200. As shown, the clip assembly 2240 can include a ring 2242 at or near its distal end. In some arrangements, the distal end of the clip assembly 2240 comprises a recessed surface 2243 to which a tip 2280 can be removably secured (FIGS. 29A and 29B). Further, a central portion of the recessed surface 2243 can include an outlet opening 2248 into which an inlet portion of the tip 2280 may be positioned. In addition, the interior and/or exterior of the ring 2242 can comprise one or more tabs 2246 and/or recesses 2244 to help secure the clip assembly 2240 to the tip 2280, the core 2210 and/or any other portion of the handpiece assembly 2200.

With continued reference to FIGS. 31A-31D, the clip assembly 2240 can include a main body 2256, which in some embodiments is configured to at least partially define an exterior surface of the handpiece assembly 2200. At the proximal end of the main body 2256, the clip 2240 can include one or more elongate members 2258 that are sized, shaped and otherwise adapted to mate with corresponding portions of the core 2210 (FIGS. 30A and 30B). For example, the elongate members 2258 can slide within corresponding slots 2215 (FIG. 30A) of the core 2210. In the illustrated arrangement, at least one of the elongate members 2258 comprises a locking tab 2259 that is adapted to snap into a matching hole 2216 (FIG. 30A) along the outer surface of the core 2210. Thus, if the elongate members 2258 are inserted sufficiently far into the corresponding slots 2215 of the core 2210, the locking tab 2259 of the clip 2240 will resiliently engage the matching hole 2216 of the core 2210. Consequently, the clip 2240 can be advantageously locked relative to the core 2210. In order to separate the clip 2240 from the core 2210, the locking tab 2259 can be pressed inwardly so that the tab 2259 disengages from the matching hole 2216.

Figure 31A:
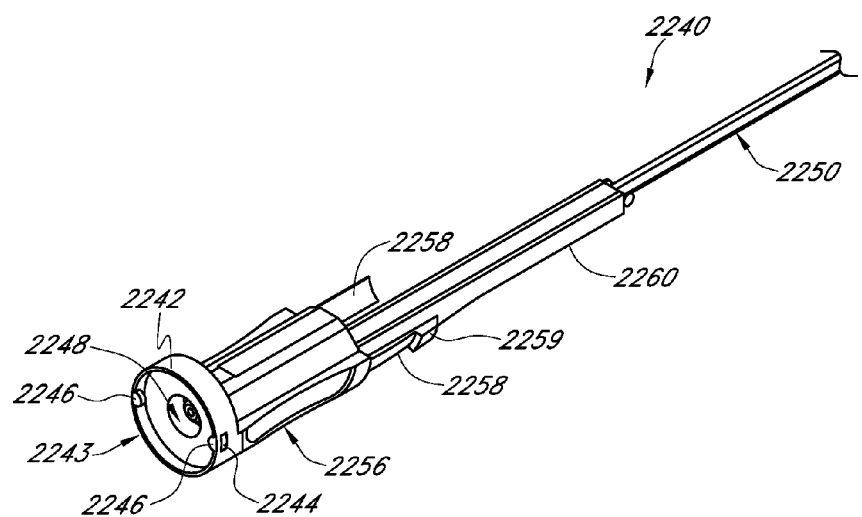
FIG. 31A illustrates a perspective view of a clip of a handpiece assembly according to one embodiment.
Figure 31B:
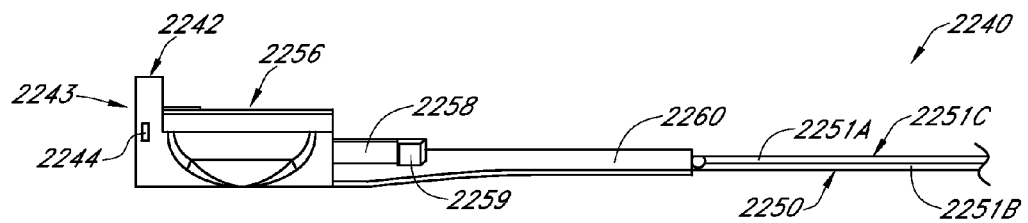
FIG. 31B illustrates a side view of the clip of FIG. 31A.
Figure 31C:
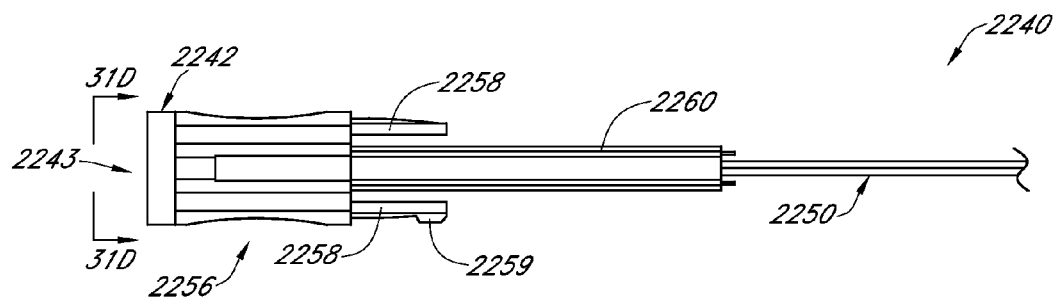
FIG. 31C illustrates a top view of the clip of FIG. 31A.
Figure 31D:
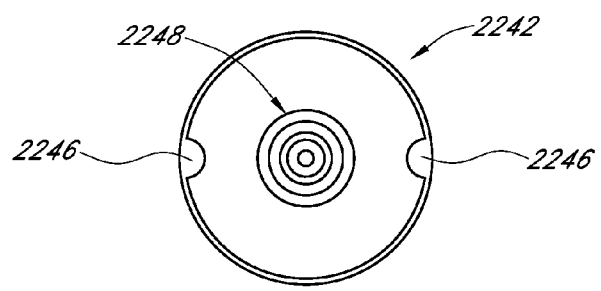
FIG. 31D illustrates a front view of the clip of FIG. 31A.

As illustrated in FIGS. 31A-31C, the clip 2240 can include a channel 2260 or other portion that is configured to receive the delivery line 2250. As discussed herein with reference to other components, the delivery line 2250 can include one, two or more of the individual conduits 2251A-2251C that are in fluid communication with the outlets of the various cassette manifolds. Thus, in some arrangements, the channel 2260 of the clip 2240 is preferably sized and shaped to accommodate all the individual conduits 2251A-2251C of the delivery line 2250. In other embodiments, as illustrated herein with reference to, inter alia, FIGS. 4, 8 and 14, the various fluids and/or other materials being injected into the anatomy can be combined within the fluid delivery module (e.g., upstream of a luer lock or other outlet fitting of a cassette or other portion of the fluid delivery module). Thus, for such arrangements, a single-lumen delivery line 2251 can be used to selectively deliver the fluid and/or other material streams to the handpiece assembly 2200. Consequently, the design of the clip 2240 and/or other portions of the assembly 2200 illustrated herein can be modified accordingly.

Figure 32A:
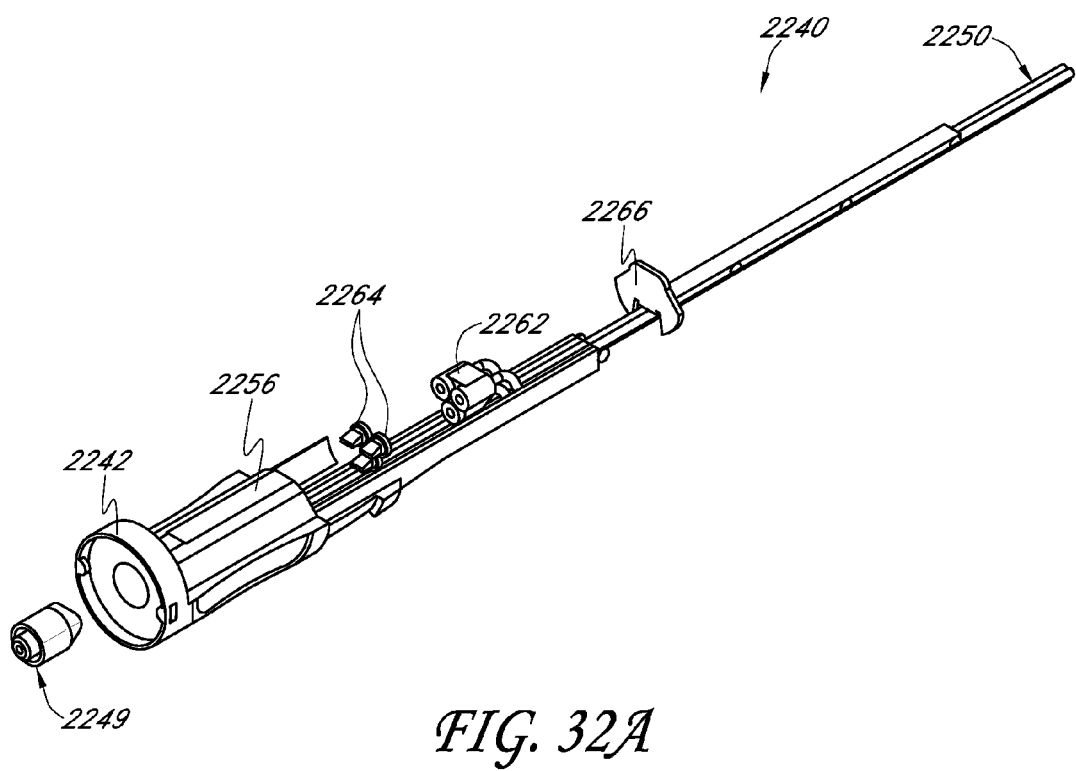
FIGS. 32A-32C illustrate perspective views of a clip of a handpiece assembly according to another embodiment.
Figure 32B:
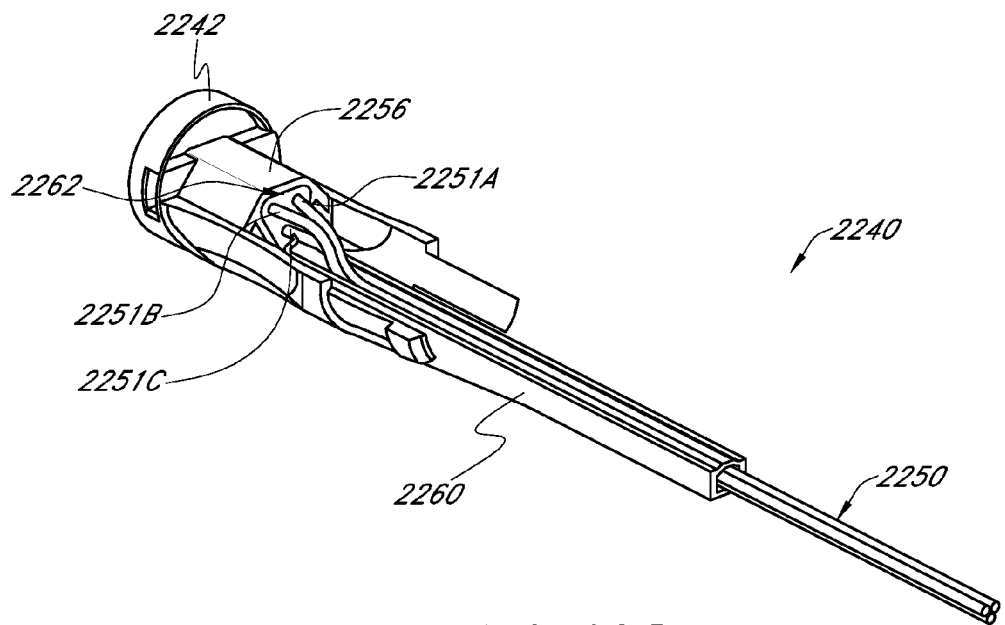
Figure 32C:
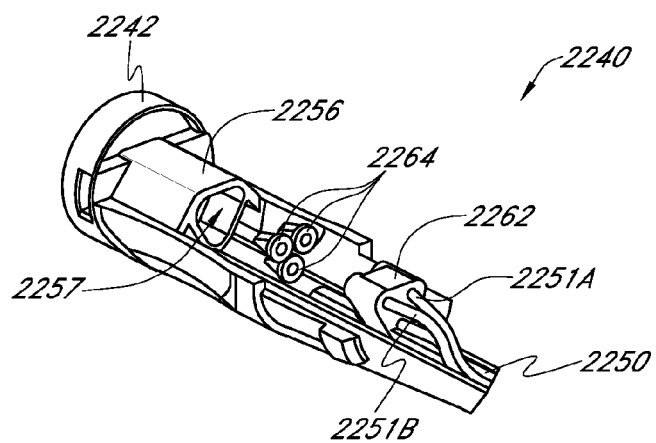

One embodiment of the manner in which the individual conduits 2251A-2251C of the delivery line 2250 are attached to the clip 2240 is illustrated in FIGS. 32A-32C. As shown, the conduits 2251A-2251C can be routed to a main coupling 2262. In the depicted arrangement, the main coupling 2262 comprises a generally triangular shape and is adapted to fit within a corresponding recessed area 2257 of the main body 2256. As best illustrated in FIGS. 32A and 32C, a duckbill valve 2264 (or other type of backflow prevention valve or device) can be positioned immediately downstream of the main coupling 2262. Thus, fluids and/or other materials passing through the passages of the main coupling 2262 are not permitted to reverse direction through the main coupling 2262. This helps ensure that there is no cross contamination of the individual conduits 2251A-2251C upstream of the main coupling 2262.

Figure 33A:
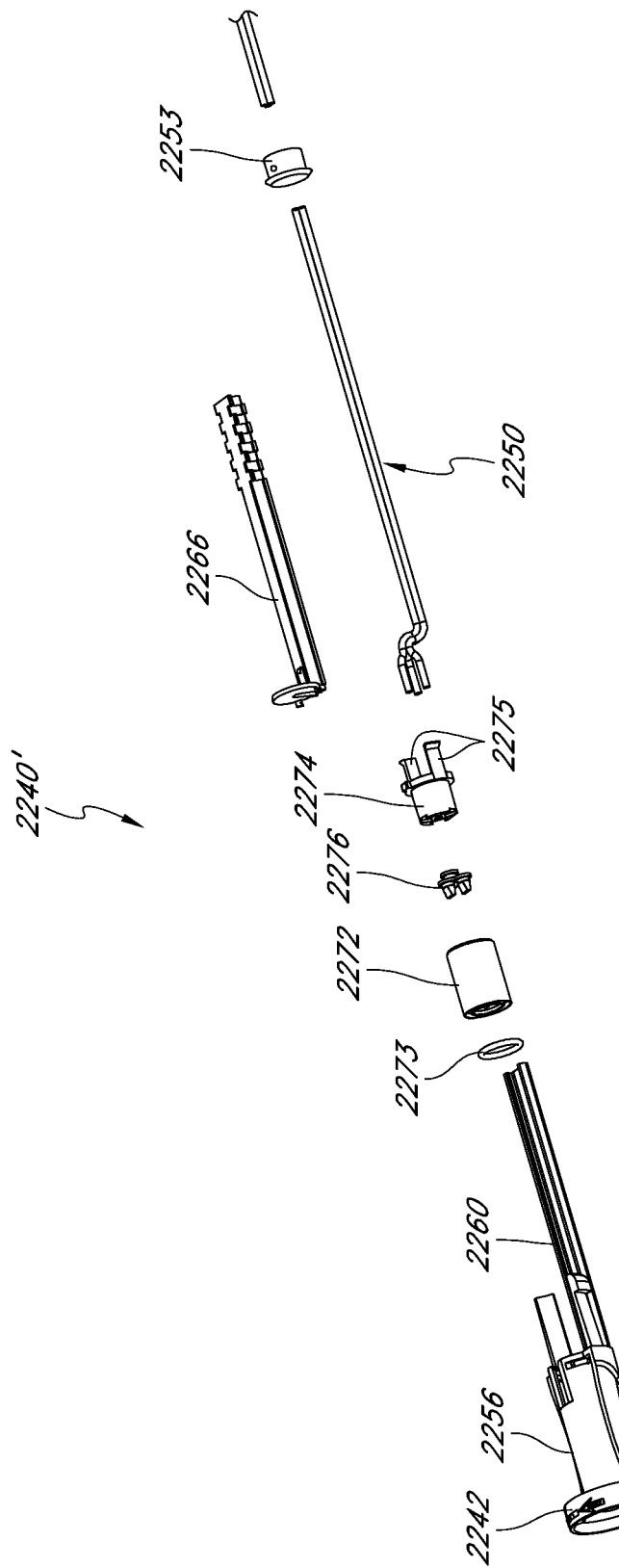
FIG. 33A illustrates an exploded perspective view of a clip of a handpiece assembly according to another embodiment.
Figure 33B:
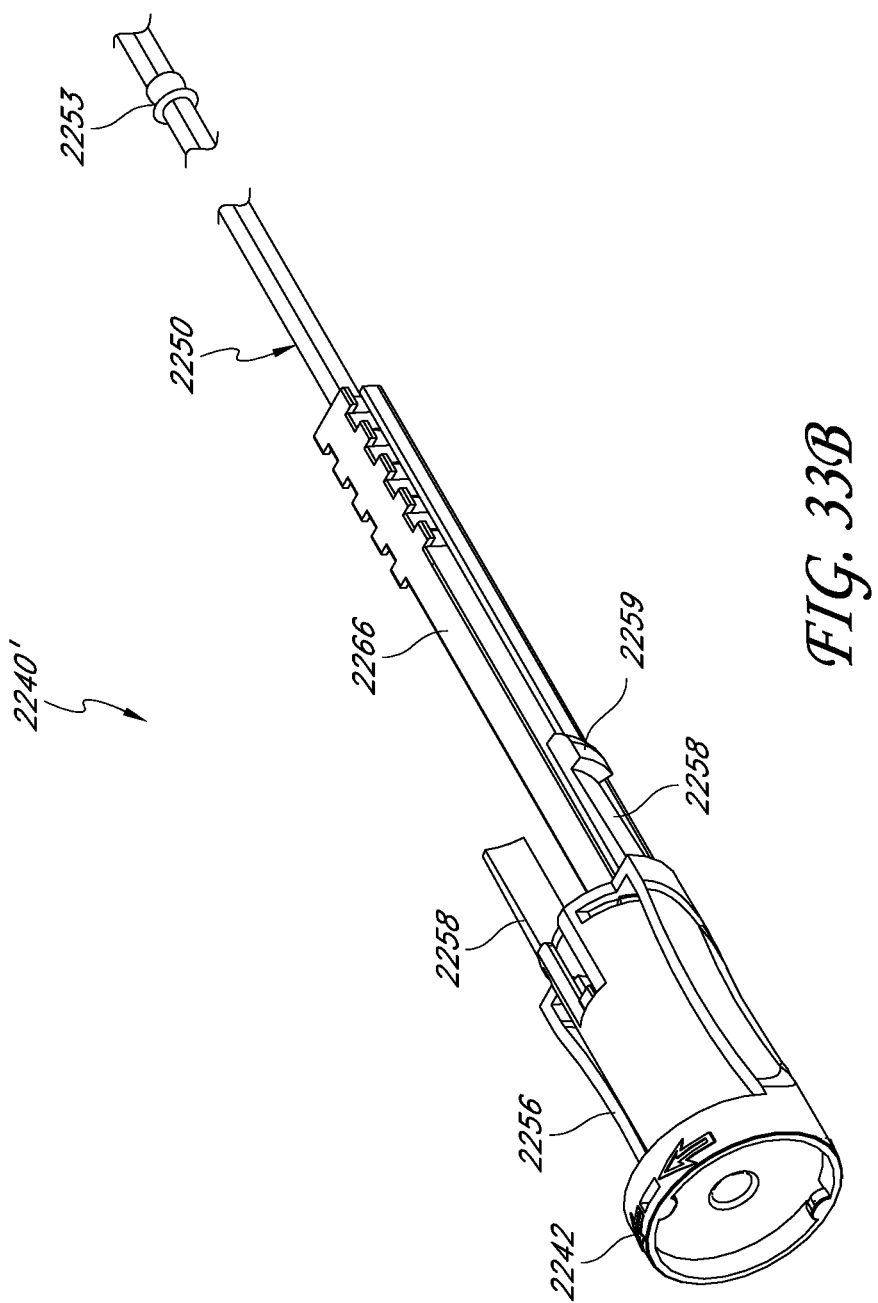
FIG. 33B illustrates a perspective view of the clip of FIG. 33A.
Figure 34A:
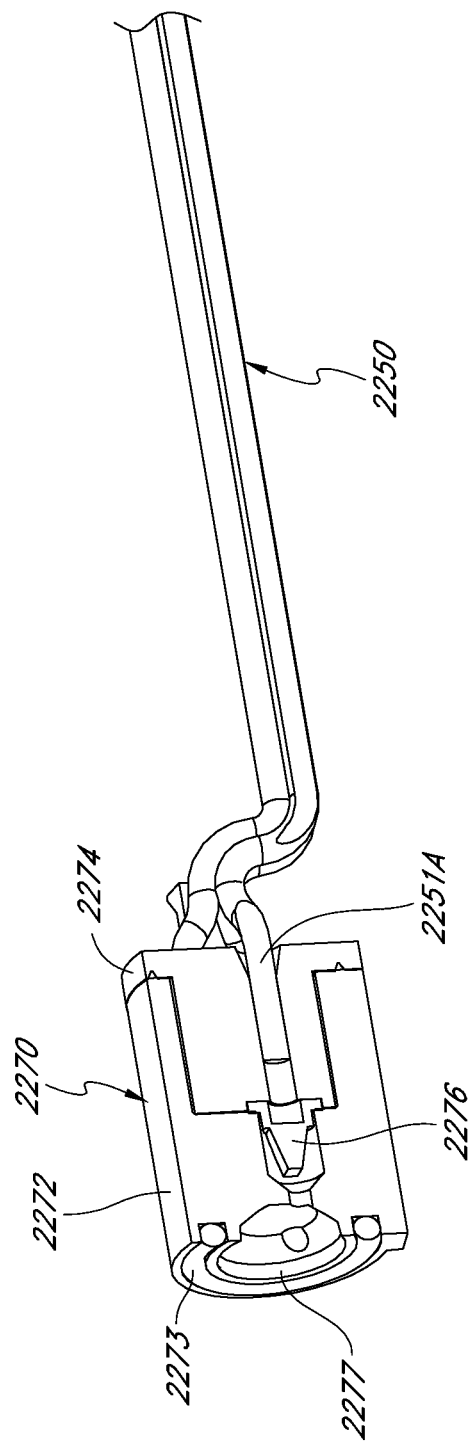
FIGS. 34A-34C illustrate various perspective views of the delivery line and portions of the clip of FIG. 33A.
Figure 34B:
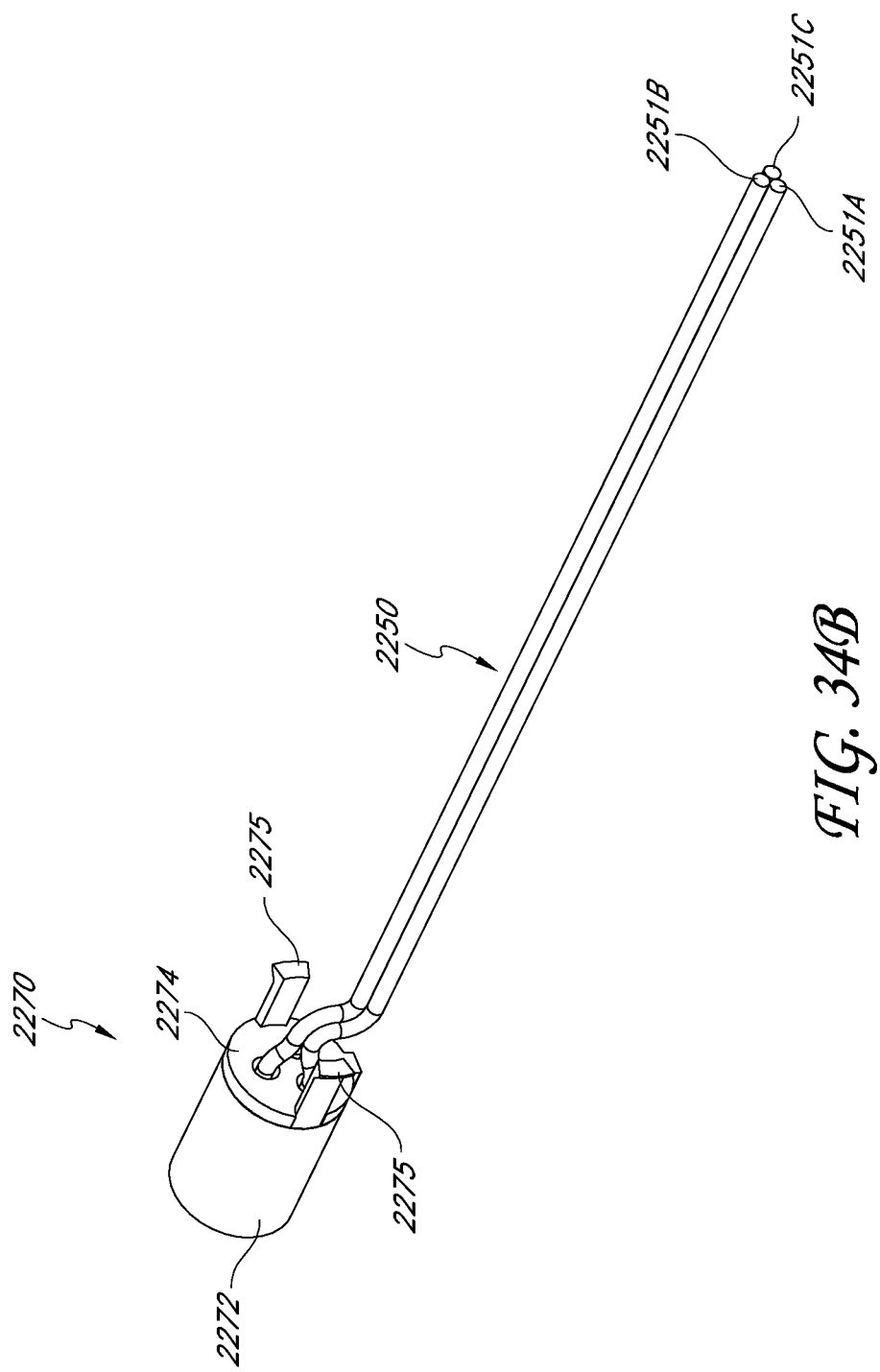
Figure 34C:
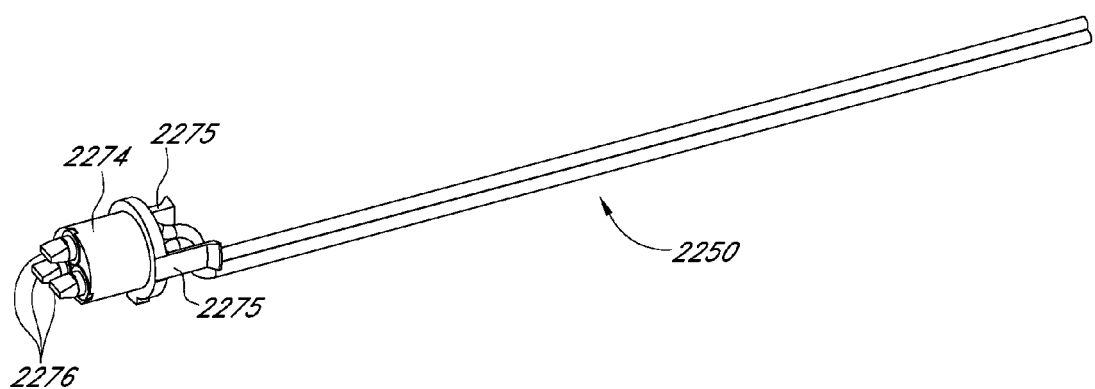

Another embodiment of the connection of individual conduits 2251A-2251C in the clip 2240' is illustrated in FIGS. 33A-34C. As with the clip 2240 of FIGS. 32A-32C, the depicted arrangement includes a main body 2256 that can be selectively attached to and/or removed from the core 2210. However, as discussed in greater detail below, there are some variations in the manner in which the conduits 2251A-2251C are connected to the distal end of the clip 2240'. As best illustrated in the views of FIGS. 34A-34C, the conduits 2251A-2251C can separate from each other a short distance upstream of a multi-piece coupling 2270. The coupling 2270 can include an inner portion 2274 fitted within an outer portion 2272 located immediately downstream of the inner portion 2274. According to some embodiments, a duckbill valve 2276 or other backflow prevention valve or device can be positioned in the fluid path of each conduit 2251A-2251C, generally between the outer and inner portions 2272, 2274. Thus, as discussed above with reference to FIGS. 32A-32C, the valves 2276 can help prevent cross-contamination of the individual conduits 2251A-2251C when fluids and/or other materials are moving through the clip 2240'. In the illustrated embodiments, once they have passed through the duckbill valves 2276, such fluids and/or other materials enter a common chamber 2277 or collection chamber 2277 located at the distal end of the outer portion 2272. Accordingly, fluids and/or other materials can exit the outlet opening 2248 (FIGS. 31A and 31D), toward a tip 2280 attached at the distal end of the ring 2242.

According to some configurations, the inner portion 2274 comprises one or more prongs 2275 that are adapted to secure to corresponding areas of the main body 2256. Thus, the inner portion 2274 and other components of the coupling 2270 can be conveniently attached to the rest of the clip 2240. It will be appreciated that one or more other devices or methods can be used to secure the coupling 2270 to the clip 2240. Further, as shown in FIGS. 33A and 33B, a closure 2266 can be used to completely or partially cover the interior of the channel 2260 through which the delivery line 2250 is routed.

The delivery line 2250A-2250E can include one, two or more different conduits or lumens. Accordingly, the depicted arrangements can advantageously provide a simple design for conveying two or more different types of fluids and/or other materials through a single member. For example, the handpiece assembly 2200 in fluid communication with the fluid delivery module using only a single multi-lumen tubular member. In addition, the internal configuration and overall design of the clip 2240 and/or other portions of the handpiece assembly 2200 can be improved by using such a multi-lumen delivery line, especially where available space within the clip or other portion of the handpiece assembly is limited.

Single-lumen or multi-lumen delivery lines 2250 can be manufactured using one or more methods (e.g., extrusion, injection molding, etc.) and/or one or more suitable materials (e.g., rubber, polymeric materials and/or the like). In some embodiments, the delivery lines are at least partially transparent or translucent so that an optical sensor can detect the presence of undesirable air or other gas bubbles passing therethrough. The materials used in the manufacture of the delivery lines and other portions of the articular injection system that may come into contact with medications, formulations and/or any other materials being injected into the anatomy preferably satisfy all regulatory standards and requirements (e.g., medical-grade quality, FDA regulations, etc.). According to some embodiments, the inner diameter of each lumen of the delivery line is approximately 0.01-0.04 inches (e.g., 0.030 inches). However, the inner diameter can be greater than 0.04 or smaller than 0.01, as desired or required.

The structural integrity, diameter, other dimensions, materials of construction, durability, flexibility, pH resistance, chemical/biological resistance, temperature resistance and/or other characteristics of the delivery line or other conduits used in the injection system can be advantageously selected for the particular application. For example, the delivery line or other conduit can be manufactured from medical-grade silicone, polymers, glass, stainless steel, copper and/or the like.

Further, the delivery line or other conduit can be configured so it adequately resists the fluids and/or other materials which it may contact. Further, such delivery lines or conduits can be advantageously adapted to withstand the pressures (e.g., positive, negative/vacuum, etc.) to which they may be exposed. Also, in some embodiments, the lines or conduits are configured to withstand a minimum of 2 pounds of joint tensile strength. However, in other embodiments, the structural characteristics of the delivery lines, conduits and/or other components of the system can be different. As discussed, some or all of the conduits used in the injection system can be constructed or otherwise assembled as a single unit. For hygienic, regulatory and/or other purposes, the delivery lines and other conduits can be sterile and disposable.

Figure 35:
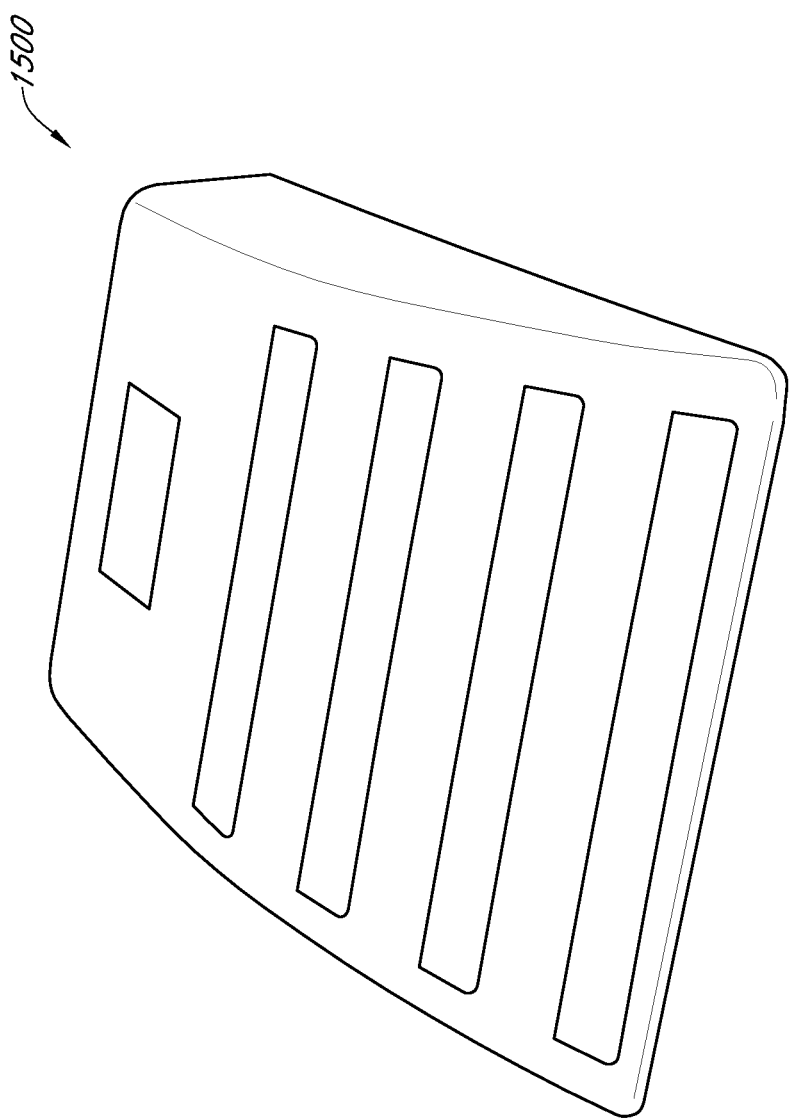
FIG. 35 illustrates a perspective view of one embodiment of a foot pedal configured to regulate one or more aspects of an injection system.

As discussed herein, a clinician can regulate the operation of the fluid delivery module and/or any other component of the injection system using one or more controllers. Such controllers can include one or more buttons, dials, knobs and/or the like. In some embodiments, the controllers can be permanently or removably attached to a handpiece assembly (e.g., a part of a control module, a core, etc.). Alternatively, the controller can be located on a device, component or portion that is not part of a handpiece assembly. For example, such controllers can be provided along the fluid delivery module, an imaging wand and/or the like. In yet other embodiments, as illustrated in FIG. 35, the controller comprises a foot pedal 1500 that can be regulated by the clinician's foot. For example, the clinician or other user can press or release the foot pedal 1500 in order to regulate the delivery of fluids from the injection system to a patient's anatomy. As discussed herein, by pressing or otherwise moving the foot pedal 1500 or other controller, an injection sequence can be initiated, terminated, paused and/or otherwise modified (e.g., increase or decrease flow rate, change the sequence of fluid delivery, etc.), as desired or required. The foot pedal or other controller can be operatively connected to a fluid delivery module and/or another component or portion of the injection system using one or more hardwired and/or wireless connections (e.g., RF, Bluetooth, Wi-Fi, etc.).

As discussed in greater detail herein, the use of a disposable handpiece assembly can offer several advantages. For example, such a configuration can improve the hygiene and general safety of an injection system. Further, the complexity and expense of a multi-piece handpiece assembly having various buttons, other controllers and/or other electrical features can be eliminated. Consequently, the handpiece assembly can be conveniently replaced, along with the tubing, the cassette and/or any other portions of the injection system that come in contact with fluids and other materials being delivered to a patient. Relatedly, the cleaning and other maintenance procedures associated with an injection system are simplified.

According to certain embodiments, the handpiece assembly, the tubing and the cassette are replaced according to a specific time frequency (e.g., once a day, twice a day, etc.), whenever the properties (e.g., type, concentration, etc.) of the various fluids and/or other materials being injected to patients are modified and/or based on some other protocol or requirements. The needle assembly attached to the distal end of the handpiece assembly is replaced between patients.

As noted above, according to some arrangements, the delivery of fluids and/or other materials from the fluid delivery module to the handpiece assembly, and thus to the patient, is controlled by the user using a foot pedal or some other controller. For example, in one embodiment, a foot pedal is connected to the fluid delivery module using a hardwired (e.g., USB, ethernet, etc.) or a wireless connection (e.g., Bluetooth, radio frequency, etc.), as desired or required. In order to commence, pause or terminate a particular procedure, the physician, nurse, technician or other user can selectively press or depress such a foot pedal, button or other controller. In some arrangements, the pedals, buttons or other controllers are configured to permit the user to select between two, three or more different settings. In other embodiments, a foot pedal is of the multi-depth type (e.g., dual-depth, tri-depth, etc.), enabling a user to selectively press the pedal to two or more distinct depths or other levels. Each distinct depth or level can correspond to a particular setting (e.g., flowrate, selection of which fluids or other materials to deliver, etc.). For example, depressing the pedal or other controller to the first level can cause the desired fluids and/or other materials to be injected at the maximum or minimum rate. Further, continuing to press the pedal to subsequent lower levels can cause the rate of delivery to increase, decrease or terminate. In other embodiments, such pedals do not include distinct depths, such as, for example, a rheostat. Thus, a particular setting (e.g., flowrate) can be varied based on the depth to which a foot pedal or other controller is depressed.

In embodiments, where the user is not able to control the injection sequence of the various fluids and/or other materials loaded onto a fluid delivery module, the system may be programmed for a desired protocol prior to the commencement of a procedure. Thus, a user can program the injection system (e.g., using the touchscreen or other entry device) to deliver one, two or more medicaments and/or other substances, either simultaneously, sequentially or individually, according to a desired sequence. Subsequently, the user can initiate, pause, terminate and otherwise control such a protocol using a foot pedal or some other controller.

According to certain embodiments, the injection system can be advantageously configured to detect the presence of air or other gas bubbles within one or more of the conduits of the cassette or other portion of the system. Once one or more bubbles are detected, the injection system can be configured to terminate the injection procedure, provide a warning to the clinician or other user and/or take any other action. According to some embodiments, the air or other gas bubbles are purged from the system before the injection procedure can be resumed. For example, a predetermined volume of fluid and/or other substance being conveyed in the conduits where air or gas was detected can be wasted or otherwise sacrificed to ensure that it has been eliminated from the system.

In one embodiment, air bubbles are detected by the optical sensors, mechanical sensors, pressure sensors, ultrasonic sensors, capacitance sensors, or combinations thereof. However, in other arrangements, the presence of air bubbles is detected using a pressure transducer of the fluid delivery module's drive system. A pressure measurement taken along the back side of the drive system can help determine if air or other fluids are present within any of the conduits or other hydraulic components of the system.

As discussed in greater detail below, FIGS. 39A-39J and 40A-40T illustrate various screenshots of a touchscreen display of the fluid delivery module that can be advantageously configured to permit a clinician or other user to control and/or view the status of a delivery of medications and/or other fluids or materials loaded onto the fluid delivery module. In the embodiments illustrated herein, the fluid delivery module is adapted to receive up to three vials or other containers, the contents of which may be selectively delivered through a handpiece assembly as described in greater detail herein. However, in other embodiments, the articular delivery system may include more or fewer vials or other containers, as desired or required.

According to some embodiments, a fluid delivery module and/or any other component of an injection system can be selectively configured to integrate or cooperate with one or more other devices, such as, for example, an ultrasound device or system, another type of imaging device or system and/or the like. As a result, a physician or other user can more accurately determine the location of the needle as it is being inserted into a patient's anatomy. In such arrangements, data, images and/or other information regarding the injection procedure can be provided to the user on a display of the fluid delivery module, on a display of an ultrasound or other imaging device, a separate display and/or as otherwise required or desired. Regardless of the level of integration between the injection system, an imaging device and/or another device or system, providing important data, images and other information in a single display can advantageously permit a user to more efficiency and effectively execute an injection procedure.

Figure 36A:
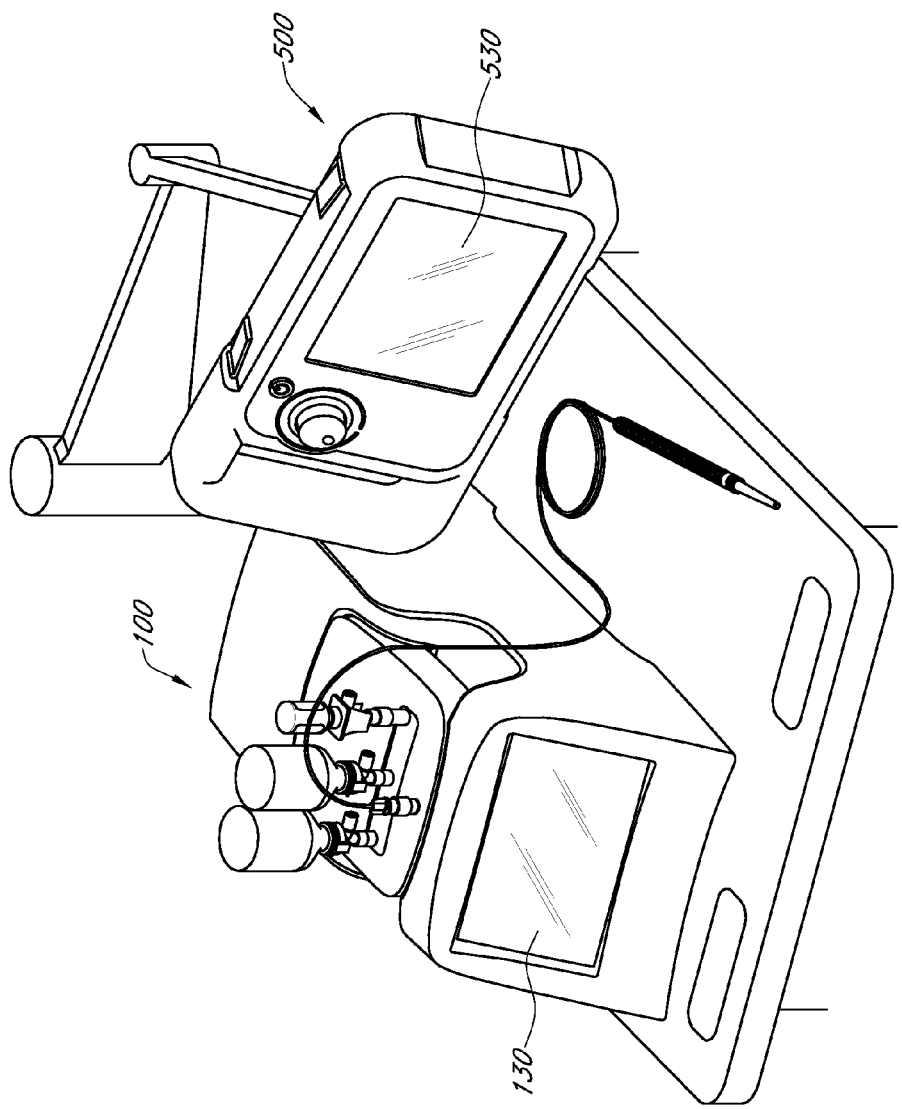
FIGS. 36A-36E illustrate various embodiments of a fluid delivery module operatively coupled to an ultrasound device or other imaging system.
Figure 36B:
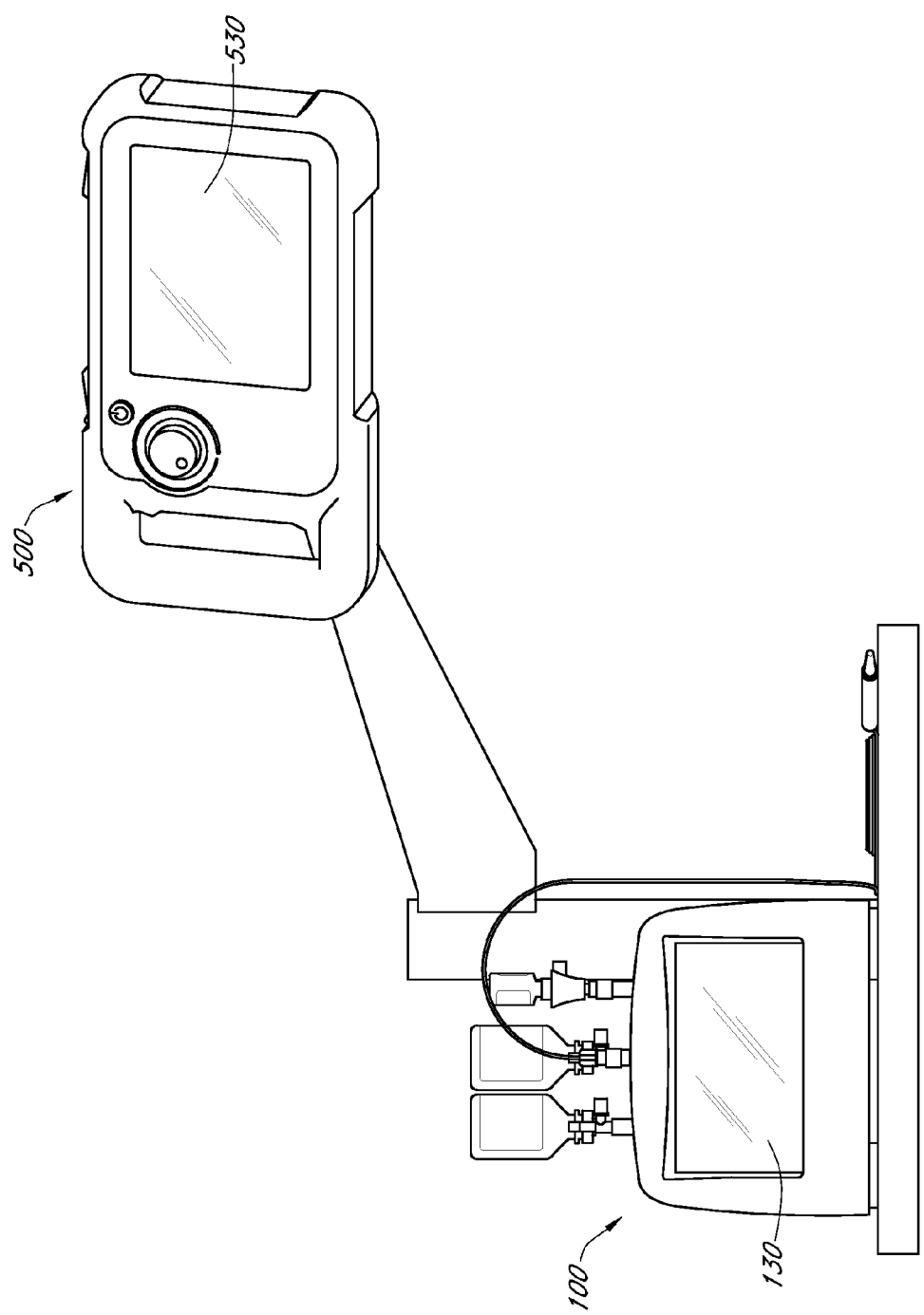

FIGS. 36A and 36B illustrate one embodiment of such an integrated set-up, in which the fluid delivery module 100 is operatively connected to an ultrasound or other imaging device 500. The fluid delivery module 100 can be configured to communicate with the imaging device 500 using one or more hardwired (e.g., USB, Ethernet, other cables, etc.) and/or wireless (e.g., radio frequency, Bluetooth, etc.) connections. As shown, once operatively connected to each other, one or both of the displays 130, 530 can be configured to provide data, images and/or other information obtained by both the injection and the imaging systems. In the illustrated embodiment, the imaging system's display 530 is configured to show the status (e.g., volume of a fluid delivered, volume of a fluid remaining within the cassette, pressure, flowrate, etc.) of the injection procedure in addition to an ultrasound image.

Thus, either or both displays 130, 530 can be configured to simultaneously provide information regarding both the imaging and the injection aspects associated with a particular procedure. Accordingly, a clinician can use a single display of the fluid delivery module or other portion of an injection system to help perform an injection procedure. Further, in some embodiments, color Doppler technology can be used to permit a clinician or other user to visualize the various steps of an injection procedure in real time. As discussed in greater detail herein, such screenshots and other images can be saved for billing, recordkeeping and/or other evidentiary purposes.

Figure 36C:
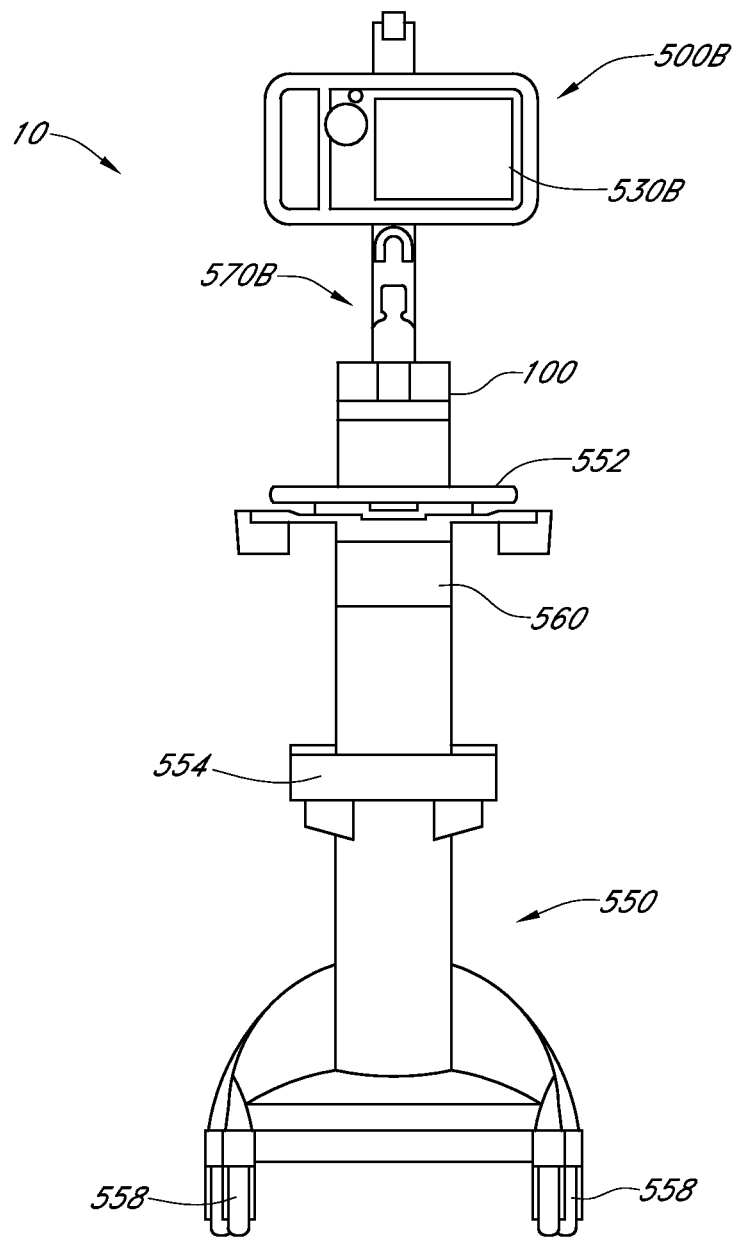
Figure 36D:
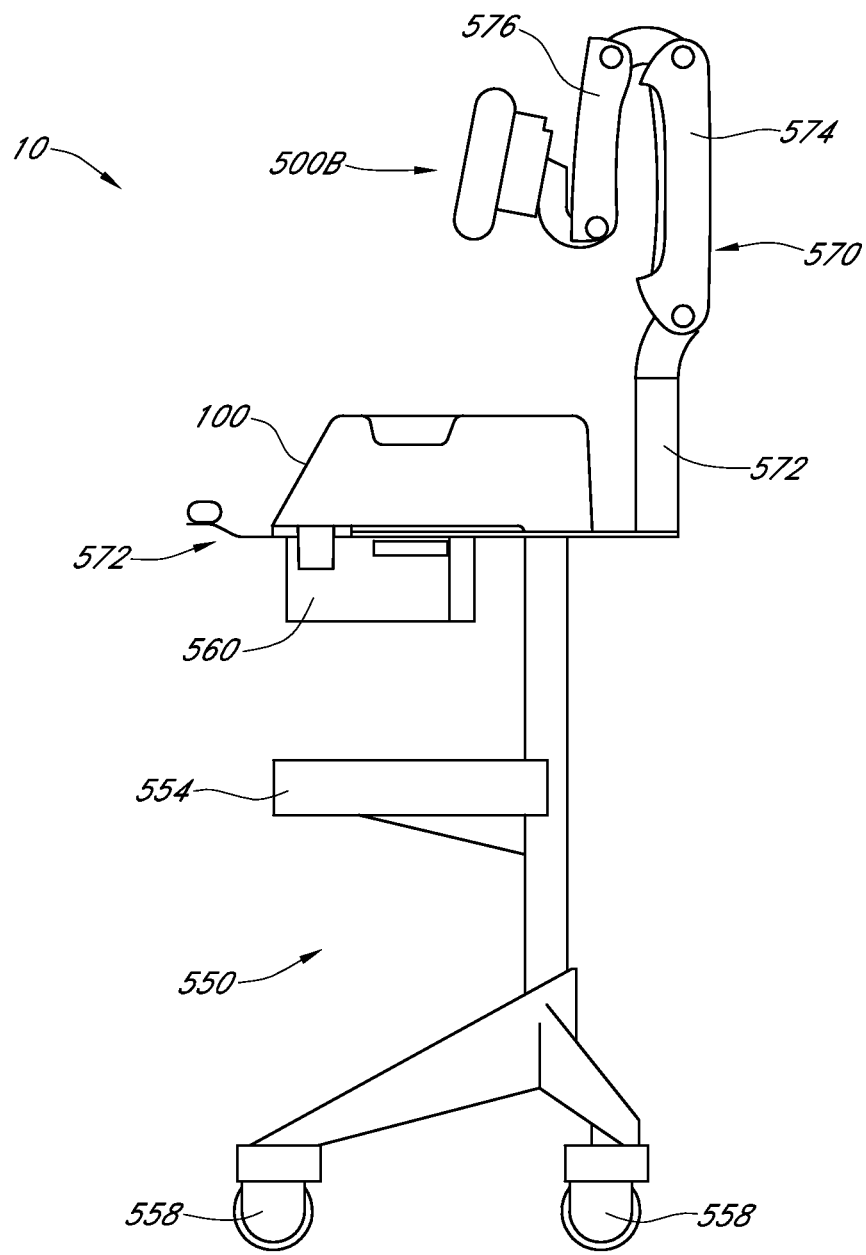

Another embodiment of an injection system 100 operatively coupled to an imaging (e.g., ultrasound) device or system 500B is illustrated in FIGS. 36C and 36D. In the depicted arrangement, the injection system 10 comprises a fluid delivery module 10 that can be removably positioned on a tray or other platform 552 of a cart 550. As shown, the cart 550 can include wheels 558 or other devices that allow it to be easily and conveniently moved to a desired location. In addition, the cart 550 can include one or more other trays 554, platforms and/or other features to further enhance its storage capabilities and overall functionality. The ultrasound or other imaging device 500, which in some embodiments includes a display 530B, can also be secured to the cart 550.

Figure 36E:
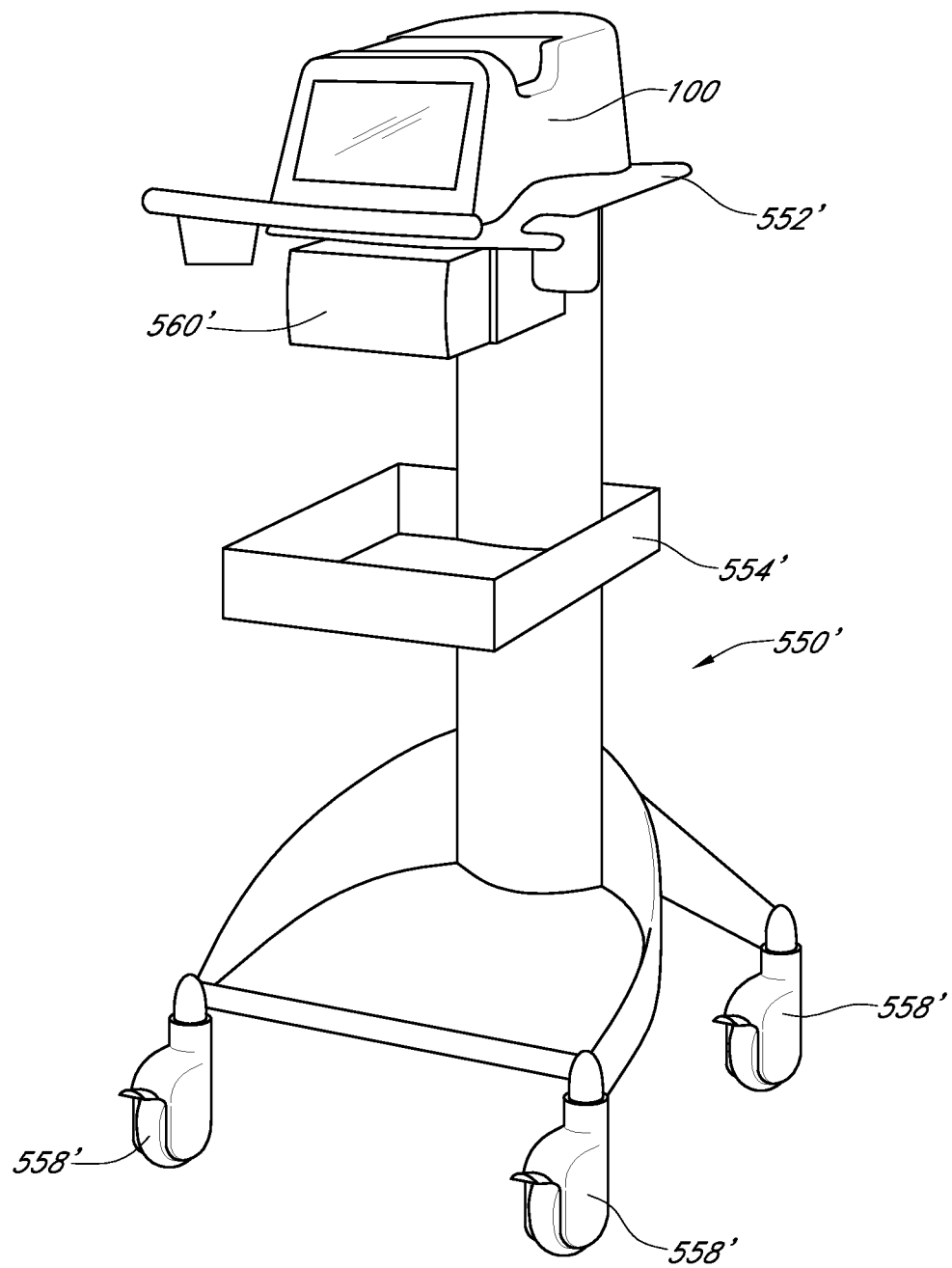

As illustrated in FIGS. 36C and 36D, the display 530B and/or any other component or portion of the imaging device 500B can be mounted on a pivotable support member 570. In some embodiments, the support member 570 comprises one or more arms 572, 574, 576 that can be moved relative to each other (e.g., using hinges, joints, etc.) to position the display 530B and/or other portions or components of the imaging device 500B in a desired location or orientation. In some embodiments, as illustrated in FIGS. 36C and 36D, the cart 550 can be configured to receive a printer 560 or other output device. For example, as discussed with reference to FIGS. 38A and 38B herein, such a printer can be used to generate a report or summary of an injection or other treatment procedure. A different embodiment of a cart 550' configured to retain a fluid delivery module 100, a printer 560, other devices, components or portions of (or operatively coupled to) an injection system is illustrated in FIG. 36E.

Figure 37A:
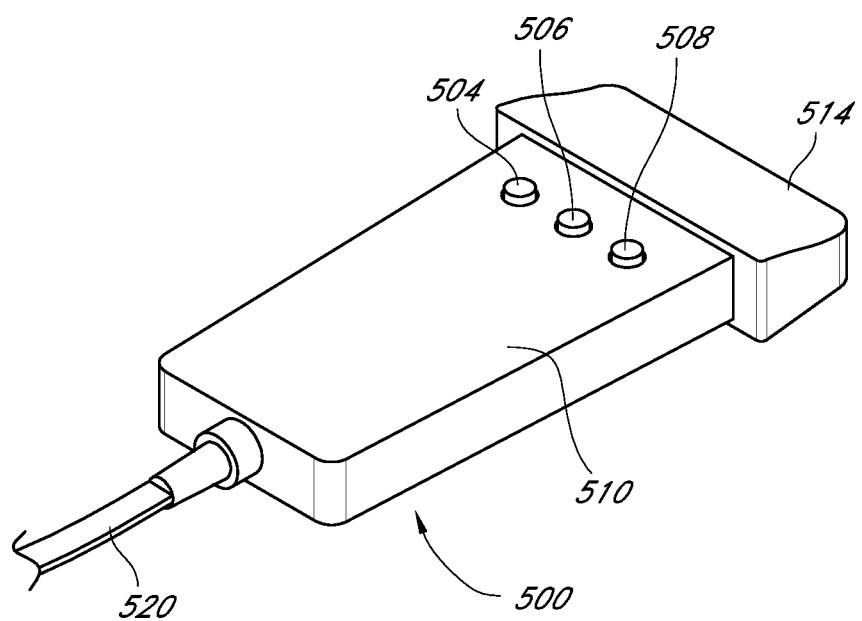
FIG. 37A illustrates a detailed perspective view of one embodiment of an imaging wand configured to be operatively coupled to an injection system.
Figure 37B:
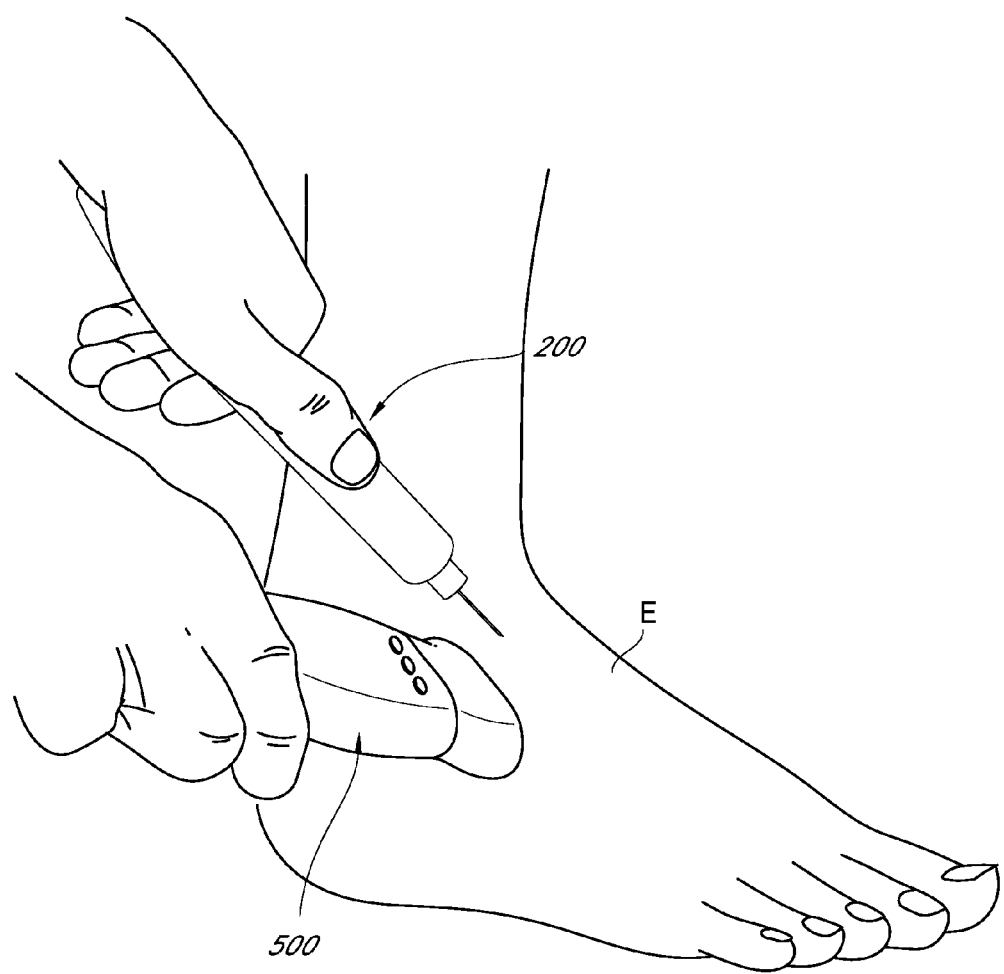
FIG. 37B illustrates a perspective view of a user simultaneously manipulating both an imaging wand and a handpiece assembly of an injection system to treat a patient's foot according to one embodiment.

One embodiment of an ultrasound or other imaging wand configured for use with an injection system is illustrated in FIGS. 37A and 37B. As shown, the wand 500 can include a main body 510 and a head 514 that is configured to contact the patient's skin during the imaging procedure. In addition, the wand 500 can include one or more buttons 504, 506, 508, knobs, levers, switches and/or other controllers that allow the clinician to operate one or more aspects of the imaging system and/or the injection system. For example, the buttons and/or other controller can be configured to adjust or capture an ultrasound or other type of image. In some embodiments, the buttons are configured to regulate the injection of fluids and/or other materials through the handpiece assembly 200 (e.g., initiate or terminate an injection procedure, alter the flowrate or sequence of delivery, etc.).

Accordingly, a clinician or other user can control various aspects of an injection procedure through a single device. Alternatively, the handpiece assembly 200 can include one or more buttons, knobs and/or other adjustment devices or controllers that are adapted to control the delivery of fluids and/or other materials through the handpiece assembly 200 and the operation of an imaging system, either in lieu of or in addition to button or controllers on the imaging wand. As discussed herein, this can advantageously permit a user to locate a targeted anatomical space (e.g., a joint, an organ, a cavity, etc.), control the delivery of one, two or more different fluids and/or substances to such a targeted space and/or regulate one or more other aspects of an injection procedure without having to remove his or her hands from the handpiece assembly 200. In other embodiments, both the injection and imaging systems are controlled by buttons or other adjustment devices located on the fluid delivery module 100 (e.g., touchscreen display), another portion of the injection system and/or a separate device, either in lieu of or in addition to buttons located on the handpiece assembly 200 and/or the imaging wand 500.

As noted above, incorporating imaging technologies (e.g., ultrasound, radio frequency spectroscopy, CT, MRI, etc.) into an articular injection system that is also configured to selectively transfer fluids and/or other materials into or out of a targeted anatomical location can facilitate an injection/aspiration procedure for a clinician or other user. In some embodiments, an imaging-enabled injection system can facilitate execution of a particular injection procedure. In addition, such devices and systems can enable an injection procedure to be completed with fewer clinicians and other resources. For example, when a separate imaging device is utilized, two or more physicians or clinicians are typically needed to properly and safely complete the procedure. As illustrated in the embodiment of FIG. 37B, a clinician or other user can perform an injection procedure by manipulating an imaging (e.g., ultrasound, radio frequency spectroscopy, etc.) wand 500 in one hand to locate the targeted anatomical location (e.g., toe, foot, knee, other joint, etc.), while simultaneously handling the handpiece assembly 200 in the other hand to selectively transfer fluids or other materials to (or from) such location.

Consequently, incorporating imaging technologies into the articular injection system can offer a number of advantages. For example, such a combination unit can be operated using a single power supply. In addition, such a configuration can be operated using a single logic board, computer chip or other processor. Further, as discussed, the combination unit can allow a clinician to use "multi function" buttons and controls. For instance, a button, soft key or other adjustment device can be used to control both an ultrasound unit (or other imaging or location device) and the injection system.

As discussed, in any of the embodiments disclosed herein, a target intra-articular location or other anatomical space can be located using one or more imaging techniques, such as, for example, ultrasound, fluoroscopy, CT, MRI and/or the like. Ultrasound technology uses sound waves of a particular frequency to image internal structures (e.g., tissue, organs, joints, etc.). In some arrangements, pulsed and/or continuous sound waves can be directed to the area of interest using one or more transducers. Redirected sound waves that bounce off anatomical structures are detected by the transducers or other devices (e.g., wand 500). These data can then be processed to generate an image or other visual display of the targeted area.

Ultrasound transducers and other components used to locate a desired anatomical location can be directly or indirectly incorporated into a fluid injection system. For example, in some embodiments, a separate ultrasound probe or wand is used to visually confirm the location of the needle relative to the target location (e.g., a joint or intra-articular space, an organ, etc.). The ultrasound equipment can be configured to operate either continuously or intermittently during the course of the procedure, as desired or required. In other embodiments, an ultrasound transducer and/or other ultrasound devices is incorporated directly into one or more components of an injection system. For instance, a small ultrasound transducer can be positioned at or near the tip of the delivery or aspiration needle. The ultrasound transducer can be placed in data communication with a processing apparatus and/or other components using one or more hardwired and/or wireless connections. In addition, the injection system can be configured so that the imaging results are advantageously viewed on the display 130 (FIG. 1) of the fluid delivery module.

Thus, as the needle is inserted into the body, a physician or other clinician can accurately detect the position of the distal end of the needle. Such imaging techniques can be used alone or in conjunction with one or more other locating methods or devices. For example, in one embodiment, tissue response measurements can be used to locate a target intra-articular space. In other embodiments, ultrasound and/or other imaging technologies are used to locate a targeted intra-articular space. In other embodiments, both tissue response measurements and ultrasound and/or other imaging technologies are used to locate a joint space. In still other embodiments, one or more other joint locating methods or devices can be used, either in lieu of or in addition to methods, systems and methods disclosed herein.

In some embodiments, ultrasound imaging is particularly advantageous because it permits real-time visualization of a joint or other target location. By way of example, in one embodiment, the delivery module and system include an ultrasound device using a broadband curved array transducer working at about 2-5 MHz and a broadband linear array working at about 4-7 MHz. Imaging errors can be kept at a minimum by taking the linear array for measurements. Curved array may be desirable and used for better penetration depth.

Several embodiments of the present application provide a system and method of using ultrasound guidance to inject fluids into small joint spaces. Further, ultrasound and other imaging technologies can assist in the visualization of internal structures (e.g., bones, joints, organs, other tissue, etc.) within the anatomy. Thus, such imaging technologies can be used to visually display the orientation of the needle with respect to such internal structures. Consequently, ultrasound can assist a user in correctly positioning and directing the needle during an injection and/or aspiration procedure.

In addition, a contrast media can be used with the ultrasound devices and methods described herein to further enhance the user's ability to verify the location of the needle tip relative to the targeted anatomical location (e.g., intraarticular location, organ, etc.). This can provide additional assurances that the medication, other fluid and/or other substances are being delivered to the desired location within the patient being treated. A contrast media can also be used in embodiments where aspiration of a fluid or other material is desired. For example, if acceptable, a contrast media can be delivered to or near the desired location. Then, once placement of the aspiration needle has been confirmed, the fluid module can be used to aspirate as required. In some embodiments, if the aspiration procedure is therapeutic in nature (e.g., being used to relieve pressure within the targeted anatomical location), the use of contrast media may be acceptable. However, in one or more other circumstances, the use of contrast media may not be acceptable or desirable. For example, if the purpose of the aspirating is to withdraw a fluid for diagnostic reasons (e.g., testing the extracted fluid sample), initially injecting a contrast media or other substance may contaminate the desired sample.

As discussed herein, in some embodiments, data and other information regarding the types, volumes or other amounts, dosages and/or other details of the various medications and/or other substances administered during a particular injection procedure, as displayed to the user in a touchscreen or other interface, are automatically stored within a memory of the fluid delivery module, another component or portion of the injection system or an external processor or network with which the injection system is in data communication. In addition data and information related to ultrasound or other imaging procedures that were conducted can also be saved for later processing (e.g., documentation, billing, etc.) or retrieval. Such data and information can include actual ultrasound images, details regarding the imaging equipment used, the extent to which a particular imaging device was used and/or the like.

In addition, as discussed, other details related to a specific procedure can also be recorded, maintained and linked to a delivery sequence of various medicaments and/or other substances. For example, the injection system can be configured to receive and maintain the name of the patient, the date and time that the procedure was performed, the duration of the procedure, the physicians, clinicians and/or other personnel that participated in the preparation and/or execution of the procedure, the disease or condition being treated, specific treatment codes and other administrative information and/or the like. Such data collection capabilities can assist with billing, insurance processing, patient record keeping, generation of reports, reordering of medicaments and other injectable materials and/or other functions. In some embodiments, such records or summaries (e.g., printouts, electronic file, etc.) can be included in or otherwise connected with (e.g., physically, electronically, etc.) a patient's file or chart. In addition, the use of the summaries or reports can provide one or more additional benefits to a user. For example, such summaries and reports can improve the economic return on an injection procedure for the service provider by leveraging the relatively favorable reimbursement of the corresponding ultrasound-guided (or other imaging-guided) procedures.

According to some embodiments, an injection system includes a printer, another output device, memory and/or the like to help memorialize the details associated with a specific injection procedure. As noted herein, the corresponding output resulting from such recordkeeping can assist with billing, insurance processing, patient record keeping, generation of reports and/or the like. In addition, such printouts or alternative forms of output (e.g., electronic reports) can memorialize the details of a particular procedure, serving as evidence of what was performed (e.g., which and how much of each medicament and/or other substance was injected, the sequence of delivery, visual confirmation via an ultrasound or other imaging technology of the needle location and other details of the injection, etc.), to whom the injection was administered, who performed the injection procedure, when and where the procedure was executed and/or the like. As noted above, such summaries can be provided on a paper printout (e.g., a printer that is incorporated with or operatively coupled to an injection system), electronic form (e.g., a summary generated as a pdf, an image or some other standard or non-standard viewable format, etc.) and/or the like.

Figure 38A:
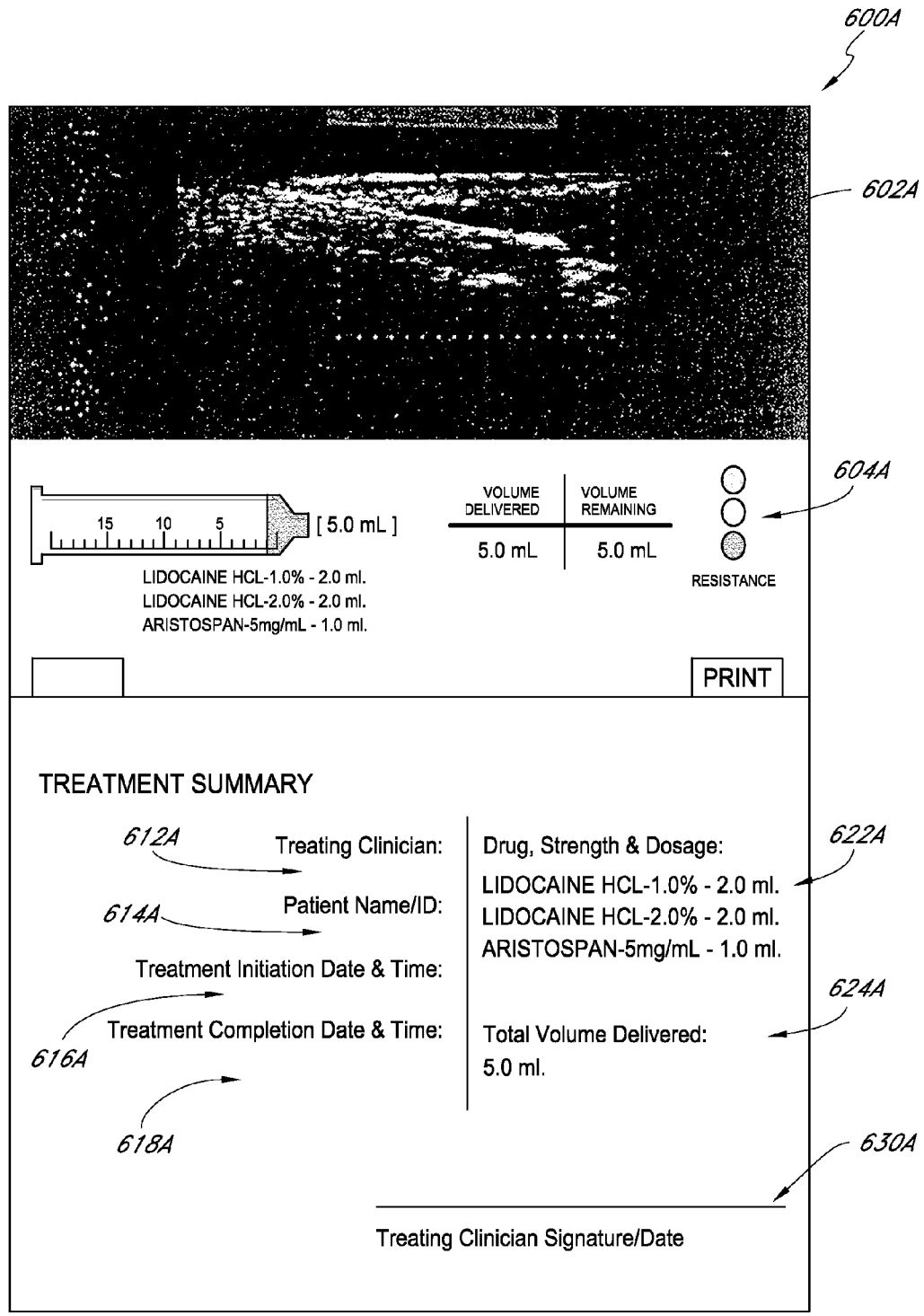
FIGS. 38A and 38B illustrate embodiments of summaries or reports configured to be generated in relation to injection procedures.
Figure 38B:
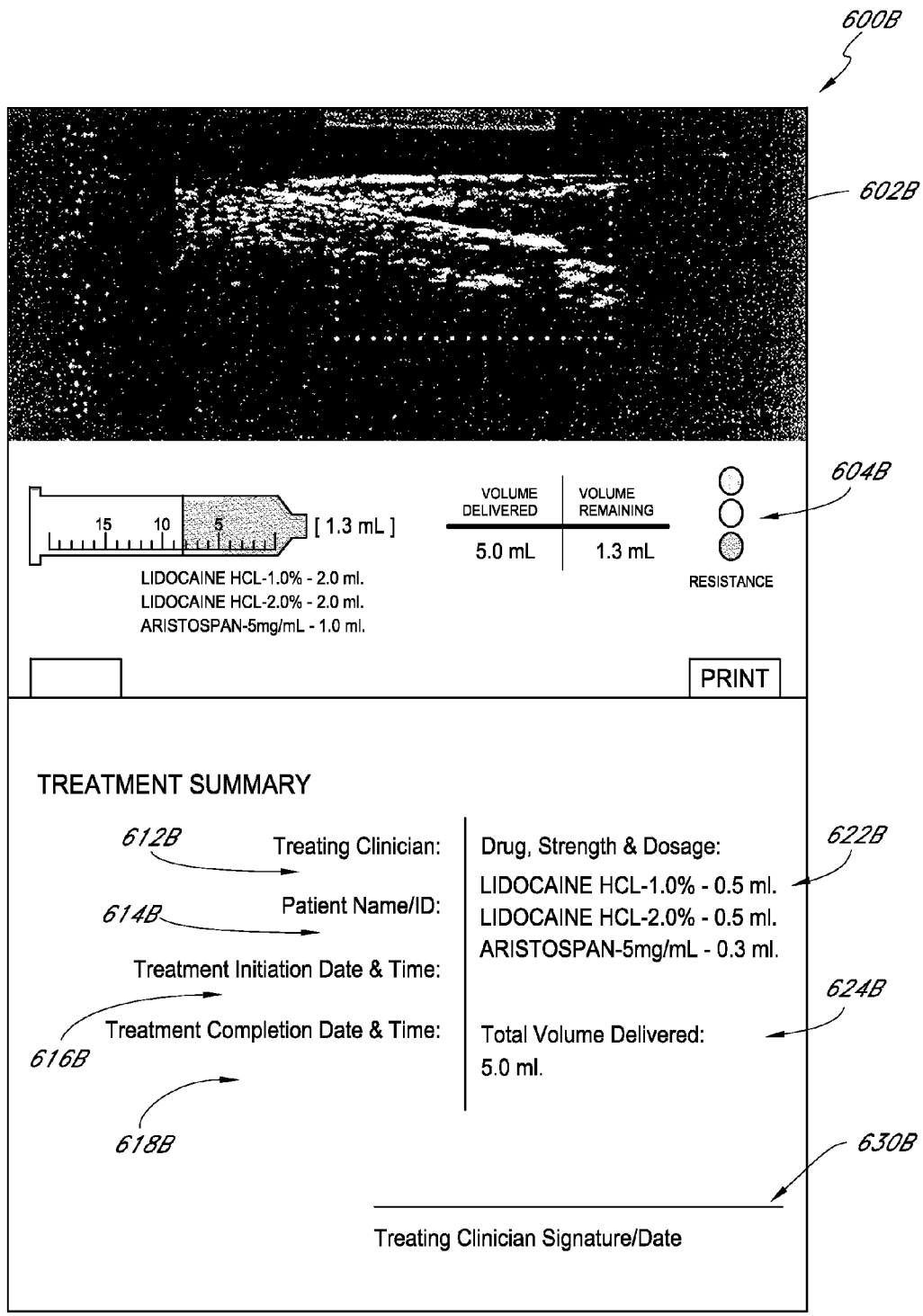
Figure 39A:
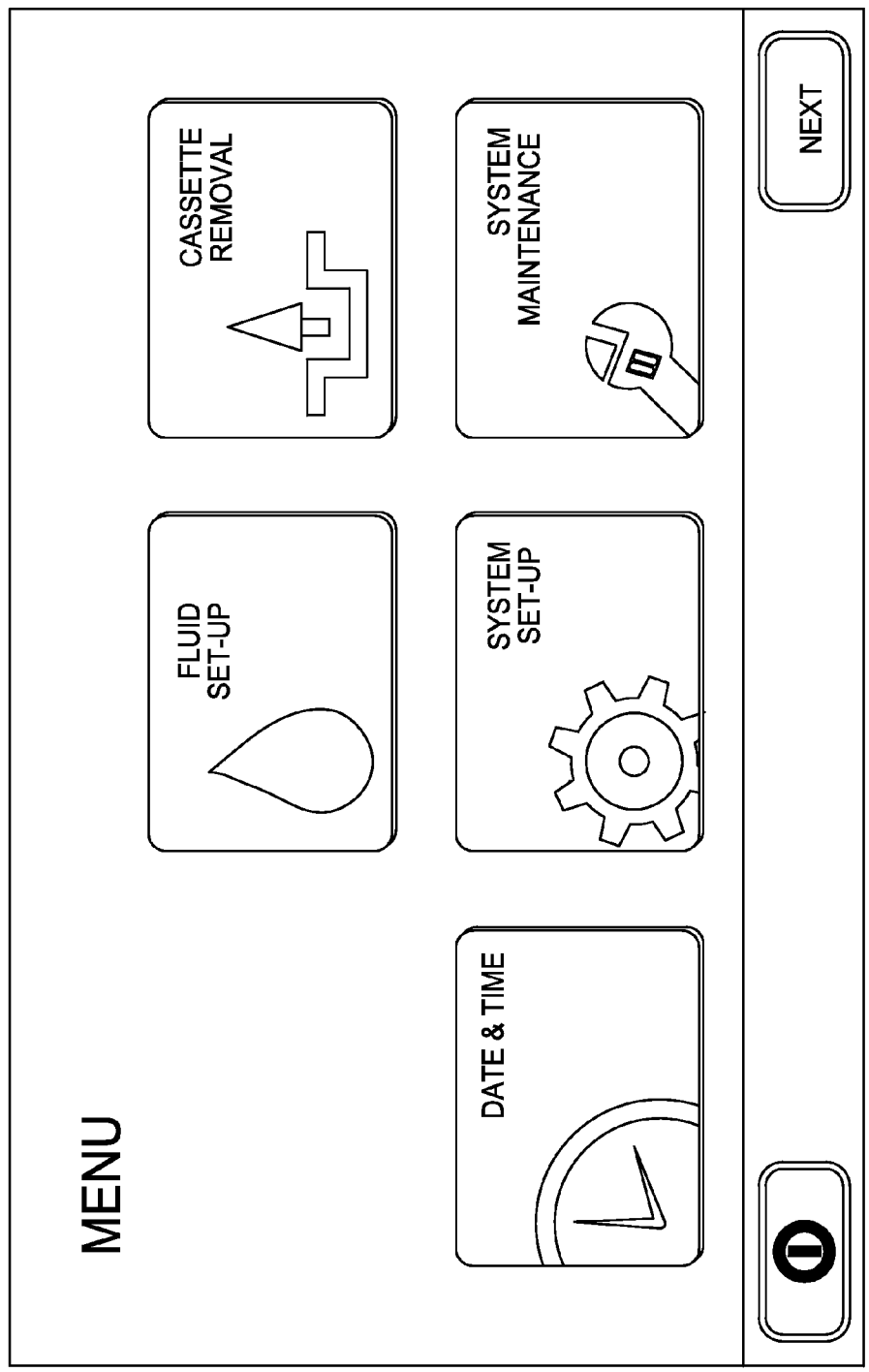
FIGS. 39A-39J illustrate various screenshots from the visual display of a fluid delivery module related to an injection procedure according to some embodiments.
Figure 39B:
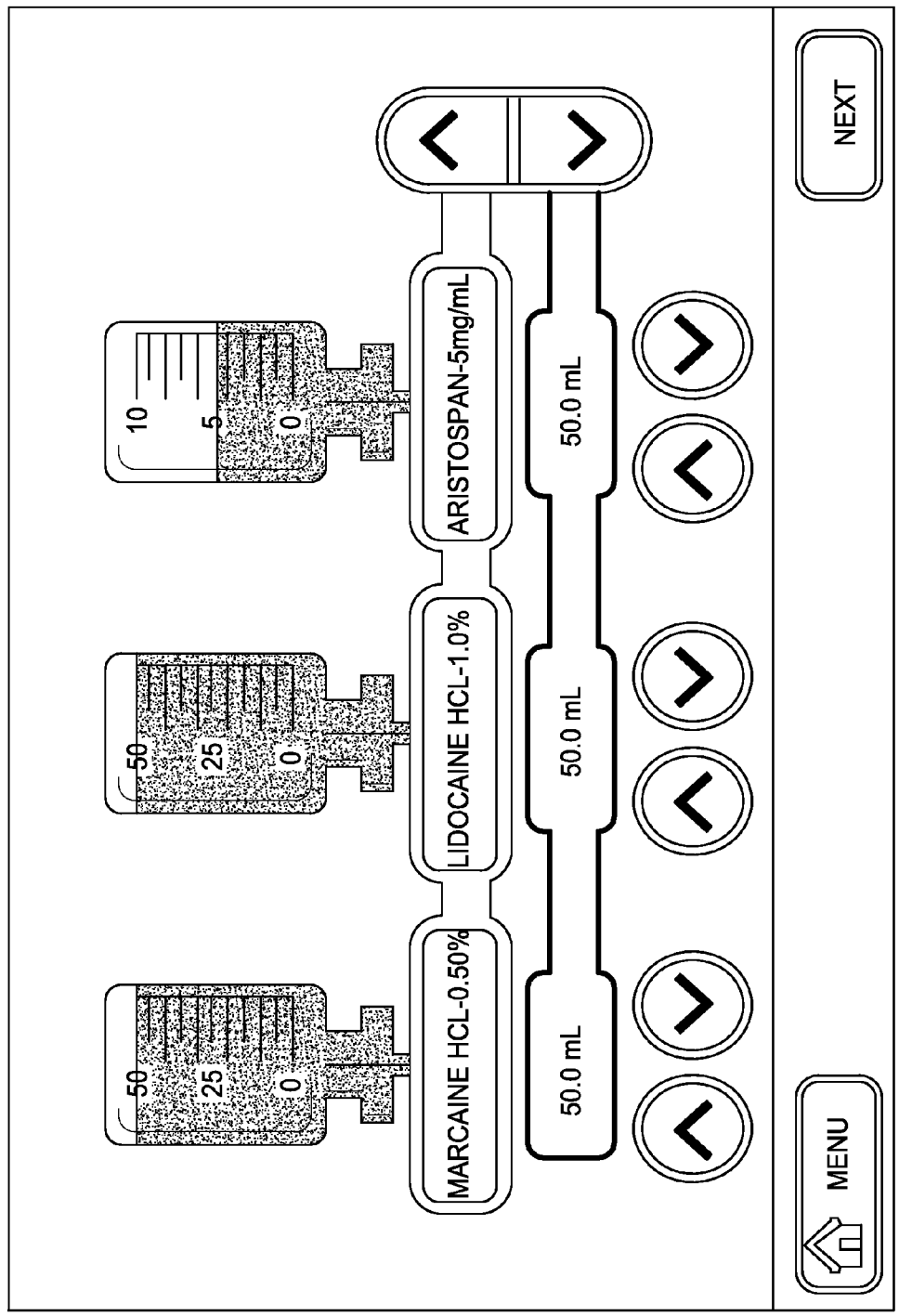
Figure 39C:
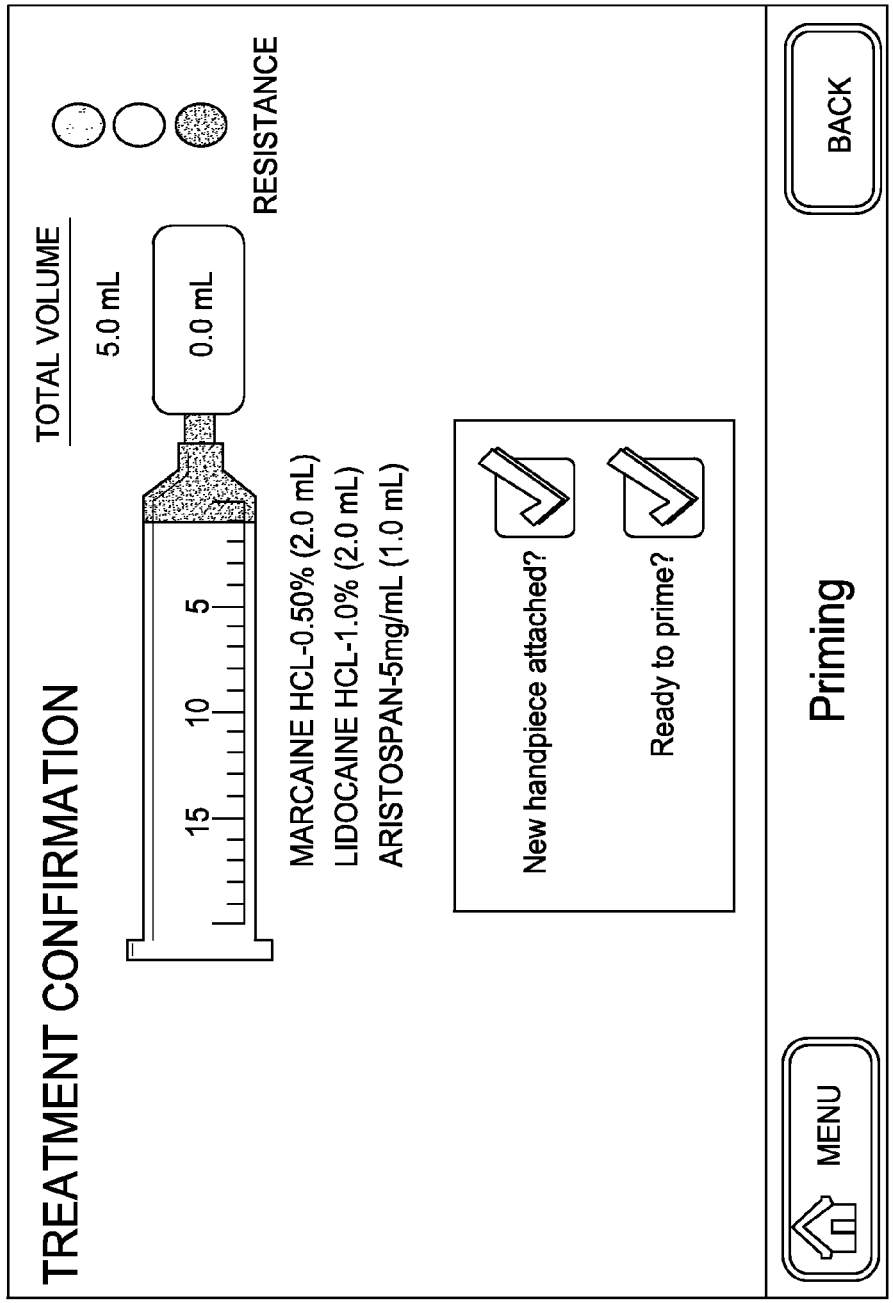
Figure 39D:
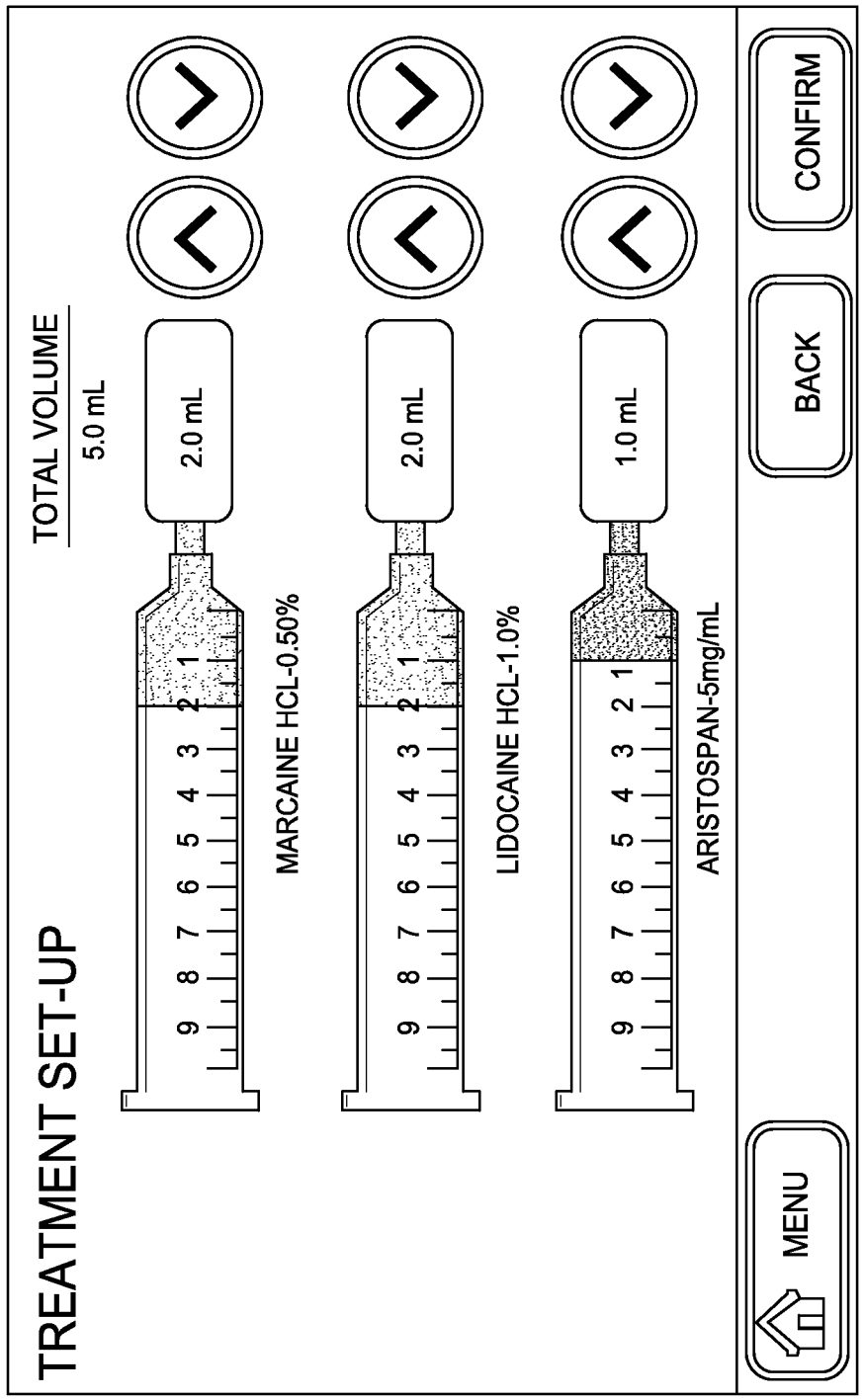
Figure 39E:
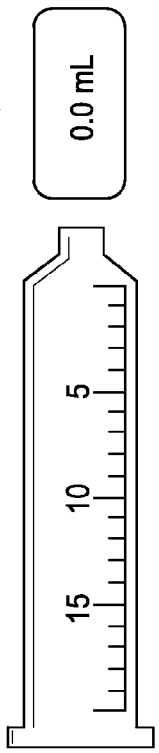
Figure 39F:
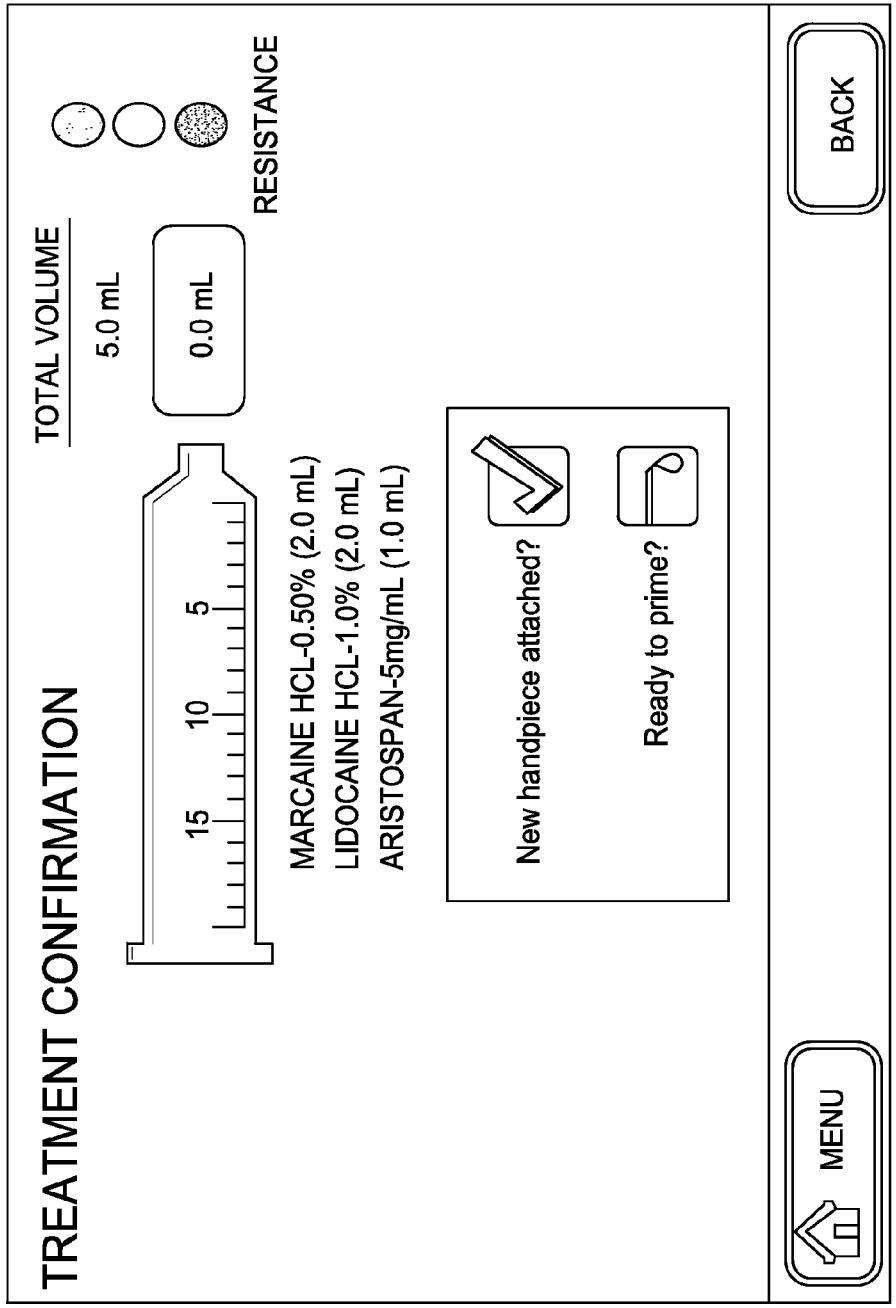
Figure 39G:
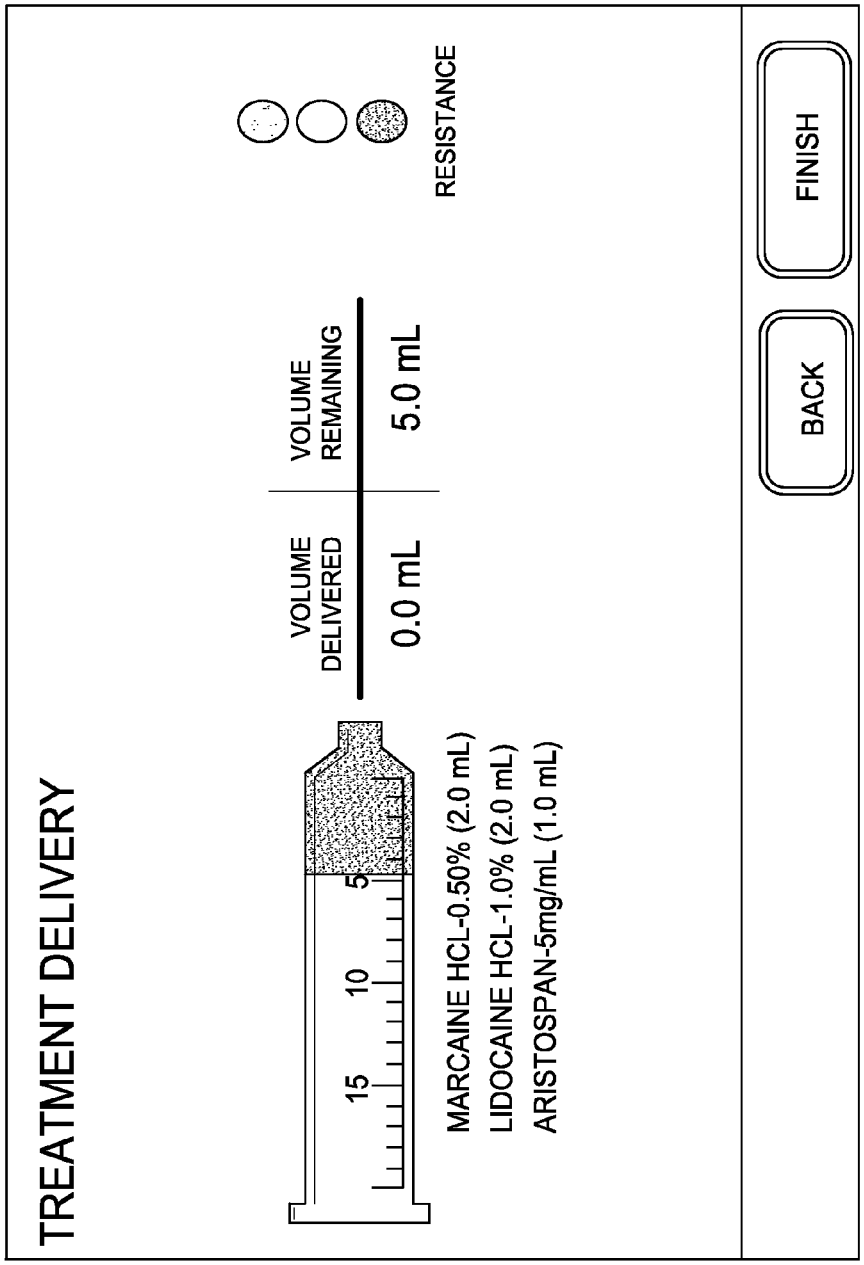
Figure 39H:
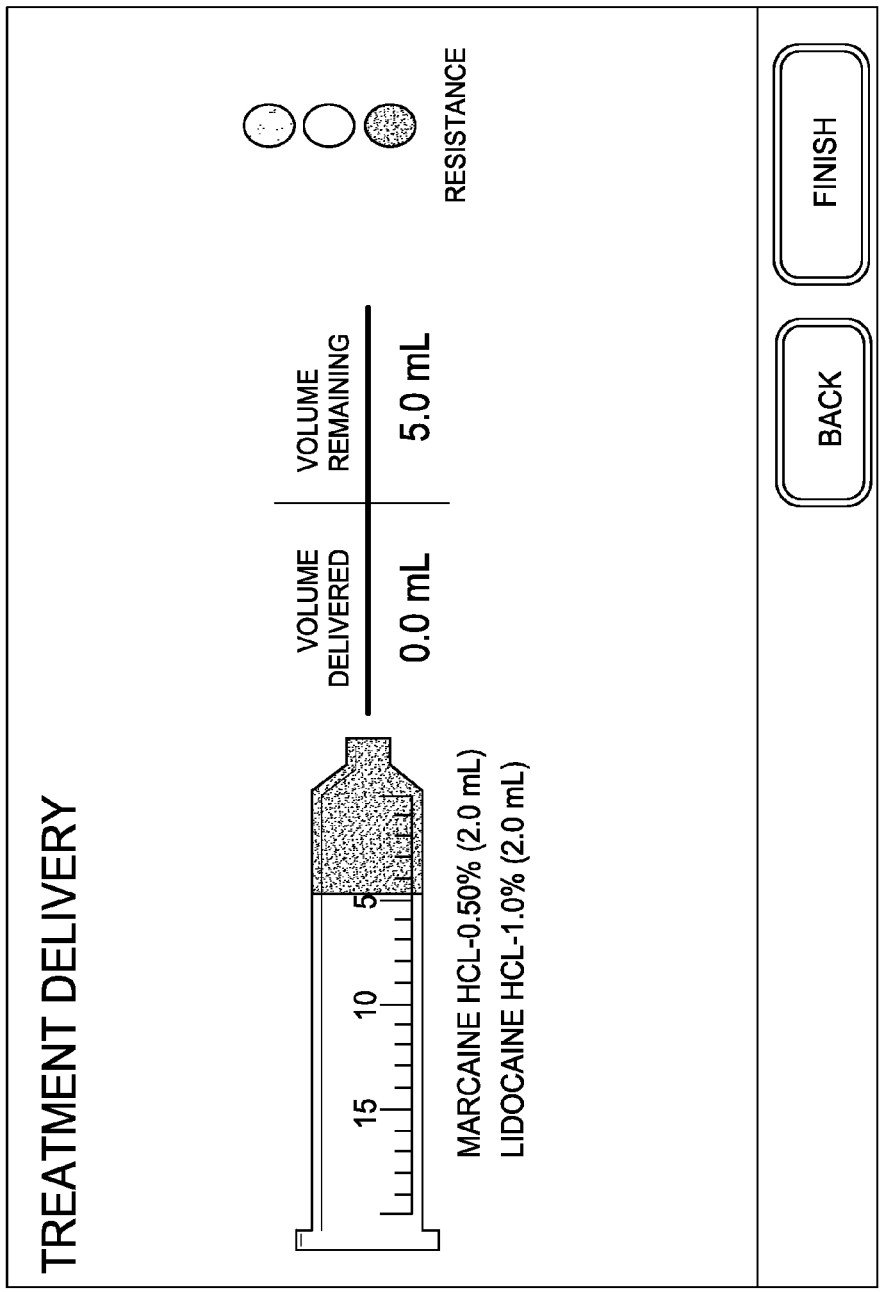
Figure 39I:
Figure 39J:
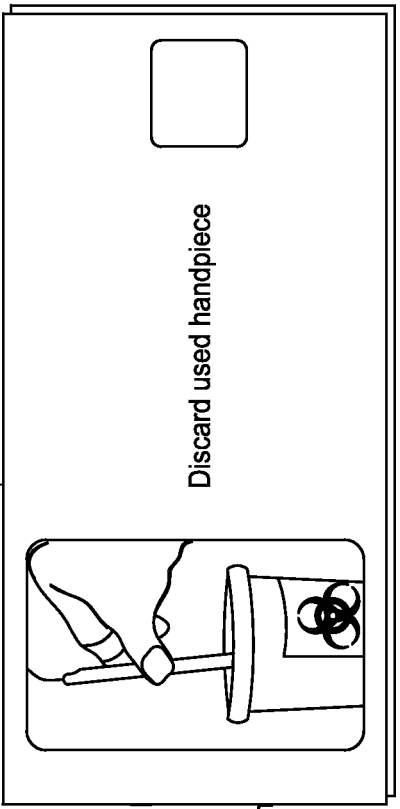
Figure 40A:
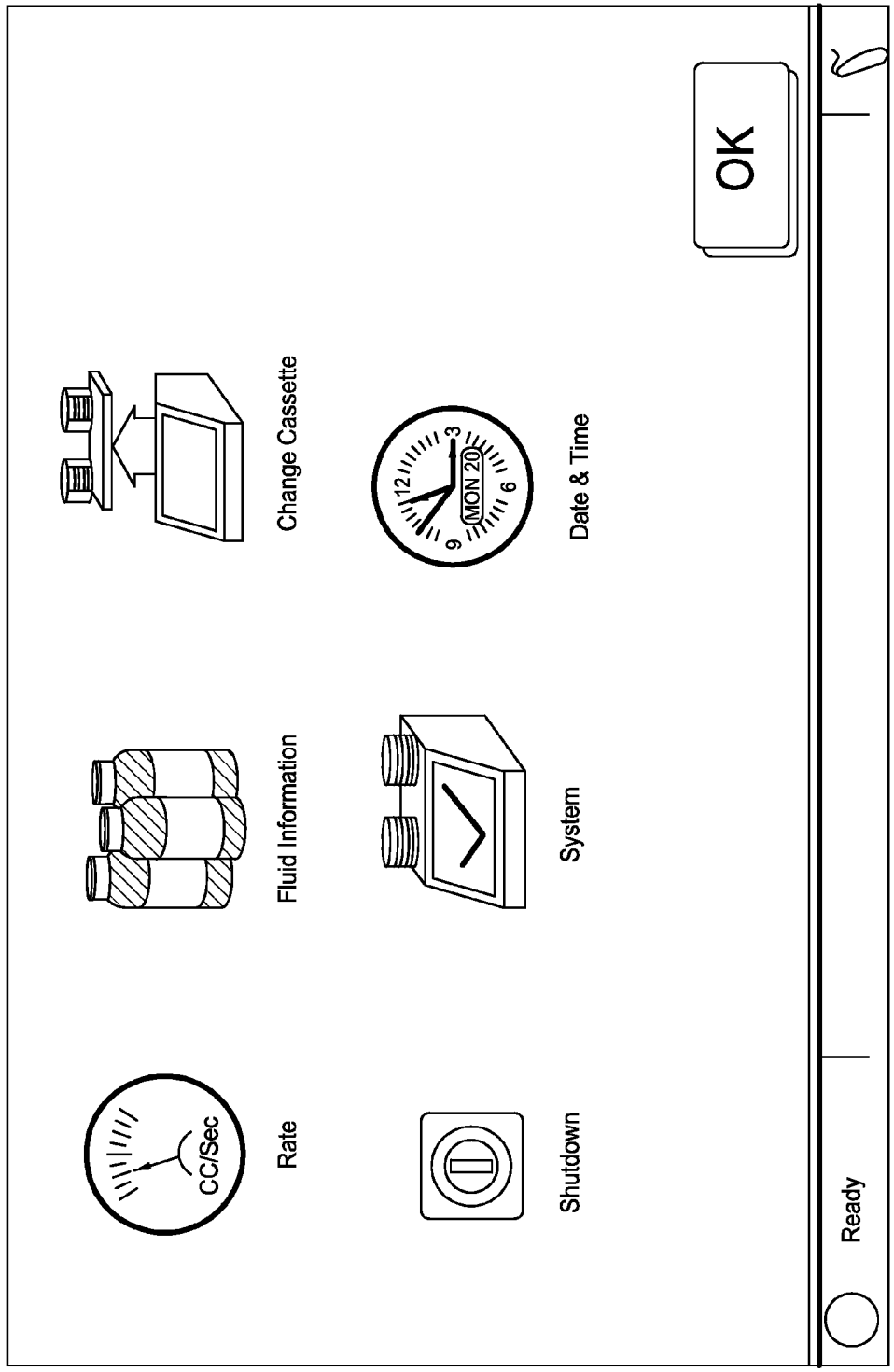
FIGS. 40A-40T illustrate various screenshots from the visual display of a fluid delivery module related to an injection procedure according to other embodiments.
Figure 40B:
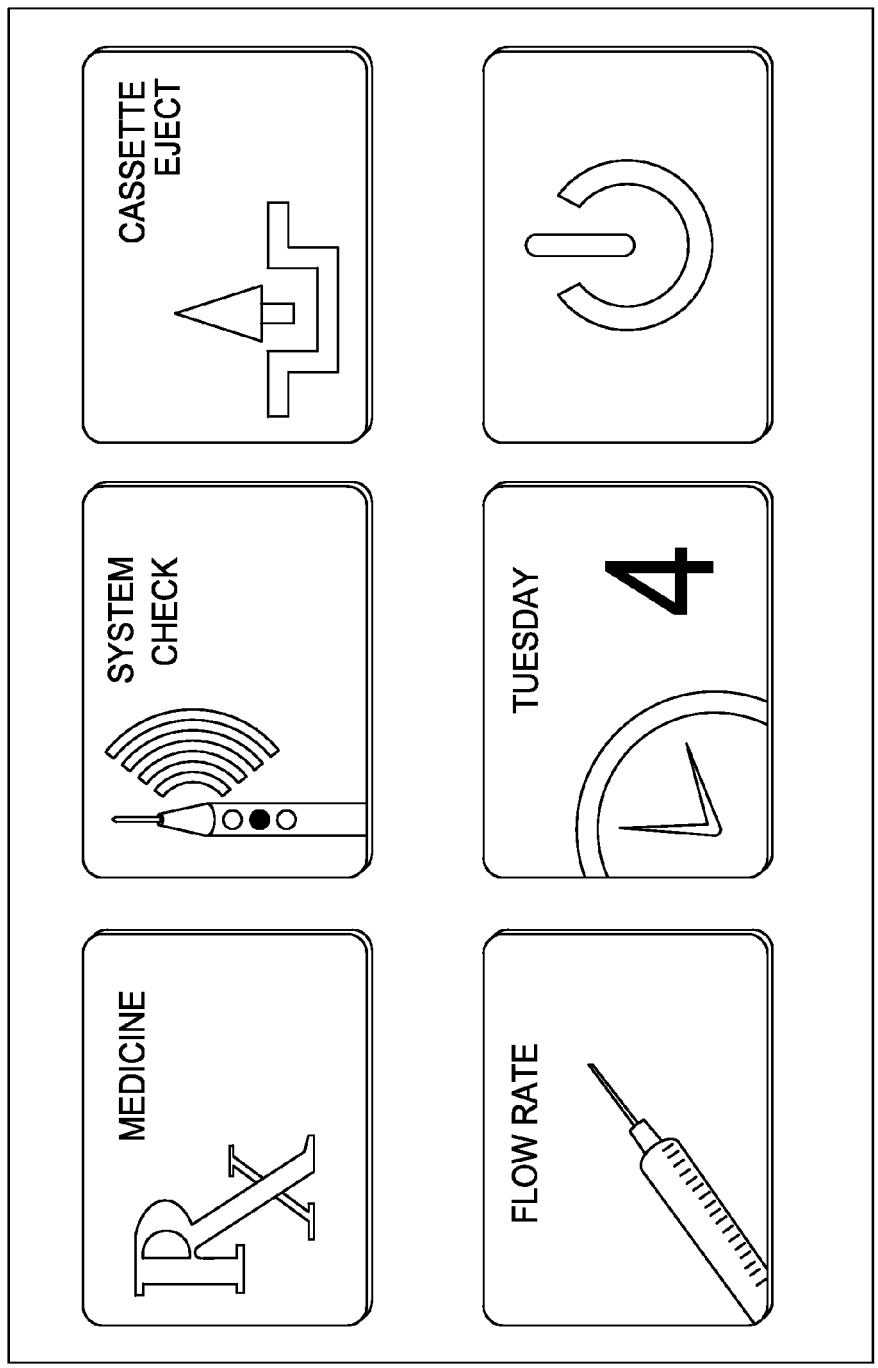
Figure 40C:
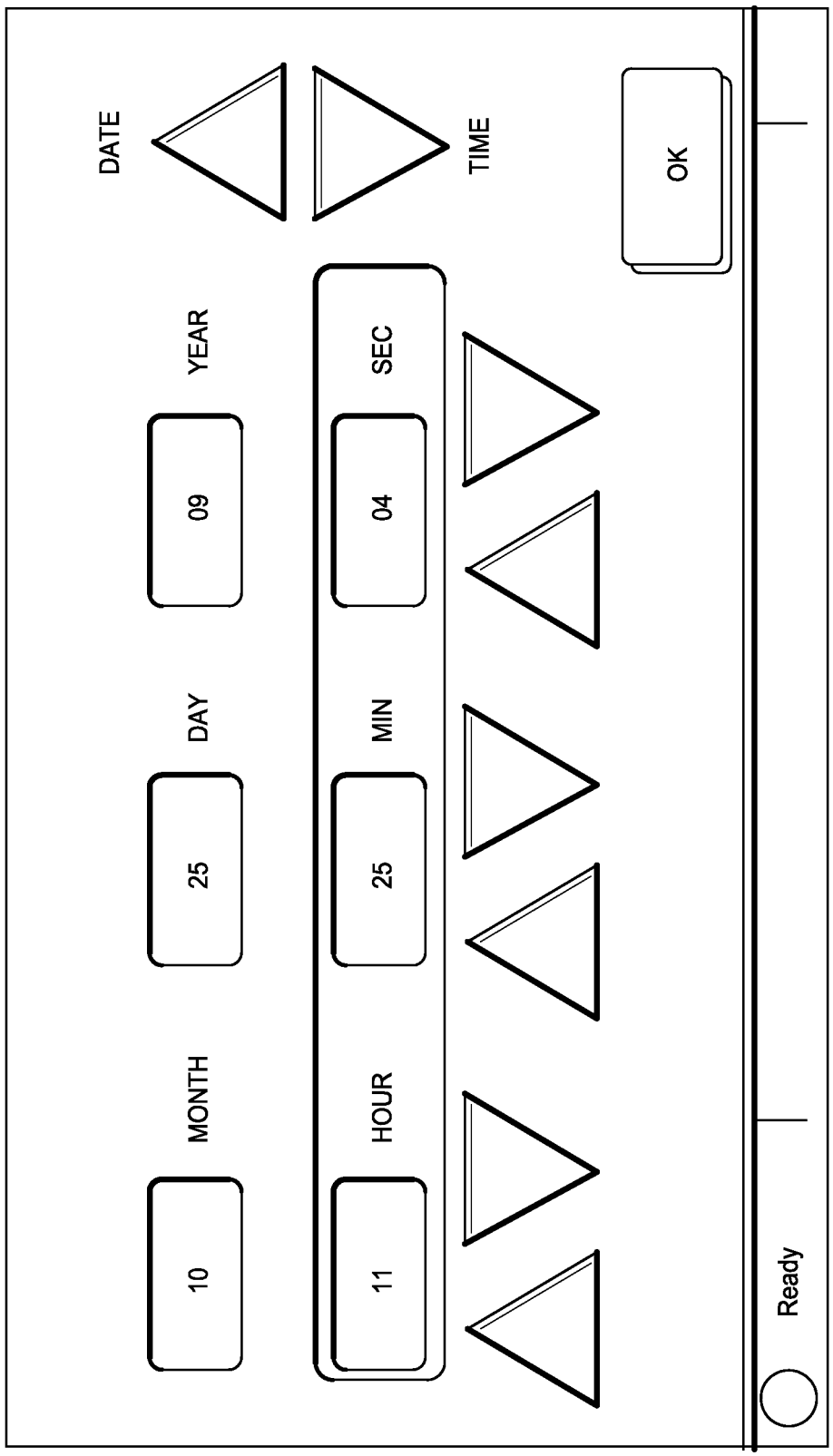
Figure 40D:
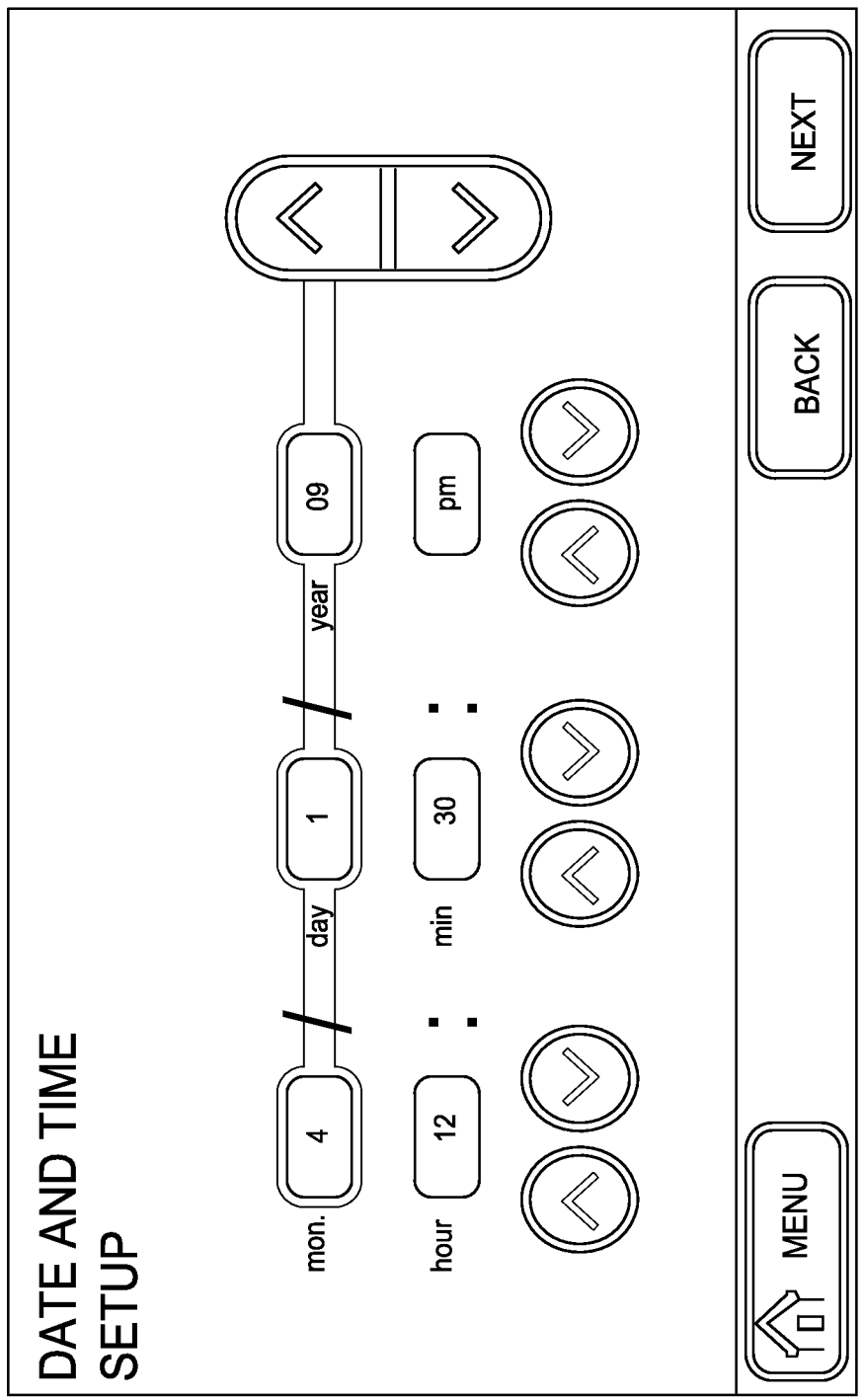
Figure 40E:
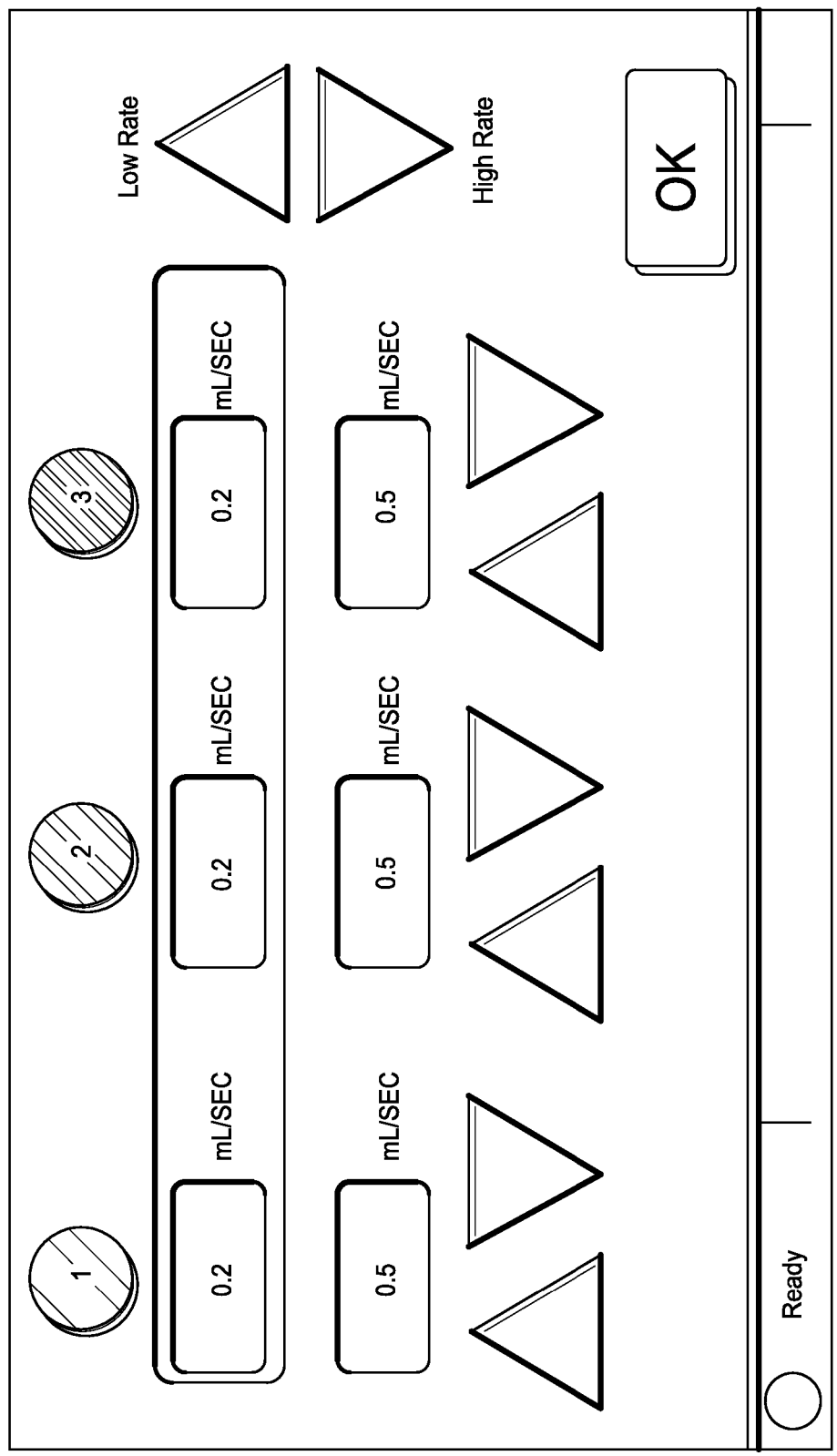
Figure 40F:
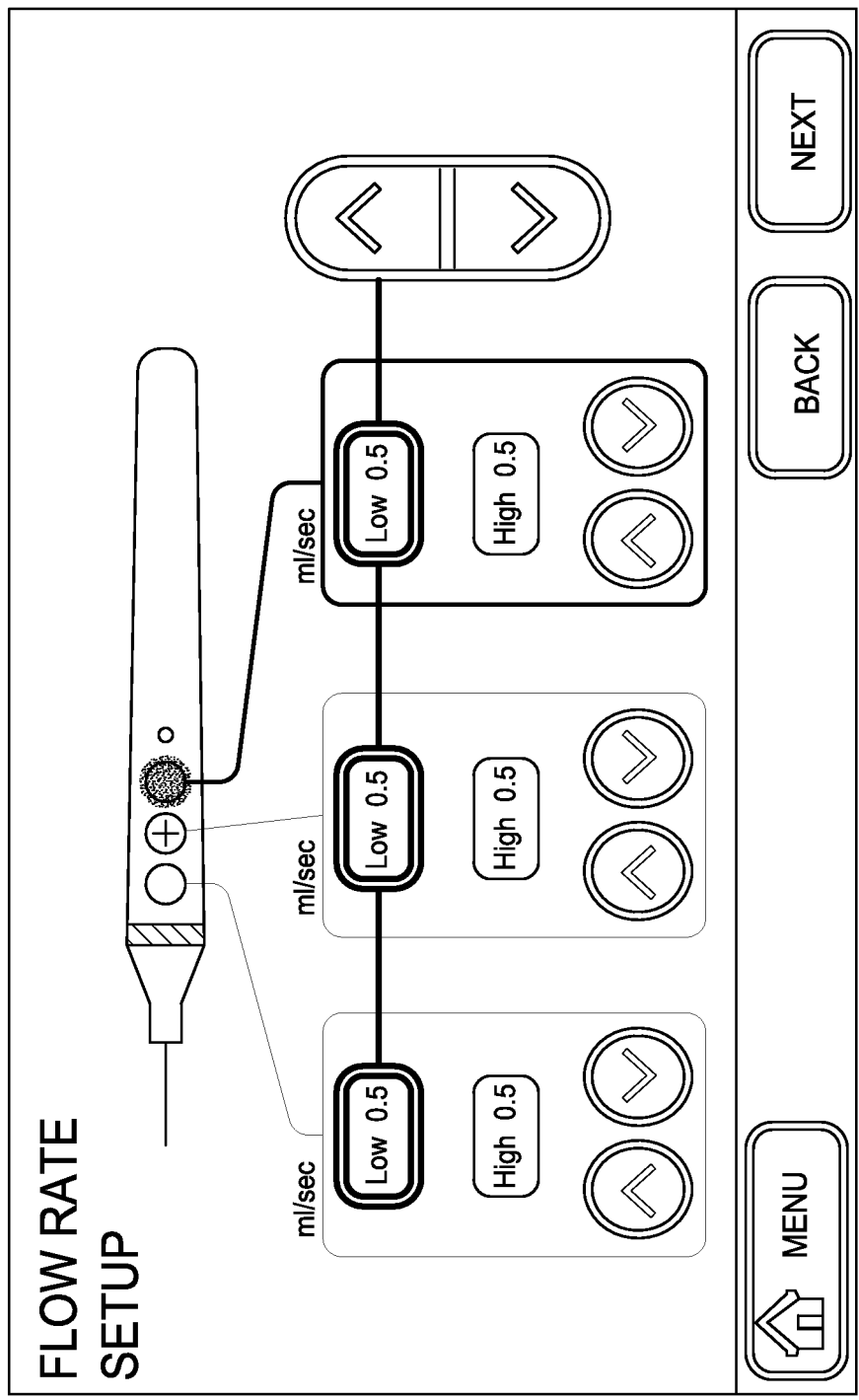
Figure 40G:
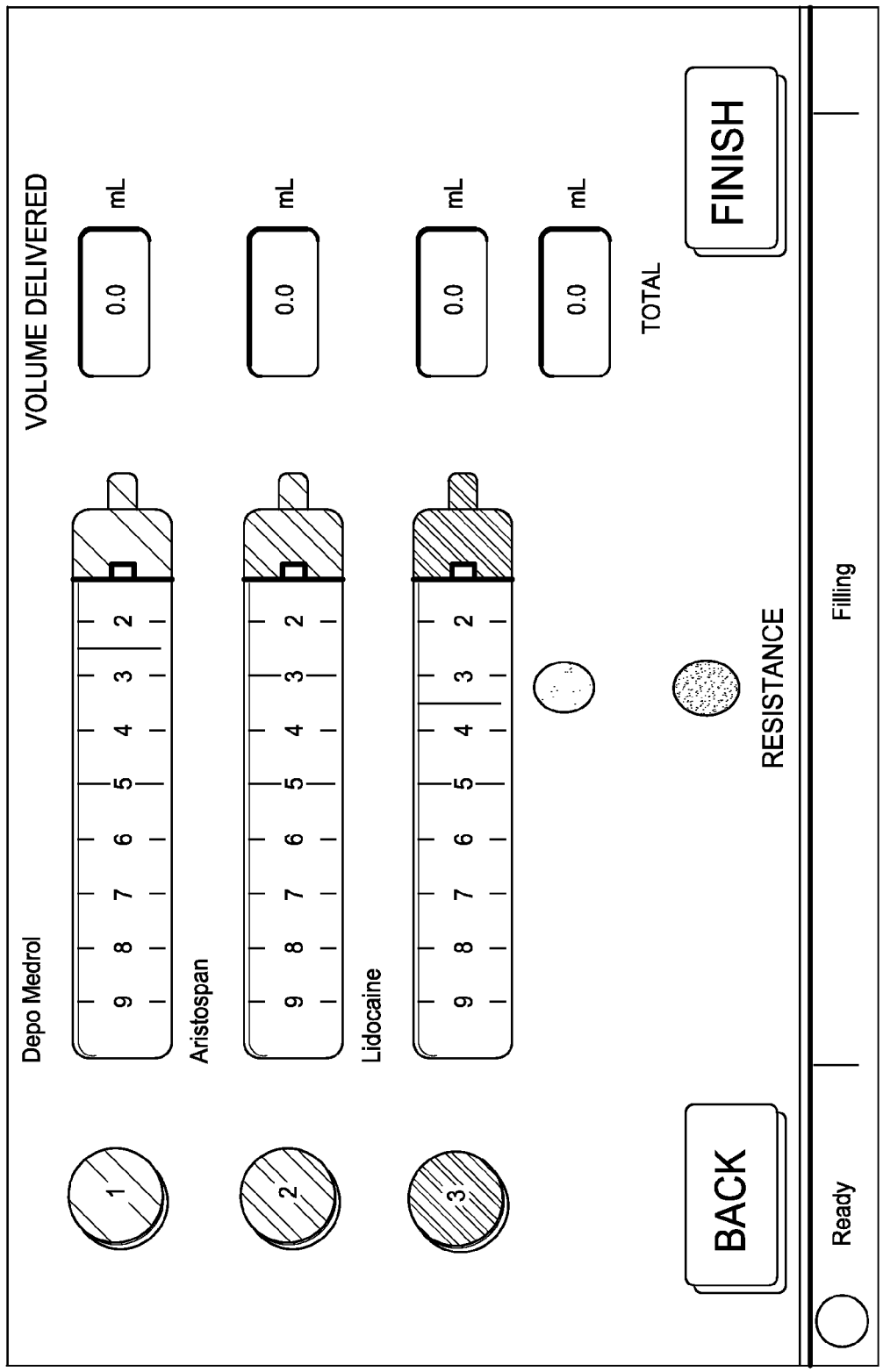
Figure 40H:
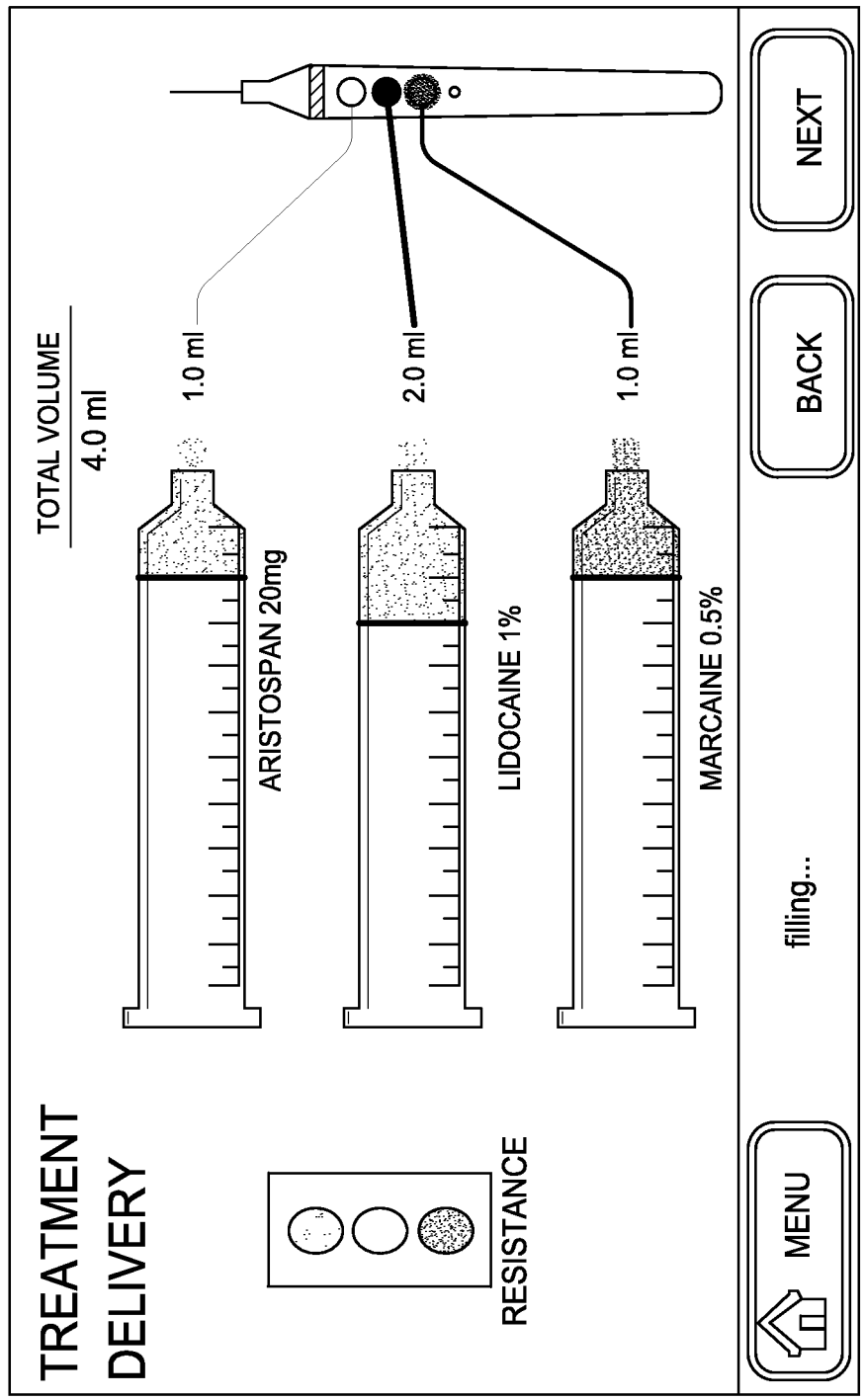
Figure 40I:
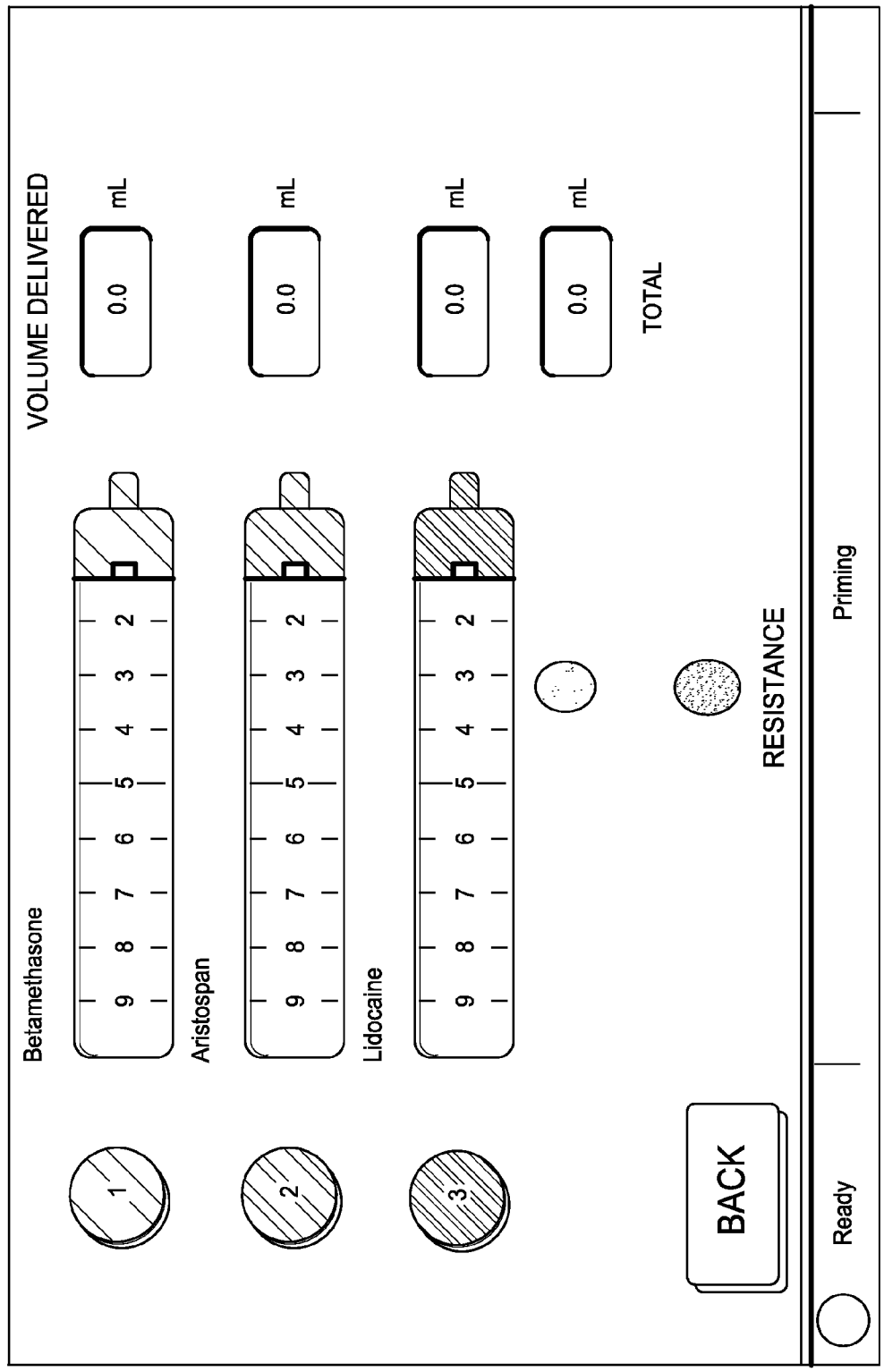
Figure 40J:
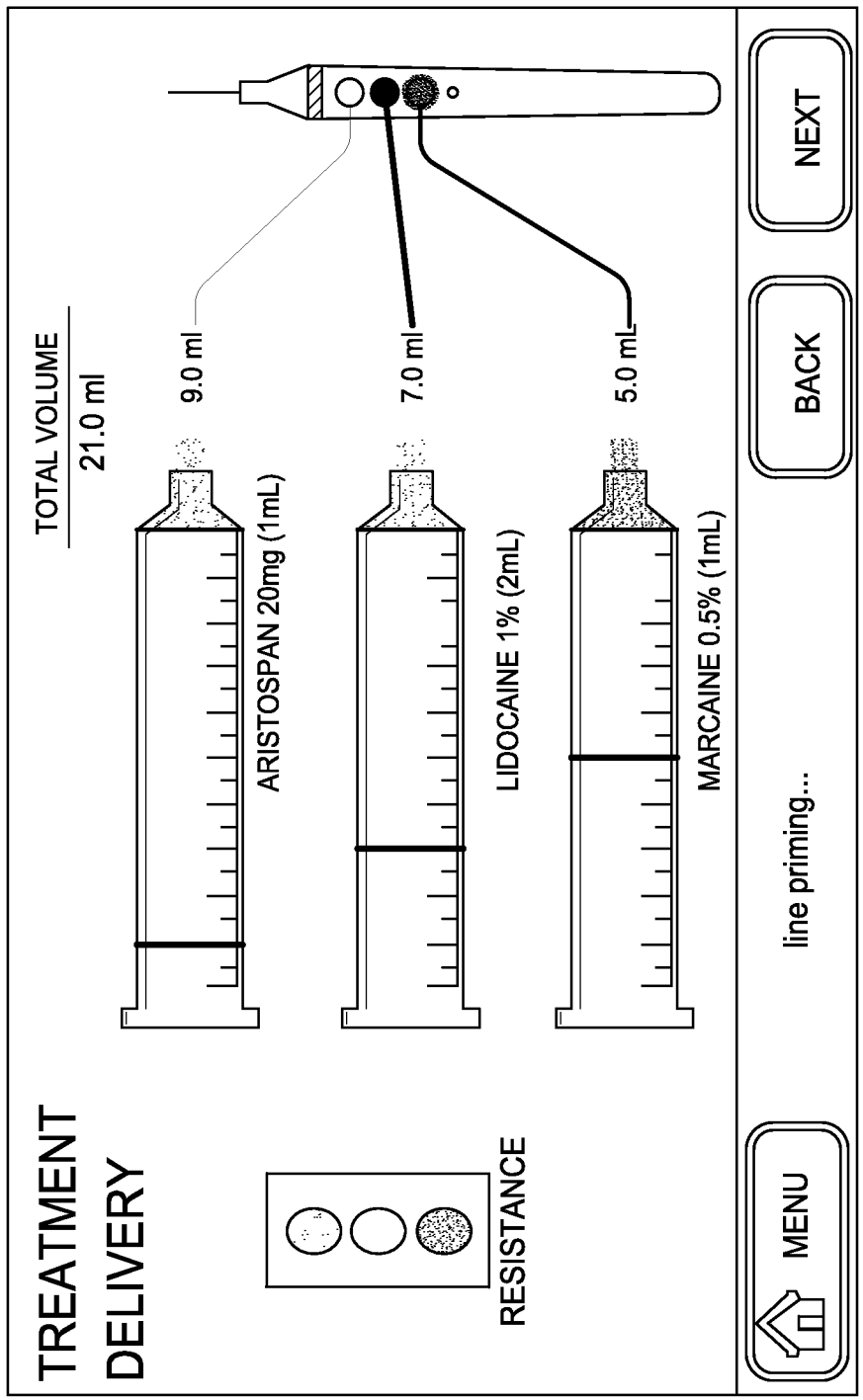
Figure 40K:
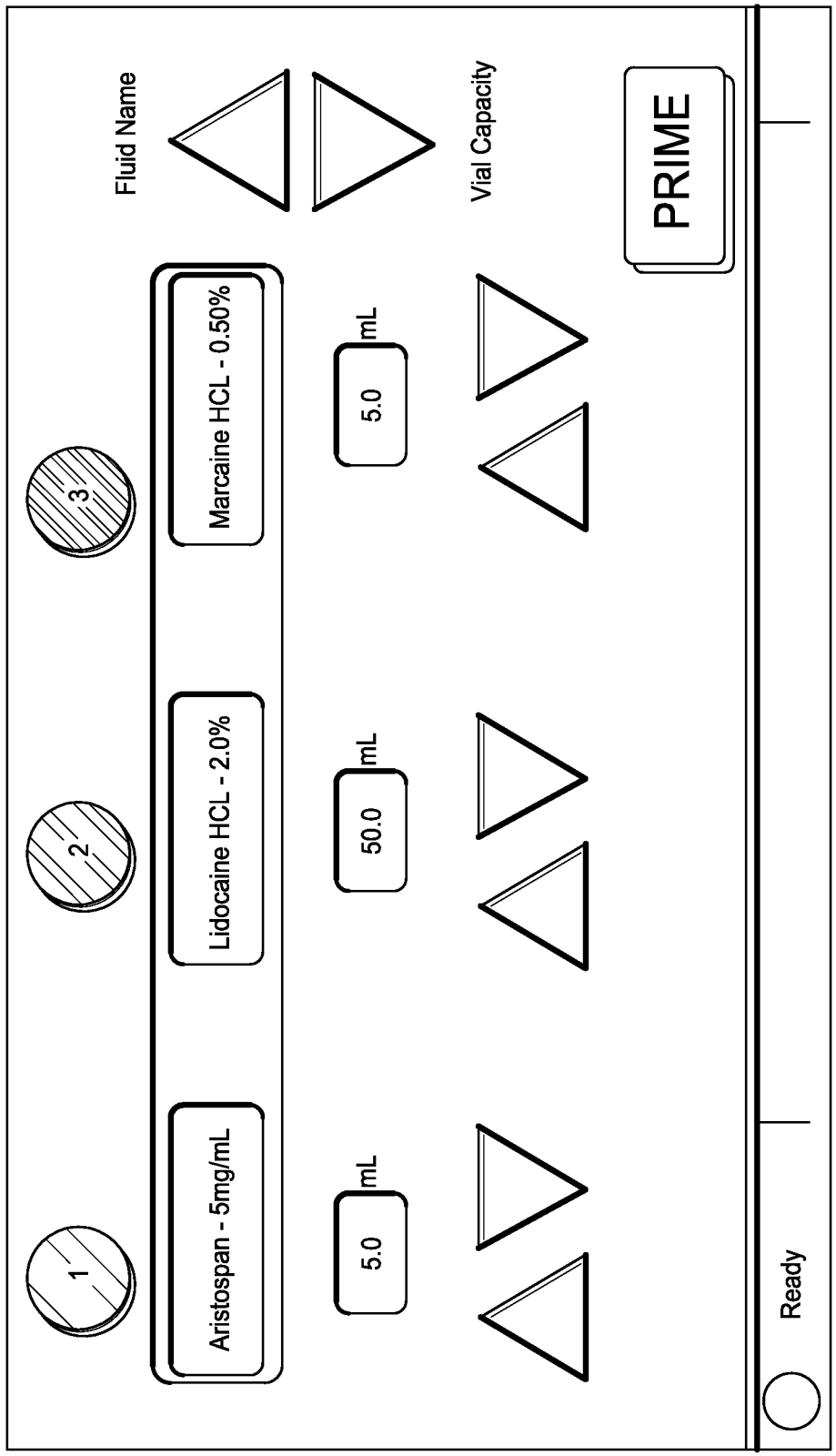
Figure 40C:
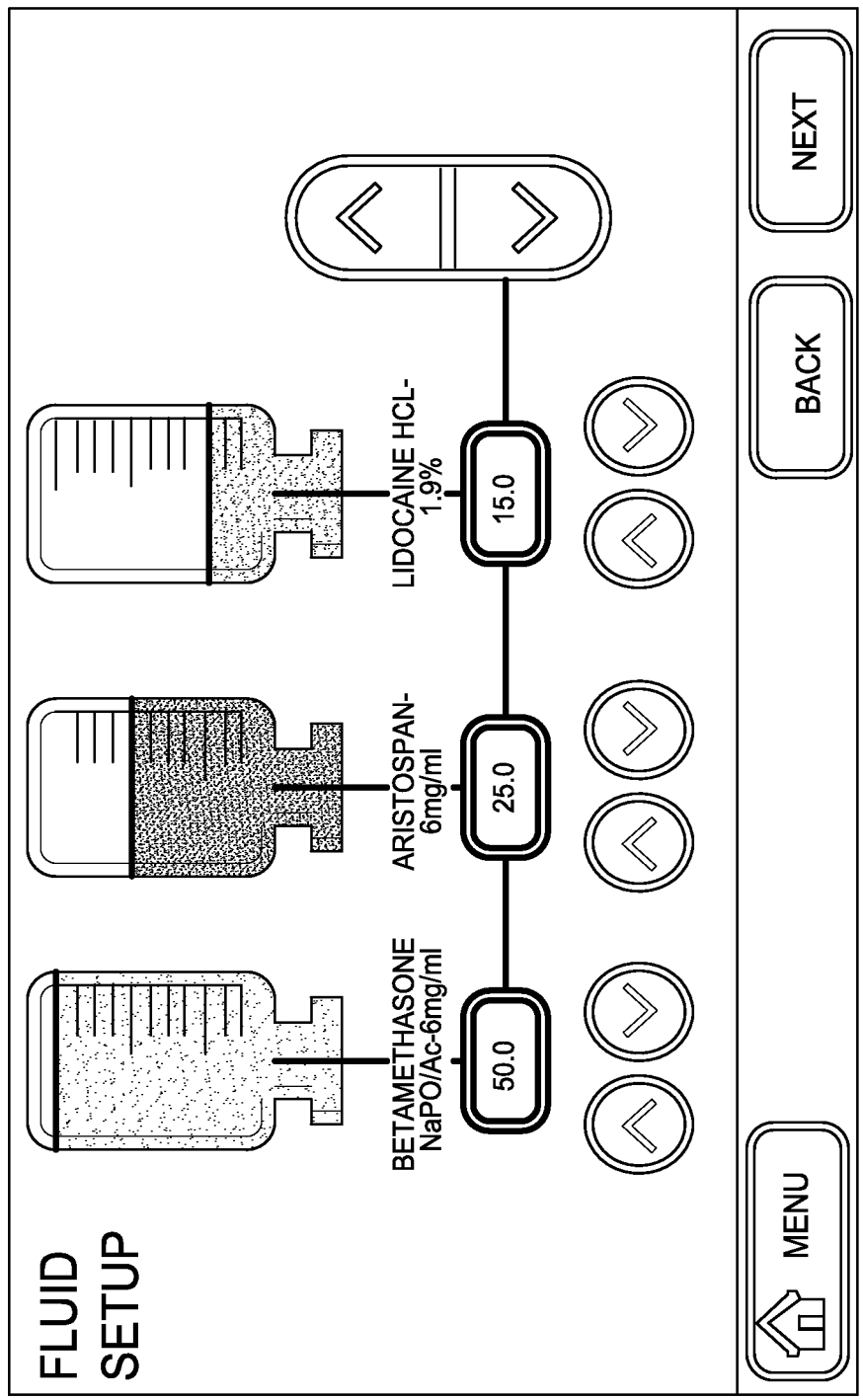
Figure 40M:
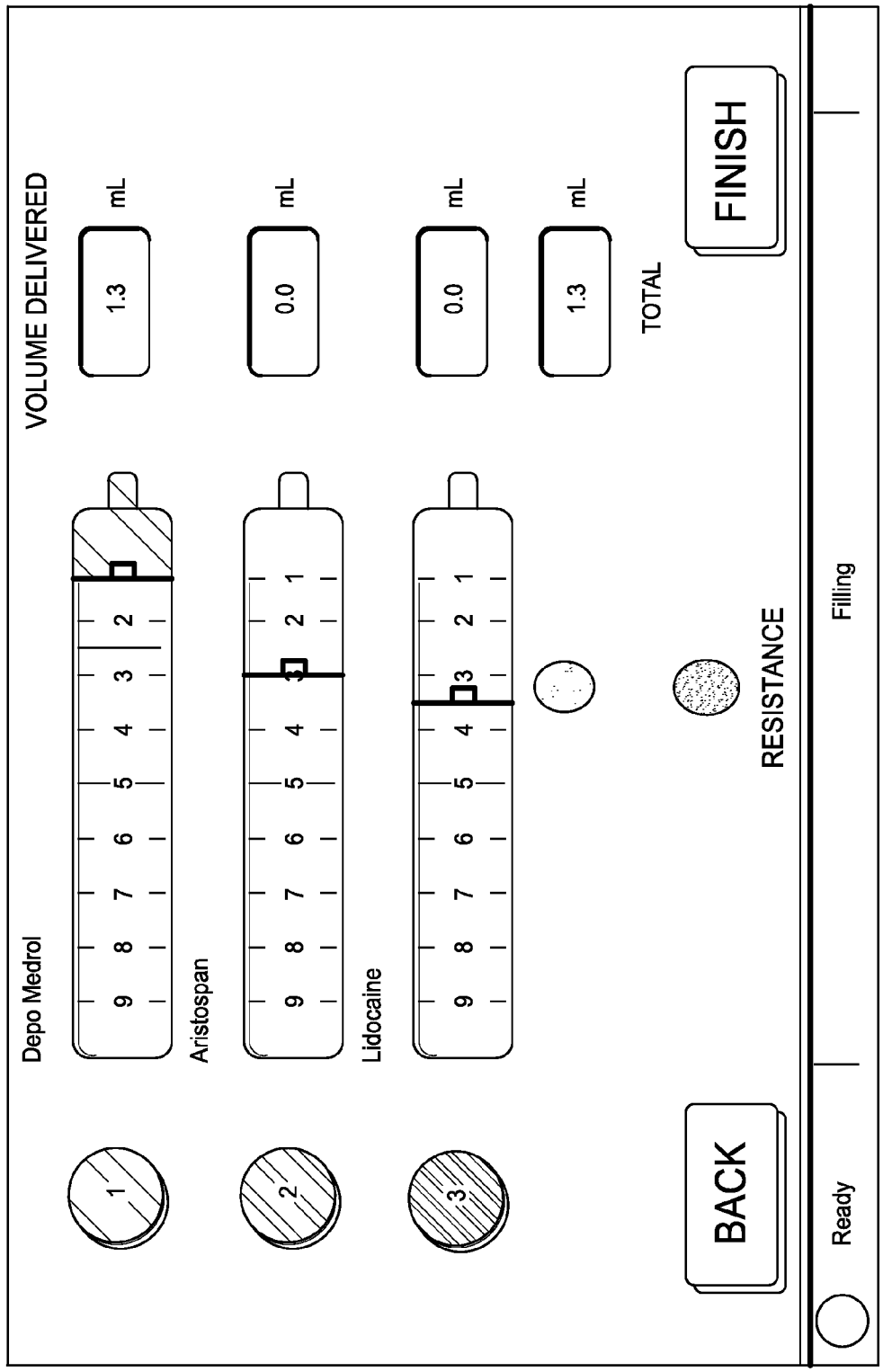
Figure 40N:
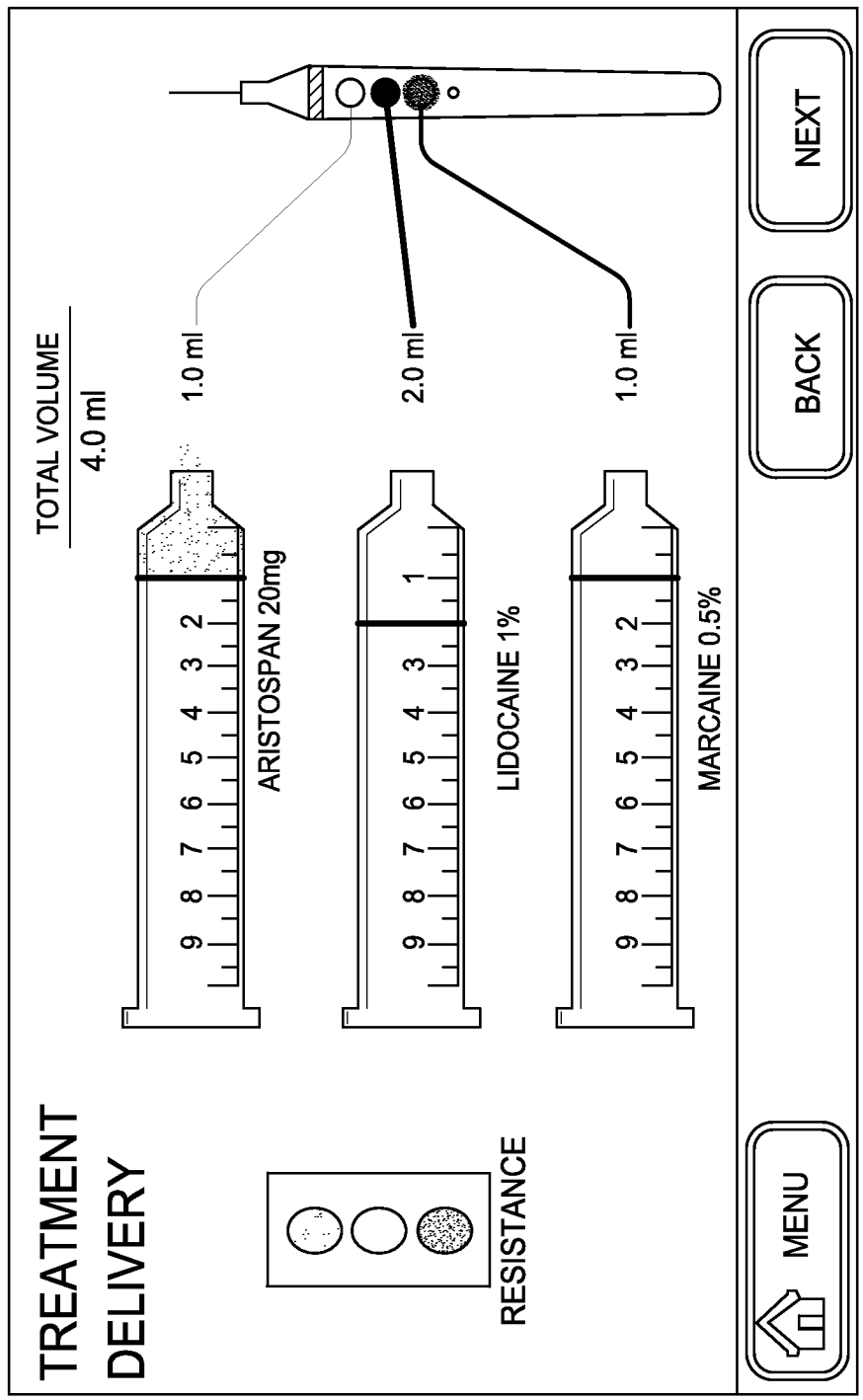
Figure 400:
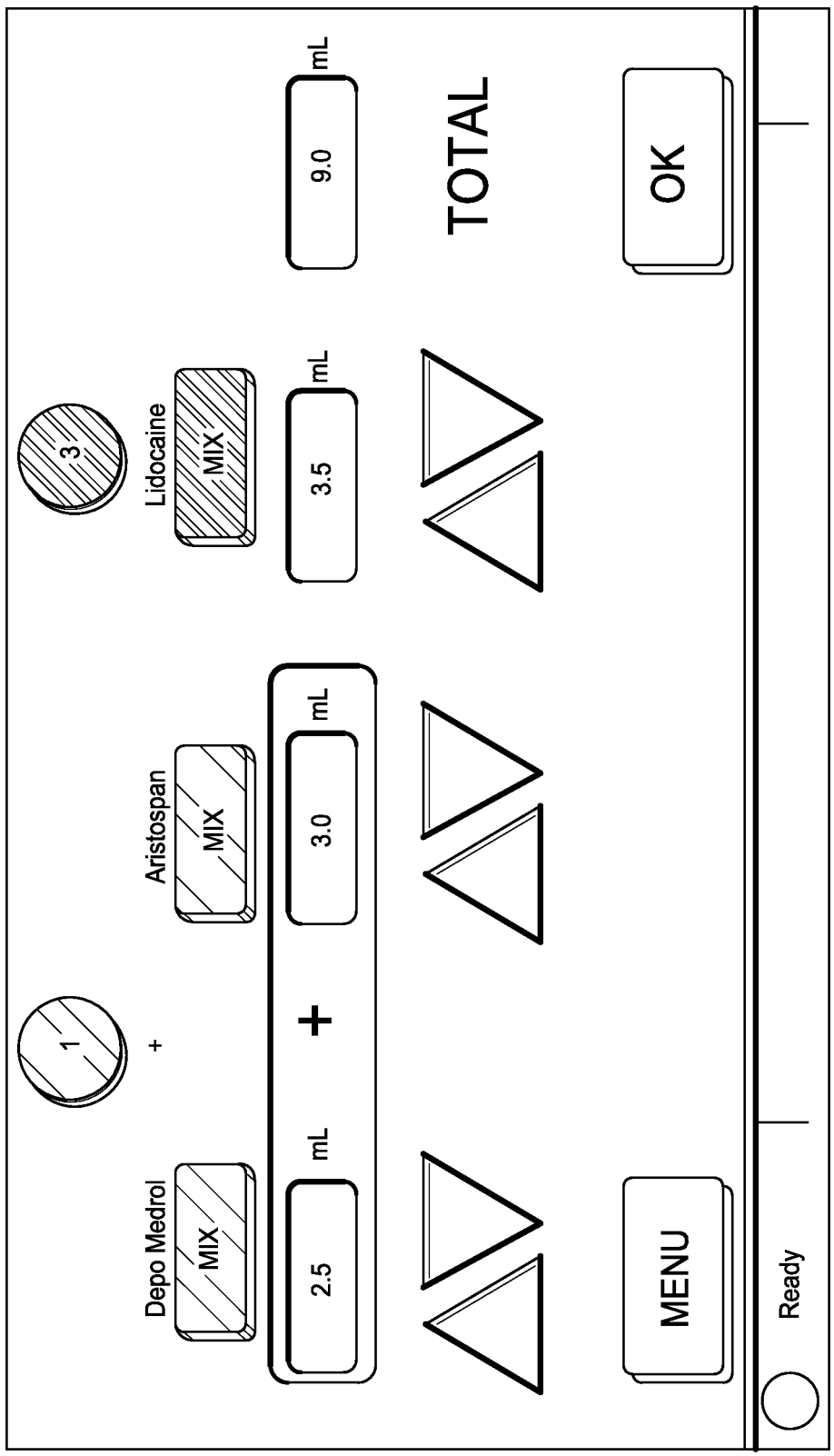
Figure 40P:
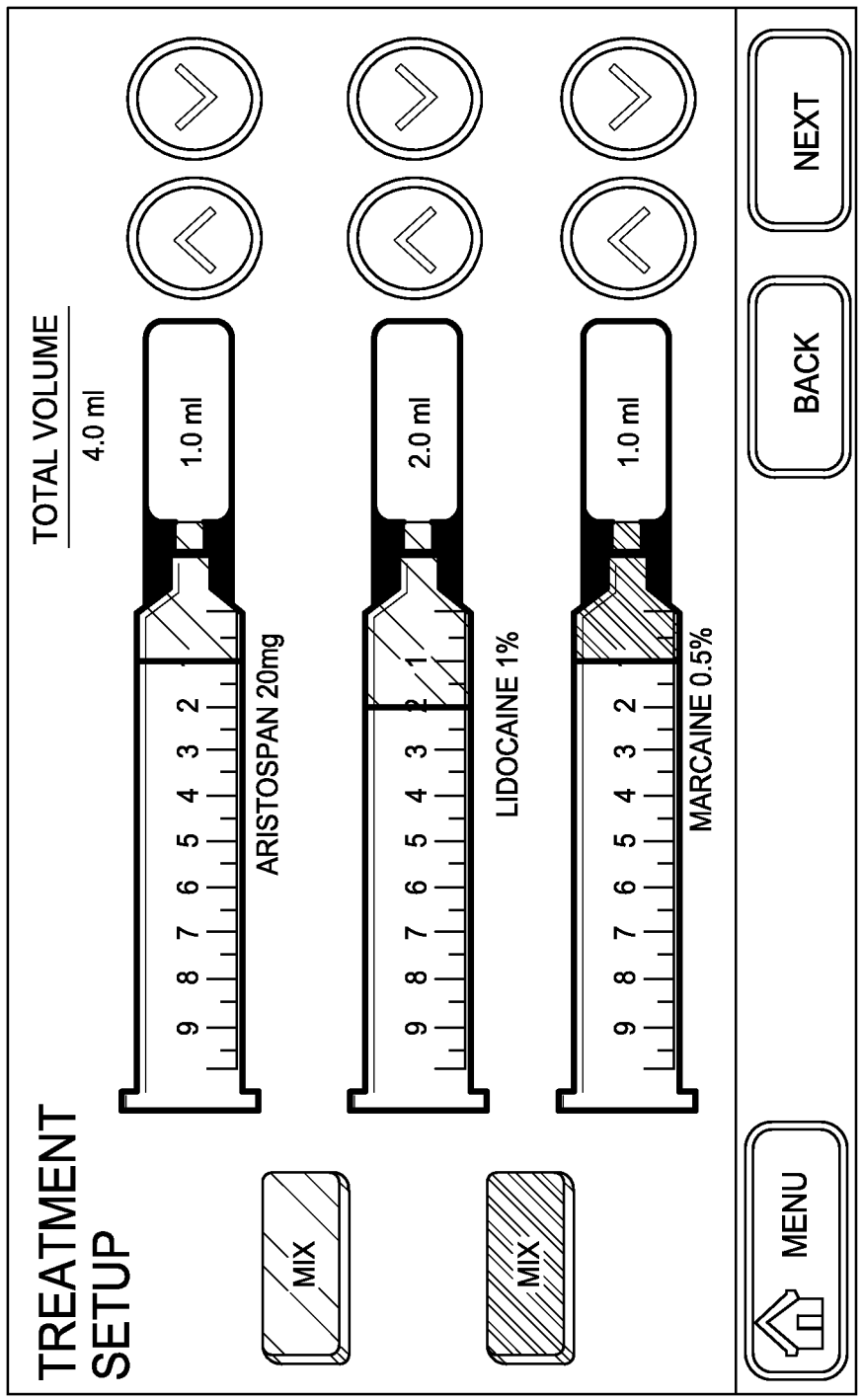
Figure 40Q:
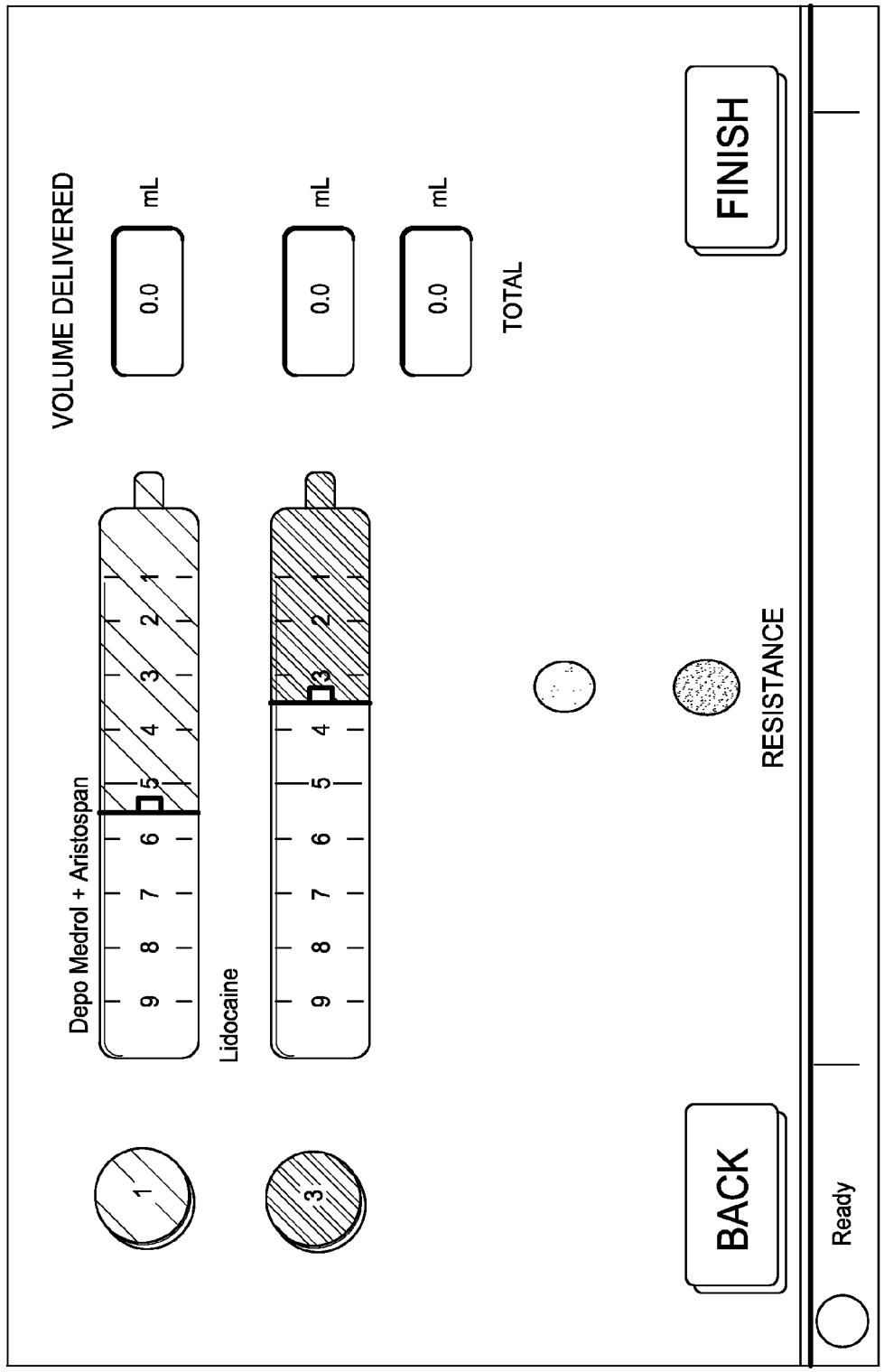
Figure 40R:
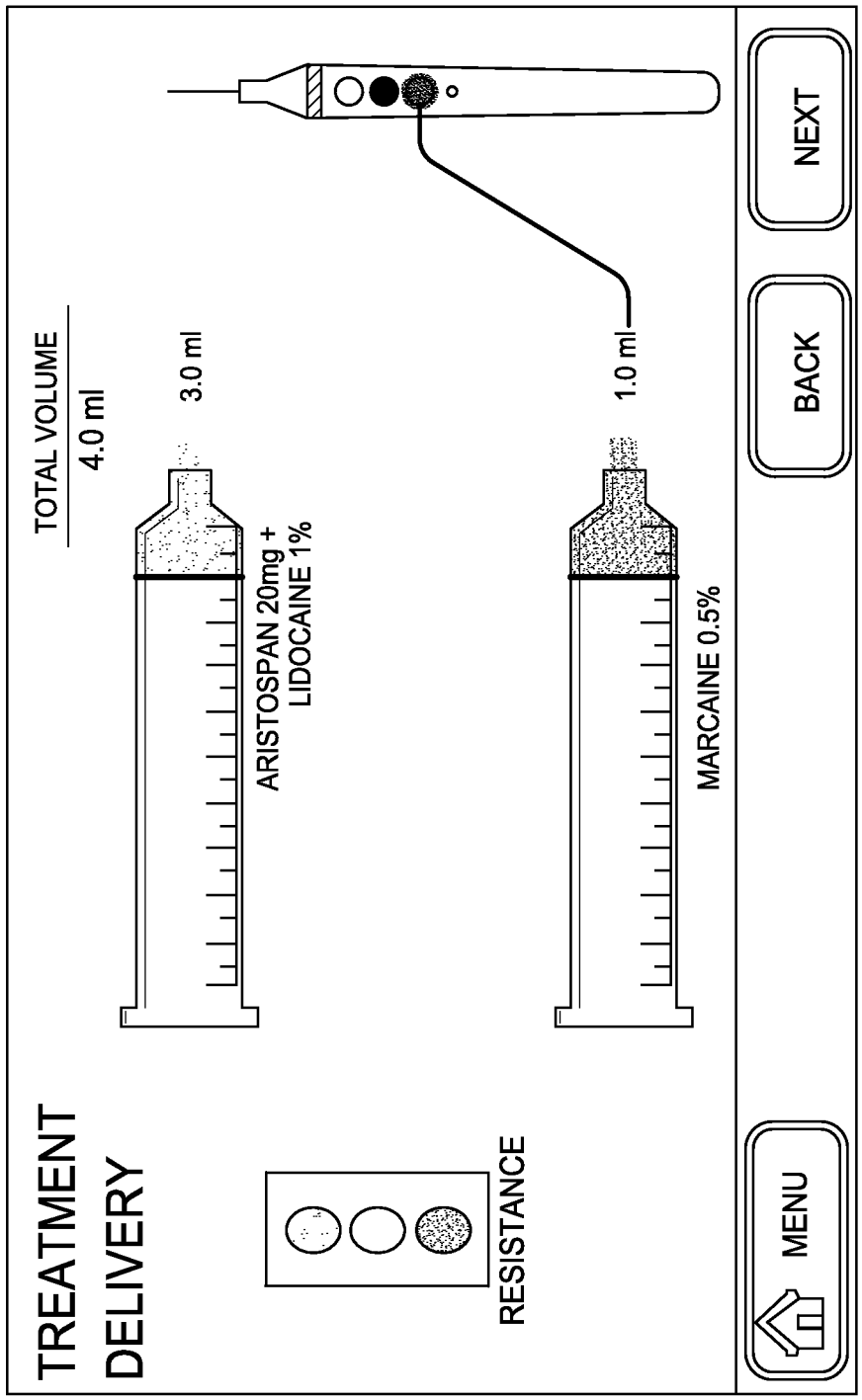
Figure 40T:
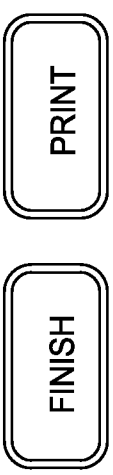

FIGS. 38A and 38B illustrate embodiments of reports or summaries 600A, 600B that can be generated in relation to the execution of a particular injection procedure. Such reports or summaries 600A, 600B can comprise paper printouts, electronic files and/or the like, as desired or required. As shown, the report or summary 600A, 600B can include one or more images 602A, 602B of the patient's joint or other targeted anatomical location. Such images can be generated using ultrasound or other imaging technologies. In some embodiments, the images 602A, 602B provide visual confirmation of the location of the injection system's needle in relation to the patient's anatomy. In addition, the images 602A, 602B can provide details related to the injection of fluids and/or other materials to or near the targeted joint or other anatomical location. For example, Doppler or other technologies can be used to verify that the various fluid and/or other material streams were properly delivered to the patient.

With continued reference to FIGS. 38A and 38B, the summary or report 600A, 600B can also include images and/or text 604A, 604B related to the prescribed or selected injection protocol (e.g., types and volumes of medicaments and/or other materials), the details of the actual injection procedure that was performed (e.g., which and how much of each medicament and/or other materials were actually delivered), the back-pressure or resistance against which the injection was performed and/or the like. In some embodiments, the reports or summaries 600A, 600B include additional data and other information, such as, for example, the name of the clinician and/or facility 612A, 612B, the name and/or other personal information of the patient 614A, 614B, the date and time the treatment procedure was initiated and completed 616A, 618A, 616B, 618B, the details (e.g., type, dosage, volume, etc.) regarding the drugs, medicaments and/or other materials delivered to the patient during the injection procedure 622A, 622B, the total volume of fluids and/or other materials that were actually delivered to the patient 624A, 624B and/or the like. In addition, the summary or report can include one or more locations 630A, 630B for the signature, date and/or other information to be completed by a clinician, a witness or any other person associated with the administration of the injection procedure. In other embodiments, the summary or report 600A, 600B can be customized according to the user's specific desires and requirements. Thus, the summary or report 600A, 600B can include more or less (and/or different) data and information than provided in the illustrated embodiments.

FIGS. 39A-39J and 40A-40T illustrate various screenshots of a touchscreen display 130 of the fluid delivery module 100 (e.g., FIG. 1) that can be advantageously permit a clinician or other user to control the delivery of one or more medications and/or other fluids or materials loaded onto the fluid delivery module. As discussed in greater detail herein, the fluid delivery module can be adapted to receive up to three vials or other containers, the contents of which may be selectively delivered through a downstream handpiece assembly. However, in other embodiments, the injection system is configured to receive more or fewer than three vials and/or other containers, as desired or required.

With reference to the screenshots illustrated in FIGS. 39B-39H and 40C-40R, a touchscreen display can provide flowrate and/or other data for each type of medication, formulation and/or other fluid or material loaded onto the fluid delivery module. For example, the contents of the vial or other container positioned on a first nest or loading area of the fluid delivery module (and subsequently placed in fluid communication with the handpiece assembly as discussed herein) can be visually and schematically represented on the on the display.

In some embodiments, other data or information about the fluids and/or other materials that are loaded onto a fluid delivery module can be provided on the screenshots. For example, information about the name of the composition and/or other fluid or material can be provided. In other arrangements, a code (e.g., NDC) and/or other identifier about the particular medication or formulation loaded onto the fluid delivery module can be displayed. Further, as discussed in greater detail herein, the vials, ampoules, syringes and/or other containers secured to the cassette or other portion of the fluid delivery module can be configured to be automatically or manually identified (e.g., using an identification flag or other member, using a barcode scanner or other identification device positioned along the outside of the fluid delivery module, etc.). Thus, information detected by such devices (e.g., type of medication, dosage or concentration, manufacturer, expiration date, etc.) can be advantageously provided on the display of the fluid delivery module. In addition, other data or other information can also be included on the display, such as, for example, imaging data for locating the distal end of the needle, date, time, name of the patient, name of the physician or other clinician performing the procedure and/or the like, as desired or required.

The touchscreen display can include up and down arrows (e.g., see FIGS. 39B, 39D, 40C-40F, 40K, 40L, 40O and 40P) associated with each type of medication, formulation and/or other fluid or material to be delivered to a patient in a scheduled injection procedure. Thus, a clinician or other user can select the volume, mass and/or other amount of a particular substance that should be delivered within a targeted anatomical location for an injection procedure. The volume or other amount selected at any particular time can be displayed in a corresponding area of the display. In addition, as shown in some of the depicted screenshots, the total volumetric or other amount of fluids and/or other materials to be delivered within an anatomy for a particular injection procedure can also be displayed.

According to some embodiments, the touchscreen display offers a convenient way of modifying a particular protocol using the up and down arrows. In addition, the touchscreen display can include one or more softkeys or other buttons (e.g., "FLUID SET-UP", "SYSTEM SET-UP", "CASSETTE REMOVAL", "DATE TIME", "MENU", "OK", etc.) that enable a user to input desired settings (e.g., maneuver through the various screens) and/or adjust the details associated with a specific injection procedure.

Once the details of a desired injection protocol have been entered, a user can use the buttons and/or other control devices positioned along the exterior of the handpiece assembly (e.g., either incorporated as a part of a core design, included as part of a removable control module, etc.) or other component of the system to selectively deliver one or more of the medications, formulations and/or other fluids or materials to a patient. In other embodiments, as discussed herein, a foot pedal is used to regulate the delivery of fluids and/or other materials to a patient.

In some embodiments, a clinician or other user presses a button of the handpiece assembly 2200 (e.g., FIGS. 29A and 29B) to deliver the internal contents of a first vial or other container corresponding to that button. Thus, a name, number or other identifier (e.g., shape, color, graphic, etc.) on the display of the fluid delivery module can match or substantially match an identifier on or near the corresponding button of the handpiece assembly. Thus, a clinician or other user can easily determine which button or other controller of the handpiece assembly should be pressed or otherwise manipulated to deliver a particular medication, formulation and/or other fluid or material into a patient's anatomy.

Alternatively, a clinician or other user initially programs the details of a desired injection protocol using the fluid delivery module. For example, the clinician can select which fluids to deliver, in which order to deliver them (e.g., whether delivery of fluids and/or other materials will be sequential or simultaneous), the volume or other amount of each fluid and/or other material to be injected and/or the like. After the clinician has entered the necessary data and other information, he or she can use a button, foot pedal and/or any other controller or device to start or stop the injection procedure. In some embodiments, as discussed in greater detail herein, the button, foot pedal and/or other controller can advantageously permit a user to speed up or slow down the injection procedure, to pause the procedure, to operate an ultrasound or other imaging device operatively coupled to the injection system and/or perform any other function or task, as desired or required.

In order to stop delivering such a fluid or other material to the patient, the physician can release a corresponding button, foot pedal and/or other controller (or press such a button again). Accordingly, the screenshot information provided on the display can be used to control the manner in which medications, formulations and/or other fluids or materials are delivered to a patient. The display can be configured to change to a different screenshot (e.g., FIGS. 39G, 39H, 40H-40L, 40N and 40R) during the delivery phase of the various fluids and/or other materials. As discussed in greater detail herein, a button or other controller can be located on the handpiece assembly. For example, a handpiece assembly can include one or more buttons as part of core design (e.g., FIGS. 29A and 29B). Alternatively, one or more buttons can be included on a control module that is configured to removably attach to a handpiece assembly (e.g., FIGS. 23A-27B). In yet other embodiments, a foot pedal (e.g., FIG. 35) and/or any other type of controller can be used to regulate the flow of fluids and/or other materials from an injection system to a patient's anatomy.

In some embodiments, two or more medications, formulations and/or other fluids or materials can be combined and delivered together through the handpiece assembly by pressing a single button and/or other controller (e.g., permanently or removably located on a handpiece assembly,] a foot pedal, the fluid delivery module, any other component of the injection system, a separate device or system, etc.). In some embodiments, a single button or other controller can be used to simultaneously or sequentially delivery two or more fluid and/or other material streams to a patient.

With continued reference to the screenshots of FIGS. 39A-39J and 40A-40T, once a user chooses to deliver two or more different medications, formulations and/or other fluids or materials using a single button or other controller, the display can be configured to visually assign a single button number to such a combination. Further, the windows or other portions of the screenshot displaying the volume or other amount of the corresponding medications, formulations and/or the like can be visually combined (e.g., using a larger window or area) in order to make it clear that such materials will be delivered simultaneously.

According to some embodiments, the rate of delivery of the medications, formulations and/or materials being simultaneously delivered is adjusted so that the desired volumes or other amounts of such materials expire at the same time for a particular injection procedure. In other words, the rate of delivery of the first fluid can be slow relative to the rate of delivery of the second fluid so that the first fluid and the second fluid are used up at the same time or approximately the same time during an injection procedure. Alternatively, the rate of delivery of the fluids and/or other materials that are simultaneously delivered through the handpiece can be adjusted so that one or some of the fluids or materials are used up before the others. As discussed in greater detail herein, one or more aspects of a delivery procedure can be customized, as desired or required by the clinician.

In some embodiments, the clinician or other user can program the injection system so that three or more medications, formulations and/or other fluids or materials loaded onto the fluid delivery module are delivered using a single button of the handpiece assembly, a foot pedal and/or any other controller. Such fluid and/or other material streams can be delivered simultaneously or sequentially, in accordance with a desired protocol.

According to some embodiments, each fluid and/or other material loaded onto the fluid delivery module can be schematically represented by a syringe, vial, other container or image on the screenshots. Further, the volume or other amount of each type of medication or formulation remaining within the cassette or other portion of the fluid delivery module for injection into a patient can be graphically represented on the screenshot. For example, the syringes, vials or other images representing the various medicaments and/or other materials loaded onto a fluid delivery module can be shown filled with the remaining volume of fluids and/or other materials. As fluids and/or other materials are delivered into an anatomy, a line representing the level of each syringe or other container can move to reflect the change in volume for a corresponding fluid and/or other material. Accordingly, the clinician or other user is permitted to graphically follow the status of the injection procedure. As shown in the various screenshot embodiments provided herein, the volume or other amount of each medication or formulation can also be numerically displayed within corresponding windows or other portions of the screenshots. A screenshot can also provide information relating to the total volume of fluids and/or other materials delivered into an anatomy during an injection procedure.

In addition, the display can be configured to provide information regarding the pressure at or near the distal end of the needle, either while the needle is being delivered to the target anatomical location (e.g., a joint) or while fluids and/or other materials are being delivered to such a location during the course of an injection procedure. According to some arrangements, in part for patient safety, the fluid delivery module is configured to accurately measure and regulate the flowrate and/or pressure of a medication, fluid or other material being delivered to the target anatomical location. Thus, the system can comprise pressure and/or flow measurement devices (e.g., pressure transducers, flowmeters, etc.). Pressure sensing devices can be used to ensure that the pressure or vacuum created by the discharge of the medications, compositions, fluids and/or other materials within the anatomy does not exceed a particular threshold level. This can help prevent or reduce the likelihood of damage occurring to the patient being treated using the injection system. Such an internal force measurement system can be configured to automatically shut off the fluid transfer device (e.g., movement of the stepper motor, other pump, etc.) when the discharge pressure exceeds a maximum level (e.g., 3 psi). In other arrangements, the fluid delivery module can include a visual and/or audible alarm or other similar feature to alert the user than a threshold pressure has been attained, either in lieu of or in addition to any automatic shut-off mechanism. For example, the clinician or other user can track real-time pressure and/or flowrate data on corresponding portions of the display during an injection procedure. Other types of feedback that indicates position or placement to a user may also be used (e.g., mechanical or tactile feedback). Such safety features can be included in any of the embodiments of the modules or systems disclosed herein.

As shown in FIGS. 39A-39J and 40A-40T, the screenshots can comprise various graphical and/or numeric portions that are adapted to provide data and other information to the user, either before or during an injection procedure. In addition, the display can include softkeys, buttons and/or other data input devices that permit a user to adjust and customize an injection procedure as desired or required. For example, the screenshots can assist a user to set up the injection system (e.g., update the time and date, inform the system that a cassette is being replaced, etc.).

Non-limiting examples of injection procedures that may be performed using the various embodiments of systems, devices and methods disclosed herein (or equivalents thereof) are provided below. It should be noted that these examples are provided to simply demonstrate only some of the features and/or other details of injection systems, devices and methods discussed and illustrated herein. As such, the following examples or any other portion of the specification or figures should not be used to limit the present application in any manner.

Figure 41:
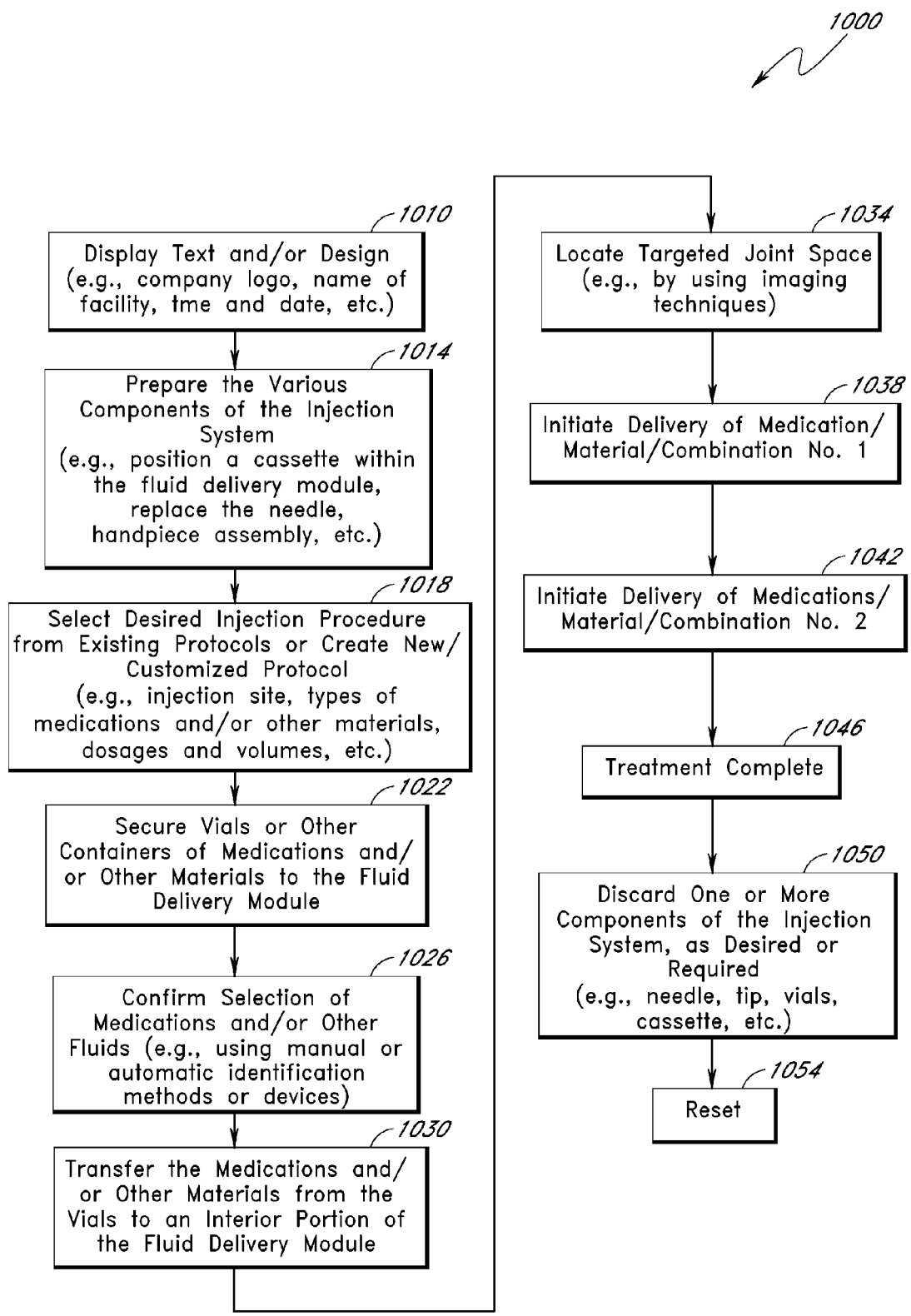
FIG. 41 schematically illustrates a flowchart of one embodiment of a sequence for delivering medication to a joint or another anatomical location.

The flowchart in FIG. 41 schematically illustrates one non-limiting example of a sequence 1000 for delivering medications, formulations and/or other fluids or substances to a target anatomical site (e.g., a joint, an organ, etc.) using an injection system in accordance with the embodiments disclosed herein. A touchscreen or other visual display of a fluid delivery module or other portion of the system can be configured to initially display 1010 a logo, the time, date, patient and/or physician identifying information, hospital or facility name or logo and/or any other image, design or other alphanumeric text. However, in other embodiments, such a display is configured to not display anything at all. In fact, the fluid delivery module may not include a display at all.

With continued reference to FIG. 41, a physician, clinician or other user can prepare the system 1014 for the subsequent delivery of fluids into a patient. For example, as discussed in greater detail herein, a cassette (or other portion of the fluid delivery module) can be positioned within a corresponding recess or other portion of a fluid delivery module. If a cassette is already secured to the fluid delivery module, the user may need to replace it with a new cassette. In some embodiments, used needle assemblies, handpiece assemblies, delivery lines, other conduits, clips and/or any other components or portions of the injection system are removed and replaced. For example, the clinician or other user can secure an appropriately sized (e.g., length, diameter, etc.) sterile needle assembly to the distal end of the handpiece device (e.g., using a luer lock or other standard or non-standard connection or fitting). As discussed in greater detail herein, the entire handpiece assembly (e.g., including the handpiece portion and the upstream tubing that connects to the fluid delivery module) can be replaced between patients. In arrangements having a removable control module, the clinician can reposition the control module to the new handpiece assembly prior to use.

As discussed in greater detail herein, a handpiece assembly, a needle assembly, a cassette and/or any other component of the injection system can be replaced between injection/aspiration treatments or procedures. Thus, in accordance with standard practices, cross-contamination of fluids and/or other materials (e.g., between different patients) can be prevented. In some embodiments, assuming that there is no need to change the medications or other materials loaded within the delivery module (e.g., no changes in types or dosages), replacement of only the handpiece assembly or the needle assembly can advantageously permit a clinician to quickly and easily perform injection procedures in many different patients. For example, in some embodiments, a physician can perform injection procedures in 20-40 or more different patients per day without having to replace the cassette and/or any other portion of the handpiece assembly. Therefore, for practical reasons, a clinician can dedicate a particular delivery module to a specific combination of medications or other substances so that he or she only needs to replace the handpiece assembly and/or the tip between uses, depending on the particular injection system embodiment being utilized.

In other embodiments, where the type, dosage or other characteristics of the medications or other substances secured within the loading area of the delivery module change, the clinician or other user may also be required to replace the cassette, clip, delivery line or other conduits and/or any component, subcomponent or portion of the injection system that may contact the medications, formulations and/or other fluids or materials being delivered within an anatomy. Thus, as discussed with respect to the various embodiments disclosed herein, certain components and portions of the injection system (e.g., the handpiece assembly, fluid delivery module, etc.) can be advantageously configured to be easily and quickly removed and replaced as desired or required (e.g., between injection procedures, when the characteristics of the medications and/or other materials being injected are modified, according to some predetermined schedule, etc.). The foregoing disclosure regarding the replacement of handpiece assemblies, needle assemblies, tips, clips, delivery lines, other conduits and/or the like can be applied to any embodiments disclosed herein or variations thereof.

Once the injection system has been adequately prepped, the clinician can select 1018 the details of the particular injection procedure to be performed. For example, in some embodiments, the clinician uses the interactive menus provided on a display of the fluid delivery module or other component of the system to choose one of various protocols already recognized by the injection system (e.g., saved within the memory of the fluid delivery module). In other arrangements, the clinician enters the details (e.g., types, volumes or other amounts, dosages and/or other information) regarding the medications, formulations and/or other materials to be injected into a patient. Thus, a clinician or other user can customize a particular injection protocol, as desired or required. In some embodiments, the injection system is configured to save the details of the various injection protocols, thereby allowing a clinician or other user to access them in the future (e.g., for purposes of repeating the same injection protocol, for record keeping and/or for any other purpose). Such data and other information can be shared with another network (e.g., the hospital's or other faculty's main network, the internet, etc.).

Next, the clinician or other user can secure 1022 one or more vials containing the medications, formulations and/or other fluids or materials to a cassette, another portion of the fluid delivery module and/or the like in preparation for a desired injection procedure. For example, each vial or other container can comprise anesthetics or other pain-relieving medications (e.g., Lidocaine, other slow or fast acting anesthetics, etc.) steroids (e.g., Depo-Medrol®, methylprednisolone acetate, etc.), hyaluronic acid, saline, pharmaceutical compositions, other medications or drugs, cells, liquid and non-liquid fluids and flowable materials, nanoparticles, cement, microbeads and/or combinations of such fluids and other materials. In any of the embodiments disclosed herein, an intra-articular injection can include the selective delivery of three different drugs into a patient, a corticosteroid, a short-acting anesthetic and a long-acting anesthetic.

In some embodiments, the vials, ampoules, syringes and/or other containers are secured to a nest, loading area or other receiving area of the fluid delivery module (e.g., cassette). Alternatively, the vials can be positioned along a different portion of the fluid delivery module or other component of the injection system, as desired or required.

According to some arrangements, the vials or other containers secured to the fluid delivery module or other portion of the system are optionally verified 1026 to confirm that the characteristics (e.g., type, dosage, volume, expiration date, etc.) of the medications, formulations and/or other fluids or materials that will be delivered into a patient are in accordance with the intended protocol. This can improve the safety and accuracy of the injection procedure, as the likelihood of delivering incorrect substances to a patient is advantageously eliminated or reduced.

Confirmation of the medications and/or other materials contained within the vials secured to the fluid delivery module or other portion of the injection system can be performed manually or automatically. As a result, when a vial is secured to the fluid delivery module, a reader or other identification device can be configured to automatically detect the contents of such a vial. In other arrangements, the fluid delivery module or other portion of the injection system comprises a barcode scanner, RFID reader or other device adapted to identify a machine-readable machine code (e.g., barcode or other textual code, color or graphical pattern, etc.) and/or the like. In still other embodiments, the clinician or other user manually confirms the contents of a vial or other container. For such systems, a user may be required to enter certain data and/or other information about the vials or other containers into one or more components of the injection system. For instance, a user can use a touchscreen, a keypad or keyboard or other data entry device to input the NDC, the name of the medication and/or any other information, to confirm the identity of the vials and/or the like.

With continued reference to the example injection procedure that is schematically illustrated in FIG. 41, the clinician can then transfer 1030 all or some of the medications, formulations and/or other materials contained in the vials or other container to an interior portion of the fluid delivery module or other component of the injection system. For example, as discussed in greater detail herein, the internal contents of such vials or other containers can be conveyed to syringes or other reservoirs within a cassette or other portion of the fluid delivery module. Once within such reservoirs, one or more of the various medications and/or other materials can be selectively administered into a patient through a downstream handpiece assembly.

In any of the embodiments disclosed herein, a preliminary priming step may precede any transfer of fluids within or out of the injection system. For example, such a priming step can be used to transfer fluids and/or other materials from a vial to an internal reservoir of a cassette, from a cassette reservoir to the handpiece assembly and/or the like. In addition, in order to ensure that no gas bubbles are injected into a patient, the injection system can be configured to expel a certain volume of fluids and/or other materials before an injection procedure is commenced. One or more other ways of detecting potentially dangerous gas bubbles within a cassette, a conduit and/ or other portions of the injection system can be used.

In some embodiments, before any medications and/or other materials can be injected into a patient, the needle at the distal end of the handpiece assembly is accurately positioned within the targeted anatomical location (e.g., joint, organ, cavity, etc.). In some embodiments, imaging techniques can be used to locate 1034 such a joint or other targeted location. Alternatively, one or more other devices or methods can be used to accurately position the needle within a patient's body. For example, as discussed in greater detail herein, the injection system can comprise ultrasound, radio frequency spectroscopy and/or other imaging capabilities to assist in accurately positioning the needle of the handpiece assembly within the anatomy of a patient. Incorporating imaging technologies (e.g., ultrasound, radio frequency spectroscopy, CT, MRI, etc.) into an injection/aspiration system can facilitate the injection and/or aspiration procedures for a physician or other clinician. For example, as noted herein, such injection systems can permit a single user to conduct the entire procedure alone.

In other embodiments, locating the targeted anatomical location (e.g., joint) comprises measuring one or more tissue characteristics at or near the tip or distal end of the needle being inserted into the anatomy. Each type of intra-articular space can be associated with a particular tissue response range within which the tissue response value at the distal end of the needle should be. Thus, as the needle is advanced through skin, subcutaneous tissue and/or other anatomical layers, the tissue response value at or near the tip of the needle may fluctuate. In one embodiment, the tissue response value at the needle tip decreases as the needle enters into the desired intra-articular space. Therefore, the system can be configured to instruct the user to advance the needle until the tissue response value drops below a specific threshold level.

In some embodiments, an optical fiber, electrode or other type of sensing device can be located at or near the distal end of the needle. A processor of the delivery module can be programmed or otherwise configured so when a tissue response value is measured, received or detected by the corresponding sensor (e.g., optical fiber, electrode, etc.), the fluid delivery module can determine whether the targeted anatomical area has been reached. The delivery module can be configured to indicate relevant information regarding the needle's position using one or more devices, components or methods, such as, for example, via the touchscreen or other display (e.g., visual readouts, charts, etc.), via audible indicia (e.g., tones, voice commands, etc.) and/or the like.

A display of the fluid delivery module (e.g., touchscreen, LCD screen, other monitor, etc.) can be configured to provide a textual and/or graphic representation of the tissue response value, its rate of change and/or any other details related to locating an intra-articular space. For example, the tissue response value at or near the tip of the needle can be displayed as the actual value (as text) or as a chart or graph (e.g., X-Y plot, a circular target chart, etc.).

After the needle has been properly positioned within a patient, the clinician can initiate delivery 1038 of one or more medications, formulations and/or other fluids or materials, as required by a particular injection protocol. As discussed, the clinician can use the buttons or other controllers on the handpiece assembly or other portion of the injection system to accurately control the delivery of a particular fluid or material stream into the patient. The buttons can be located on a removable control module, on a core and/or any other portion or component of the handpiece assembly. In other embodiments, a button and/or other controller used to regulate the delivery of fluids and/or other materials through the injection system can be included in a foot pedal, on the fluid delivery module, on another portion or component of the injection system, on an imaging wand operatively coupled to the injection system and/or any other device or system. For example, in some arrangements, the clinician initiates delivery of Lidocaine or another anesthetic. As discussed, the delivery of such anesthetics can be initiated as the clinician begins to advance the needle through the patient's anatomy or after the tip of the needle has been accurately positioned within a joint or another targeted anatomical location (e.g., muscle tissue, organ, etc.).

The incorporation of mechanically (e.g., using a stepper motor), hydraulically, pneumatically or differently driven delivery of medications, formulations and/or other fluids or materials from the fluid delivery module to the patient can facilitate the execution of an injection procedure. For example, a physician or other clinician can simply use one or more buttons or other controllers (e.g., on a control module, core, other portion of a handpiece assembly, touchscreen of fluid delivery module, imaging wand, etc.) to accurately deliver a volume or other amount of a particular substance to a joint or another targeted anatomical location. This can be particularly helpful when the manual delivery of such fluids and/or other materials could be difficult, strenuous, repetitive or otherwise problematic. A relatively high and persistent force and effort may be required by the physician or other clinician to deliver one or more medicaments and/or other substances to a targeted anatomical location. This can be particularly problematic when attempting to inject dense, viscous or high-solids fluids or other materials to small joints (e.g., toes, fingers, midfoot joints, etc.) or another high back-pressure locations within an anatomy (e.g., to or near bones, certain organs, etc.). Thus, at least some of the embodiments of the injection systems, devices and methods disclosed herein permit the delivery of one or more medicaments and/or other materials from a fluid delivery module to a target anatomical location within a patient without the need to push or exert the necessary force or effort to physically administer such substances. Consequently, the clinician or other user can dedicate more of his or her time and effort in accurately locating a joint or other targeted anatomical location and executing the desired injection procedure.

As discussed, the clinician can selectively deliver 1042 one or more other fluid and/or material streams into a patient, either alone or concurrently with the delivery of another stream. In some embodiments, this is accomplished by pressing or otherwise manipulating buttons or other controller on the handpiece assembly or another portion of the injection system. Alternatively, a single button or other controller can regulate the sequential or simultaneous delivery of all fluid and/or other material streams from the fluid delivery module to a patient's anatomy. Further, the injection system can be configured so that operation of such a button or other controller causes two or more different fluid and/or material streams to be simultaneously delivered through the needle. Screenshots (e.g., FIGS. 39A-39J and 40A-40T) visually provided on a display (e.g., of a fluid delivery module) or other output device can assist the clinician with selecting an injection protocol and/or executing an injection procedure.

According to some embodiments, a treatment procedure comprises the injection of a volume of an anesthetic and/or a steroid (Depo-Medrol®) after a volume of a first medication (e.g., Lidocaine or another anesthetic or pain-relieving medication) has been injected into the targeted area. In other arrangements, one or more other fluids and/or other materials (e.g., hyaluronic acid, saline, pharmaceutical compositions, cells, nanoparticles, cement, microbeads, etc.) can be contained within one or more of the vials or other containers loaded onto the cassette or other portion of the fluid delivery module, either in lieu of or in addition to the anesthetics, pain-relieving medications and steroids, as required or desired. In one embodiment, an intra-articular injection can include the selective delivery of three different drugs into a patient, a corticosteroid, a short-acting anesthetic and a long-acting anesthetic. In alternative embodiments, more or fewer (or different) medicaments and/or other materials can be included in a particular injection protocol. According to some embodiments of injection modes or sequences, two or more of the various medications, other fluids and/or other materials loaded onto a fluid delivery module can be delivered simultaneously with one another or sequentially.

Once the desired volumes or other quantities of medications, formulations and/or other substances have been delivered, the clinician can remove the needle from the patient and terminate the procedure 1046. However, in other embodiments, one or more additional treatment steps or procedures may remain after the delivery of the desired medications and/or other substances. Depending on the particular embodiment being utilized, the handpiece assembly, the needle assembly, the tip and/or any other component of the injection system (e.g., cassette, vials or other containers, clip, delivery line, etc.) can be properly discarded 1050 to reset 1054 the system in preparation for a subsequent injection procedure.

In any of the embodiments disclosed herein, certain cleaning protocols can be used to help prevent or reduce the likelihood of viral ingress or other forms of contamination. For example, whenever a removable component is detached from a corresponding fitting or area of the injection system, a user may need to clean the exposed surfaces (e.g., swab, wipe, etc.) with one or more materials (e.g., wipes or swabs comprising isopropanol, other alcohols, sterilizing agents, disinfectants and/or the like). In some embodiments, for example, a clinician or other user can swab, wipe or otherwise clean the exposed recess of a fluid delivery module (e.g., when a cassette is being replaced), a core (e.g., when a clip is being replaced), the distal end of a handpiece assembly (e.g., when a needle assembly is being replaced), the nest or receiving areas (e.g., when a vial, ampoule, syringe or other container is being replaced) and/or the like.

To assist in the description of the disclosed embodiments, words such as upward, upper, bottom, downward, lower, rear, front, vertical, horizontal, upstream, downstream have been used above to describe different embodiments and/or the accompanying figures. It will be appreciated, however, that the different embodiments, whether illustrated or not, can be located and oriented in a variety of desired positions.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

What is claimed is:

1. An injection system for delivering at least one fluid into a subject, comprising:

a fluid delivery module comprising a first loading area configured to receive a container, the fluid delivery module further comprising a first internal reservoir, the first internal reservoir being configured to selectively receive a volume of fluid contained within a container secured to the first loading area;

a handpiece assembly comprising at least one conduit, the at least one conduit comprising a distal end configured to receive a needle, wherein the at least one conduit of the handpiece assembly is configured to be placed in fluid communication with the first internal reservoir;

at least one controller configured to regulate, at least in part, a delivery of a fluid from the first internal reservoir to the at least one conduit of the handpiece assembly;

a fluid transfer device for selectively generating a vacuum and a positive pressure within the first internal reservoir;

wherein the fluid transfer device transfers a first volume of a fluid from a container secured to the first loading area to the first internal reservoir by generating a vacuum within the first internal reservoir; and when the first volume of fluid is located in the first internal reservoir, the fluid transfer device transfers at least a portion of the first volume of the fluid transferred to the first internal reservoir to the at least one conduit of the handpiece assembly by generating a positive pressure within the first internal reservoir; and wherein the injection system is configured to generate a negative pressure within the at least one conduit in order to aspirate a bodily fluid of the subject at least partially through a needle secured along the distal end of the at least one conduit when the needle is positioned with the subject.

2. The injection system of claim 1, wherein the first loading area is configured to receive nonspecific fluid containers.

3. The injection system of claim 1, wherein the first loading area is configured to directly receive an original manufacturer's vial.

4. The injection system of claim 1, wherein the fluid delivery module further comprises a second loading area and a second internal reservoir, wherein the second internal reservoir is configured to selectively receive a volume of fluid contained within a container secured to the second loading area, and wherein the second internal reservoir is in fluid communication with the at least one conduit of the handpiece assembly.

5. The injection system of claim 1, wherein the first loading area is located along an exterior of the fluid delivery module to facilitate securing a container to the first loading area.

6. The injection system of claim 1, wherein the first loading area and the first internal reservoir are included in a cassette assembly, the cassette assembly being configured to be removably secured to the fluid delivery module.

7. The injection system of claim 1, wherein the at least one controller comprises at least one of a button, a dial, a knob, a switch, a rollerball, a rollerwheel and a foot pedal.

8. The injection system of claim 1, wherein the fluid delivery module comprises a display, the display being configured to provide status information of an injection procedure.

9. The injection system of claim 8, wherein the status information comprises at least one of (i) a volume of fluid delivered from the first internal reservoir to the handpiece assembly, and (ii) a volume remaining in the first internal reservoir of the fluid delivery module.

10. The injection system of claim 1, wherein the fluid delivery module is in data communication with an imaging device configured to help locate a targeted anatomical location within the subject.

11. The injection system of claim 10, wherein the imaging device comprises an ultrasound device.

12. The injection system of claim 1, wherein a proximal end of the at least one conduit is configured to removably attach to the fluid delivery module.

13. The injection system of claim 1, wherein a proximal end of the at least one conduit is configured to removably attach to the fluid delivery module.

14. An injection system for delivering at least one fluid into a subject, comprising:
   a fluid delivery module comprising a first loading area configured to receive a container, the fluid delivery module further comprising a first internal reservoir, the first internal reservoir being configured to selectively receive a volume of fluid contained within a container secured to the first loading area;
   at least one conduit, wherein the at least one conduit is configured to be placed in fluid communication with the first internal reservoir; and
   a fluid transfer device configured to generate a vacuum and a positive pressure within the first internal reservoir;
   wherein the fluid transfer device transfers a first volume of a fluid from a container secured to the first loading area to the first internal reservoir by generating a vacuum within the first internal reservoir; and when the first volume of fluid is located in the first internal reservoir, the fluid transfer device transfers at least a portion of the first volume of the fluid transferred to the first internal reservoir to the at least one conduit by generating a positive pressure within the first internal reservoir; and
   wherein the first loading area and the first internal reservoir are included in a cassette assembly, the cassette assembly being configured to be removably secured to the fluid delivery module.

15. The injection system of claim 14, wherein the first loading area is located along an exterior of the fluid delivery module to facilitate securing a container to the first loading area.

16. The injection system of claim 14, wherein a proximal end of the at least one conduit is configured to removably couple to at least a portion of the cassette assembly in order to place the at least one conduit in fluid communication with the first reservoir.

17. The injection system of claim 14, wherein the fluid delivery module is configured to be placed in data communication with an imaging device configured to help locate a targeted anatomical location within the subject.

18. An injection system for delivering at least one fluid into a subject, comprising:
   a fluid delivery module comprising a first loading area configured to receive a container, the fluid delivery module further comprising a first internal reservoir, the first internal reservoir being configured to selectively receive a volume of fluid contained within a container secured to the first loading area;
   a handpiece assembly comprising at least one conduit, the at least one conduit comprising a distal end configured to receive a needle, wherein the at least one conduit of the handpiece assembly is configured to be placed in fluid communication with the first internal reservoir;
   at least one controller configured to regulate, at least in part, a delivery of a fluid from the first internal reservoir to the at least one conduit of the handpiece assembly;
   a fluid transfer device for selectively generating a vacuum and a positive pressure within the first internal reservoir;
   wherein the fluid transfer device transfers a first volume of a fluid from a container secured to the first loading area to the first internal reservoir by generating a vacuum within the first internal reservoir; and when the first volume of fluid is located in the first internal reservoir, the fluid transfer device transfers at least a portion of the first volume of the fluid transferred to the first internal reservoir to the at least one conduit of the handpiece assembly by generating a positive pressure within the first internal reservoir; and
   wherein the first loading area and the first internal reservoir are included in a cassette assembly, the cassette assembly being configured to be removably secured to the fluid delivery module.

\* \* \* \* \*